United States Patent
Audia et al.

(12) 
(10) Patent No.: US 6,552,013 B1
(45) Date of Patent: Apr. 22, 2003

(54) DEOXYAMINO ACID COMPOUNDS, PHARMACEUTICAL COMPOSITIONS COMPRISING SAME, AND METHODS FOR INHIBITING β-AMYLOID PEPTIDE RELEASE AND/OR ITS SYNTHESIS BY USE OF SUCH COMPOUNDS

(75) Inventors: James E. Audia, Indianapolis, IN (US); Warren J. Porter, Indianapolis, IN (US); Richard C. Thompson, Frankfort, IN (US); Stephen C. Wilkie, Indianapolis, IN (US); Douglas R. Stack, Fishers, IN (US); Qing Shi, Carmel, IN (US)

(73) Assignees: Elan Pharmaceuticals, Inc., South San Francisco, CA (US); Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/338,121

(22) Filed: Jun. 22, 1999

Related U.S. Application Data

(60) Provisional application No. 60/160,067, filed on Jun. 22, 1998, and provisional application No. 60/150,704, filed on Sep. 30, 1998.

(51) Int. Cl.[7] .................... C07D 243/24; C07D 223/18; C07D 223/16; C07D 409/12; A61K 31/55
(52) U.S. Cl. ........................... 514/212.04; 514/212.07; 540/522; 540/523
(58) Field of Search ................ 514/212.04, 212.07; 540/522, 523

(56) References Cited

U.S. PATENT DOCUMENTS

| | | | |
|---|---|---|---|
| 4,410,520 A | 10/1983 | Watthey | 424/244 |
| 4,473,575 A | 9/1984 | Watthey | 424/263 |
| 5,015,639 A | 5/1991 | Berger et al. | 514/213 |
| 5,206,235 A | 4/1993 | Fisher et al. | 514/213 |
| 5,247,080 A | 9/1993 | Berger et al. | 540/523 |
| 5,486,541 A | 1/1996 | Sterling et al. | 514/657 |
| 5,502,048 A | 3/1996 | Chapdelaire et al. | 514/213 |
| 5,519,061 A | 5/1996 | Youdim et al. | 514/647 |
| 5,532,415 A | 7/1996 | Youdim et al. | 564/308 |
| 5,656,626 A | 8/1997 | Chapdelaine et al. | 514/213 |
| 5,672,598 A | 9/1997 | De et al. | 514/212 |

FOREIGN PATENT DOCUMENTS

| | | |
|---|---|---|
| WO | WO 92/16524 | 10/1992 |
| WO | WO 97/16410 | 5/1997 |
| WO | WO 98/22430 | 5/1998 |
| WO | WO 98/22494 | 5/1998 |
| WO | WO 98/38177 | 9/1998 |

*Primary Examiner*—Bruck Kifle
(74) *Attorney, Agent, or Firm*—Burns, Doane, Swecker & Mathis LLP

(57) ABSTRACT

Disclosed are compounds which inhibit β-amyloid peptide release and/or its synthesis, and, accordingly, have utility in treating Alzheimer's disease. Also disclosed are pharmaceutical compositions comprising a compound which inhibits β-amyloid peptide release and/or its synthesis as well as methods for treating Alzheimer's disease both prophylactically and therapeutically with such pharmaceutical compositions.

34 Claims, No Drawings

DEOXYAMINO ACID COMPOUNDS, PHARMACEUTICAL COMPOSITIONS COMPRISING SAME, AND METHODS FOR INHIBITING β-AMYLOID PEPTIDE RELEASE AND/OR ITS SYNTHESIS BY USE OF SUCH COMPOUNDS

CROSS REFERENCE TO RELATED APPLICATIONS

This application claims the benefit of U.S. Provisional Application No. 60/160,067, which was converted pursuant to 37 C.F.R. §1.53(b) from U.S. patent application Ser. No. 09/102,507, filed Jun. 22, 1998 and U.S. Provisional Application No. 60/150,704, which was converted pursuant to 37 C.F.R. §1.53(b) from U.S. patent application Ser. No. 09/162,757, filed Sep. 30, 1998, the disclosures of which is incorporated herein by reference in its entirety.

BACKGROUND OF THE INVENTION

FIELD OF THE INVENTION

This invention relates to compounds which inhibit β-amyloid peptide release and/or its synthesis, and, accordingly, have utility in treating Alzheimer's disease.

REFERENCES

The following publications, patents and patent applications are cited in this application as superscript numbers:

[1] Glenner, et al., *Biochem. Biophys. Res. Commun.* (1984) 120:885–890.
[2] U.S. Pat. No. 4,666,829, issued May 19, 1987, to G. G. Glenner et al., entitled "Polypeptide Marker for Alzheimer's Disease and Its Use for Diagnosis."
[3] Selkoe, *Neuron.* (1991) 6:487–498.
[4] Goate, et al., *Nature* (1990) 349:704–706.
[5] Chartier Harlan, et al., *Nature* (1989) 353:844–846.
[6] Murrell, et al., *Science* (1991) 254:97–99.
[7] Mullan, et al., *Nature Genet.* (1992) 1:345–347.
[8] Schenk, et al., International Patent Application Publication No. WO 94/10569, "Methods and Compositions for the Detection of Soluble β-Amyloid Peptide", published May 11, 1994.
[9] Selkoe, Scientific American, "Amyloid Protein and Alzheimer's Disease", pp. 2–8, November, 1991.
[10] Yates et al., U.S. Pat. No. 3,598,859.
[11] *Tetrahedron Letters* 1993, 34(48), 7685.
[12] R. F. C. Brown et al., *Tetrahedron Letters* 1971, 8, 667–670.
[13] A. O. King et al., *J. Org. Chem.* 1993, 58, 3384–3386.
[14] U.S. Provisional Application Serial No. 60/019,790, filed Jun. 14, 1996.
[15] R. D. Clark et al., *Tetrahedron* 1993, 49(7), 1351–1356.
[16] Citron, et al., *Nature* (1992) 360:672–674.
[17] P. Seubert, *Nature* (1992) 359:325–327.
[18] Hansen, et al., *J. Immun. Meth.* (1989) 119:203–210.
[19] Games et al., *Nature* (1995) 373:523–527.
[20] Johnson-Wood et al., *PNAS USA* (1997) 94:1550–1555.

All of the above publications, patents and patent applications are herein incorporated by reference in their entirety to the same extent as if each individual publication, patent or patent application was specifically and individually indicated to be incorporated by reference in its entirety.

STATE OF THE ART

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (PAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

Compounds which inhibit β-amyloid peptide release and/or its synthesis in vivo are disclosed in U.S. patent application Ser. No. 08/996,422, filed Dec. 22, 1997, and entitled "Cycloalkyl, Lactam, Lactone and Related Compounds, Pharmaceutical Compositions Comprising Same, and Methods for Inhibiting β-Amyloid Peptide Release, and/or its Synthesis by Use of Such Compounds," the disclosure of which is incorporated herein by reference in its entirety. The present invention is directed to deoxy derivatives of such compounds.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition.

Accordingly, in one of its composition aspects, the present invention provides compounds of formula I:

wherein:

W is a cyclic group selected from the group consisting of:

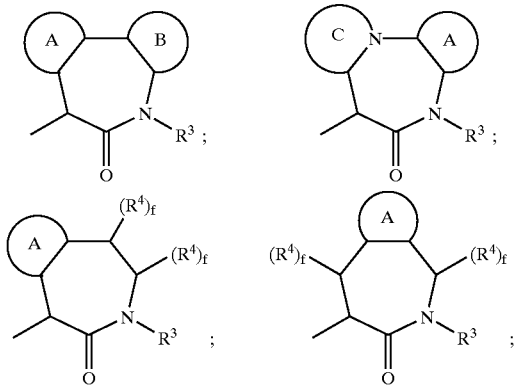

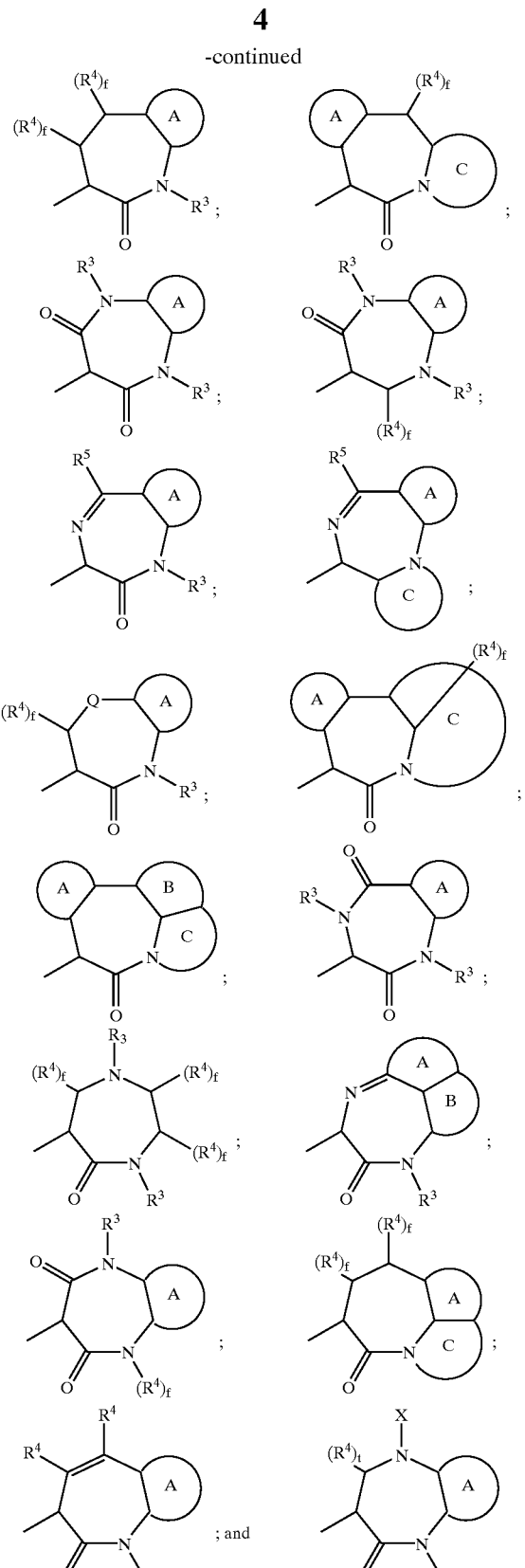

wherein:
ring A, together with the atoms to which it is attached, forms a carbocyclic or heterocyclic ring selected from the group consisting of aryl, cycloalkyl, substituted cycloalkyl, cycloalkenyl, substituted cycloalkenyl, heteroaryl and heterocyclic;

ring B, together with the atoms to which it is attached, forms a carbocyclic or heterocyclic ring selected from the group consisting of aryl, cycloalkyl, substituted cycloalkyl, cycloalkenyl, substituted cycloalkenyl, heteroaryl and heterocyclic;

ring C, together with the atoms to which it is attached, forms a heteroaryl or heterocyclic ring;

Y is represented by the formula:

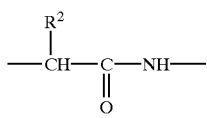

$R^1$ is selected from the group consisting of alkyl, alkenyl, alkynyl, cycloalkyl, cycloalkenyl, substituted alkyl, substituted alkenyl, substituted alkynyl, substituted cycloalkyl, substituted cycloalkenyl, aryl, heteroaryl and heterocyclic;

$R^2$ is selected from the group consisting of alkyl, substituted alkyl, alkenyl, substituted alkenyl, alkynyl, substituted alkynyl, cycloalkyl, aryl, heteroaryl and heterocyclic;

each $R^3$ is independently selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;

each $R^4$ is independently selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic;

$R^5$ is selected from the group consisting of hydrogen, alkyl, substituted alkyl, alkenyl, substituted alkenyl, alkynyl, substituted alkynyl, alkoxy, substituted alkoxy, aryl, aryloxy, cycloalkyl, substituted cycloalkyl, cycloalkenyl, substituted cycloalkenyl, substituted amino, heteroaryl, heterocyclic, thioalkoxy and substituted thioalkoxy;

Q is oxygen, sulfur, —S(O)—, —S(O)$_2$—, —C(O)— or —C(S)—;

Z is represented by the formula —T—CX'X"V—, wherein T is selected from the group consisting of a bond covalently linking $R^1$ to —CX'X"—, oxygen, sulfur and —NR$^6$—, wherein $R^6$ is hydrogen, acyl, alkyl, aryl or heteroaryl;

X' is hydrogen, hydroxy or fluoro;

X" is hydrogen, hydroxy or fluoro, or X' and X" together form an oxo group; and

V is selected from the group consisting of alkylene or substituted alkylene, or $R^1$ and Z together form an aryl, cycloalkyl, substituted cycloalkyl, cycloalkenyl, substituted cycloalkenyl, heterocyclic or substituted heterocyclic;

X is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted alkenyl, heteroaryl and heterocyclic; or X and one of $R^4$ and the atoms to which they are attached form a double bond;

t is an integer from 0 to 2;
f is an integer from 0 to 2;
n is an integer equal to 1 or 2;
and pharmaceutically acceptable salts thereof provided that neither of X' and X" can be hydroxy or fluoro when T is other than a covalent bond linking $R^1$ to —CX'X"—.

This invention also provides for novel pharmaceutical compositions comprising a pharmaceutically acceptable carrier and a compound of the formula I above.

Additionally, in one of its method aspects, this invention is directed to a method for inhibiting β-amyloid peptide release and/or its synthesis in a cell which method comprises administering to such a cell an amount of a compound or a mixture of compounds of formula I above effective in inhibiting the cellular release and/or synthesis of β-amyloid peptide.

Because the in vivo generation of β-amyloid peptide is associated with the pathogenesis of AD[8,9], the compounds of formula I can also be employed in conjunction with a pharmaceutical composition to prophylactically and/or therapeutically prevent and/or treat AD. Accordingly, in another of its method aspects, this invention is directed to a prophylactic method for preventing the onset of AD in a patient at risk for developing AD which method comprises administering to said patient a pharmaceutical composition comprising a pharmaceutically inert carrier and an effective amount of a compound or a mixture of compounds of formula I above.

In yet another of its method aspects, this invention is directed to a therapeutic method for treating a patient with AD in order to inhibit further deterioration in the condition of that patient which method comprises administering to said patient a pharmaceutical composition comprising a pharmaceutically inert carrier and an effective amount of a compound or a mixture of compounds of formula I above.

In formula I above, rings A and B may be the same or different and are preferably independently selected from the group consisting of aryl, cycloalkyl, cycloalkenyl, heteroaryl and heterocyclic. More preferably, rings A and B are independently selected from the group consisting of aryl and cycloalkyl. Still more preferably, rings A and B are independently aryl.

Particularly preferred A and B rings include, by way of example, phenyl, substituted phenyl, including fluorosubstituted phenyl, cyclohexyl and the like.

Preferred C rings include, by way of example, pyrrolidinyl, piperidinyl, morpholino and the like.

Preferred $R^1$ groups include unsubstituted aryl groups such as phenyl, 1-naphthyl, 2-naphthyl, etc.; substituted aryl groups such as monosubstituted phenyls (preferably substituents at 3 or 5 positions); disubstituted phenyls (preferably substituents at 3 and 5 positions); and trisubstituted phenyls (preferably substituents at the 3,4,5 positions). Preferably, the substituted phenyl groups do not include more than 3 substituents. Examples of substituted phenyls include, for instance, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl)phenyl, 3,5-dimethoxyphenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 4-fluoro-2-trifluoromethylphenyl, 2-fluoro-4-trifluoromethylphenyl, 4-benzyloxyphenyl, 2-chloro-6-fluorophenyl, 2-fluoro-6-cholrophenyl, 2,3,4,5,6-pentafluorophenyl, 2,5-dimethylphenyl, 4-phenylphenyl and 2-fluoro-3-trifluoromethylphenyl.

Other preferred $R^1$ groups include, by way of example, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopenten-1-yl, cyclopenten-2-yl, cyclohexen-1-yl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyridin-2-yl, pyridin-3-yl, pyridin4-yl, fluoropyridyls (including 5-fluoropyridin-3-yl), chloropyridyls (including 5-chloropyridin-3-yl), thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetrazol-5-yl, allyl, 2-(cyclohexyl)ethyl, (CH$_3$)CH=CHCH$_2$CH$_2$CH(CH$_3$)—, (CH$_3$)$_2$C=CHCH$_2$CH$_2$CH(CH$_3$)—, φC(O)CH$_2$—, thien-2-ylmethyl, 2-(thien-2-yl)ethyl, 3-(thien-2-yl)-n-propyl, 2-(4-nitrophenyl)ethyl, 2-(4-methoxyphenyl)-ethyl, norboran-2-yl, (4-methoxyphenyl)-methyl, (2-methoxyphenyl)methyl, (3-methoxyphenyl)methyl, (3-hydroxyphenyl)-methyl, (4-hydroxyphenyl)methyl, (4-methoxyphenyl)methyl, (4-methylphenyl)-methyl, (4-fluorophenyl)methyl, (4-flourophenoxy)methyl, (2,4-dichlorophenoxy)-ethyl, (4-chlorophenyl)methyl, (2-chlorophenyl)methyl, (1-phenyl)ethyl, (1-(p-chlorophenyl)ethyl, (1-triflouromethyl)ethyl, (4-methoxyphenyl)ethyl, CH$_3$OC(O)CH$_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH$_3$CH=CH—, CH$_3$CH$_2$CH=CH—, (4-chlorophenyl)C(O)CH$_2$—, (4-fluorophenyl)C(O)CH$_2$—, (4-methoxyphenyl)C(O)CH$_2$—, 4-(fluorophenyl)-NHC(O)CH$_2$—, 1-phenyl-n-butyl, (φ)$_2$CHNHC(O)CH$_2$CH$_2$—, (CH$_3$)$_2$NC(O)CH$_2$—, (φ)$_2$CHNHC(O)CH$_2$CH$_2$—, methylcarbonylmethyl, (2,4-dimethylphenyl)-C(O)CH$_2$—, phenylC(O)CH$_2$—, CH$_3$C(O)N(φ)—, ethenyl, methylthiomethyl, (CH$_3$)$_3$CNHC(O)CH$_2$—, diphenylmethyl, phenoxymethyl, 3,4-methylenedioxyphenyl-CH$_2$—, benzo[b]thiophen-3-yl, (CH$_3$)$_3$COC(O)NHCH$_2$—, trans-styryl, H$_2$NC(O)CH$_2$CH$_2$—, 2-trifluoromethylphenyl-C(O)CH$_2$, φC(O)NHCH(φ)CH$_2$—, mesityl, CH$_3$C(=NHOH)CH$_2$—, 4-CH$_3$-φ-NHC(O)CH$_2$CH$_2$—, φC(O)CH(φ)CH$_2$—, (CH$_3$)$_2$CHC(O)NHCH(φ)—, CH$_3$CH$_2$OCH$_2$—, CH$_3$OC(O)CH(CH$_3$)(CH$_2$)$_3$—, 2,2,2-trifluoroethyl, 1-(trifluoromethyl)ethyl, 2-CH$_3$-benzofuran-3-yl, 2-(2,4-dichlorophenoxy)ethyl, φSO$_2$CH$_2$—, 3-cyclohexyl-n-propyl, CF$_3$CH$_2$CH$_2$CH$_2$— and N-pyrrolidinyl.

$R^2$ is preferably selected from the group consisting of alkyl, substituted alkyl, alkenyl, cycloalkyl, aryl, heteroaryl and heterocyclic.

Particularly preferred $R^2$ substituents include, by way of example, methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-buten-2-yl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyridin-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, -2-methylcyclopentyl, -cyclohexen-2-yl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl (e.g., 2-pyridyl, 3-pyridyl and 4-pyridyl), pyridyl (2-pyridyl, 3-pyridyl and 4-pyridyl), —CH$_2$-naphthyl (e.g., 1-naphthyl and 2-naphthyl), —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynapth-2-yl, —CH$_2$CH$_2$SCH$_3$, thien-2-yl, thien-3-yl, and the like.

Preferably, $R^3$ is selected from the group consisting of hydrogen, alkyl, substituted alkyl and cycloalkyl.

Particularly preferred $R^3$ substituents include, by way of example, hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, cyclohexyl, and the like.

When present, $R^4$ is preferably alkyl or substituted alkyl.

$R^5$ is preferably alkyl; substituted alkyl; aryl; substituted aryl, such as 2-fluorophenyl, 3-fluorophenyl, 4-fluorophenyl, 2-chlorophenyl and the like; cycloalkyl, such as cyclohexyl and the like; or heteroaryl or heterocyclic, such as piperdin-1-yl, 2-pyridyl, 2-thiazolyl, 2-thienyl and the like.

Preferably, f is 0 or 1. More preferably, f is 0.
Preferably, n is 1.

In one preferred embodiment of this invention, W is a cyclic group of the formula:

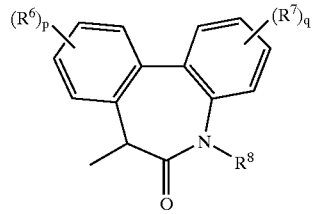

wherein
  each $R^6$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;

each $R^7$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;

$R^8$ is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;

p is an integer from 0 to 4; and q is an integer from 0 to 4.

Preferably, $R^6$ and $R^7$ are independently selected from the group consisting of alkoxy, substituted alkoxy, alkyl, substituted alkyl, amino, substituted amino, carboxyl, carboxyalkyl, cyano, halo, nitro, thioalkoxy and substituted thioalkoxy. More preferably, when present, $R^6$ and $R^7$ are fluoro.

$R^8$ is preferably selected from the group consisting of hydrogen, alkyl, substituted alkyl, acyl, aryl, cycloalkyl and substituted cycloalkyl. More preferably, $R^8$ is selected from the group consisting of hydrogen, alkyl, substituted alkyl and cycloalkyl.

Particularly preferred $R^8$ substituents include, by way of example, hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, cyclohexyl, and the like.

In another preferred embodiment of this invention, W is a cyclic group of the formula:

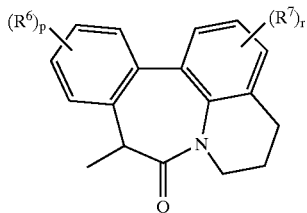

wherein $R^6$, $R^7$, and p are as defined herein and r is an integer from 0 to 3.

In still another preferred embodiment of this invention, W is a cyclic group of the formula:

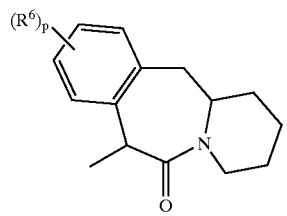

wherein $R^6$ and p are as defined herein.

In yet another preferred embodiment of this invention, W is a cyclic ring of the formula:

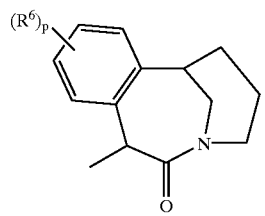

wherein $R^6$ and p are as defined herein.

In still another preferred embodiment of this invention, W is a cyclic ring of the formula:

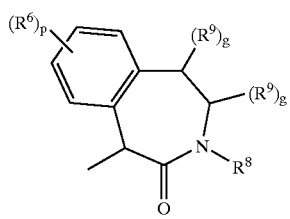

wherein $R^6$, $R^8$ and p are as defined herein; and each $R^9$ is independently selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic; and g is an integer from 0 to 2.

When present, $R^9$ is preferably alkyl or substituted alkyl.

In another preferred embodiment of this invention, W is a cyclic ring of the formula:

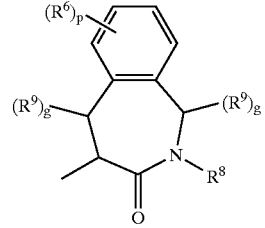

wherein $R^6$, $R^8$, $R^9$, g and p are as defined herein.

In yet another preferred embodiment of this invention, W is a cyclic ring of the formula:

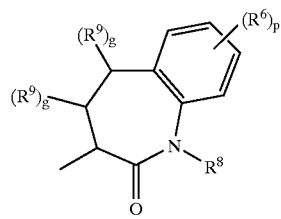

wherein $R^6$, $R^8$, $R^9$, g and p are as defined herein.

In still another preferred embodiment of this invention, W is a cyclic ring of the formula:

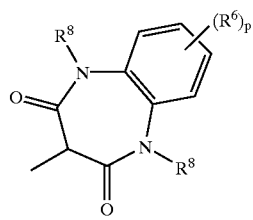

wherein $R^6$, each $R^8$ and p are as defined herein.

In another preferred embodiment of this invention, W is a cyclic ring of the formula:

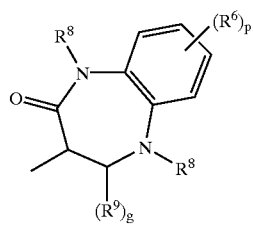

wherein each $R^6$, each $R^8$, $R^9$, g and p are as defined herein.

In another preferred embodiment of this invention, W is a cyclic ring of the formula:

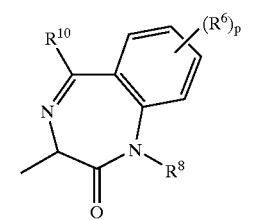

wherein $R^6$, $R^8$ and p are as defined herein; and $R^{10}$ selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic.

In another preferred embodiment of this invention, W is a cyclic ring of the formula:

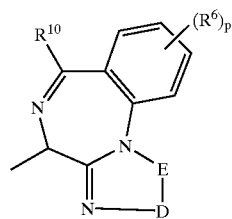

wherein $R^6$, $R^{10}$ and p are as defined herein; and

D—E is selected from the group consisting of alkylene, alkenylene, substituted alkylene, substituted alkenylene and —N=CH—.

In another preferred embodiment of this invention, W is a cyclic ring of the formula:

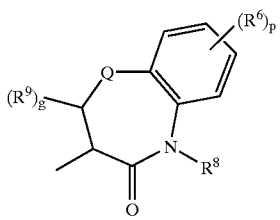

wherein $R^6$, $R^8$, $R^9$, g and p are as defined herein; and

Q is oxygen, sulfur, —S(O)— or —S(O)$_2$—.

In another preferred embodiment of this invention, W is a cyclic ring of the formula:

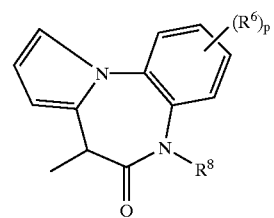

wherein $R^6$, $R^8$ and p are as defined herein.

In another preferred embodiment of this invention, W is a cyclic ring of the formula:

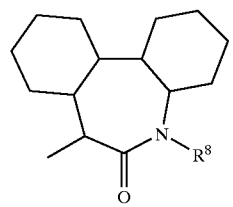

wherein $R^8$ is as defined herein.

In another preferred embodiment of this invention, W is a cyclic ring of the formula:

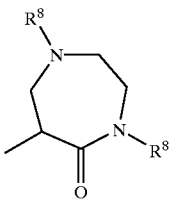

wherein R⁸ is as defined herein.

In another preferred embodiment of this invention, W is a cyclic ring of the formula:

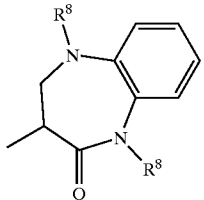

wherein R⁸ is as defined herein.

In another preferred embodiment of this invention, W is a cyclic ring of the formula:

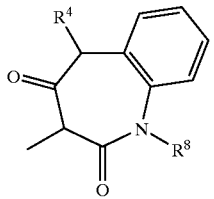

wherein R⁴ and R⁸ are as defined herein.

In another preferred embodiment of this invention, W is a cyclic ring of the formula:

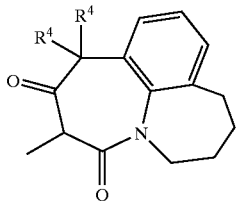

wherein R⁴ is as defined herein.

In another preferred embodiment of this invention, W is a cyclic ring of the formula:

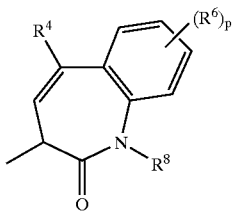

wherein R⁴, R⁶, R⁸ and p are as defined herein.

In another preferred embodiment of this invention, W is a cyclic ring of the formula:

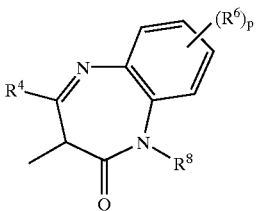

wherein R⁴, R⁶, R⁸ and p are as defined herein.

Compounds of this invention include, by way of example, the following:

5-(S)-(N'-(2-(3,5-difluorophenyl)ethyl)-L-alaninyl)-amino-7-methyl-5,7-dihydro-6H-dibenz[b,d]azepin-6-one 5(S)-(N'-(2(R)-hydroxy-2-(3,5-difluorophenyl)ethyl)-L-alaninyl)-amino-7-methyl-5,7-dihydro-6H-dibenz[b,d]azepin-6-one 5(S)-(N'-(2(S)-hydroxy-2-(3,5-difluorophenyl)ethyl)-L-alaninyl)-amino-7-methyl-5,7-dihydro-6H-dibenz[b,d]azepin-6-one 5(S)-(N'-(2(R/S)-hydroxy-3-isopropyloxypropyl)-L-alaninyl)-amino-7-methyl-5,7-dihydro-6H-dibenz[b,d]azepin-6-one 5(S)-(N'-(2(R/S)-hydroxybutyl)-L-alaninyl)-amino-7-methyl-5,7-dihydro-6H-dibenz[b,d]azepin-6-one 5(S)-(N'-(2(R/S)-3-dihydroxypropyl)-L-alaninyl)-amino-7-methyl-5,7-dihydro-6H-dibenz[b,d]azepin-6-one 5(S)-(N'-(2(R/S)-hydroxy-3-morpholinopropyl)-L-alaninyl)-amino-7-methyl-5,7-dihydro-6H-dibenz[b,d]azepin-6-one 5(S)-(N'-(2(R/S)-hydroxytetradecyl)-L-alaninyl)-amino-7-methyl-5,7-dihydro-6H-dibenz[b,d]azepin-6-one 5(S)-(N'-(2(R/S)-hydroxyoctyl)-L-alaninyl)-amino-7-methyl-5,7-dihydro-6H-dibenz[b,d]azepin-6-one 5(S)-(N'-(2(R)-hydroxy-2-(3,4,5-trifluorophenyl)ethyl)-L-alaninyl)-amino-7-methyl-5,7-dihydro-6H-dibenz[b,d]azepin-6-one 5(S)-(N'-(2(S)-hydroxy-2-(3,4,5-trifluorophenyl)ethyl)-L-alaninyl)-amino-7-methyl-5,7-dihydro-6H-dibenz[b,d]azepin-6-one 5(S)-(N'-(2(R)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,3,3-trifluoro)propyl)-L-alaninyl)-amino-7-methyl-5,7-dihydro-6H-dibenz[b,d]azepin-6-one 5(S)-(N'-(2(S)-hydroxy-2-(3,3,3-trifluoro)propyl)-L-alaninyl)-amino-7-methyl-5,7-dihydro-6H-dibenz[b,d]azepin-6-one 5-(S)-(N'-(3-methyl-2-butanone)-L-alaninyl)-amino-7-methyl-5,7-dihydro-6H-dibenz[b,d]azepin-6-one 5-(S)-(N'-(3-methyl-2-(S)-hydroxybutyl)-L-alaninyl)-amino-7-methyl-5,7-dihydro-6H-dibenz[b,d]azepin-6-one 3-(N'-(3-methyl-2-(S)-2-hydroxybutyl)-L-Alaninyl)-amino-2,4-dioxo-1-methyl-5-phenyl-2,3,4,5-tetrahydro-1H-1,5-benzodiazepine 3-(N'-(2-(R/S)-3,5-difluorophenyl-2-hydroxyethyl)-L-alaninyl)-amino-2,4-dioxo-1-methyl-5-phenyl-2,3,4,5-tetrahydro-1H-1,5-benzodiazepine 5-[N'-(S)-2-(4-methylpentyl)amino-3-methylbutyryl-L-alaninyl]-amino-7-methyl-5,7-dihydro-6H-dibenz[b,d]azepin-6-one 5-(S)-{N'-[(1RS,2SR)-1,2,3,4-tetrahydro-1-hydroxy-2-naphthyl]alaninyl}-amino-7-methyl-5,7-dihydro-6H-dibenz[b,d]azepin-6-one 5-(S)-{N'-[(1RS,2RS)-1,2,3,4-tetrahydro-1-hydroxy-2-naphthyl]alaninyl}-amino-7-methyl-5,7-dihydro-6H-dibenz[b,d]azepin-6-one 5-(S)-[N'-(2-α-tetralone)-L-alaninyl]-amino-7-methyl-5,7-dihydro-6H-dibenz[b,d]azepin-6-one hydrochloride 5-(S)-[N'-(1,2,3,4-tetrahydro-2-naphthyl)-L-alaninyl]-amino-7-methyl-5,7-dihydro-6H-dibenz[b,d]azepin-6-one 5-(S)-{N'-[(1RS,2SR)-1-hydroxy-2-cyclohexyl]alaninyl}-amino-7-methyl-5,7-dihydro-6H-dibenz[b,d]azepin-6-one 5-(S)-[N'-(4-methylpentyl)-L-alaninyl]-amino-7-methyl-5,7-dihydro-6H-dibenz[b,d]azepin-6-one Other examples are set forth in the Table below:

TABLE

The compounds listed below conform to formula I as shown below:

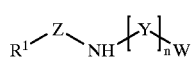

I

W is the following structure, unless otherwise indicated:

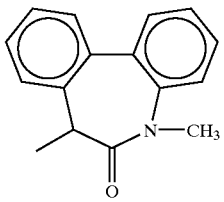

| R¹ | Z | Y | n | W |
|---|---|---|---|---|
| 3,5-di-fluoro-Φ- | —CH₂—CH₂— | —HC(CH₃)—C(O)—NH— | 1 | as above |
| 3,5-di-fluoro-Φ- | CH(OH)—CH₂ | —HC(CH₃)—C(O)—NH— | 1 | as above |
| (CH₃)₂CH— | —O—CH₂—CH(OH)—CH₂— | —HC(CH₃)—C(O)—NH— | 1 | as above |
| CH₃— | —CH₂—CH(OH)—CH₂— | —HC(CH₃)—C(O)—NH— | 1 | as above |
| HO—CH₂— | —CH(OH)—CH₂— | —HC(CH₃)—C(O)—NH— | 1 | as above |
| morpholine- | —CH₂—CH(OH)—CH₂— | —HC(CH₃)—C(O)—NH— | 1 | as above |
| CH₃—(CH₂)₅— | —(CH₂)₆—CH(OH)—CH₂— | —HC(CH₃)—C(O)—NH— | 1 | as above |
| CH₃— | —(CH₂)₅—CH(OH)—CH₂— | —HC(CH₃)—C(O)—NH— | 1 | as above |
| 3,4,5-tri-fluoro-Φ- | —CH(OH)—CH₂— | —HC(CH₃)—C(O)—NH— | 1 | as above |
| p-F₃C-Φ- | —CH(OH)—CH₂— | —HC(CH₃)—C(O)—NH— | 1 | as above |
| 3,5-di-F₃C-Φ- | —CH(OH)—CH₂— | —HC(CH₃)—C(O)—NH— | 1 | as above |
| F₃C— | —CH(OH)—CH₂— | —HC(CH₃)—C(O)—NH— | 1 | as above |
| (CH₃)₂—CH— | —C(O)—CH₂— | —HC(CH₃)—C(O)—NH— | 1 | as above |
| (CH₃)₂—CH— | —CH(OH)—CH₂— | —HC(CH₃)—C(O)—NH— | 1 | as above |
| (CH₃)₂—CH— | —CH(OH)—CH₂— | —HC(CH₃)—C(O)—NH— | 1 | 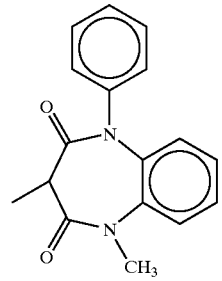 |
| 3,5-di-fluoro-Φ- | —CH(OH)—CH₂— | —HC(CH₃)—C(O)—NH— | 1 | 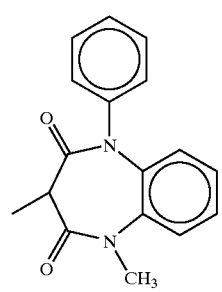 |

TABLE-continued

The compounds listed below conform to formula I as shown below:

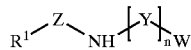

W is the following structure, unless otherwise indicated:

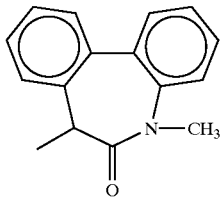

| R¹ | Z | Y | n | W |
|---|---|---|---|---|
| R'Z = [2-methyl-1-hydroxy-tetralin] | | —HC(CH₃)—C(O)—NH— | 1 | [dibenzazepine-N-CH₃] |
| R'Z = [2-methyl-1-oxo-tetralin] | | —HC(CH₃)—C(O)—NH— | 1 | [dibenzazepine-N-CH₃] |
| R'Z = [2-methyl-tetralin] | | —HC(CH₃)—C(O)—NH— | 1 | [dibenzazepine-N-CH₃] |
| R'Z = [2-methyl-1-hydroxy-cyclohexyl] | | —HC(CH₃)—C(O)—NH— | 1 | [dibenzazepine-N-CH₃] |
| (CH₃)₂—CH— | —CH₂—CH₂—CH₂— | —HC(CH₃)—C(O)—NH— | 1 | [dibenzazepine-N-CH₃] |

As is appreciated by the skilled person, compounds of the present invention exist as isomers. Herein, the Cahn-Prelog-Ingold designations of (R)- and (S)- and, for amino acid derived portions of the compounds, the L- and D-designations of stereochemistry relative to the isomers of glyceraldehyde are used to refer to specific isomers where designated. The specific isomers can be prepared by stereospecific synthesis or can be resolved and recovered by techniques known in the art, such as, chromatography on chiral stationary phases, and fractional recrystallization of addition salts formed by reagents used for that purpose. Useful methods of resolving and recovering specific stereoisomers are known in the art and described, for example, in Stereochemistry of Organic Compounds, E. L. Eliel and S. H. Wilen (Wiley-Interscience 1994), Enantiomers, Racemates and Resolutions, J. Jacques, A. Collet and S. J. Wilen (Wiley-Interscience 1981), and European Patent Application No. EP-A-838448, published Apr. 29, 1998. It is to be understood that the invention extends to all of the isomeric forms of the compounds of the present invention, including the diastereomeric, enantiomeric and racemic forms of the compounds.

Also included within the scope of this invention are prodrugs of the compounds of formula I above including acylated forms of alcohols and thiols, aminals of one or more amines, and the like.

DETAILED DESCRIPTION OF THE INVENTION

As above, this invention relates to compounds which inhibit β-amyloid peptide release and/or its synthesis, and, accordingly, have utility in treating Alzheimer's disease. However, prior to describing this invention in further detail, the following terms will first be defined.

DEFINITIONS

The term "β-amyloid peptide" refers to a 39–43 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is an approximate 39–43 amino acid fragment of a large membrane-spanning glycoprotein, referred to as the β-amyloid precursor protein (APP). Its 43-amino acid sequence is:

| Asp Ala Glu Phe Arg His Asp Ser Gly Tyr | 1 |
| Glu Val His His Gln Lys Leu Val Phe Phe | 11 |
| Ala Glu Asp Val Gly Ser Asn Lys Gly Ala | 21 |
| Ile Ile Gly Leu Met Val Gly Gly Val Val | 31 |
| Ile Ala Thr (SEQ ID NO: 1) | 41 | or a sequence which is substantially homologous thereto.

"Alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkylene" refers to divalent alkylene groups preferably having from 1 to 10 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to an alkylene group, preferably of from 1 to 10 carbon atoms, having from 1 to 3 substituents selected from the group consisting of alkoxy, substituted alkoxy, cycloalkyl, substituted cycloalkyl, cycloalkoxy, substituted cycloalkoxy, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$^2$-heteroaryl. Additionally, such substituted alkylene groups include those where 2 substituents on the alkylene group are fused to form one or more cycloalkyl, aryl, heterocyclic or heteroaryl groups fused to the alkylene group. Preferably, such fused cycloalkyl groups contain from 1 to 3 fused ring structures.

"Alkenylene" refers to divalent alkenylene groups preferably having from 2 to 10 carbon atoms and more preferably 2 to 6 carbon atoms. This term is exemplified by groups such as ethenylene (—CH═CH—), the propenylene isomers (e.g., —CH$_2$CH═CH— and —C(CH$_3$)═CH—), and the like.

"Substituted alkenylene" refers to an alkenylene group, preferably of from 2 to 10 carbon atoms, having from 1 to 3 substituents selected from the group consisting of alkoxy, substituted alkoxy, cycloalkyl, substituted cycloalkyl, cycloalkoxy, substituted cycloalkoxy, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl. Additionally, such substituted alkylene groups include those where 2 substituents on the alkylene group are fused to form one or more cycloalkyl, aryl, heterocyclic or heteroaryl groups fused to the alkylene group.

"Alkaryl" refers to -alkylene-aryl groups preferably having from 1 to 8 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O—". Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—" where substituted alkyl is as defined above.

"Alkylalkoxy" refers to the group "-alkylene-O-alkyl" which includes by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

"Alkylthioalkoxy" refers to the group "-alkylene-S-alkyl" which includes by way of example, methylenethiomethoxy (—CH$_2$SCH$_3$), ethylenethiomethoxy (—CH$_2$CH$_2$SCH$_3$), n-propylene-thio-iso-propoxy (—CH$_2$CH$_2$CH$_2$SCH(CH$_3$)$_2$), methylenethio-t-butoxy (—CH$_2$SC(CH$_3$)$_3$) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), isopropenyl (—C(CH$_3$)=CH$_2$), and the like.

"Substituted alkenyl" refers to an alkenyl group as defined above having from 1 to 3 substituents selected from the group consisting of alkoxy, substituted alkoxy, cycloalkyl, substituted cycloalkyl, cycloalkoxy, substituted cycloalkoxy, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH$_2$C≡CH) and the like.

"Substituted alkynyl" refers to an alkynyl group as defined above having from 1 to 3 substituents selected from the group consisting of alkoxy, substituted alkoxy, cycloalkyl, substituted cycloalkyl, cycloalkoxy, substituted cycloalkoxy, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

"Acylamino" refers to the group —C(O)NRR where each R is independently selected from the group consisting of hydrogen, alkyl, substituted alkyl, aryl, heteroaryl, heterocyclic and where both R groups are joined to form a heterocyclic group, wherein alkyl, substituted alkyl, aryl, heteroaryl and heterocyclic are as defined herein.

"Amino" refers to the group —NH$_2$.

"Substituted amino" refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, heteroaryl, heterocyclic and where both R groups are joined to form a heterocyclic group. When both R groups are hydrogen, —N(R)$_2$ is an amino group. Examples of substituted amino groups include, by way of illustration, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like.

The term "amino-blocking group" or "amino-protecting group" refers to any group which, when bound to an amino group, prevents undesired reactions from occurring at the amino group and which may be removed by conventional chemical and/or enzymatic procedures to reestablish the amino group. Any known amino-blocking group may be used in this invention. Typically, the amino-blocking group is selected so as to render the resulting blocked-amino group unreactive to the particular reagents and reaction conditions employed in a subsequent pre-determined chemical reaction or series of reactions. After completion of the reaction(s), the amino-blocking group is selectively removed to regenerate the amino group. Examples of suitable amino-blocking groups include, by way of illustration, tert-butoxycarbonyl (Boc), benzyloxycarbonyl (Cbz), acetyl, 1-(1'-adamantyl)-1-methylethoxycarbonyl (Acm), allyloxycarbonyl (Aloc), benzyloxymethyl (Bom), 2-p-biphenylisopropyloxycarbonyl (Bpoc), tert-butyldimethylsilyl (Bsi), benzoyl (Bz), benzyl (Bn), 9-fluorenylmethyloxycarbonyl (Fmoc), 4-methylbenzyl, 4-methoxybenzyl, 2-nitrophenylsulfenyl (Nps), 3-nitro-2-pyridinesulfenyl (NPys), trifluoroacetyl (Tfa), 2,4,6-trimethoxybenzyl (Tmob), trityl (Trt), and the like. If desired, amino-blocking groups covalently attached to a solid support may also be employed.

"Aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

"Aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

"Acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

"Aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heterocyclic, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

"Carboxyalkyl" refers to the groups "—C(O)O-alkyl" and "—C(O)O-substituted alkyl" where alkyl is as defined above.

"Cycloalkyl" refers to cyclic alkyl groups of from 3 to 12 carbon atoms having a single cyclic ring or multiple condensed rings, including bridged, fused and spiro rings and combinations thereof. The cycloalkyl ring may optionally be fused to an aryl, heteroaryl, or heterocycle ring. Such cycloalkyl groups include, by way of example, single ring structures such as cyclopropyl, cyclobutyl, cyclopentyl, cyclooctyl, and the like, or multiple ring structures such as adamantanyl, and the like.

"Substituted cycloalkyl" refers to cycloalkyl groups having from 1 to 5 (preferably 1 to 3) substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Cycloalkenyl" refers to cyclic alkenyl groups of from 4 to 8 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like. p "Substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Halo" or "halogen" refers to fluoro, chloro, bromo and iodo and preferably is either fluoro or chloro.

"Heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heterocyclic, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroaryloxy" refers to the group "—O-heteroaryl".

"Heterocycle" or "heterocyclic" refers to a monovalent saturated or unsaturated group having a single ring or multiple condensed rings having from 1 to 15 carbon atoms and from 1 to 4 hetero atoms selected from nitrogen, sulfur or oxygen within at least one ring.

Unless otherwise constrained by the definition for the heterocyclic substituent, such heterocyclic groups can be optionally substituted with 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl. Such heterocyclic groups can have a single ring or multiple condensed rings. Preferred heterocyclics include morpholino, piperidinyl, and the like.

"Monocyclic heterocyclics" refer to single ring heterocycle groups which are exemplified by, for example, pyrrolidinyl, morpholino, and the like.

"Bicyclic heterocyclics" refer to heterocyclic groups comprised of two ring systems which may be fused, spiro or bridged wherein at least one of the rings contains a heteroatom and the other ring is selected from the group consisting of cycloalkyl, cycloalkenyl, aryl, heteroaryl and heterocyclic. Examples of fused bicyclic heterocyclic ring systems include, for instance, 3-(1,2,3,4-tetrahydro-isoquinolinyl) and the like.

"Tricyclic heterocyclics" refer to heterocyclic groups comprised of three ring systems wherein each of the ring systems is independently fused, spiro or bridged wherein at least one of the rings contains a heteroatom and the remaining two rings are selected from the group consisting of cycloalkyl, cycloalkenyl, aryl, heteroaryl and heterocyclic. When the remaining two rings are cycloalkyl, cycloalkenyl or heterocyclic, these rings may optionally be spiro linked.

Examples of heterocycles and heteroaryls include, but are not limited to, pyrrole, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Heterocyclooxy" refers to the group "—O-heterocycle".

"Keto" or "oxo" refers to the group "═O".

"Oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioalkoxy" refers to the group —S-alkyl.

"Substituted thioalkoxy" refers to the group —S-substituted alkyl.

"Thioaryloxy" refers to the group aryl-S— wherein the aryl group is as defined above including optionally substituted aryl groups also defined above.

"Thioheteroaryloxy" refers to the group heteroaryl-S— wherein the heteroaryl group is as defined above including optionally substituted aryl groups as also defined above.

"Thioketo" refers to the group "═S".

The term "5,7-dihydro-6H-dibenz[b,d]azepin-6-one" refers to a polycyclic ε-caprolactam ring system having the formula:

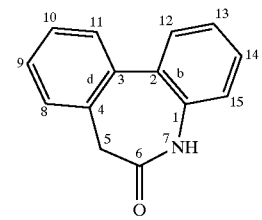

wherein, for nomenclature purposes, the atoms and bonds are numbered and lettered, respectively, as shown.

The term "5,6-dihydro-4H-quino[8,1-ab][3]benzazepin-8 (9H)-one" refers to a polycyclic ε-caprolactam ring system having the formula:

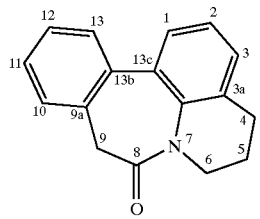

wherein, for nomenclature purposes, the atoms and bonds are numbered and lettered, respectively, as shown.

The term "1,3,4,7,12,12a-hexahydropyrido[2,1-b][3] benzazepin-6(2H)-one" refers to a polycyclic ε-caprolactam ring system having the formula:

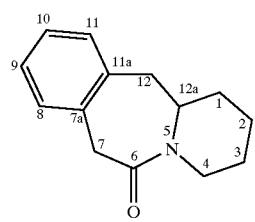

wherein, for nomenclature purposes, the atoms and bonds are numbered and lettered, respectively, as shown.

The term "4,5,6,7-tetrahydro-3,7-methano-3H-3-benzazonin-2(1H)-one" refers to a polycyclic ε-caprolactam ring system having the formula:

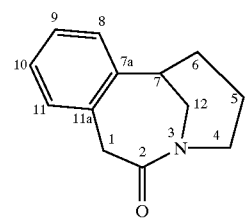

wherein, for nomenclature purposes, the atoms and bonds are numbered and lettered, respectively, as shown.

As to any of the above groups which contain 1 or more substituents, it is understood, of course, that such groups do not contain any substitution or substitution patterns which are sterically impractical and/or synthetically non-feasible.

"Pharmaceutically acceptable salt" refers to pharmaceutically acceptable salts of a compound of formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, thiol, carboxyl groups or other protectable functional group of the compounds prevents reactions from occurring at these groups and which protecting group can be removed by conventional chemical or enzymatic steps to reestablish the unprotected functional group. The particular removable blocking group employed is not critical and preferred removable hydroxyl blocking groups include conventional substituents such as allyl, benzyl, acetyl, chloroacetyl, thiobenzyl, benzylidine, phenacyl, t-butyldiphenylsilyl and any other group that can be introduced chemically onto a hydroxyl functionality and later selectively removed either by chemical or enzymatic methods in mild conditions compatible with the nature of the product.

Preferred carboxyl protecting groups include esters such as methyl, ethyl, propyl, t-butyl, etc., which can be removed by mild hydrolysis conditions compatible with the nature of the product.

Compound Preparation

When n is one, compounds of formula I are readily prepared by conventional acylation, followed by reductive amination as illustrated in Scheme 1.

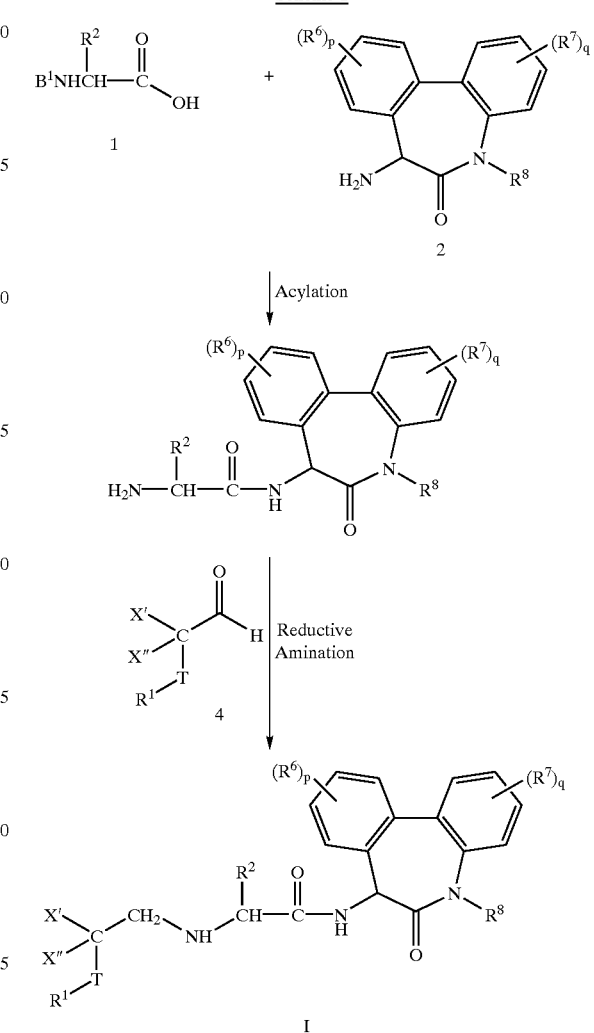

As shown in Scheme 1, a protected amino acid 1 (where B is a protecting group) can be coupled with an amine compound, such as 2 (where $R^6$, $R^7$, $R^8$, p and q are as defined herein), by conventional acylation reactions to provide, after deprotection, intermediate 3. It should be recognized by one skilled in the art that amine 2 is merely representative and those skilled in the art will recognize that amino derivatives of any of the other ring systems described herein may be employed in this reaction. Typically, this reaction is conducted using conventional coupling reagents and procedures and at least a stoichiometric amount of amino acid 1 and amine 2. For example, well known coupling reagents such as carbodiimides with or without the use of well known additives such as N-hydroxysuccinimide, 1-hydroxybenzotriazole, etc. can be used to facilitate coupling. The reaction is conventionally conducted in an inert aprotic polar diluent such as dimethylformamide, dichloromethane, chloroform, acetonitrile, tetrahydrofuran and the like.

Acid 1 can also be coupled to amine 2 prepared by use of polymer supported forms of carbodiimide peptide coupling reagents. A polymer supported form of EDC, for example, has been described (*Tetrahedron Letters*, 34(48), 7685 (1993))[11]. Additionally, a new carbodiimide coupling reagent, PEPC, and its corresponding polymer supported forms have been discovered and are very useful for the preparation of such compounds.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethylphenyl-acetamidomethyl resin (Pam Resin) and 4-benzyloxybenzyl alcohol resin (Wang Resin) available from Advanced Chemtech of Louisville, Ky., USA (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis., USA (see Aldrich 1994–1995 catalog, page 899). Methods for the preparation of PEPC and its polymer supported forms are outlined in Scheme 1A below.

Scheme 1A

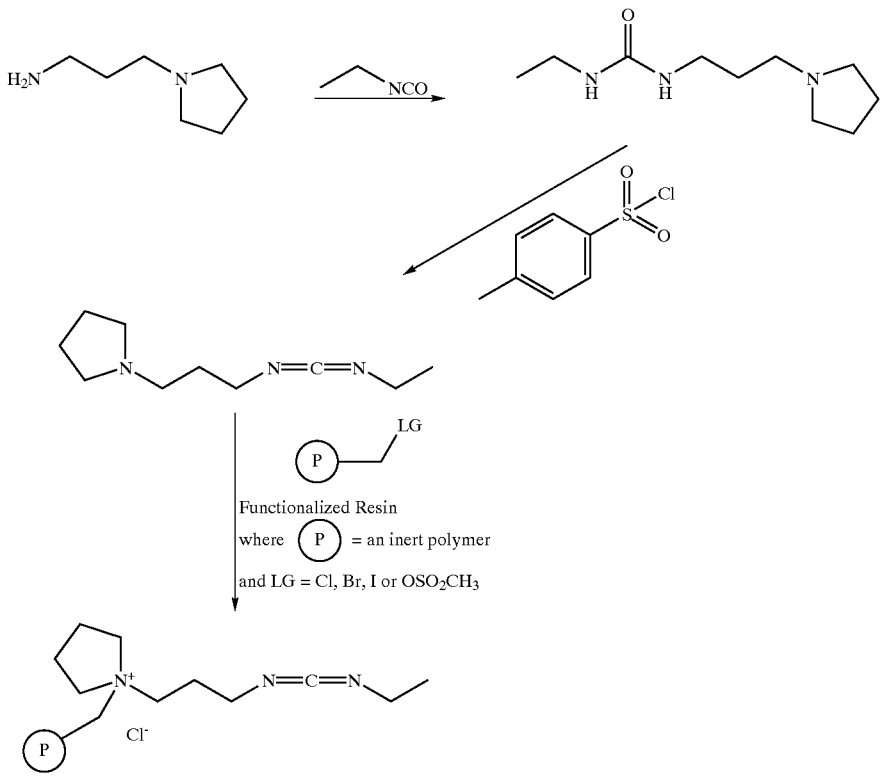

Such methods are described more fully in U.S. patent application Ser. No. 60/019,790 filed Jun. 14, 1996 which application is incorporated herein by reference in its entirety. Briefly, PEPC is prepared by first reacting ethyl isocyanate with 1-(3-aminopropyl)pyrrolidine. The resulting urea is treated with 4-toluenesulfonyl chloride to provide PEPC. The polymer supported form is prepared by reaction of PEPC with an appropriate resin under standard conditions to give the desired reagent.

The carboxylic acid coupling reactions employing these reagents are performed at about ambient to about 45° C., for from about 3 to 120 hours. Typically, the product may be isolated by washing the reaction with CHCl$_3$ and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

Alternatively, the acid halide of compound 1 can be employed in reaction (1) and, when so employed, it is typically employed in the presence of a suitable base to scavenge the acid generated during the reaction. Suitable bases include, by way of example, triethylamine, diisopropylethylamine, N-methylmorpholine and the like. Removal of the amine protecting group using conventional procedures and reagents then affords intermediate 3.

Intermediate 3 is then coupled with an excess of aldehyde 4, preferably with 1.1 to 2 equivalents of 4 and an excess, preferably 1.1 to 1.5 equivalents, of a reducing agent, such as sodium cyanoborohydride, to provide for compound of Formula I. Generally, this reaction is conducted in an essentially inert diluent, such as methanol, at a temperature ranging from about 0° C. to about 50° C., preferably at ambient temperature, for about 0.5 to 3 hours.

Alternatively, a compound of Formula I can be prepared by reacting an acid of formula 5:

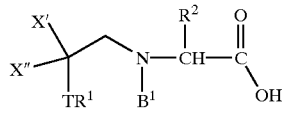

where $R^1$, $R^2$, $B^1$, T, X' and X" are as defined herein, with amine 2 under acylating reaction conditions described above, followed by deprotection of the amino protecting group ($B^1$) using conventional reagents and procedures known in the art.

Compounds of formula I where n is 2, can be prepared as illustrated in Scheme 2 below, by first coupling an amine, such as 2, with a protected amino acid 9, and then, after deprotection, converting the resulting intermediate 10 as described in Scheme 1 above.

Scheme 2

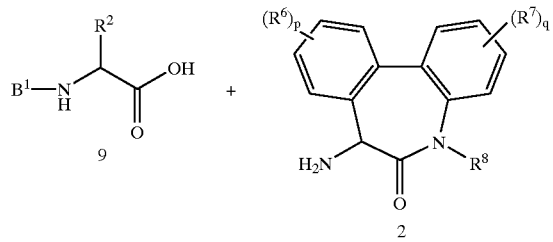

1) Acylation
2) Deprotection

-continued

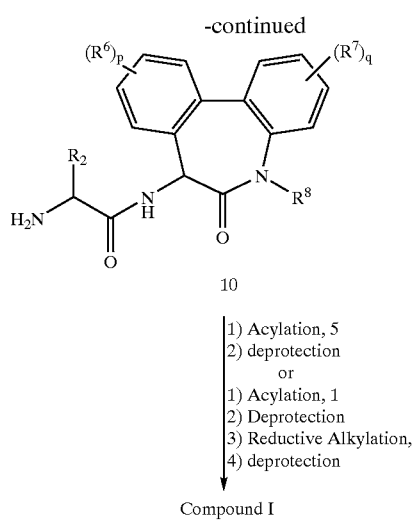

10

1) Acylation, 5
2) deprotection
or
1) Acylation, 1
2) Deprotection
3) Reductive Alkylation, 4
4) deprotection Compound I Alternatively, when n is 2, the aldehyde, or carboxylic acid units may also be coupled together prior to reaction with an amine using the reductive amination or acylation procedures described above, as appropriate. The resulting intermediate is then coupled to the amine, such as 2, to afford precursors of the compounds of formula I.

The compounds of formula I may also be prepared by any one of the following methods by conventional means as known to one of ordinary skill in the art. Some such methods are described below (a) reductive alkylation, as shown in Scheme 3 below:

Scheme 3

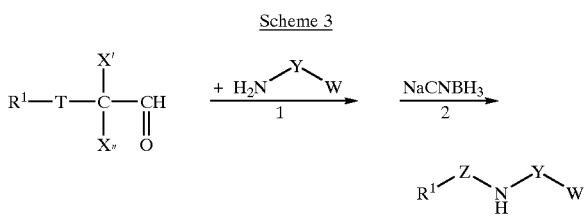

wherein $R^1$, T, X', X", Y, W and Z are as defined herein and is described in detail in Scheme 1 above;

(b) epoxide opening, as shown in Scheme 4 below:

Scheme 4

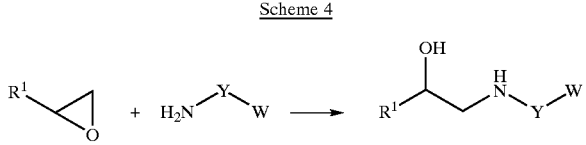

wherein $R^1$, Y and W are as defined herein;

(c) or nucleophilic displacement, as shown in Scheme 5 below:

Scheme 5

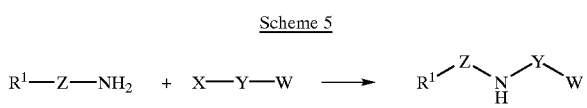

wherein $R^1$, Y, W and Z are as defined herein, and X is a leaving group such as halogen, tosylate, mesylate, triflate, and the like, as known to one of ordinary skill in the art.

Epoxide ring opening reactions provide for β-hydroxyl groups (β to the amine). The conditions employed for such reactions are well known in the art. Similarly, nucleophilic displacement reactions provide for facile methods for reacting, e.g., a primary amine with, for example, an α-haloacetic acid derivative, to provide for an amino acid derivative which reaction is described in detail in International Patent Application Publication No. WO98/22441.

In any of the above reaction schemes 3–5, substituents may be protected as necessary by protecting groups as known to one of ordinary skill in the art in order to prevent reaction with the reactive group.

Synthesis of Aldehyde and Carboxylic Acid Starting Materials

The aldehyde and carboxylic acids employed in the above reactions can be readily prepared by several divergent synthetic routes with the particular route selected relative to the ease of compound preparation, commercial availability of starting materials, whether n is one or two, etc.

A. Synthesis of Aldehydes

The aldehyde of formula 4, employed in this invention can be readily prepared by oxidizing the corresponding alcohol using conventional oxidizing agents. For example, Swern oxidation of primary alcohols affords the corresponding aldehyde. Typically, this reaction is conducted by contacting the alcohol with a mixture of oxalyl chloride and dimethyl sulfoxide in the presence of a tertiary amine, such as triethylamine. Generally, this reaction is conducted in an inert diluent, such as dichloromethane, at an initial temperature of about −78° C. and then at ambient temperature for about 0.25 to 2 hours to afford the aldehyde. The alcohols employed in this reaction are either commercially available or can be prepared using conventional reagents and procedures. For example, suitable alcohols can be prepared by reduction of the corresponding amino acids or amino acid esters using conventional reducing agents such as lithium aluminum hydride and the like.

B. Synthesis of Carboxylic Acids

The carboxylic acids of formula 1 are commercially available or they can be prepared by esterification of corresponding alpha amino acids by methods well known in the art. The acid of formula 5, can be prepared by conventional coupling of an aldehyde of formula 4 with the amino group of an esterified alpha-amino acid under reductive amination reaction conditions described above.

Preparation of Cyclic Compounds (e.g. Benzaepinones, Dibenzazepinones, Benzodiazepines and Related Compounds)

The cyclic compounds and amino-substituted derivatives thereof, such as 2, employed in the reactions described above are either known in the art or can be prepared by art-recognized procedures using commercially available starting materials and reagents.

For example, 5,7-dihydro-6H-dibenz[b,d]azepin-6-one may be prepared by cyclizing a chloromethyl amide intermediate using the procedures set forth in R. F. C. Brown et al., *Tetrahedron Letters* 1971, 8, 667–670[12] and references cited therein.

Additionally, the synthesis of a representative cyclic compound, i.e., a 5,7-dihydro-6H-dibenz[b,d]azepin-6-one, is illustrated in Scheme 6. As will be readily apparent to those of ordinary skill in the art, the synthetic procedure illustrated in Scheme 6 and the reaction conditions described below can be modified by selecting the appropriate starting materials and reagents to allow the preparation of other cyclic amines suitable for use in this invention.

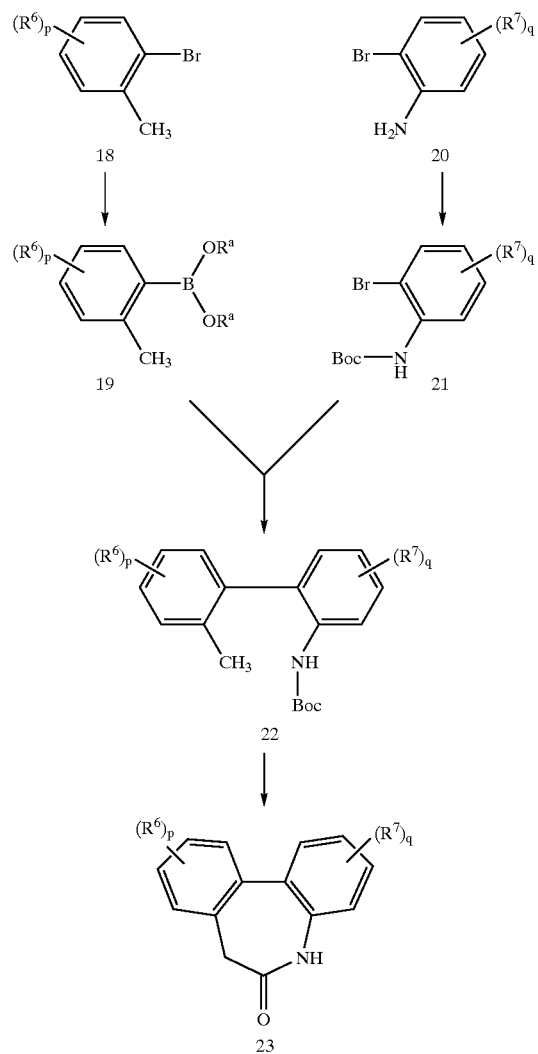

Scheme 6

As shown in Scheme 6, 5,7-dihydro-6H-dibenz[b,d] azepin-6-one derivatives, 23, wherein $R^6$, $R^7$, p and q are as defined above, can be readily prepared in several steps from a 2-bromotoluene derivative 18 and a 2-bromoaniline derivative 20. In this synthetic procedure, the 2-bromotoluene derivative, 18, is first converted into the corresponding 2-methylphenylboronate ester, 19. This reaction is typically conducted by treating 18 with about 1.0 to about 2.1 equivalents of an alkyl lithium reagent, preferably sec-butyl lithium or tert-butyl lithium, in an inert diluent, such as THF, at a temperature ranging from about −80° C. to about −60° C. for about 0.25 to about 1 hour. The resulting lithium anion is then treated in situ with an excess, preferably 1.5 equivalents, of a trialkylborate, such as trimethylborate. This reaction is initially conducted at −80° C. to about −60° C. and then allowed to warm to about 0° C. to about 30° C. for about 0.5 to about 3 hours. The resulting methyl boronate ester is typically not isolated, but is preferably converted in situ into the pinacol ester by treating the reaction mixture with an excess, preferably about 2.0 equivalents, of pinacol. This reaction is typically conducted at ambient temperature for about 12 to about 24 hours to afford the 2-methylphenylboronate ester, 19, in which both $R^a$ groups are preferably joined together to form —C(CH$_3$)$_2$C(CH$_3$)$_2$—.

In a separate reaction, the amino group of a 2-bromoaniline derivative, 20, is converted into the N-Boc derivative 21 by treating 20 with about 1.0 to about 1.5 equivalents of di-tert-butyl-dicarbonate. Typically, this reaction is conducted at a temperature ranging from 25° C. to about 100° C. for about 12 to 48 hours to afford the N-Boc-2-bromoaniline derivative 21.

As further illustrated in Scheme 6, the 2-methylphenylboronate ester, 19, and the N-Boc-2-bromoaniline derivative 21 can then be coupled to form the biphenyl derivative 22. This reaction is typically conducted by contacting 21 with about 1.0 to about 1.2 equivalents of 19 and about 1.0 to about 1.2 equivalents of potassium carbonate in the presence of a pallidium catalyst, preferably tetrakis(triphenylphosphine)pallidium(0). Generally, this coupling reaction is conducted in a diluent, preferably 20% water/dioxane, under an inert atmosphere at a temperature ranging from about 50° C. to about 100° C. for about 6 to 24 hours.

Biphenyl derivative 22 is then readily converted into the 5,7-dihydro-6H-dibenz[b,d]azepin-6-one 23 by carboxylation of the 2-methyl group, followed by cyclization to form the ε-caprolactam. The carboxylation reaction is typically conducted by contacting 22 with about 2.0 to about 2.5 equivalents of a suitable base, such as sec-butyllithium, tert-butyllithium and the like, in an inert diluent, such as THF, at a temperature ranging from about –100° C. to about –20° C. for about 0.5 to 6 hours. The resulting dianion is then treated with excess anhydrous carbon dioxide to form the carboxylate. Treatment of the carboxylate with excess hydrogen chloride in a suitable diluent, such as methanol, at a temperature ranging from about 25° C. to about 100° C. then affords the 5,7-dihydro-6H-dibenz[b,d]azepin-6-one 23. Various other cyclic compounds can be prepared by routine modifications of the above described procedures.

Preferred synthetic procedures for aminating a representative compound are illustrated in Scheme 7. It will be readily apparent to those of ordinary skill in the art that the synthetic procedure illustrated in Scheme 7 and the following reaction conditions can be modified by selecting the appropriate starting materials and reagents to allow the preparation of other amino compounds suitable for use in this invention.

Scheme 7

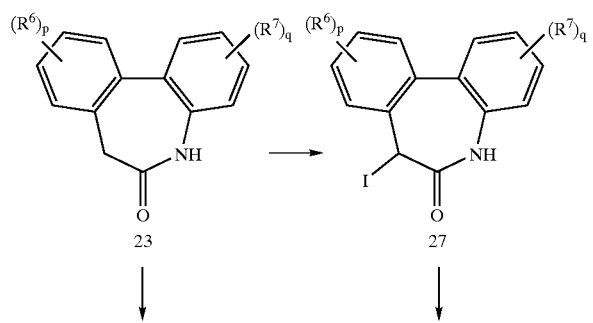

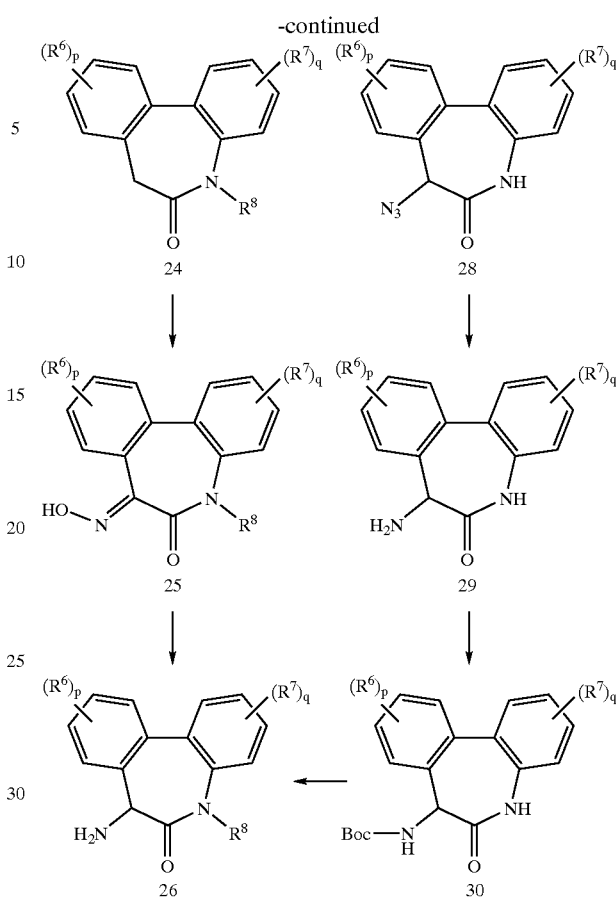

As shown in Scheme 7, 5,7-dihydro-6H-dibenz[b,d] azepin-6-one, 23, is optionally N-alkylated using conventional reagents and conditions to provide a 7-alkyl-5,7-dihydro-6H-dibenz[b,d]azepin-6-one derivative, 24. Typically, this reaction is conducted by first contacting 23 with about 1.0 to 1.5 equivalents of a suitable base, such as sodium hydride, sodium bis(trimethysilyl)amide and the like, in an inert diluent, such as DMF, THF and the like, at a temperature ranging from about –78° C. to about 50° C. for about 0.25 to about 6 hours. The resulting anion is then treated in situ with an excess, preferably about 1.1 to about 2.0 equivalents, of an alkyl, substituted alkyl, cycloalkyl halide, etc., typically a chloride, bromide or iodide. This reaction is typically conducted at a temperature ranging from about 0° C. to about 60° C. for about 1.0 to about 48 hours to afford the 7-alkyl-5,7-dihydro-6H-dibenz[b,d] azepin-6-one derivative, 24.

The 7-alkyl-5,7-dihydro-6H-dibenz[b,d]azepin-6-one 24 is then oximated by contacting 24 with an excess, preferably with about 1.0 to 1.5 equivalents of a suitable base, such as sodium bis(trimethysilyl)amide and the like, in the presence of about 1.0 to about 2.0 equivalents of an alkyl nitrite. Suitable alkyl nitrites for use in this reaction include, by way of example, butyl nitrite, isoamyl nitrite and the like. This reaction is typically conducted in an inert diluent, such as THF and the like, at a temperature ranging from about –10° C. to about 20° C. for about 0.5 to about 6 hours to afford the 7-alkyl-5-oximo-5,7-dihydro-6H-dibenz[b,d]azepin-6-one derivative 25.

Reduction of 25 using conventional reagents and conditions then affords the 5-amino-7-alkyl-5,7-dihydro-6H-dibenz[b,d]azepin-6-one 26. Preferably, this reduction reaction is conducted by hydrogenating the oxime 25 in the presence of a catalyst, such as Raney nickel. This reaction is typically conducted under about 200 psi to about 600 psi of hydrogen at a temperature of about 70° C. to about 120° C. for about 8 to 48 hours in a diluent, preferably a mixture of ethanol and ammonia (about 20:1). Alternatively, in another preferred procedure, the oxime may be reduced using 10% Pd/C and between about 30 to about 60 psi of hydrogen at a temperature ranging from about 20° C. to about 50° C. for about 4 hours. The resulting 5-amino-7-alkyl-5,7-dihydro-6H-dibenz[b,d]azepin-6-one 26 is generally purified using well known procedures, such as recrystallization and/or chromatography.

Alternatively, 5-amino-7-alkyl-5,7-dihydro-6H-dibenz[b,d]azepin-6-ones, 26, can be prepared by first forming the 5-iodo derivative 27 of 5,7-dihydro-6H-dibenz[b,d]azepin-6-one, 23. This reaction is typically conducted as described in A. O. King et al.[13] by treating 23 with an excess, preferably about 1.2 to about 2.5 equivalents, of trimethylsilyl iodide in the presence of an excess of a trialkylamine, such as triethylamine, diisopropylethylamine, TMEDA and the like, at a temperature ranging from about −20° C. to about 0° C. for about 3 to 30 minutes and then adding about 1.1 to about 2.0 equivalents of iodine ($I_2$). Typically, after addition of the iodine, the reaction is stirred at a temperature ranging from about 0° C. to about 20° C. for about 2 to about 4 hours to afford 5-iodo-5,7-dihydro-6H-dibenz[b,d]azepin-6-one, 27.

Displacement of iodide from 27 using an alkali metal azide then affords 5-azido-5,7-dihydro-6H-dibenz[b,d]azepin-6-one, 28. Typically, this reaction is conducted by contacting 27 with about 1.1 to about 1.5 equivalents of sodium azide in an inert diluent, such as DMF, at a temperature ranging from about 0° C. to about 50° C. for about 12 to about 48 hours.

The azido derivative 28 is then reduced to the corresponding amino derivative 29 using conventional procedures and reagents. For example, the azido group is preferably reduced by contacting 28 with an excess, preferably with about 3 equivalents, of triphenylphosphine in a diluent, preferably a mixture of THF and water. This reduction reaction is typically conducted at a temperature ranging from about 0° C. to about 50° C. for about 12 to 48 hours to afford 5-amino-5,7-dihydro-6H-dibenz[b,d]azepin-6-one, 29.

The amino group of 29 is then protected or blocked using a conventional amino blocking group. Preferably, compound 29 is treated with about 1.0 to about 1.1 equivalents of di-tert-butyl dicarbonate in the presence of an excess, preferably about 2 to about 3 equivalents, of a trialkylamine, such as triethylamine. This reaction is typically conducted in an inert diluent, such as THF, at a temperature ranging from about 0C to about 50° C. for 3 to about 24 hours to provide 5-(N-Boc-amino)-5,7-dihydro-6H-dibenz[b,d]azepin-6-one, 30.

Compound 30 is then optionally N-alkylated to afford, after de-blocking of the amino group, a 5-amino-7-alkyl-5,7-dihydro-6H-dibenz[b,d]azepin-6-one, 26. The N-alkylation reaction is typically conducted by treating 30 with about 1.0 to 1.5 equivalents of an alkyl halide, a substituted alkyl halide or a cycloalkyl halide in the presence of about 1.0 to about 1.5 equivalents of a suitable base, such as cesium carbonate and the like. This reaction is generally conducted in an inert diluent, such as DMF and the like, at a temperature ranging from about 25° C. to about 100° C. for about 12 to about 48 hours.

Representative alkyl, substituted alkyl and cycloalkyl halides suitable for use in this N-alkylation reaction include, by way of illustration, 1-iodo-2-methylpropane, methyl bromoacetate, 1-chloro-3,3-dimethyl-2-butanone, 1-chloro-4-phenylbutane, bromomethylcyclopropane, 1-bromo-2,2,2-trifluoroethane, bromocyclohexane, 1-bromohexane and the like.

The N-Boc protecting group is then removed using conventional procedures and reagents to afford the 5-amino-7-alkyl-5,7-dihydro-6H-dibenz[b,d]azepin-6-one, 26. This deblocking reaction is typically conducted by treating the N-Boc compound 30 with anhydrous hydrogen chloride in an inert diluent, such as 1,4-dioxane, at a temperature ranging from about 0° C. to about 50° C. for about 2 to about 8 hours. The resulting 5-amino-7-alkyl-5,7-dihydro-6H-dibenz[b,d]azepin-6-one 26 is generally purified using well known procedures, such as recrystallization and/or chromatography.

The 5-amino-7-alkyl-5,7-dihydro-6H-dibenz[b,d]azepin-6-ones, 26, can also be prepared via an azide transfer reaction as illustrated in Scheme 8.

Scheme 8

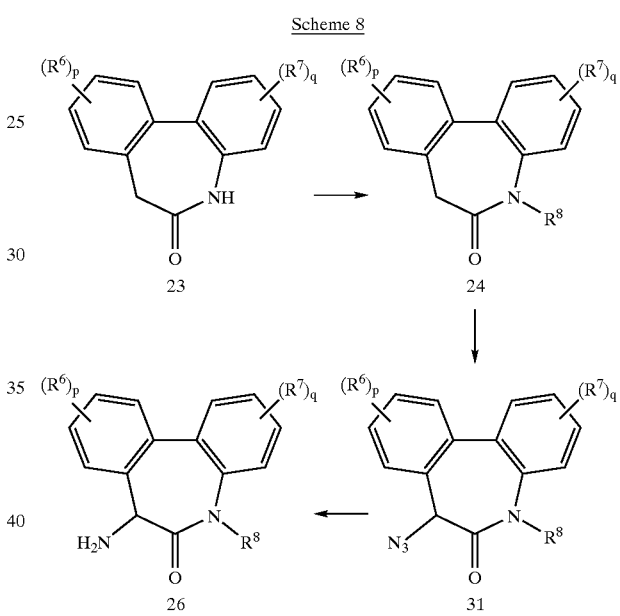

As shown in Scheme 8, 5,7-dihydro-6H-dibenz[b,d]azepin-6-one, 23, is first N-alkylated as described above using conventional reagents and conditions to provide a 7-alkyl-5,7-dihydro-6H-dibenz[b,d]azepin-6-one derivative, 24.

The 7-alkyl-5,7-dihydro-6H-dibenz[b,d]azepin-6-one 24 is then reacted with an azide transfer reagent to afford 5-azido-7-alkyl-5,7-dihydro-6H-dibenz[b,d]azepin-6-one 31. Typically, this reaction is conducted by first contacting 24 with an excess, preferably with about 1.0 to 1.5 equivalents of a suitable base, such as lithium diisopropylamine and the like, in an inert diluent such as THF, at a temperature ranging from about −90° C. to about −60° C. for about 0.25 to about 2.0 hours. The resulting anion is then treated with an excess, preferably with about 1.1 to about 1.2 equivalents, of an azide transfer reagent, such as 2,4,6-triisopropylbenzenesulfonyl azide (trisyl azide). This reaction is typically conducted at a temperature ranging from about −90° C. to about −60° C. for about 0.25 to about 2.0 hours. The reaction mixture is then typically treated with an excess of glacial acetic acid and the mixture is allowed to warm to ambient temperature and then heated at about 35°

C. to about 50° C. for about 2 to 4 hours to afford the 5-azido-7-alkyl-5,7-dihydro-6H-dibenz[b,d]azepin-6-one derivative 31. Reduction of 31 as described above using conventional reagents and conditions then affords the 5-amino-7-alkyl-5,7-dihydro-6H-dibenz[b,d]azepin-6-one 26.

If desired, the aryl rings of 5-amino-7-alkyl-5,7-dihydro-6H-dibenz[b,d]azepin-6-ones, 26, and similar or related compounds may be partially or fully saturated by treatment with hydrogen in the presence of a hydrogention catalyst. Typically, this reaction is conducted by treating 26 with hydrogen at a pressure of about 10 to about 100 psi in the presence of a catalyst, such as rhodium on carbon. This reaction is typically conducted at a temperature ranging from about 20° C. to about 100° C. for about 12 to 96 hours in a suitable diluent, such as ethyl acetate/acetic acid (1:1) and the like.

Other methods for preparing intermediates useful in this invention are described in U.S. patent application Ser. No. 09/102,726, filed on Jun. 22, 1998, and entitled "Polycyclic α-Amino-ε-caprolactams and Related Compounds", the disclosure of which is incorporated herein by reference in its entirety.

Additionally, the synthesis of various benzapinones and related compounds are described in Busacca et al., *Tetrahedron Lett.*, 33, 165–168 (1992); Crosisier et al., U.S. Pat. No. 4,080,449; J. A. Robl et al. *Tetrahedron Lett.*, 36(10), 1593–1596 (1995); Flynn et al. *J. Med. Chem.* 36, 2420–2423 (1993); Orito et al. *Tetrahedron,* 36, 1017–1021 (1980); Kawase et al., *J. Org. Chem.*, 54, 3394–3403 (1989); Lowe et al., *J. Med. Chem.* 37, 3789–3811 (1994); Robl et al., *Bioorg. Med. Chem. Lett.*, 4, 1789–1794 (1994); Skiles et al., *Bioorg. Med. Chem. Lett.*, 3, 773–778 (1993); Grunewald et al., *J. Med. Chem.*, 39(18), 3539 (1996); Warshawsky et al., *Bioorg. Med. Chem. Lett.*, 6, 957–962 (1996); Ben-Ishai, et al., *Tetrahedron,* 43, 439–450 (1987); van Neil et al, *Bioorg. Med. Chem.* 5, 1421–1426 (1995); and references cited therein. These publications and patents are incorporated herein by reference in their entirety.

Similarly, various benzodiazepine derivatives suitable for use in this invention can be prepared using conventional procedures and reagents. For example, a 2-aminobenzophenone can be readily coupled to α-(isopropylthio)-N-(benzyloxycarbonyl)glycine by first forming the acid chloride of the glycine derivative with oxayl chloride, and then coupling the acid chloride with the 2-aminobenzophenone in the presence of a base, such as 4-methylmorpholine, to afford the 2-[α-(isopropylthio)-N-(benzyloxycarbonyl)glycinyl]-aminobenzophenone. Treatment of this compound with ammonia gas in the presence of an excess, preferably about 1. 1 to about 1.5 equivalents, of mercury (II) chloride then affords the 2-[N-(α-amino)-N'-(benzyloxycarbonyl)-glycinyl]aminobenzophenone. This intermediate can then be readily cyclized by treatment with glacial acetic acid and ammonium acetate to provide the 3-(benzyloxycarbonyl)amino-2,3-dihydro-5-phenyl-1H-1,4-benzodiazepin-2-one. Subsequent removal of the Cbz group affords the 3-amino-2,3-dihydro-5-phenyl-1H-1,4-benzodiazepin-2-one.

Alternatively, 2,3-dihydro-5-phenyl-1H-1,4-benzodiazepin-2-ones can be readily aminated at the 3-position using conventional azide transfer reactions followed by reduction of the resulting azido group to form the corresponding amino group. The conditions for these and related reactions are described in the examples set forth below. Additionally, 2,3-dihydro-5-phenyl-1H-1,4-benzodiazepin-2-ones are readily alkylated at the 1-position using conventional procedures and reagents. For example, this reaction is typically conducted by first treating the benzodiazepinone with about 1.1 to about 1.5 equivalents of a base, such as sodium hydride, potassium tert-butoxide, potassium 1,1,1,3,3,3-hexamethyldisilazane, or cesium carbonate, in an inert diluent, such as DMF. This reaction is typically conducted at a temperature ranging from about −78° C. to about 80° C. for about 0.5 to about 6 hours. The resulting anion is then contacted with an excess, preferably about 1.1 to about 3.0 equivalents, of an alkyl halide, typically an alkyl chloride, bromide or iodide. Generally, this reaction is conducted at a temperature of about 0° C. to about 100° C. for about 1 to about 48 hours.

Additionally, the 3-amino-2,4-dioxo-2,3,4,5-tetrahydro-1H-1,5-benzodiazepines employed in this invention are typically prepared by first coupling malonic acid with a 1,2-phenylenediamine. Conditions for this reaction are well known in the art and are described, for example, in PCT Application WO 96-US8400 960603. Subsequent alkylation and amination using conventional procedures and reagents affords various 3-amino-1,5-bis(alkyl)-2,4-dioxo-2,3,4,5-tetrahydro-1H-1,5-benzodiazepines. Such procedures are described in further detail in the examples set forth below.

In the synthesis of compounds of formula I using the synthetic methods described herein, the starting materials can contain a chiral center (e.g., alanine) and, when a racemic starting material is employed, the resulting product is a mixture of R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of R,S enantiomers. Preferably, however, when a chiral product is desired, the chiral product corresponds to the L-amino acid derivative. Alternatively, chiral products can be obtained via purification techniques which separate enantiomers from a R,S mixture to provide for one or the other stereoisomer. Such techniques are well known in the art.

Pharmaceutical Formulations

When employed as pharmaceuticals, the compounds of formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within a carrier which can be in the form of a capsule, sachet, paper or other container. When the excipient serves as a diluent, it can be a solid, semi-solid, or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120.0 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%)/ Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 560 mg quantities.

FORMULATION EXAMPLE 9

A subcutaneous formulation may be prepared as follows:

| Ingredient | Quantity |
| --- | --- |
| Active Ingredient | 1.0 mg |
| corn oil | 1 mL |

(Depending on the solubility of the active ingredient in corn oil, up to about 5.0 mg or more of the active ingredient may be employed in this formulation, if desired).

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, carboxyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in diagnosing and treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028, each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as a "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 1 to about 500 mg/kg/day.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The compounds described herein are also suitable for use in the administration of the compounds to a cell for diagnostic and drug discovery purposes. Specifically, the compounds may be used in the diagnosis of cells releasing and/or synthesizing β-amyloid peptide. In addition the compounds described herein are useful for the measurement and evaluation of the activity of other candidate drugs on the inhibition of the cellular release and/or synthesis of β-amyloid peptide.

The following synthetic and biological examples are offered to illustrate this invention and are not to be construed in any way as limiting the scope of this invention.

EXAMPLES

In the examples below, the following abbreviations have the following meanings. If an abbreviation is not defined, it has its generally accepted meaning.

| | |
|---|---|
| BEMP = | 2-tert-butylimino-2-diethylamino-1,3-dimethylperhydro-1,3,2-diazaphosphorine |
| Boc = | t-butoxycarbonyl |
| BOP = | benzotriazol-1-yloxy-tris(dimethylamino)phosphonium hexafluorophosphate |
| bd = | broad doublet |
| bs = | broad singlet |
| bt = | broad triplet |
| CBZ = | benzyloxycarbonyl |
| d = | doublet |
| dd = | doublet of doublets |
| DIC = | diisopropylcarbodiimide |
| DIPEA = | diisopropylethylamine |
| DMF = | dimethylformamide |
| DMAP = | dimethylaminopyridine |
| DMSO = | dimethylsulfoxide |
| EDC = | ethyl-1-(3-dimethyaminopropyl)carbodiimide |
| ee = | enantiomeric excess |
| eq. = | equivalents |
| EtOAc = | ethyl acetate |
| g = | grams |
| HMDS = | 1,1,1,3,3,3-hexamethyldisilazane |
| HOBT = | 1-hydroxybenzotriazole hydrate |
| Hunig's base = | diisopropylethylamine |
| L = | liter |
| LDA = | lithium diisopropylamide |
| m = | multiplet |
| M = | molar |
| max = | maximum |
| meq = | milliequivalent |
| mg = | milligram |
| mL = | milliliter |
| mm = | millimeter |
| mmol = | millimole |
| MOC = | methoxyoxycarbonyl |
| N = | normal |
| N/A = | not available |
| ng = | nanogram |
| nm = | nanometers |
| OD = | optical density |
| PEPC = | 1-(3-(1-pyrrolidinyl)propyl)-3-ethylcarbodiimide |
| PP-HOBT = | piperidine-piperidine-1-hydroxybenzotrizole |
| psi = | pounds per square inch |
| φ | phenyl |
| q = | quartet |
| quint. = | quintet |
| rpm = | rotations per minute |
| RT = | room temperature |
| s = | singlet |
| sat. = | saturated |
| t = | triplet |
| t-BuOK = | potassium tert-butoxide |
| TFA = | trifluoroacetic acid |
| THF = | tetrahydrofuran |
| tlc = | thin layer chromatography |
| TMSI = | trimethylsilyl iodide |
| μL = | microliter |
| UV = | ultra-violet |

In the examples below, all temperatures are in degrees Celsius (unless otherwise indicated). The compounds set forth in the examples below were prepared using the following general procedures as indicated.

In the following examples and procedures, the term "Aldrich" indicates that the compound or reagent used in the procedure is commercially available from Aldrich Chemical Company, Inc., 1001 West Saint Paul Avenue, Milwaukee, Wis. 53233, USA; the term "Fluka" indicates that the compound or reagent is commercially available from Fluka Chemical Corp., 980 South 2nd Street, Ronkonkoma, N.Y. 11779, USA; the term "Lancaster" indicates that the compound or reagent is commercially available from Lancaster Synthesis, Inc., P.O. Box 100 Windham, N.H. 03087, USA; the term "Sigma" indicates that the compound or reagent is commercially available from Sigma, P.O. Box 14508, St. Louis, Mo. 63178, USA; the term "Chemservice" indicates that the compound or reagent is commercially available from Chemservice Inc., Westchester, Pa., USA; the term "Bachem" indicates that the compound or reagent is commercially available from Bachem Biosciences Inc., 3700 Horizon Drive, Renaissance at Gulph Mills, King of Prussia, Pa. 19406, USA; the term "Maybridge" indicates that the compound or reagent is commercially available from Maybridge Chemical Co. Trevillett, Tintagel, Cornwall PL34 0HW, United Kingdom; the term "TCI" indicates that the compound or reagent is commercially available from TCI America, 9211 North Harborgate Street, Portland Oreg. 97203, USA; the term "Alfa" indicates that the compound or reagent is commercially available from Johnson Matthey Catalog Company, Inc. 30 Bond Street, Ward Hill, Mass. 01835-0747, USA; the term "Novabiochem" indicates that the compound or reagent is commercially available from Calbiochem-Novabiochem Corp., 10933 North Torrey Pines Road, P.O. Box 12087, La Jolla, Calif. 92039-2087, USA; the term "Oakwood" indicates that the compound or reagent is commercially available from Oakwood, Columbia, S.C., USA; the term "Advanced Chemtech" indicates that the compound or reagent is commercially available from Advanced Chemtech, Louisville, Ky. USA; and the term "Pfaltz & Bauer" indicates that the compound or reagent is commercially available from Pfaltz & Bauer, Waterbury, Conn., USA.

I. COUPLING PROCEDURES

The following coupling procedures may be used to prepare compounds of this invention:

General Procedure A

First EDC Coupling Procedure

To a 1:1 mixture of the corresponding carboxylic acid and the corresponding amino acid ester or amide in $CH_2Cl_2$ at 0° C. was added 1.5 equivalents triethylamine, followed by 2.0 equivalents hydroxybenzotriazole monohydrate and then 1.25 equivalents of ethyl-3-(3-dimethylamino)propyl carbodiimide.HCl. The reaction mixture was stirred overnight at room temperature and then transferred to a separatory funnel. The mixture was washed with water, saturated aqueous $NaHCO_3$, 1N HCl and saturated aqueous NaCl, and then dried over $MgSO_4$. The resulting solution was stripped free of solvent on a rotary evaporator to yield the crude product.

General Procedure B

Second EDC Coupling Procedure

A mixture of the corresponding acid (1 eqv), N-1-hydroxybenzotriazole (1.6 eqv), the corresponding amine (1 eqv), N-methylmorpholine (3 eqv) and dichloromethane (or DMF for insoluble substrates) was cooled in an ice-water bath and stirred until a clear solution was obtained. EDC (1.3 eqv) was then added to the reaction mixture. The cooling bath was then allowed to warm to ambient temperature over 1–2 h and the reaction mixture was stirred overnight. The reaction mixture was then evaporated to dryness under vacuum. To the residue was added 20% aqueous potassium carbonate and the mixture was shaken throughly and then allowed to stand until the oily product solidified (overnight if necessary). The solid product was then collected by filteration, washed thoroughly with 20% aqueous potassium carbonate, water, 10% HCl, and water to give the product, usually in pure state. No racemization was observed.

General Procedure C

Third EDC Coupling Procedure

The carboxylic acid was dissolved in methylene chloride. The corresponding amino acid ester or amide (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product.

General Procedure D

Fourth EDC Coupling Procedure

A round bottom flask was charged with the corresponding carboxylic acid (1.0 eq.), hydroxybenzotriazole hydrate (1.1 eq.) and the corresponding amine (1.0 eq.) in THF under nitrogen atmosphere. An appropriate amount (1.1 eq for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in ethyl acetate (or similar solvent) and water, washed with saturated aqueous sodium bicarbonate solution, 1 N HCl, brine, dried over anhydrous sodium sulfate and the solvent removed at reduced pressure to provide the product.

General Procedure E

BOP Coupling Procedure

To a stirred solution of N-(3,5-difluorophenylacetyl) alanine (2 mmol) in DMF, cooled in an ice-water bath, was added BOP (2.4 mmol) and N-methylmorpholine (6 mmol). The reaction mixture was stirred for 50 min. and then a solution of α-amino-γ-lactam (2 mmol) in DMF cooled at 0° C. was added. The cooling bath was allowed to warm to ambient temperature over 1–2 h and the reaction mixture was then stirred overnight. A 20% aqueous potassium carbonate solution (60 mL) was added and this mixture shaken throughly. No solid formed. The mixture was then washed with ethyl acetate (150 mL) and evaporated to dryness under vacuum to give a white solid. Water (50 mL) was then added and this mixture shaken throughly. The precipitate that formed was collected by filtration, then washed thoroughly with water, followed by 1 mL of diethyl ether to give the product (51 mg, 0.16 mmol, 7.8%).

General Procedure F

Coupling of an Acid Chloride with an Amino Acid Ester

To a stirred solution of (D,L)-alanine isobutyl ester hydrochloride (4.6 mmol) in 5 ml of pyridine was added 4.6 mmol of the acid chloride. Precipitation occurred immediately. The mixture was stirred for 3.5 h, dissolved in 100 mL of diethyl ether, washed with 10% HCl three times, brine once, 20% potassium carbonate once and brine once. The solution was dried over magnesium sulfate, filtered, and evaporated to yield the product. Other amino acid esters may also be employed in this procedure.

General Procedure G

Coupling of a Carboxylic Acid with an Amino Acid Ester

A solution of the carboxylic acid (3.3 mmol) and 1,1'-carbodiimidazole (CDI) in 20 mL THF was stirred for 2 h. (D,L)-alanine isobutyl ester hydrochloride (3.6 mmol) was added, followed by 1.5 mL (10.8 mmol) of triethylamine. The reaction mixture was stirred overnight. The reaction mixture was dissolved in 100 mL of diethyl ether, washed with 10% HCl three times, brine once, 20% potassium carbonate once and brine once. The solution was dried over magnesium sulfate, filtered, and evaporated to yield the product. Other amino acid esters may also be employed in this procedure.

General Procedure H

Fifth EDC Coupling Procedure

In a round bottom flask was added a carboxylic acid (1.1 eq.) in THF, an amine hydrochloride (1.0 eq.), 1-hydroxybenzotriazole hydrate (1.1 eq.), N,N-diisopropylethylamine (2.1 eq.), followed by 1-(3-dimethylaminopropyl)-3-ethylcarbodiimide hydrochloride (EDC) (1.1 eq.). The reaction mixture was stirred at room temperature for 10–20 hours under an atmosphere of nitrogen. The mixture was diluted with EtOAc and washed with 0.1 M HCl (1×10 mL), saturated NaHCO$_3$ (1×10 mL), H$_2$O (1×10 mL), and brine and dried over MgSO$_4$. The drying agent was removed by filtration and the filtrate was concentrated in vacuo. The residue was purified by flash column chromatography on silica gel followed by trituration from EtOAc and hexanes.

General Procedure I

Sixth EDC Coupling Procedure

To a solution or suspension of the amine or amine hydrochloride (1.0 eq.) in THF (0.05–0.1 M) under N$_2$ at 0° C. was added the carboxylic acid (1.0–1.1 eq.), hydroxybenzotriazole monohydrate (1.1–1.15 eq.), Hunig's base (1.1 eq. for free amines and 1.1–2.3 eq. for hydrochloride amine salts), followed by 1-(3-dimethylaminopropyl)-3-ethylcarbodiimide hydrochloride (1.1–1.15 eq.). The cooling bath was removed and the mixture allowed to warm to room temperature for 10–24 hours. The solution or mixture was diluted with EtOAc, in a 3–5 volume multiple of the initial THF volume, and washed with 0.1–1.0 M aq. HCl (1 or 233 ), dilute NaHCO$_3$ (1 or 2×), and brine (1×). Then, the organic phase was dried over either MgSO$_4$ or Na$_2$SO$_4$, filtered, concentrated to provide the crude product, which was either further purified or utilized without further purification.

General Procedure J

EEDQ Coupling Procedure

To a solution of the amine in THF (1.0 eq., 0.05–0.08 M, final molarity) under N$_2$ at room temperature was added the N-t-Boc protected amino acid (1.1 eq., either as a solid or in THF via cannula), followed by EEDQ (Aldrich, 1.1 eq.). The pale yellow solution was stirred at room temperature for 16–16.5 hours, then diluted with EtOAc (in a 3–5 volume multiple of the initial THF volume), and washed with 1M aq. HCl (2×), dilute aq. NaHCO$_3$ (2×), and brine (1×). The organic phase was dried over either Na$_2$SO$_4$ or MgSO$_4$, filtered, and concentrated.

II. CARBOXYLIC ACIDS

The following procedures may be used to prepare carboxylic acid intermediates useful in the present invention:

General Procedure II-A

Ester Hydrolysis to Free Acid

Ester hydrolysis to the free acid was conducted by conventional methods. Below are two examples of such conventional de-esterification methods.

Method A

To a carboxylic ester compound in a 1:1 mixture of $CH_3OH/H_2O$ was added 2–5 equivalents of $K_2CO_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over $MgSO_4$. The solution was stripped free of solvent on a rotary evaporator to yield the product.

Method B

The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was dissolved in water and washed with ether. The layers were separated and the aqueous layer was acidified to pH 2. The aqueous layer was extracted with ethyl acetate. The ethyl acetate extracts were dried over $Na_2SO_4$ and the solvent was removed under reduced pressure after filtration. The residue was purified by conventional methods (e.g., recrystallization).

General Procedure II-B

Acid Chloride Preparation 3,5-Difluorophenylacetic acid (30 g, 0.174 mol) (Aldrich) was dissolved in dichloromethane and this solution was cooled to 0° C. DMF (0.5 mL, catalytic) was added followed by the dropwise addition of oxalyl chloride (18 mL, 0.20 mol) over a 5 minute period. The reaction was stirred for 3 h and then rotoevaporated at reduced pressure to give an oil which was placed on a high vacuum pump for 1 h to afford 3,5-difluorophenylacetyl chloride as a thin yellow oil. Other acid chlorides can be prepared in a similar manner.

General Procedure II-C

Schotten-Baumann Procedure 3,5-Difluorophenylacetyl chloride (from General Procedure II-B) was added dropwise to a 0° C. solution of L-alanine (Aldrich) (16.7 g, 0.187 mol) in 2 N sodium hydroxide (215 mL, 0.43 mol). The reaction was stirred for 1 h at 0° C. and then overnight at room temperature. The reaction was diluted with water (100 mL), then extracted with ethyl acetate (3×150 mL). The organic layer was then washed with brine (200 mL), dried over $MgSO_4$, and rotoevaporated at reduced pressure to a residue. Recrystallization of the residue from ethyl acetate/hexanes afforded the desired product (34.5 g, 82% yield). Other acid chlorides may be used in this procedure to provide for intermediates useful in this invention.

General Procedure II-D

Reductive Amination

To a solution of the arylamine in ethanol in a hydrogenation flask was added 1 equivalent of the 2-oxocarboxylic acid ester (e.g., pyruvate ester), followed by 10% palladium on carbon (25 weight percent based on the arylamine). The reaction was hydrogenated at 20 psi $H_2$ on a Parr shaker until complete reaction was indicated by tlc (30 minutes to 16 hours). The reaction mixture was then filtered through a pad of Celite 545 (available from Aldrich Chemical Company, Inc.) and stripped free of solvent on a rotary evaporator. The crude product residue was then further purified via chromatography.

III. CYCLIC COMPOUNDS

The following procedures illustrate the synthesis of various cyclic compound intermediates useful for preparing compounds of this invention:

A. Benzazepinone Derivatives and Related Compounds

General Procedure 1-A

Alkylation of 1-Amino-1,3,4,5-tetrahydro-2H-3-benzazepin-2-one

Step A

1-Ethoxycarbonylamino-1,3,4,5-tetrahydro-2H-3-benzazepin-2-one was prepared according to the procedure of Ben-Ishai et al., *Tetrahedron*, 1987, 43, 430, incorporated herein by reference.

Step B

1-Ethoxycarbonylamino-1,3,4,5-tetrahydro-2H-3-benzazepin-2-one (2.0 g, 100 M %) was dissolved in DMF (30 mL) and NaH (95%, 0.17 g, 100M %) was added in one portion. The reaction mixture was stirred for 1 hour and then the appropriate alkyl iodide (300M %) was added and the mixture was stirred for 12 hours. The reaction was poured into water and extracted with ethyl acetate (3×). The ethyl acetate extracts were then washed with water (3×) and brine (1×). Treatment with $MgSO_4$, rotoevaporation, and chromatography (30% EtOAc/hexanes) yielded 1-ethoxycarbonylamino-3-alkyl-1,3,4,5-tetrahydro-2H-3-benzazepin-2-one in 87% yield.

Step C

1-Ethoxycarbonylamino-3-alkyl-1,3,4,5-tetrahydro-2H-3-benzazepin-2-one (1.0 g, 100M %) was suspended in 30 mL of 30% HBr/HOAc and heated to 100° C. The reaction mixture was stirred for 5 hours at this temperature and then the reaction was cooled and rotoevaporated to yield 1-amino-3-alkyl-1,3,4,5-tetrahydro-2H-3-benzazepin-2-one as the hydrobromide salt (100% yield).

General Procedure 1-B

Alkylation of 3-Amino-1,3,4,5-tetrahydro-2H-1-benzazepin-2-one

Step A

3-Amino-1,3,4,5-tetrahydro-2H-1-benzazepin-2-one was prepared from α-tetralone using the methods described in Armstrong et al. *Tetrahedron Letters*, 1994, 35, 3239, incorporated herein by reference. The following compounds were as prepared by this procedure for use in the following steps:

5-methyl-3-amino-1,3,4,5-tetrahydro-2H-1-benzazepin-2-one (from 4-methyl-α-tetralone (Aldrich)); and
5,5-dimethyl-3-amino-1,3,4,5-tetrahydro-2H-1-benzazepin-2-one (from 4,4-dimethyul-α-tetralone (Aldrich)).

Step B

3-Amino-1,3,4,5-tetrahydro-2H-1-benzazepin-2-one (4.43 g, 100M %) was suspended in t-butanol (30 mL) and BOC-anhydride (7.5 mL, 130M %) was added dropwise. The reaction mixture was stirred for 2 hours and then it was rotoevaporated to a residue which was chromatographed with 60% ethyl acetate/hexanes to yield BOC-protected 3-amino-1,3,4,5-tetrahydro-2H-1-benzazepin-2-one in 87% yield.

Step C

BOC-protected 3-amino-1,3,4,5-tetrahydro-2H-1-benzazepin-2-one (1.5 g, 100M %) was dissolved in DMF (20 mL) and NaH (95%, 0.13 g, 100M %) was added in one portion. The reaction mixture was stirred for 1 hour and then the appropriate alkyl iodide (300M %) was added and stirring was continued for 12 hours. The reaction mixture was poured into water and extracted with ethyl acetate (3×). The ethyl acetate extracts were washed with water (3×) and then brine (1×). Treatment with $MgSO_4$, rotoevaporation, and chromatography (30% EtOAc/hexanes) yielded a BOC-protected 3-amino-1-alkyl-1,3,4,5-tetrahydro-2H-1-benzazepin-2-one in 80% yield.

Step D

The BOC-protected 3-amino-1-alkyl-1,3,4,5-tetrahydro-2H-1-benzazepin-2-one (1.0 g, 100M %) was suspended in 30 mL of 1:1 $CH_2Cl_2$/triflouroacetic acid and the mixture was stirred for 4 hours. The reaction was then rotoevaporated to yield the 3-amino-1-alkyl-1,3,4,5-tetrahydro-2H-1-benzazepin-2-one (100% yield).

EXAMPLE 1-A

Synthesis of 3-Amino-1,5-dimethyl-1,3,4,5-tetrahydro-2H-1-benzazepin-2-one

Step A

3-Amino-5-methyl-1,3,4,5-tetrahydro-2H-1-benzazepin-2-one was prepared from 4-methyl-α-tetralone using the methods described in Armstrong et al. *Tetrahedron Letters*, 1994, 35, 3239, incorporated herein by reference.

Step B

3-Amino-5-methyl-1,3,4,5-tetrahydro-2H-1-benzazepin-2-one (9.3 g 100M %) was dissolved in dioxane (300 mL) and the solution was chilled to 0° C. BOC-anhydride (13.89 g 130M %) was added and the ice bath was removed allowing the solution to come to room temperature and stirring was continued for 16 hours. The solution was rotory evaporated to remove dioxane to provide an off white solid. This solid was recrystallized from $CHCl_3$ to yield BOC-protected 3-amino-5-methyl-1,3,4,5-tetrahydro-2H-1-benzazepin-2-one in 55% yield.

Step C

BOC-protected 3-amino-5-methyl-1,3,4,5-tetrahydro-2H-1-benzazepin-2-one (100 M %) was dissolved in DMF (20 mL) and NaH (95%, 100 M %) was added in one portion and the reaction mixture was stirred for 1 hour. Methyl iodide (300 M %) was added and this mixture was stirred for 12 hours. The reaction mixture was then poured into water and extracted with ethyl acetate (3×) then backwashed with water (3×) and then brine (1×). Treatment with $MgSO_4$, rotoevaporation, and chromotography (5% MeOH/$CH_2Cl_2$) yielded BOC-protected 3-amino-1,5-dimethyl-1,3,4,5-tetrahydro-2H-1-benzazepin-2-one in 75% yield.

Step D

BOC-protected 3-amino-1,5-dimethyl-1,3,4,5-tetrahydro-2H1-benzazepin-2-one (100 M %) was suspended in 30 mL of 1:1 $CH_2Cl_2$/triflouroacetic acid. The reaction mixture was stirred for 4 hours. The reaction was then rotoevaporated to yield 3-amino-1,5-dimethyl-1,3,4,5-tetrahydro-2H-1-benzazepin-2-one (100% yield).

EXAMPLE 1-B

Synthesis of 5-(L-Alaninyl)-amino-3,3,7-trimethyl-5,7-dihydro-6H-benz[b]azepin-6-one Hydrochloride Following the General Procedure H and using N-t-Boc-L-alanine and 5-amino-3,3,7-trimethyl-5,7-dihydro-6H-benz[b]azepin-6-one hydrochloride (Example 1-C), 5-(N-t-Boc-L-alaninyl)amino-3,3,7-trimethyl-5,7-dihydro-6H-benz[b]azepine-6-one was prepared. Following the General Procedure (Example 1-C, Step B) and using 5-(N-t-Boc-L-alaninyl)amino-3,3,7-trimethyl-5,7-dihydro-6H-benz[b]azepin-6-one, 5-(L-alaninyl)amino-3,3,7-trimethyl-5,7-dihydro-6H-benz[b]azepin-6-one hydrochloride was prepared.

EXAMPLE 1-C

Synthesis of 5-Amino-3,3,7-trimethyl-5,7-dihydro-6H-benz[b]azepin-6-one Hydrochloride General Procedure N-Alkylation of Lactams Step A To a stirred solution of a BOC-protected α-aminocaprolactam (6.87 g, 30 mmol) in DMF (150 mL) was added in portions 97% NaH (1.08 g, 45 mmol). Bubbling occured immediately and followed by heavy precipitation. After 10 minutes, benzyl bromide (3.93 mL, 33 mmol) was added. The precipitate dissolved quickly and in about 10 min. a clear solution was obtained. The reaction mixture was stirred overnight and then evaporated as completely as possible on a rotovap at 30° C. Ethyl acetate (100 mL) was added to the residue and this mixture was washed with water, brine, and dried over magnesium sulfate. After filtration and concentration, a thick liquid (10 g) was obtained which was then chromatographed over silica gel with 1:3 ethyl acetate/hexane as the eluant to provide 5.51 g (58%) of the N-benzylated product as an oil. Other lactams and alkylating agents may be used in this procedure to obtain a wide variety of N-alkylated lactams. Various bases, such as LiN($SiMe_3$), may also be employed.

Following this General Procedure and using N-t-Boc-5-amino-3,3-dimethyl-5,7-dihydro-6H-benz[b]azepin-6-one (General Procedure 1-B, followed by Boc protection) and methyl iodide, N-t-Boc-5-amino-3,3,7-trimethyl-5,7-dihydro-6H-benz[b]azepin-6-one was prepared.

General Procedure

BOC Removal Procedure

Step A

A stream of anhydrous HCl gas was passed through a stirred solution of the N-t-Boc protected amino acid in 1,4-dioxane (0.03–0.09 M), chilled in a ice bath to ~10° C. under $N_2$, for 10–15 minutes. The solution was capped, the cooling bath removed, and the solution was allowed to warm to room temperature with stirring for 2–8 hours, monitoring by TLC for the consumption of starting material. The solution was concentrated (and in some instances dissolved in $CH_2Cl_2$ then re-concentrated and placed in vacuum oven at 60–70° C. to remove most of the residual dioxane) and used without further purification.

Following this General Procedure and using N-t-Boc-5-amino-3,3,7-trimethyl-5,7-dihydro-6H-benz[b]azepin-6-one, the title compound was prepared.

EXAMPLE 1-D

Synthesis of 3-(S)-Amino-1-methyl-5-oxa-1,3,4,5-tetrahydro-2H-1-benzazepin-2-one

Step A 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286, incorporated herein by reference.

Step B

Following the General Procedure of Step A of Example 1-C and using the product from Step A of this example, the title compound was prepared.

EXAMPLE 1-E

Synthesis of 3-(S)-Amino-1-ethyl-5-oxa-1,3,4,5-tetrahydro-2H-1-benzazepin-2-one

Step A 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286, incorporated herein by reference.

Step B

Following the General Procedure of Step A of Example 1-C and using the product from Step A of this example, the title compound was prepared.

EXAMPLE 1-F

Synthesis of 3-(S)-Amino-1-methyl-5-thia-1,3,4,5-tetrahydro-2H-1-benzazepin-2-one The title compound was prepared from N-Boc-cystine (Novabio) and 2-fluoro-1-nitrobenzene (Aldrich) using the method of R. J. DeVita et al., *Bioorganic and Medicinal Chemistry Lett.* 1995, 5(12) 1281–1286, incorporated herein by reference, followed by the General Procedure of Step A of Example 1-C.

EXAMPLE 1-G

Synthesis of 7-Amino-1,3,4,7,12,12a-hexahydropyrido[2,1-b][3]-benzazepin-6(2H)-one

Step A

Synthesis of N-Chloroacetyl-2-benzylpiperidine

Following General Procedure F and using 2-benzylpyridine, the title compound was prepared.

Physical data were as follows:
(MW=251.8); mass spectroscopy (MH+) 252.0.

Step B

Synthesis of 1,3,4,7,12,12a-hexahydropyrido[2,1-b][3]benzazepin-6(2H)-one

Following General Procedure G and using N-chloroacetyl-2-benzylpiperidine, the title compound was prepared.

Physical data were as follows:
$^1$H-nmr (CDCl$_3$): δ=1.3–1.9 (6H); 2.42 (t, 1H); 3.08 (m, 2H); 3.47 (m, 1H); 3.96 (q, 2H); 4.66 (d, 1H); 7.2 (m, 4H). (MW=215.3); mass spectroscopy (MH+) 216.1.

Step C

Synthesis of 7-Oximo-1,3,4,7,12,12a-hexahydropyrido[2,1-b][3]benzazepin-6(2H)-one Following General Procedure 3A (Step B) and using 1,3,4,7,12,12a-hexahydropyrido[2,1-b][3]benzazepin-6(2H)-one (from Step B above), the title compound was prepared.

Physical data were as follows:
(MW=244.3); mass spectroscopy (MH+) 245.0.

Step D

Synthesis of 7-Amino-1,3,4,7,12,12a-hexahydropyrido[2,1-b][3]benzazepin-6(2H)-one Following General Procedure 3A (Step C) and using 7-oximo-1,3,4,7,12,12a-hexahydropyrido[2,1-b][3] benzazepin-6(2H)-one (from Step C above), the title compound was prepared.

Physical data were as follows:
$^1$H-nmr (CDCl$_3$): δ=1.3–1.9 (6H); 2.42 (t, 1H); 3.08 (m, 2H); 3.47 (m, 1H); 3.96 (q,2H); 4.66 (d,1H); 7.2 (m,4H).
(MW=230.3); mass spectroscopy (MH+) 231.1.

EXAMPLE 1-H

Synthesis of 1-(N'-L-Alaninyl)amino-4,5,6,7-tetrahydro-3,7-methano-3H-3-benzazonin-2(1H-one

Step A

Synthesis of N-Chloroacetyl-3-phenylpiperidine

Following General Procedure F and using 3-phenylpyridine hydrochloride (Aldrich), the title compound was prepared.

Step B

Synthesis of 4,5,6,7-Tetrahydro-3,7-methano-3H-3-benzazonin-2(1H)-one

Following General Procedure G and using N-chloroacetyl-3-phenylpiperidine, the title compound was prepared.

Physical data were as follows:
$^1$H-nmr (CDCl$_3$): d=1.32–1.57 (2H); 2.08 (m, 2H); 2.81 (t, 1H); 3.13 (bs, 1H); 3.37 (m, 2H); 4.36 (m, 2H); 4.50 (d, 1H).
(MW=201.3); mass spectroscopy (MH+) 202.1.

Step C

Synthesis of 1-Oximo-4,5,6,7-tetrahydro-3,7-methano-3H-3-benzazonin-2(1H)-one

Following General Procedure 3A (Step B) and using the product from Step B above, the title compound was prepared.

Step D

Synthesis of 1-Amino-4,5,6,7-tetrahydro-3,7-methano-3H-3-benzazonin-2(1H)-one

Following General Procedure 3A (Step C) and using the product from Step C above, the title compound was prepared.

Physical data were as follows:

$^1$H-nmr (CDCl$_3$): δ=2.86 (t, 1H); 3.17 (bs, 1H); 3.39 (dd, 1H); 4.40 (d, 1H); 4.50 (d, 1H); 5.39 (s, 1H).

(MW=216.3); mass spectroscopy (MH+) 217.4.

Step E

Synthesis of 1-(N'-Boc-L-Alaninyl)amino-4,5,6,7-tetrahydro-3,7-methano-3H-3-benzazonin-2(1H)-one Following General Procedure D and using N-tert-Boc-L-alanine (Aldrich) and the product from Step D above, the title compound was prepared.

Physical data were as follows:

(MW=387.48); mass spectroscopy (MH+) 388.1.

Step F

Synthesis of 1-(N'-L-Alaninyl)amino4,5,6,7-tetrahydro-3,7-methano-3H-3-benzazonin-2(1H)-one Following General Procedure E and using the product from Step E, the title compound was prepared.

Physical data were as follows:

$^1$H-nmr (CDCl$_3$): δ=2.85 (t, 1H); 3.16 (bs, 1H); 3.40 (dd, 1H); 3.67 (m, 1H); 4.35 (d, 1H); 4.56 (d, 1H); 6.40 (d, 1H).

(MW=287.4); mass spectroscopy (MH+) 288.1.

EXAMPLE 2-A

Synthesis of 5-Amino-5,7-dihydro-6H-dibenzo[a,c]cyclohepten-6-ol Hydrochloride

Step A

Synthesis of 5-Oximo-5,7-dihydro-6H-dibenzo[a,c]cyclohepten-6-one

A round bottom flask was charged with 5,7-dihydro-6H-dibenzo[a,c]cyclohepten-6-one (1.0 g, 4.81 mmol) (CAS#1139-82-8, prepared as described in *Tetrahedron Letters*, Vol. 28, No. 23, (1987), pp 2633–2636, incorporated herein by reference) and butyl nitrite (0.673 mL, 5.77 mmol) (Aldrich) in Et$_2$O. The solution was cooled to 0° C. and treated drop-wise with a saturated solution of HCl(g)/Et$_2$O. After 5 hours at 0° C., the resulting precipitate was filtered, rinsed with cold Et$_2$O and vacuum dried to give the title compound as a colorless solid.

NMR data was as follows:

$^1$H-nmr (CDCl$_3$): δ=7.26–7.74 (m, 8H), 3.84 (m, 2H).

C$_{15}$H$_{11}$NO$_2$ (MW=237.26); mass spectroscopy (MH+) 238.

Anal. Calcd for C$_{15}$H$_{11}$NO$_2$; C, 75.93 H, 4.67 N, 5.90. Found: C, 75.67 H, 4.83 N, 5.67.

Step B

Synthesis of 5-Amino-5,7-dihydro-6H-dibenzo[a,c]-cyclohepten-6-ol Hydrochloride

The compound isolated above (0.489 g, 2.04 mmol) was dissolved in THF and added drop-wise to a well-stirred mixture of LAH (10.2 mL, 10.2 mmol)/THF. After heating to reflux for 25 hours under N$_2$ atmosphere the solution was quenched and worked-up according to Fieser's method. The resulting solid, was rinsed with NH$_3$ sat/CHCl$_3$, the filtrate evaporated and the title compound purified by chromatography (SiO$_2$, CHCl$_3$).

C$_{15}$H$_{15}$NO (MW=225.290); mass spectroscopy (MH+) 226.

Anal. Calcd for C$_{15}$H$_{15}$NO; C, 79.97 H, 6.71 N, 6.22. Found: C, 80.19 H, 6.71 N, 5.91.

EXAMPLE 2-B

Synthesis of 5-[L-alaninyl]-amino-5,7-dihydro-6H-dibenzo[a,c]cyclohepten-6-one

Following General Procedure D above using Boc-L-alanine (Aldrich) and 5-amino-5,7-dihydro-6H-dibenzo[a,c]cyclohepten-6-ol hydrochloride (Example 2-A), the compound was prepared as a tan foam.

The resulting alcohol was oxidized as follows. To a stirred mixture of oxalyl chloride (0.15 mL, 1.2 mmol) in 10 mL of dichloromethane cooled to −78° C. was added DMSO (0.106 mL, 1.5 mmol) and the mixture was stirred for 10 minutes. A solution of the alcohol (0.1828 g, 0.60 mmol) in 20 mL of chloroform was added dropwise. The reaction mixture was stirred at −78° C. for 2 hours, and then 0.5 mL (3.6 mmol) of triethylamine was added. Stirring was continued for 1 hour and then the mixture was allowed to warm to room temperature and stirring was continued at ambient temperature overnight. The mixture was then diluted with 50 mL of dichloromethane, washed with brine (3×), dried over magnesium sulfate, filtered and evaporated to dryness to give the crude product which was typically purified by column chromatography.

The Boc group was removed using 2.0 M HCl/dioxane. The title compound was isolated as an orange foam.

C$_{18}$H$_{18}$N$_2$O$_2$HCl (MW=330.4); mass spectroscopy (MH+ of freebase) 295.

C. Dibenzazepinone Derivatives and Related Compounds

General Procedure 3-A

Preparation of 5-Amino-7-alkyl-5,7-dihydro-6H-dibenz[b,d]azepin-6-one Derivatives

Step A

Following the General Procedure of Step A of Example 1-C and using 5,7-dihydro-6H-dibenz[b,d]azepin-6-one and an alkyl halide, the 7-alkyl-5,7-dihydro-6H-dibenz[b,d]azepin-6-one was prepared.

Step B

The 7-alkyl-5,7-dihydro-6H-dibenz[b,d]azepin-6-one (1 eq.) was dissolved in THF and isoamylnitrite (1.2 eq.) was added. The mixture was cooled to 0° C. in an ice bath. NaHMDS (1.1 eq., 1M in THF) was added dropwise. After stirring for 1 hour or until the reaction was complete, the mixture was concentrated then acidified with 1N HCl and extracted with EtOAc. The organic portion was dried and concentrated to yield a crude product which was purified by silica gel chromatography.

Step C

The resulting oxime was dissolved in EtOH/NH$_3$ (20:1) and hydrogenated in a bomb using Raney nickel and hydrogen (500 psi) at 100° C. for 10 hours. The resulting mixture was filtered and concentrated to provide an oil which was purified by silica gel chromatography to yield the title compound.

General Procedure 3-B

Preparation of Fluoro-substituted 5,7-dihydro-6H-dibenz[b,d]azepin-6-one Derivatives A modification of the procedure of Robin D. Clark and Jahangir, Tetrahedron, Vol. 49, No. 7, pp. 1351–1356, 1993[15] was used. Specifically, an appropriately substituted N-t-Boc-2-amino-2'-methylbiphenyl was dissolved in THF and cooled to –78° C. s-Butyl lithium (1.3M in cyclohexane, 2.2 eq.) was added slowly so that the temperature remained below –65° C. The resulting mixture was allowed to warm to –25° C. and was stirred at that temperature for 1 hour. The mixture was cooled to –78° C. Dry $CO_2$ was bubbled through the mixture for 30 seconds. The mixture was allowed to warm to ambient temperature then was carefully quenched with water. The mixture was concentrated under reduced pressure then was adjusted to pH 3 with 1N HCl. The mixture was extracted with EtOAc and the organic portion was dried and concentrated to yield a crude material. The crude material was dissolved in methanol and the solution was saturated with HCl. The mixture was heated at reflux for 12 hours then was allowed to cool. The mixture was concentrated to provide crude lactam which was purified by chromatography or crystallization.

General Procedure 3-C

Resolution of 5-Amino-7-methyl-5,7-dihydro-6H-dibenz[b,d]azepin-6-one

In a round bottom flask was added the racemic freebase amine (1.0 eq.) in methanol followed by di-p-toluoyl-D-tartaric acid monohydrate (1.0 eq.). The mixture was concentrated in vacuo to a residue and redissolved in a moderate volume of methanol and allowed to stir at room temperature open to the atmosphere (8–72 hours). The solid was removed by filtration. The enantiomeric excess was determined by chiral HPLC (Chiracel ODR) using 15% acetonitrile and 85% $H_2O$ with 0.1% trifluoroacetic acid and a flow rate of 1.0 mL/minute at 35° C. The resolved di-p-toluoyl-D-tartaric salt was then dissolved in EtOAc and saturated $NaHCO_3$ until pH 9–10 was reached. The layers were separated and the organic layer was washed again with saturated $NaHCO_3$, $H_2O$, and brine. The organic layer was dried over $MgSO_4$ and the drying agent was removed by filtration. The filtrate was concentrated in vacuo. The free amine was dissolved in MeOH and HCl (12M, 1.0 eq.) was added. The salt was concentrated in vacuo and the resulting film was triturated with EtOAc. The HCl salt was filtered and rinsed with EtOAc. The ee was determined by chiral HPLC.

EXAMPLE 3-A

Synthesis of 5-Amino-7-methyl-5,7-dihydro-6H-dibenz[b,d]azepin-6-one Hydrochloride Step A Synthesis of 7-Methyl-5,7-dihydro-6H-dibenz[b,d]azepin-6-one A round bottom flask was charged with sodium hydride (0.295 g, 7.46 mmol) in 9.0 mL of DMF and treated with 5,7-dihydro-6H-dibenz[b,d]azepin-6-one (1.3 g, 6.22 mmol) (CAS #20011-90-9, prepared as described in Brown, et. al., Tetrahedron Letters, No. 8, 667–670, (1971) and references cited therein, which are incorporated herein by reference). After stirring at 60° C. for 1 hour, the solution was treated with methyl iodide (1.16 mL, 18.6 mmol) and stirring continued for 17 hours with the exclusion of light. After cooling, the reaction was diluted with $CH_2Cl_2/H_2O$, washed with $NaHSO_4$ solution, $H_2O$, and dried over $Na_2SO_4$. Evaporation and flash chromatography ($SiO_2$, $CHCl_3$) gave 0.885 g (63%) of the title compound as a colorless solid.

NMR data was as follows:

$^1$H-nmr (CDCl$_3$): δ=7.62 (d, 2H), 7.26–7.47 (m, 6H), 3.51 (m, 2H), 3.32 (s, 3H).

$C_{15}H_{13}NO$ (MW=223.27); mass spectroscopy (MH+) 223.

Anal. Calcd for $C_{15}H_{13}NO$; C, 80.69 H, 5.87 N, 6.27. Found: C, 80.11 H, 5.95 N, 6.23.

Step B

Synthesis of 7-Methyl-5-oximo-5,7-dihydro-6H-dibenz[b,d]azepin-6-one

The compound isolated above (0.700 g, 3.14 mmol) was dissolved in 20 mL of toluene and treated with butyl nitrite (0.733 mL, 6.28 mmol). The reaction temperature was lowered to 0° C. and the solution was treated with KHMDS (9.42 mL, 0.5 M) under $N_2$ atmosphere. After stirring for 1 hour the reaction was quenched with a saturated solution of $NaHSO_4$, diluted with $CH_2Cl_2$ and separated. The organic layer was dried over $Na_2SO_4$ and the title compound purified by chromatography ($SiO_2$, 98:2 $CHCl_3$/MeOH) giving 0.59 g (80%) as a colorless solid.

$C_{15}H_{12}N_2O_2$ (MW=252.275); mass spectroscopy (MH+) 252.

Anal. Calcd for $C_{15}H_{12}N_2O_2$; C, 71.42 H, 4.79 N, 11.10. Found: C, 71.24 H, 4.69 N, 10.87.

Step C

Synthesis of 5-Amino-7-Methyl-5,7-dihydro-6H-dibenz[b,d]azepin-6-one Hydrochloride The oxime isolated above (0.99 g, 3.92 mmol) was hydrogenated in a Parr apparatus at 35 psi over 10% Pd/C (0.46 g) in 3 A ethanol. After 32 hours, the reaction mixture was filtered through a plug of celite, the filtrate evaporated to a foam and treated with a saturated solution of HCl (g) in $Et_2O$. The resulting colorless solid was filtered, rinsed with cold $Et_2O$ and vacuum dried to give 0.66 g (61%) of the title compound.

NMR data was as follows:

$^1$H-nmr (DMSOd6): δ=9.11 (bs, 3H), 7.78–7.41(m, 8H), 4.83 (s, 1H), 3.25 (s, 3H).

$C_{15}H_{14}N_2O\cdot HCl$ (MW=274.753); mass spectroscopy (MH+ free base) 238.

Anal. Calcd for $C_{15}H_{14}N_2O \cdot HCl$; C, 65.57 H, 5.50 N, 10.19 Found: C, 65.27 H, 5.67 N, 10.13.

EXAMPLE 3-B

Synthesis of (S)- and (R)-5-(L-Alaninyl)-amino-7-methyl-5,7-dihydro-6H-dibenz[b,d]azepin-6-one

Step A

Synthesis of (S)- and (R)-5-(N-Boc-L-Alaninyl)-amino-7-methyl-5,7-dihydro-6H-dibenz[b,d]azepin-6-one Boc-L-Alanine (0.429 g, 2.26 mmol) (Aldrich) was dissolved in THF and treated with HOBt (0.305 g, 2.26 mmol), and 5-amino-7-methyl-5,7-dihydro-6H-dibenz[b,d]azepin-6-one (0.45 g, 1.89 mmol) (Example 3-A). The temperature was lowered to 0° C. and the reaction mixture treated with EDC (0.449 g, 2.26 mmol) (Aldrich) and stirred 17 hours under $N_2$. The reaction mixture was evaporated, the residue diluted with EtOAc/$H_2O$, washed 1.0 N HCl, sat. $NaHCO_3$, brine and dried over $Na_2SO4$. The diastereomers were separated on a Chiralcel OD column using 10% IPA/heptane at 1.5 mL/minute.

Isomer 1: Retention time 3.37 minutes.

NMR data was as follows:

$^1$H-nmr (CDCl$_3$): δ=7.62–7.33 (m, 9H), 5.26 (d, 1H), 5.08 (m, 1H), 4.34 (m, 1H), 3.35 (s, 3H), 1.49 (s, 9H), 1.40 (d, 3H).

Optical Rotation: $[\alpha]_{20}$=–96@589 nm (c=1, MeOH).

$C_{23}H_{27}N_3O_4$ (MW=409.489); mass spectroscopy (MH+) 409.

Anal. Calcd for $C_{23}H_{27}N_3O_4$; C, 67.46 H, 6.64 N, 10.26. Found: C, 68.42 H, 7.02 N, 9.81.

Isomer 2: Retention time 6.08 minutes.

NMR data was as follows:

$^1$H-nmr (CDCl$_3$): δ=7.74 (bd,1H), 7.62–7.32 (m, 8H), 5.28 (d, 1H), 4.99 (m, 1H), 4.36 (m, 1H), 3.35 (s, 3H), 1.49 (s, 9H), 1.46 (d, 3H).

Optical Rotation: $[\alpha]_{20}$=69@589 nm (c=1, MeOH).

$C_{23}H_{27}N_3O_4$ (MW=409.489); mass spectroscopy (MH+) 409.

Anal. Calcd for $C_{23}H_{27}N_3O_4$; C, 67.46 H, 6.64 N, 10.26. Found: C, 67.40 H, 6.62 N, 10.02

Step B

Synthesis of (S)- and (R)-5-(L-Alaninyl)-amino-7-methyl-5,7-dihydro-6H-dibenz[b,d]azepin-6-one Hydrochloride The compounds isolated in Step A (each isomer separately) were dissolved in dioxane and treated with excess HCl (g). After stirring for 17 hours, the title compounds were isolated as colorless solids after evaporation and vacuum drying.

Isomer 1

$C_{18}H_{19}N_3O_2 \cdot HCl$ (MW=345.832); mass spectroscopy (MH+ free base) 309.

Optical Rotation: $[\alpha]_{20}$=–55@589 nm (c=1, MeOH).

Isomer 2

$C_{18}H_{19}N_3O_2 \cdot HCl$ (MW=345.832); mass spectroscopy (MH+ free base) 309.

Optical Rotation: $[\alpha]_{20}$=80@589 nm (c=1, MeOH).

EXAMPLE 3-C

Synthesis of (S)- and (R)-5-(L-Valinyl)-amino-7-methyl-5,7-dihydro-6H-dibenz[b,d]azepin-6-one

Step A

Synthesis of (S)- and (R)-5-(N-Boc-L-Valinyl)-amino-7-methyl-5,7-dihydro-6H-dibenz[b,d]azepin-6-one Boc-L-Valine (0.656 g, 3.02 mmol) (Aldrich) was dissolved in THF and treated with HOBt (0.408, 3.02 mmol), DIPEA (1.05 mL, 6.05 mmol) and 5-amino-7-methyl-5,7-dihydro-6H-dibenz[b,d]azepin-6-one hydrochloride (0.75 g, 2.75 mmol) (Example 3-A). The temperature was lowered to 0° C. and the reaction mixture treated with EDC (0.601 g, 3.02 mmol) (Aldrich) and stirred 17 hours under $N_2$. The reaction mixture was evaporated, the residue diluted with EtOAc/$H_2O$, washed 1.0 N HCl, sat. $NaHCO_3$, brine and dried over $Na_2SO_4$. The diastereomers were separated on a Chiralcel OD column using 10% IPA/heptane at 1.5 mL/minute.

Isomer 1: Retention time 3.23 minutes.

Optical Rotation: $[\alpha]_{20}$=–120@589 mn (c=1, MeOH).

$C_{25}H_{31}N_3O_4$ (MW=437.544); mass spectroscopy (MH+) 438

Isomer 2: Retention time 6.64 minutes.

Optical Rotation: $[\alpha]_{20}$=50@589 nm (c=1, MeOH).

$C_{25}H_{31}N_3O_4$ (MW=437.544); mass spectroscopy (MH+) 438

Step B

Synthesis of (S)- and (R)-5-(L-Valinyl)-amino-7-methyl-5,7-dihydro-6H-dibenz[b,d]azepin-6-one Hydrochloride The compounds isolated in Step A (each isomer separately) were dissolved in dioxane and treated with excess HCl (g). After stirring for 17 hours, the title compounds were isolated as colorless solids after evaporation and vacuum drying.

Isomer 1

$C_{20}H_{23}N_3O_2 \cdot HCl$ (MW=373.88); mass spectroscopy (MH+ free base) 338.

Optical Rotation: $[\alpha]_{20}$=–38@589 nm (c=1, MeOH).

Isomer 2

$C_{20}H_{23}N_3O_2 \cdot HCl$ (MW=373.88); mass spectroscopy (MH+ free base) 338.

Optical Rotation: $[\alpha]_{20}$=97@589 nm (c=1, MeOH).

EXAMPLE 3-D

Synthesis of (S)- and (R)-5-(L-tert-Leucine)-amino-7-methyl-5,7-dihydro-6H-dibenz[b,d]azepin-6-one

Step A

Synthesis of (S)- and (R)-5-(N-Boc-L-tert-Leucinyl)-amino-7-methyl-5,7-dihydro-6H-dibenz[b,d]azepin-6-one Boc-L-tert-Leucine (0.698 g, 3.02 mmol) (Fluka) was dissolved in THF and treated with HOBt (0.408, 3.02 mmol), DIPEA (1.05 mL, 6.05 mmol) and 5-amino-7-methyl-5,7-dihydro-6H-dibenz[b,d]azepin-6-one hydrochloride (0.75 g, 2.75 mmol) (Example 3-A). The temperature was lowered to 0° C. and the reaction mixture treated with EDC (0.601 g, 3.02 mmol) (Aldrich) and stirred 17 hours under $N_2$. The reaction mixture was evaporated, the residue diluted with EtOAc/$H_2O$, washed 1.0 N HCl, sat. $NaHCO_3$, brine and dried over $Na_2SO_4$. The diastereomers were separated on a Chiralcel OD column using 10% IPA/heptane at 1.5 mL/minute.

Isomer 1: Retention time 3.28 minutes.

Optical Rotation: $[\alpha]_{20}$=−128@589 nm (c=1, MeOH).

$C_{26}H_{33}N_3O_4$ (MW=451.571); mass spectroscopy (MH+) 452

Isomer 2: Retention time 5.52 minutes.

Optical Rotation: $[\alpha]_{20}$=26@589 nm (c=1, MeOH).

$C_{26}H_{33}N_3O_4$ (MW=451.571); mass spectroscopy (MH+) 452

Step B

Synthesis of (S)- and (R)-5-(L-tert-Leucinyl)-amino-7-methyl-5,7-dihydro-6H-dibenz[b,d]azepin-6-one Hydrochloride The compounds isolated in Step A (each isomer separately) were dissolved in dioxane and treated with excess HCl (g). After stirring for 17 hours, the title compounds were isolated as colorless solids after evaporation and vacuum drying.

Isomer 1

$C_{21}H_{25}N_3O_2 \cdot HCl$ (MW=387.91); mass spectroscopy (MH+ free base) 352.

Optical Rotation: $[\alpha]_{20}$=−34@589 nm (c=1, MeOH).

Isomer 2

$C_{21}H_{25}N_3O_2 \cdot HCl$ (MW=387.91); mass spectroscopy (MH+ free base) 352.

Optical Rotation: $[\alpha]_{20}$=108@589 nm (c=1, MeOH).

EXAMPLE 3-E

Synthesis of 5-(N-Boc-Amino)-5,7-dihydro-6H.7H-dibenz[b,d]azepin-6-one

Step A

Synthesis of 5-Iodo-5,7-dihydro-6H-dibenz[b,d]azepin-6-one

A solution of 5,7-dihydro-6H-dibenz[b,d]azepin-6-one (1.0 g, 4.77 mmol) (Example 3-A) and $Et_3N$ (2.66 mL, 19.12 mmol) was stirred for 5.0 minutes at −15° C. in $CH_2Cl_2$ and treated with TMSI (1.36 mL, 9.54 mmol). After stirring for 15 minutes $I_2$ (1.81 g, 7.16 mmol) was added in a single portion and the reaction allowed to warm to 5–10° C. over 3 h. The reaction was quenched with sat. $Na_2SO_3$, diluted with $CH_2Cl_2$. and separated. The organics were washed with $Na_2SO_3$ and $NaHSO_3$ and dried over $MgSO_4$. After filtration, the organics were concentrated to approximately 20 mL and diluted with an additional 20 mL of hexanes. The title compound was isolated as a tan precipitate by filtration.

Step B

Synthesis of 5-Azido-5,7-dihydro-6H-dibenz[b,d]azepin-6-one

The iodide isolated above was dissolved in DMF and treated with 1.2 equivalents of $NaN_3$. After stirring 17 hour at 23° C., the mixture was diluted with EtOAc/$H_2O$, separated, washed with brine and dried over $MgSO_4$. The title compound was triturated from hot EtOAc as a tan powder.

Step C

Synthesis of 5-(N-Boc-Amino)-5,7-dihydro-6H,7H-dibenz[b,d]azepin-6-one

The azide was dissolved in THF/$H_2O$ and stirred at 23° C. for 17 hours in the presence of 3.0 equivalents of $Ph_3P$. The reaction was diluted with 50% HOAc/toluene, separated, the aqueous layer extracted with toluene and evaporated to an oily residue. This was taken to pH 7.0 by the addition of 1 N NaOH, the resulting HOAc salt was collected and vacuum dried. Finally, the compound was treated with Boc anhydride (1.05 equivalents) and $Et_3N$ (2.1 equivalents) in THF. After stirring for 5 hours at 23° C., the reaction was filtered and the title compound isolated as a colorless powder.

EXAMPLE 3-F

Synthesis of 5-Amino-7-(2-methylpropyl)-5,7-dihydro-6-H-dibenz[b,d]azepin-6-one Hydrochloride Step A Synthesis of 5-(N-Boc-Amino)-7-(2-methylpropyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 3-E) in DMF was treated with $Cs_2CO_3$ (0.22 g, 0.678 mmol) and warmed to 60° C. To the reaction mixture was added 1-iodo-2-methylpropane (0.078 mL, 0.678 mmol) and stirring continued for 17 hours. After cooling to 23° C. the mixture was diluted with $CH_2Cl_2$, washed with several portions of brine and dried over $Na_2SO_4$. The title compound was purified by chromatography ($SiO_2$, $CHCl_3$/MeOH 9:1).

$C_{23}H_{28}N_2O_3$ (MW=380.41); mass spectroscopy (MH+) 381

Anal. Calcd for $C_{23}H_{28}N_2O_3$; C, 72.61 H, 7.42 N, 7.36. Found: C, 72.31 H, 7.64 N, 7.17.

Step B

Synthesis of 5-Amino-7-(2-methylpropyl)-5,7-dihydro-6H-dibenz[b,d]azepin-6-one Hydrochloride The compound isolated in Step A was deprotected in dioxane saturated with gaseous HCl. The title compound was isolated as a slightly colored solid after evaporation and vacuum drying.

EXAMPLE 3-G

Synthesis of 5-Amino-7-(methoxyacetyl)-5,7-dihydro-6H-dibenz[b,d]azepin-6-one Hydrochloride Step A Synthesis of 5-(N-Boc-Amino)-7-(methoxyacetyl)-5,7-dihydro-6H-dibenz[b,d]azepin-6-one A solution of 5-(N-Boc-amino)-5,7-dihydro-6H-dibenz[b,d]azepin-6-one (1.03, 3.08 mmol) (Example 3-E) in DMF was treated with $Cs_2CO_3$ (1.10 g, 3.39 mmol) and warmed to 60° C. To the reaction mixture was added bromomethyl acetate (0.321 mL, 3.39 mmol) (Aldrich) and stirring continued for 17 hours. After cooling to 23° C., the mixture was diluted with $CH_2Cl_2$, washed with several portions of brine and dried over $Na_2SO_4$. The title compound was purified by chromatography ($SiO_2$, $CHCl_3$).

$C_{22}H_{24}N_2O_5$ (MW=396.44); mass spectroscopy (MH+) 397

Anal. Calcd for $C_{22}H_{24}N_2O_5$; C, 66.65 H, 6.10 N, 7.07. Found: C, 66.28 H, 5.72 N, 6.50.

Step B

Synthesis of 5-Amino-7-(methoxyacetyl)-5,7-dihydro-6H-dibenz[b,d]azepin-6-one Hydrochloride The compound isolated in Step A was deprotected in dioxane saturated with gaseous HCl. The title compound was isolated as a colorless solid after evaporation and vacuum drying.

$C_{17}H_{16}N_2O_3$ HCl (MW=332.78); mass spectroscopy (MH+ free base) 297.

EXAMPLE 3-H

Synthesis of 5-Amino-7-(3,3-dimethyl-2-butanonyl)-5,7-dihydro-6H-dibenz[b,d]azepin-6-one Hydrochloride Step A Synthesis of 5-(N-Boc-Amino)-7-(3,3-dimethyl-butanonyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 3-E) in DMF was treated with $Cs_2CO_3$ (0.3 g, 0.925 mmol) and warmed to 60° C. To the reaction mixture was added 1-chloro-3,3-dimethyl-2-butanone (0.096 mL, 0.74 mmol) (Aldrich) and stirring continued for 17 hours. After cooling to 23° C., the mixture was diluted with $CH_2Cl_2$, washed with several portions of brine and dried over $Na_2SO_4$. The title compound was isolated as a colorless solid.

$C_{25}H_{30}N_2O_4$ (MW=422.522); mass spectroscopy (MH+) 423

Step B

Synthesis of 5-Amino-7-(3,3-dimethyl-2-butanonyl)-5,7-dihydro-6H-dibenz[b,d]azepin-6-one Hydrochloride The compound isolated in Step A was deprotected in dioxane saturated with gaseous HCl. The title compound was isolated as a colorless solid after evaporation and vacuum drying.

EXAMPLE 3-I

Synthesis of L-Alaninyl-5-amino-7-methyl-5,7-dihydro-6H-dibenz[b,d]azepin-6-one Hydrochloride Step A Following General Procedure D and using N-t-Boc-L-alanine and 5-amino-7-methyl-5,7-dihydro-6H-dibenz[b,d]azepin-6-one, N-t-Boc-L-alaninyl-5-amino-7-methyl-5,7-dihydro-6H-dibenz[b,d]azepin-6-one was prepared.

Step B

Following the General Procedure of Step B of Example 1-C and using the N-t-Boc-L-alaninyl-5-amino-7-methyl-5,7-dihydro-6H-dibenz[b,d]azepin-6-one, the title compound was prepared. Other substituted N-t-Boc-L-alaninyl-5-amino-7-methyl-5,7-dihydro-6H-dibenz[b,d]azepin-6-ones can also be prepared by this procedure.

EXAMPLE 3-J

Synthesis of L-Valinyl-5-amino-7-methyl-5,7-dihydro-6H-dibenz[b,d]azepin-6-one Hydrochloride Step A Following General Procedure D and using N-t-Boc-L-valine and 5-amino-7-methyl-5,7-dihydro-6H-dibenz[b,d]azepin-6-one, N-t-Boc-L-valinyl-5-amino-7-methyl-5,7-dihydro-6H-dibenz[b,d]azepin-6-one was prepared.

Step B

Following the General Procedure of Step B of Example 1-C and using the N-t-Boc-L-valinyl-5-amino-7-methyl-5,7-dihydro-6H-dibenz[b,d]azepin-6-one, the title compound was prepared. Other substituted N-t-Boc-L-valinyl-5-amino-7-methyl-5,7-dihydro-6H-dibenz[b,d]azepin-6-ones can also be prepared by this procedure.

EXAMPLE 3-K

Synthesis of 5-Amino-7-phenbutyl-5,7-dihydro-6H-dibenz[b,d]azepin-6-one

Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein, which are incorporated herein by reference) and 1-chloro-4-phenylbutane (Aldrich), the title compound was prepared.

EXAMPLE 3-L

Synthesis of 5-Amino-7-cyclopropymethyl-5,7-dihydro-6H-dibenz[b,d]azepin-6-one

Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein, which are incorporated herein by reference) and (bromomethyl)cyclopropane (Aldrich), the title compound was prepared.

EXAMPLE 3-M

Synthesis of 5-Amino-7-(2',2',2'-trifluoroethyl)-5,7-dihydro-6H-dibenz[b,d]azepin-6-one Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein, which are incorporated herein by reference) and 1-bromo-2,2,2-trifluoroethane (Aldrich), the title compound was prepared.

EXAMPLE 3-N

Synthesis of 5-Amino-7-cyclohexyl-5,7-dihydro-6H-dibenz[b,d]azepin-6-one

Following General Procedure 3-A and using 5,7-dihydro-6H-dibenz[b,d]azepin-6-one (prepared as described in Brown, et. al., *Tetrahedron Letters*, No. 8, pp. 667–670, (1971) and references cited therein, which are incorporated herein by reference) and bromocyclohexane (Aldrich), the title compound was prepared.

EXAMPLE 3-O

Synthesis of 5-(L-Alaninyl)amino-9-fluoro-7-methyl-5,7-dihydro-6H-dibenz[b,d]azepin-6-one Hydrochloride Step A 2-Bromo-5-fluorotoluene was stirred in THF at −78° C. s-BuLi (1.05 eq., 1.3 M in cyclohexane) was slowly added and the mixture was stirred for 45 minutes. Trimethylborate (1.5 eq.) was added and the mixture was allowed to warm to ambient temperature. After stirring for 1 hour, pinacol (2 eq.) was added. The mixture was stirred for 16 hours then was concentrated under reduced pressure. The resulting residue was slurried in $CH_2Cl_2$ and filtered through Celite. The filtrate was concentrated to yield an oil which was purified by chromatography on deactivated silica gel ($Et_3N$) to yield the arylboronate ester.

Step B

2-Bromoaniline (1 eq.) and di-t-butyl-dicarbonate (1.1 eq.) were stirred at 80° C. for 20 hours. The resulting mixture was allowed to cool and was directly distilled using house vacuum to provide N-t-Boc-2-bromoaniline.

Step C

N-t-Boc-2-bromoaniline (Step 2, 1 eq.), the arylboronate ester (Step 1, 1.1 eq.), $K_2CO_3$ (1.1 eq.) and tetrakis(triphenylphosphine)palladium(0) (0.02 eq.) were stirred in 20% water/dioxane under nitrogen. The solution was heated at reflux for 10 hours. The mixture was allowed to cool then was concentrated. The resulting residue was partitioned between water and chloroform. The organic portion was dried and concentrated to yield an oil which was purified by silica gel chromatography using 1:1 $CH_2Cl_2$/hexanes.

Step D

Following General Procedure 3-B and using the substituted biphenyl from step 3, the 9-fluoro-5,7-dihydro-6H-dibenz[b,d]azepin-6-one was prepared.

Step E

9-Fluoro-5,7-dihydro-6H-dibenz[b,d]azepin-6-one (1 eq., Step 4), cesium carbonate (1.1 eq., Aldrich) and methyl iodide (1.1 eq., Aldrich) were stirred in dry DMF at ambient temperature for 16 hours. The mixture was concentrated under reduced pressure to provide a residue which was partitioned between EtOAc and water. The organic portion was dried and concentrated to yield an oil which was purified by silica gel chromatography to 9-fluoro-7-methyl-5,7-dihydro-6H-dibenz[b,d]azepin-6-one.

Step F

Following General Procedure 3-A, Step B and 9-fluoro-7-methyl-5,7-dihydro-6H-dibenz[b,d]azepin-6-one from Step 5, 5-amino-9-fluoro-7-methyl-5,7-dihydro-6H-dibenz[b,d]azepin-6-one was prepared.

Step G

Following the procedure of Example 3-I and using 5-amino-9-fluoro-7-methyl-5,7-dihydro-6H-dibenz[b,d]azepin-6-one from Step 6, the title compound was prepared.

EXAMPLE 3-P

Synthesis of 5-(L-Alaninyl)amino-13-fluoro-7-methyl-5,7-dihydro-6H-dibenz[b,d]azepin-6-one Hydrochloride Following the procedure of Example 3-O and using 2-bromo-4-fluoroaniline (Step 2, Lancaster) and o-tolylboronic acid (Step 3, Aldrich), the title compound was prepared.

EXAMPLE 3-Q

Synthesis of 5-(L-Alaninyl)amino-10-fluoro-7-methyl-5,7-dihydro-6H-dibenz[b,d]azepin-6-one Hydrochloride Following the procedure of Example 3-O and using 2-bromo-4-fluorotoluene (Step 1), the title compound was prepared.

EXAMPLE 3-R

Synthesis of 5-(L-Alanyl)-amino-7-cyclopropylmethyl-5,7-dihydro-6H-dibenz[b,d]azepin-6-one Hydrochloride Following the procedure of Example 3-I and using 5-amino-7-cyclopropylmethyl-5,7-dihydro-6H-dibenz[b,d]azepin-6-one (Example 3-L), the title compound was prepared.

EXAMPLE 3-S

Synthesis of 5-(L-Alaninyl)amino-7-phenbutyl-5,7-dihydro-6H-dibenz[b,d]-azepin-6-one Hydrochloride Following the procedure of Example 3-I and using 5-amino-7-phenbutyl-5,7-dihydro-6H-dibenz[b,d]azepin-6-one (Example 3-K), the title compound was prepared.

EXAMPLE 3-T

Synthesis of 5-(L-Valinyl)amino-7-cyclopropylmethyl-5,7-dihydro-6H-dibenz[b,d]azepin-6-one Hydrochloride Following the procedure of Example 3-J and using 5-amino-7-cyclopropylmethyl-5,7-dihydro-6H-dibenz[b,d]azepin-6-one (Example 3-L), the title compound was prepared.

EXAMPLE 3-U Synthesis of 5-(L-Valinyl)amino-7-phenbutyl-5,7-dihydro-6H-dibenz[b,d]azepin-6-one Hydrochloride Following the procedure of Example 3-J and using 5-amino-7-phenbutyl-5,7-dihydro-6H-dibenz[b,d]azepin-6-one (Example 3-K), the title compound was prepared.

EXAMPLE 3-V

Synthesis of 5-(L-Valinyl)amino-7-hexyl-5,7-dihydro-6H-dibenz[b,d]azepin-6-one Hydrochloride Step A Following General Procedure 3-A and using 5,7-dihydro-6H-dibenz[b,d]azepin-6-one (prepared as described in Brown, et. al., *Tetrahedron Letters*, No. 8, 667–670, (1971) and references cited therein, which are incorporated herein by reference) and 1-bromohexane (Aldrich), 5-amino-7-hexyl-5,7-dihydro-6H-dibenz[b,d]azepin-6-one was prepared.

Step B

Following the procedure of Example 3-J and using 5-amino-7-hexyl-5,7-dihydro-6H-dibenz[b,d]azepin-6-one, the title compound was prepared.

EXAMPLE 3-W

Synthesis of 5-(L-Valinyl)amino-10-fluoro-7-methyl-5,7-dihydro-6H-dibenz[b,d]azepin-6-one Hydrochloride Following the procedure of Example 3-J and using 5-amino-10-fluoro-7-methyl-5,7-dihydro-6H-dibenz[b,d]azepin-6-one (as prepared in Example 3-Q), the title compound was prepared.

EXAMPLE 3-X

Synthesis of 5-(L-Valinyl)amino-13-fluoro-7-methyl-5,7-dihydro-6H-dibenz[b,d]azepin-6-one Hydrochloride Following the procedure of Example 3-J and using the 5-amino-13-fluoro-7-methyl-5,7-dihydro-6H-dibenz[b,d]azepin-6-one (as prepared in Example 3-P), the title compound was prepared.

EXAMPLE 3-Y

Synthesis of 5-(L-Valinyl)amino-13-fluoro-7-methyl-5,7-dihydro-6H-dibenz[b,d]azepin-6-one Hydrochloride Following the procedure of Example 3-J and using the 5-amino-9-fluoro-7-methyl-5,7-dihydro-6H-dibenz[b,d]azepin-6-one (as prepared in Example 3-O), the title compound was prepared.

EXAMPLE 3-Z

Synthesis of (5-Amino-7-methyl-1,2,3,4,5,7-hexahydro-6H-dicyclohexyl[b,d]azepin-6-one The 5-amino-7-methyl-5,7-dihydro-6H-dibenz[b,d]azepin-6-one hydrochloride (Example 3-A) was dissolved in a 1:1 mixture of EtOAc/HOAc. 5% Rh/C was added and the mixture was stirred at 60° C. under 60 psi of hydrogen. After 3 days, the mixture was filtered and the filtrate was concentrated to provide an oil which was purified by SCX-cation exchange chromatography to yield the title compound.

EXAMPLE 3-AA

Synthesis of 5-(S)-Amino-7-methyl-5,7-dihydro-6H-dibenz[b,d]azepin-6-one Hydrochloride Following General Procedure 3-C using racemic 5-amino-7-methyl-5,7-dihydro-6H-dibenz[b,d]azepin-6-one (1.0 eq.) and di-p-toluoyl-D-tartaric acid monohydrate (1.0 eq.) in methanol, the title compound was prepared as a solid. The product was collected by filtration. Enantiomeric excess was determined by chiral HPLC.

Desired enantiomer 1: retention time of 9.97 minutes.

Undesired enantiomer 2: retention time of 8.62 minutes. NMR data was as follows:

$^1$H-nmr (CDCl$_3$): δ=9.39 (s, 2H), 7.75–7.42 (m, 8H), 4.80 (s, 1H), 3.30 (s, 3H).

$C_{15}H_{15}ClN_2O$ (MW=274.75); mass spectroscopy (MH+) 239.1.

Anal Calcd for $C_{15}H_{15}ClN_2O_3$; C, 65.57; H, 5.50; N, 10.20; Found: C, 65.51, H, 5.61; N, 10.01.

EXAMPLE 3-AB

Synthesis of 9-Amino-5,6-dihydro-4H-quino[8,1-ab][3]benzazepin-8(9H)-one Hydrochlororide

Step A

Synthesis of 8-Phenylquinoline

A degassed solution of 8-bromoquinoline (1.0 g, 4.81 mmol) (Aldrich) in dioxane (50 mL)/H$_2$O (10 mL) was treated with phenylboronic acic (0.64 g, 5.29 mmol) (Aldrich), Pd(Ph$_3$P)$_4$ (0.050 g, 0.04 mmol) and K$_2$CO$_3$ (0.73 g, 5.29 mmol). After refluxing for 4 hours under a N$_2$ atmosphere the reaction was allowed to cool, diluted with EtOAc and separated. After drying over Na$_2$SO$_4$ and SiO$_2$ chromatography (95:5 Hexanes/EtOAc) the titled compound was isolated as a colorless oil.

Physical data were as follows:

$^1$H-nmr (CDCl$_3$): δ=8.97 (d, 1H), 8.22 (dd, 1H), 7.87–7.39 (m, 9H).

$C_{15}H_{11}N$ (MW=205); mass spectroscopy (MH+) 206.

Step B

Synthesis of 8-Phenyl-1,2,3,4-tetrahydroquinoline

The product from Step A (0.99 g, 4.82 mmol) was hydrogenated according to the procedure described by Honel, M., et. al., J.C.S. Perkin I, (1980), 1933–1938, incorporated herein by reference.

Physical data were as follows:

$^1$H-nmr (CDCl$_3$): δ=7.46 (m, 3H), 7.38 (m, 2H), 6.98 (m, 2H), 6.70 (m, 1H), 3.27 (t, 2H), 2.86 (t, 2H), 1.96 (m, 2H).

$C_{15}H_{15}N$ (MW=209); mass spectroscopy (MH+) 210.

Step C

Synthesis of 1-Chloromethylacetyl-8-phenyl-1,2,3,4-tetrahydroquinoline

The product from Step B (1.0 g, 4.78 mmol) was dissolved in CH$_2$Cl$_2$ (20 mL)/H$_2$O (20 mL) and treated with NaHCO$_3$ (0.602 g, 7.18 mmol) followed by chloroacetyl chloride (0.478 mL, 5.26 mmol). After stirring for 17 h at 23° C., the reaction was diluted with CH$_2$Cl$_2$, washed with saturated NaHCO$_3$, dried over Na$_2$SO$_4$ and purified by SiO$_2$ chromatography (CHCl$_3$/Hexanes 9:1). The product was isolated as a colorless solid.

Physical data were as follows:

$C_{17}H_{16}ClNO$ (MW=286.77); mass spectroscopy (MH+) 287.

Anal. Calcd for $C_{17}H_{16}ClNO$; C, 71.45 H, 5.64 N, 4.90. Found: C, 71.63 H, 5.60 N, 4.87.

Step D

Synthesis of 5,6-Dihydro-4H-quino[8,1-ab][3]benzazepin-8(9H)-one

The product from Step C (0.89 g, 3.11 mmol) was mixed thoroughly with AlCl$_3$ (0.87 g, 6.54 mmol) at 23° C. and the mixture heated neat at 100° C. for 5–7 minutes. After vigorous gas evolution, the molten mixture was allowed to cool and extracted with several portions of CH$_2$Cl$_2$/NaHCO$_3$ (sat). The combined organic layers were dried over $Na_2SO_4$ and the title compound was purified by chromatography ($SiO_2$, $CHCl_3$/hexanes 9:1), yielding a colorless oil which solidified upon standing.

Physical data were as follows:

$C_{17}H_{15}NO$ (MW=249.312); mass spectroscopy (MH+) 250.

Anal. Calcd for $C_{17}H_{15}NO$; C, 81.90 H, 6.06 N, 5.62. Found: C, 81.75 H, 6.11 N, 5.86.

Step E

Synthesis of 9-Oximo-5,6-Dihydro-4H-quino[8,1-ab][3]benzazepin-8(9H)-one

The product from Step D (0.490 g, 1.97 mmol) was dissolved in THF and butyl nitrite (0.46 mL, 3.93 mmol) and treated with KHMDS (0.5 M, 4.52 mL, 2.26 mmol) at 0° C. After stirring for 1 h, the reaction was quenched with cold 1 N HCl, extracted with EtOAc, the combined organic layers dried over $Na_2SO_4$ and the product purified by $SiO_2$ chromatography ($CHCl_3$/MeOH, 99: 1). The title compound was isolated as a colorless solid.

Physical data were as follows:

$C_{17}H_{14}N_2O_2$ (MW=278.3); mass spectroscopy (MH+) 279.

Anal. Calcd for $C_{17}H_{14}N_2O_2 \cdot 0.3317$ mol $H_2O$; C, 71.82 H, 5.19 N, 9.85. Found: C, 71.85 H, 5.09 N, 9.59.

Step F

Synthesis of 9-Amino-5,6-Dihydro-4H-quino[8,1-ab][3]benzazepin-8(9H)-one

The product from Step E (0.360 g, 1.29 mmol) was hydrogenated over Ra/Ni (0.05 g) in EtOH (50 mL)/$NH_3$ (anhydrous) (5.0 mL) at 100° C. and 500 psi for 10 h. The catalyst was removed by filtration and the resulting filtrate chromatographed over $SiO_2$ ($CHCl_3$/MeOH, 98:2) yielding the titled compound as a colorless oil which solidified upon standing.

Physical data were as follows:

$C_{17}H_{16}N_2O$ (MW=264.326); mass spectroscopy (MH+) 266.

Anal. Calcd for $C_{17}H_{16}N_2O$; C, 77.25 H, 6.10 N, 10.60. Found: C, 77.23 H, 6.15 N, 10.49.

EXAMPLE 3-AC

Synthesis of 9-(N'-L-Alaninyl)amino-5,6-dihydro-4H-quino[8,1-ab][3]benzazepin-8(9H)-one Hydrochloride Step A Synthesis of 9-(N'-Boc-L-Alaninyl)amino-5,6-Dihydro-4H-quino[8,1-ab][3]benzazepin-8(9H)-one Following General Procedure D and using N-Boc-Alanine (Aldrich) and 9-amino-5,6-dihydro-4H-quino[8,1-ab][3]benzazepin-8(9H)-one (from Example 3-AB), the title compound was prepared.

Physical data were as follows:

$C_{25}H_{29}N_3O_4$ (MW=435.521); mass spectroscopy (MH+) 436.

Anal. Calcd for $C_{25}H_{29}N_3O_4 \cdot 0.4102$ mol $H_2O$; C, 67.79 H, 6.79 N, 9.49; Found: C, 67.83 H, 6.91 N, 9.29.

Step B

Synthesis of 9-(N'-L-Alaninyl)amino-5,6-dihydro-4H-quino[8,1-ab][3]benzazepin-8(9H)-one Hydrochloride Following General Procedure E and using the product from Step A, the title compound was prepared.

Physical data were as follows:

$C_{20}H_{21}N_3O_2 \cdot HCl$ (MW=371.6); mass spectroscopy (MH+ free base) 335.

EXAMPLE 3-AD

Synthesis of 5-[L-alaninyl]-amino-7-(2-methylpropyl)-5,7-dihydro-6H-dibenz[b,d]azepin-6-one hydrochloride Following General Procedure D above using Boc-L-alanine (Aldrich) and 5-amino-7-(2-methylpropyl)-5,7-dihydro-6H-dibenz[b,d]azepin-6-one hydrochloride (Example 3-F), the compound was prepared as a tan foam. The resulting Boc group was removed using 2.0 M HCl/dioxane. The title compound was isolated as a slightly colored solid after evaporation and vacuum drying. $C_{21}H_{24}N_3O_2HCl$ (MW=386); mass spectroscopy (MH+ of freebase) 351.

EXAMPLE 3-AE

Synthesis of 5-[L-alaninyl]-amino-5,7-dihydro-6H, 7H-dibenz[b,d]azepin-6-one hydrochloride Step A Synthesis of 5-Amino-5,7-dihydro-6H,7H-dibenz[b,d]azepin-6-one hydrochloride 5-(N-Boc-Amino)-5,7-dihydro-6H,7H-dibenz[b,d]azepin-6-one (Example 3-E) was treated with 2.0 M HCl/dioxane. After stirring for 17 h at 23° C., the title compound was isolated as a slightly colored solid after filtration and vacuum drying.

$C_{14}H_{12}N_2OHCl$ (MW=260.72); mass spectroscopy (MH+ of freebase) 225.

Anal. Calcd for $C_{14}H_{12}N_2OHCl$: C, 64.50 H, 5.03 N, 10.74. Found: C, 64.35 H, 4.99 N, 10.51.

Step B

Synthesis of 5-[N-Boc-L-alaninyl]-amino-5,7-dihydro-6H,7H-dibenz[b,d]azepin-6-one The compound isolated above was coupled with Boc-L-alanine (Aldrich) following General Procedure D. The title compound was used without further purification.

$C_{22}H_{25}N_4O_4$ (MW=395.45); mass spectroscopy (MH+) 396.

Anal. Calcd for $C_{22}H_{25}N_4O_4$: C, 66.82 H, 6.37 N, 10.63. Found: C, 65.53 H, 6.16 N, 10.38.

Step C

Synthesis of 5-[L-alaninyl]-amino-5,7-dihydro-6H, 7H-dibenz[b,d]azepin-6-one hydrochloride The compound isolated above was deprotected using HCl/dioxane. The title compound was used without further purification after stirring for 17 h at 23 C and vacuum drying.

D. BENZODIAZEPINE DERIVATIVES AND RELATED COMPOUNDS

General Procedure 4-A

N-1-Methylation of Benzodiazepines

A solution of benzodiazepine (1 eq.) in DMF (0.1 M concentration) at 0° C. was treated with potassium tert-butoxide (1.0 eq., 1.0 M solution in THF). After stirring for 30 minutes at 0° C., iodomethane (1.3 eq.) was added and stirring continued for 25 minutes. The mixture was diluted with methylene chloride and washed with water and brine. The organic phase was dried over $Na_2SO_4$, filtered, and concentrated. The crude product was then either purified by trituration with 1:1 ether/hexanes or chromatographed via HPLC using ethyl acetate/hexanes as the eluent.

General Procedure 4-B

Cbz Removal Procedure

A flask was charged with the Cbz-protected 3-aminobenzodiazepine (1 eq.). To this was added HBr (34 eq.; 30% solution in acetic acid). Within 20 minutes all of the starting material dissolves. The reaction was stirred for 5 hours at ambient temperature. Ether was added to the orange solution causing the HBr.eamine salt to precipitate. The mixture was decanted. This process of adding ether and decanting was repeated thrice in an effort to remove acetic acid and benzyl bromide. Toluene was added and the mixture concentrated in vacuo. This step was also repeated. The HBr salt was partitioned between ethyl acetate and 1 M $K_2CO_3$. The aqueous layer was back-extracted with ethyl acetate. The combined organics were washed with brine, dried over $Na_2SO_4$, filtered, and concentrated.

General Procedure 4-C

Boc Removal Procedure

A solution of Boc-protected amine (1 eq.) in methylene chloride (0.15 M concentration) was cooled to 0° C. and treated with trifluoroacetic acid (30 eq.). After 10 minutes at 0° C., the cooling bath was removed and stirring continued at ambient for 20 minutes to 1 hour. The mixture was concentrated in vacuo to remove excess trifluoroacetic acid. The residue was dissolved in methylene chloride and washed with saturated aqueous $NaHCO_3$ or 1 M $K_2CO_3$ and brine. The organic layer was dried over $Na_2SO_4$, filtered, and concentrated.

General Procedure 4-D

Azide Transfer Reaction Using KHMDS

The azido derivative was prepared using the procedure described in John W. Butcher et al., *Tet. Lett.*, 37, 6685–6688 (1996), incorporated herein by reference.

General Procedure 4-E

Azide Transfer Reaction Using LDA

To a solution of diisopropylamine (1.1 eq.) in 1 mL of dry THF cooled to −78° C. was added n-butyl lithium (1.6M in hexane) (1.1 eq.) dropwise maintaining the reaction temperature at −78° C. The reaction mixture was stirred for 30 minutes at −78° C. and then the lactam (0.471 mM) was added dropwise as a solution in 1 mL of dry THF. The reaction mixture was stirred at −78° C. for 30 minutes and then a pre-cooled solution of trisyl azide (1.2 eq.) was added as a solution in 1 mL of dry THF. The reaction mixture was stirred at −78° C. for 20 minutes and then quenched with acetic acid (4.0 eq.). The reaction mixture was then stirred at 40° C. for 2 hours. The reaction was then poured into EtOAc and washed with water, sodium bicarbonate and brine, and then dried over sodium sulfate, filtered and concentrated. The residue was purified by LC 2000 chromatography.

General Procedure 4-F

Azido Group Reduction

The azido group was reduced to the corresponding primary amine using the procedure described in John W. Butcher et al., *Tet. Lett.*, 37, 6685–6688 (1996), incorporated herein by reference.

General Procedure 4-G

N-Alkylation of Amides or Lactams Using Sodium Hydride or Potassium tert-Butoxide To a slurry of sodium hydride or potassium tert-butoxide (1.1 eq) in 15 mL of dry DMF was added the appropriate amide (0.0042 moles) as a solution in 10 mL of DMF. The alkyl iodide was then added and a thick slurry resulted. The reaction became less thick as time elapsed and when complete by TLC the reaction had become homogeneous. The reaction mixture was poured over ice and extracted into ethyl acetate. The organic layer was washed with water, followed by brine. The organic layer was then dried over sodium sulfate, filtered and concentrated under reduced pressure. The residue was purified by HPLC (LC 2000), eluting with an ethyl acetate/hexane system.

General Procedure 4-H

N-Alkylation of Amides or Lactams Using KHMDS

To the appropriate amide or lactam in THF cooled to −78° C. was added KHMDS dropwise and the reaction mixture was stirred for 30 min. at −78° C. The alkyl iodide was then added dropwise while maintaining the temperature at −70° C. The cooling bath was then removed and reaction was allowed to warm to room temperature and stirring was continued for 2 hours. The reaction mixture was then poured over ice and extracted into ethyl acetate. The organic extracts were washed with water, followed by brine. The organic layer was then dried over sodium sulfate, filtered and concentrated under reduced pressure. The residue was purified by HPLC (LC 2000), eluting with an ethyl acetate/ hexane system.

General Procedure 4-I

N-Alkylation of Amides or Lactams Using Cesium Carbonate

To a solution of the amide or lactam in DMF was added cesium carbonate (1.05 eq) and an alkyl iodide (1.1 eq). The mixture was allowed to stir overnight at room temperature and then the reaction mixture was diluted with ethyl acetate and washed with water, followed by brine. The organic layer was dried over sodium sulfate, filtered and concentrated under reduced pressure. The residue was purified by HPLC (LC 2000), eluting with an ethyl acetate/hexane system.

General Procedure 4-J

BOC Removal Procedure

To an N-Boc protected compound was added $CH_2Cl_2$/TFA (4:1) at room temperature. The reaction mixture was stirred at room temperature for 3 hours and then concentrated. The residue was extracted into dichloromethane and washed with water, saturated sodium bicarbonate, dried over $Na_2SO_4$, filtered and concentrated to give the free amine.

General Procedure 4-K

Azide Transfer Procedure

This azide transfer procedure is a modification of the procedure described in Evans, D. A. et al. *J. Am. Chem. Soc.* 1990, 112, 4011–4030, incorporated herein by reference. To a solution of the lactam substrate (1.0 eq.) in THF (~0.1 M) under $N_2$ at −78° C. was added a solution of $KN(TMS)_2$ (1.1 eq. of 0.5 M in Toluene, Aldrich) dropwise over a period of 2–10 minutes. A slight exotherm was often observed by an internal thermometer, and the resulting solution was stirred for 5–15 minutes, while re-cooling to −78° C. Then, trisyl azide (1.1–1.5 eq., CAS No. 36982-84-0, prepared as described by references in the Evans reference above, which are incorporated herein by reference) in THF (~0.5 M), either precooled to −78° C. or at room temperature, was added via cannula over a period of 0.5–5 minutes. Again, a slight exotherm was generally noted. The resulting solution was stirred for from 5–10 minutes, while re-cooling to −78° C. Then, AcOH (4.5–4.6 eq., glacial) was added, the cooling bath removed and the mixture allowed to warm to room temperature with stirring for 12–16 hours. The mixture was diluted with EtOAc, in a 2–5 volume multiple of the initial THF volume, and washed with dilute aq. $NaHCO_3$ (1–2x), 0.1–1.0 M aq. HCl (0–2x), and brine (1x). The organic phase was then dried over $MgSO_4$, filtered, and concentrated to provide the crude product.

General Procedure 4-L

Azide Reduction to an Amine

A mixture of the azide in absolute EtOH (0.03–0.07 M) and 10% Pd/C (~⅓ by weight of the azide) was shaken in a Parr apparatus under $H_2$ (35–45 psi) at room temperature for 3–6 hours. The catalyst was removed by filtration through a plug of Celite, rinsing with absolute EtOH, and the filtrate was concentrated to provide the crude amine product.

General Procedure 4-M

Amide Alkylation Using Cesium Carbonate

This procedure is a modification of the procedure described in Claremon, D. A.; et al, PCT Application: WO 96/406555, incorporated herein by reference. To a mixture of 2,4-dioxo-2,3,4,5-tetrahydro-1H-1,5-benzodiazepine (CAS No. 49799-48-6) in DMF (1.0 eq., 0.7 M) under $N_2$ at room temperature was added $Cs_2CO_3$ (2.2 eq.) and the appropriate alkyl halide (2.2 eq.). The mixture was stirred at room temperature for 5.5–16 hours. The mixture was partitioned between EtOAc and sat. $NaHCO_3$. The aqueous layer was extracted with EtOAc (1–2x) and the combined EtOAc extracts were dried over $Na_2SO_4$, filtered, and concentrated to provide the crude product.

General Procedure 4-N

BOC Removal Procedure

A stream of anhydrous HCl gas was passed through a stirred solution of the N-t-Boc protected amino acid in 1,4-dioxane (0.03–0.09 M), chilled in a ice bath to ~10° C. under $N_2$, for 10–15 minutes. The solution was capped, the cooling bath removed, and the solution was allowed to warm to room temperature with stirring for 2–8 hours, monitoring by TLC for the consumption of starting material. The solution was concentrated (and in some instances dissolved in $CH_2Cl_2$ then re-concentrated and placed in vacuum oven at 60–70° C. to remove most of the residual dioxane) and used without further purification.

EXAMPLE 4-A

Synthesis of 3-Amino-1,3-dihydro-5-(1-piperidinyl)-2H-1,4-benzodiazepin-2-one

Step A

Preparation of 1,2-Dihydro-3H-1-methyl-5-(1-piperidinyl)-1,4-benzodiazepin-2-one A solution of phosphorous pentachloride (1.2 eq) in methylene chloride was added dropwise to a solution of 1-methyl-1,2,3,4-tetrahydro-3H-1,4-benzodiazepin-2,5-dione (Showell, G. A. et al. *J. Med. Chem.* 1994, 37, 719, incorporated herein by reference) in methylene chloride. The resultant yellowish-orange solution was stirred at ambient temperature for 2.5 hours; the solvent was removed in vacuo. The orange residue was redissolved in methylene chloride, cooled to 0° C., and treated with a solution of piperidine (2 eq) and triethylamine (2 eq) in methylene chloride. The cooling bath was removed and the reaction stirred for 18 hours. The reaction mixture was washed with saturated aqueous $NaHCO_3$ (back-extracted with methylene chloride) and brine. The organic phase was dried over $Na_2SO_4$, filtered, and concentrated. The residue was purified via HPLC eluting with a gradient of 4 to 10% methanol/methylene chloride affording the title intermediate as a yellow solid having a melting point of 103–105° C.

$C_{15}H_{19}N_3O$ (MW 257.37); mass spectroscopy 257.

Anal. Calcd for $C_{15}H_{19}N_3O$: C, 70.01; H, 7.44; N, 16.33. Found: C, 69.94; H, 7.58; N, 16.23.

Step B

Preparation of 1,2-Dihydro-3H-1-methyl-3-oximido-5-(1-piperidinyl)-1,4-benzodiazepin-2-one Potassium tert-butoxide (2.5 eq) was added in two portions to a −20° C. solution of 1,2-dihydro-3H-1-methyl-5-(1-piperidinyl)-1,4-benzodiazepin-2-one (1 eq.) in toluene. After stirring at −20° C. for 20 minutes, isoamyl nitrite (1.2 eq.; Aldrich) was added to the red reaction mixture. The reaction was stirred at −20° C. for 5 hours at which time the reaction was done by TLC. The cooling bath was removed and the reaction quenched with 0.5 M citric acid. After stirring for 10 minutes, diethyl ether was added. The suspension was stirred at ambient temperature overnight then filtered washing with ether. The resultant cream colored solid had a melting point of 197–200° C.

$^1$H NMR data of the E/Z isomers was as follows:

$^1$H NMR (300 MHz, $CDCl_3$): δ=7.64 (1H, bs), 7.48 (2H, d, J=7.4 Hz), 7.35–7.20 (6H, m), 6.75 (1H, bs), 3.8–3.2 (8H, m), 3.46 (3H, s), 3.42 (3H s), 1.90–1.40 (12H, m).

$C_{15}H_{18}N_4O_2$ (MW=286.37); mass spectroscopy 286.

Step C

Preparation of 1,2-dihydro-3H-1-methyl-3-[O-(ethylaminocarbonyl)-oximido]-5-(1-piperidinyl)-1,4-benzodiazepin-2-one A mixture of 1,2-dihydro-3H-1-methyl-3-oximido-5-(1-piperidinyl)-1,4-benzodiazepin-2-one (1 eq.) in THF was treated with ethyl isocyanate (1.7 eq) and triethylamine (0.6 eq). The mixture was heated to 64° C. for 4 hours. The mixture was concentrated and the residue purified by HPLC eluting with 5% methanol/methylene chloride.

$^1$H NMR data of the E/Z isomers was as follows:

$^1$H NMR (300 MHz, CDCl$_3$): δ=7.50 (2H, dd, J=8.4, 1.5 Hz), 7.35–7.22 (6H, m), 6.42 (1H, bt), 6.20 (1H, bt), 3.7–3.4 (8H, m), 3.46 (3H, s), 3.44 (3H, s), 3.25 (4H, m), 1.9–1.4 (12H, m), 1.12 (3H, t, J=6.3 Hz), 1.10 (3H, t, J=6.3 Hz).

$C_{18}H_{23}N_5O_3$ (MW=357.46); mass spectroscopy 357.

Step D

Preparation of 3-Amino-1,3-dihydro-2H-1-methyl-5-(1-piperidinyl)-1,4-benzodiazepin-2-one The 1,2-dihydro-3H-1-methyl-3-[O-(ethylaminocarbonyl)oximido]-5-(1-piperidinyl)-1,4-benzodiazepin-2-one (1 eq.) was hydrogenated in methanol over 5% palladium on carbon (0.15 eq.) at 43 psi for 3.25 hours. The reaction was filtered through celite and concentrated in vacuo. The residue was taken up in methylene chloride and filtered a second time through celite. The filtrate was concentrated and the resultant foam was used immediately.

EXAMPLE 4-B

Synthesis of 3-(L-Alaninyl)-amino-2,3-dihydro-1-methyl-5-phenyl-1H-1,4-benzodiazepin-2-one Step A Preparation of (S)-3-amino-1,3-dihydro-1-methyl-5-phenyl-2H-1,4-benzodiazepin-2-one, (1S)-7,7-dimethyl-2-oxobicyclo[2,2,1]heptane-1-methanesulfonate The title intermediate was prepared according to Reider, P. J. et al. *J. Org. Chem.* 1987, 52, 955, incorporated herein by reference, using 3-amino-1,3-dihydro-1-methyl-5-phenyl-2H-1,4-benzodiazepin-2-one (Bock M. G. et al.; *J. Org. Chem.* 1987, 52, 3232, incorporated herein by reference) as the starting material.

Step B

Preparation of 3-[N'-(tert-Butylcarbamate)-L-alaninyl]-amino-2,3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2.2.1]heptane-1-methanesulfonate was free based by partitioning between methylene chloride and 1M potassium carbonate. The free amine was then coupled with N-Boc-alanine following General Procedure D.

$C_{24}H_{28}N_4O_4$ (MW=436.56); mass spectroscopy 436.

Anal. Calc. for $C_{24}H_{28}N_4O_4$: C, 66.03; H, 6.47; N, 12.84. Found: C, 65.79; H, 6.68; N, 12.80.

Step C

Preparation of 3-(L-Alaninyl)-amino-2,3-dihydro-1-methyl-5-phenyl-1H-1,4-benzodiazepin-2-one Following General Procedure 4-C using 3-[N'-(tert-butylcarbamate)-L-alaninyl]-amino-2,3-dihydro-1-methyl-5-phenyl-1H-1,4-benzodiazepin-2-one, the title compound was prepared as a white foam.

Anal. Calc. for $C_{19}H_{19}N_4O_2$: C, 69.21; H, 6.64; N, 15.37. Found: C, 70.11; H, 6.85; N, 15.01.

EXAMPLE 4-C

Synthesis of 3-(L-Alaninyl)-amino-7-chloro-2,3-dihydro-1-methyl-5-phenyl-1H-1,4-benzodiazepin-2-one Step A Preparation of 3-(Benzyloxycarbonyl)-amino-7-chloro-2,3-dihydro-1-methyl-5-phenyl-1H-1,4-benzodiazepin-2-one A solution of 3-(benzyloxycarbonyl)-amino-7-chloro-2,3-dihydro-5-phenyl-1H-1,4-Benzodiazepin-2-one (1 eq; Neosystem) in DMF was cooled to 0° C. and treated with potassium tert-butoxide (1 eq; 1.0M solution in THF). The resultant yellow solution was stirred at 0° C. for 30 minutes then quenched with methyl iodide (1.3 eq.). After stirring an additional 25 minutes the reaction was diluted with methylene chloride and washed with water and brine. The organic phase was dried over Na$_2$SO$_4$, filtered, and concentrated. The residue was purified via HPLC chromatography eluting with a gradient of 20–30% ethyl acetate/hexanes.

$C_{24}H_{20}ClN_3O_3$ (MW=433.92); mass spectroscopy 433.

Anal. calcd for $C_{24}H_{20}ClN_3O_3$: C, 66.44; H, 4.65; N, 9.68. Found: C, 66.16; H, 4.50; N, 9.46.

Step B

Preparation of 3-Amino-7-chloro-1,3-dihydro-1-methyl-5-phenyl-2H-1,4-benzodiazepin-2-one Following General Procedure 4-B using 3-(benzyloxycarbonyl)-amino-7-chloro-2,3-dihydro-1-methyl-5-phenyl-1H-1,4-benzodiazepin-2-one, the title intermediate was prepared as a white foam which was used immediately in Step C.

Step C

Preparation of 3-[N'-tert-Butylcarbamate)-L-alaninyl]-amino-7-chloro-1,3-dihydro-1-methyl-5-phenyl-2H-1,4-benzodiazepin-2-one Following General Procedure D using N-Boc-L-alanine and 3-amino-7-chloro-1,3-dihydro-1-methyl-5-phenyl-2H-1,4-benzodiazepin-2-one, the title intermediate was prepared as a white foam.

$C_{24}H_{28}ClN_4O_4$ (MW=471.18); mass spectroscopy 471

Anal. calcd for $C_{24}H_{28}ClN_4O_4$: C, 61.21; H, 5.78; N, 11.90. Found: C, 61.24; H, 5.59; N, 11.67.

Step D

Preparation of 3-(L-Alaninyl)amino-7-chloro-1,3-dihydro-1-methyl-5-phenyl-2H-1,4-benzodiazepin-2-one Following General Procedure 4-C using 3-[N'-tert-butylcarbamate)-L-alaninyl]-amino-7-chloro-1,3-dihydro-1-methyl-5-phenyl-2H-1,4-benzodiazepin-2-one, the title intermediate was prepared as a white foam. The crude material was used immediately.

EXAMPLE 4-D

Synthesis of 3-(L-Alaninyl)amino-7-bromo-2,3-dihydro-1-methyl-5-(2-fluorophenyl)-1H-1,4-benzodiazepin-2-one Step A Preparation of 3-(Benzyloxycarbonyl)-amino-7-bromo-2,3-dihydro-1-methyl-5-(2-fluorophenyl)-1H-1,4-benzodiazepin-2-one Following General Procedure 4-A using 3-(benzyloxycarbonyl)-amino-7-bromo-2,3-dihydro-5-(2- fluorophenyl)-1H-1,4-benzodiazepin-2-one (Neosystem), the title intermediate was prepared as a white foam.

$C_{24}H_{19}BrFN_3O_3$ (MW=496.36); mass spectroscopy 497.

Anal. calcd for $C_{24}H_{19}BrFN_3O_3$: C, 58.08; H, 3.86; N, 8.47. Found: C, 57.90; H, 4.15; N, 8.20.

Step B

Preparation of 3-Amino-7-bromo-1,3-dihydro-1-methyl-5-(2-fluorophenyl)-2H-1,4-benzodiazepin-2-one Following General Procedure 4-B using 3-(benzyloxycarbonyl)-amino-7-bromo-2,3-dihydro-1-methyl-5-(2-fluorophenyl)-1H-1,4-benzodiazepin-2-one, the title intermediate was prepared as a white foam which was used immediately in Step C.

Step C

Preparation of 3-[N'-(tert-Butylcarbamate)-L-alaninyl]-amino-7-bromo-1,3-dihydro-1-methyl-5-(2-fluorophenyl)-2H-1,4-benzodiazepin-2-one Following General Procedure D using N-Boc-L-alanine (Novo) and 3-amino-7-bromo-1,3-dihydro-1-methyl-5-(2-fluorophenyl)-2H-1,4-benzodiazepin-2-one, the title intermediate was prepared as a white foam.

$C_{24}H_{26}BrFN_4O_4$ (MW=533.12); mass spectroscopy 533.2.

Anal. calcd for $C_{24}H_{26}BrFN_4O_4$: C, 54.04; H, 4.91; N, 10.50. Found: C, 53.75; H, 4.92; N, 10.41.

Step D

Preparation of 3-(L-Alaninyl)-amino-7-bromo-1,3-dihydro-1-methyl-5-(2-fluorophenyl)-2H-1,4-benzodiazepin-2-one Following General Procedure 4-C using 3-[N'-(tert-butylcarbamate)-L-alaninyl]-amino-7-bromo-1,3-dihydro-1-methyl-5-(2-fluorophenyl)-2H-1,4-benzodiazepin-2-one, the title intermediate was prepared as a white foam. The crude material was used immediately.

EXAMPLE 4-E

Synthesis of 3-(N'-Methyl-L-alaninyl)-amino-2,3-dihydro-1-methyl-5-phenyl-1H-1,4-benzodiazepin-2-one

Step A

Preparation of 3-[N'-(tert-Butylcarbamate)-N'-methyl-L-alaninyl]-amino-2,3-dihydro-1-methyl-5-phenyl-1H-1,4-benzodiazepin-2-one Following General Procedure D and using (S)-3-amino-1,3-dihydro-1-methyl-5-phenyl-2H-1,4-benzodiazepin-2-one (Example 4-B) and N-tert-Boc-N-methyl-alanine (Sigma), the title intermediate was obtained as a white solid.

$C_{25}H_{30}N_4O_4$ (MW=450.2); mass spectroscopy (M+1) 451.2.

Anal. calcd for $C_{25}H_{30}N_4O_4$: C, 66.65; H, 6.71; N, 12.44. Found: C, 66.66; H, 6.89; N, 12.21.

Step B

Preparation of 3-(N'-Methyl-L-alaninyl)-amino-2,3-dihydro-1-methyl-5-phenyl-1H-1,4-benzodiazepin-2-one Following General Procedure 4-C and using 3-[N'-(tert-butylcarbamate)-N'-methyl-L-alaninyl]-amino-2,3-dihydro-1-methyl-5-phenyl-1H-1,4-benzodiazepin-2-one, the title intermediate was prepared as a white foam.

$C_{20}H_{22}N_4O_2$ (MW=350.46); mass spectroscopy (M+1) 351.4.

Anal. calcd for $C_{20}H_{22}N_4O_2$: C, 68.55; H, 6.33; N, 15.99. Found, C, 68.36; H, 6.20; N, 15.79.

EXAMPLE 4-F

Synthesis of 3-(L-Alaninyl)amino-7-chloro-2,3-dihydro-1-methyl-5-(2-chlorophenyl)-1H-1,4-benzodiazepin-2-one

Step A

Preparation of 3-(Benzyloxycarbonyl)-amino-7-chloro-2,3-dihydro-1-methyl-5-(2-chlorophenyl)-1H-1,4-benzodiazepin-2-one Following General Procedure 4-A using 3-(benzyloxycarbonyl)-amino-7-chloro-2,3-dihydro-5-(2-chlorophenyl)-1H-1,4-benzodiazepin-2-one (Neosystem), the title intermediate was prepared as a white solid having a melting point of 232–233° C.

$C_{24}H_{19}Cl_2N_3O_3$ (MW=468.36); mass spectroscopy 468.

$^1$H NMR (300 MHz, CDCl$_3$): δ=7.67 (1H, m), 7.52 (1H, dd, J=2.4, 8.7 Hz), 7.42–7.26 (9H, m), 7.07 (1H, d, J=2.4 Hz), 6.70 (1H, d, J=8.3 Hz), 5.35 (1H, d, J=8.4 Hz), 5.14 (2H, ABq, J=19.6 Hz), 3.47 (3H, s).

$^{13}$C NMR (75 MHz, CDCl$_3$): δ=166.66, 165.65, 155.72, 140.52, 136.99, 136.0, 132.87, 131.99, 131.47, 131.40, 131.38, 131.16, 130.54, 130.06, 128.45, 128.08, 128.03, 127.72, 127.22, 123.28, 122.01, 68.95, 67.02, 35.32.

Step B

Preparation of 3-Amino-7-chloro-1,3-dihydro-1-methyl-5-(2-chlorophenyl)-2H-1,4-benzodiazepin-2-one Following General Procedure 4-B using 3-(benzyloxycarbonyl)-amino-7-chloro-2,3-dihydro-1-methyl-5-(2-chlorophenyl)-1H-1,4-benzodiazepin-2-one, the title intermediate was prepared as a white foam which was used immediately in Step C.

Step C

Preparation of 3-[N'-(tert-Butylcarbamate)-L-alaninyl]-amino-7-chloro-1,3-dihydro-1-methyl-5-(2-chlorophenyl)-2H-1,4-benzodiazepin-2-one Following General Procedure D using N-Boc-L-alanine and 3-amino-7-chloro-1,3-dihydro-1-methyl-5-(2-chlorophenyl)-2H-1,4-benzodiazepin-2-one, the title intermediate was prepared as a white foam.

$C_{24}H_{26}Cl_2N_4O_4$ (MW=505.44); mass spectroscopy 505.2.

Step D

Preparation of 3-(L-Alaninyl)-amino-7-chloro-1,3-dihydro-1-methyl-5-(2-chlorophenyl)-2H-1,4-benzodiazepin-2-one Following General Procedure 4-C using 3-[N'-(tert-butylcarbamate)-L-alaninyl]-amino-7-chloro-1,3-dihydro-1-methyl-5-(2-chlorophenyl)-2H-1,4-benzodiazepin-2-one, the title intermediate was prepared as a white foam. The crude material was used immediately.

EXAMPLE 4-G

Synthesis of 3-(L-Alaninyl)amino-5-cyclohexyl-2,3-dihydro-1-methyl-1H-1,4-Benzodiazepin-2-one

Step A

Preparation of 3-(Benzyloxycarbonyl)-amino-5-cylclohexyl-2,3-dihydro-1-methyl-1H-1,4-benzodiazepin-2-one Following General Procedure 4-A using 3-(benzyloxycarbonyl)-amino-5-cyclohexyl-2,3-dihydro-1H-1,4-benzodiazepin-2-one (Neosystem), the title intermediate was prepared as a white solid having a melting point of 205–206° C.

$C_{24}H_{27}N_3O_3$ (MW=405.54); mass spectroscopy 405.

$^1$H NMR (300 MHz, CDCl$_3$): δ=7.54 (1H, d, J=7.9 Hz), 7.48 (1H, d, J=7.7 Hz), 7.36–7.26 (7H, m), 6.54 (1H, d, J=8.3 Hz), 5.15 (1H, d, J=8.0 Hz), 5.09 (2H, ABq, J=17.1 Hz), 3.39 (3H, s), 2.77 (1H, m), 2.01 (1H, bd, J=13.6 Hz), 1.85 (1H, bd, J=12.4 Hz), 1.68–1.49 (4H, m), 1.34–1.02 (4H, m).

Step B

Preparation of 3-Amino-5-cyclohexyl-1,3-dihydro-1-methyl-2H-1,4-benzodiazepin-2-one Following General Procedure 4-B using 3-(benzyloxycarbonyl)-amino-5-cyclohexyl-2,3-dihydro-1-methyl-1H-1,4-benzodiazepin-2-one, the title intermediate was prepared as a white foam which was used immediately in Step C.

$C_{16}H_{21}N_3O$ (MW+H=272.1763); mass spectroscopy 272.1766

Step C

Preparation of 3-[N'-(tert-Butylcarbamate)-L-alaninyl]-amino-5-cyclohexyl-1,3-dihydro-1-methyl-2H-1,4-benzodiazepin-2-one Following General Procedure D using N-Boc-L-alanine and 3-amino-5-cyclohexyl-1,3-dihydro-1-methyl-2H-1,4-benzodiazepin-2-one, the title intermediate was prepared as a white foam.

$C_{24}H_{34}N_4O_4$ (MW=442.62); mass spectroscopy (M+H) 443.2.

Step D

Preparation of 3-(L-Alaninyl)amino-5-cyclohexyl-1,3-dihydro-1-methyl-2H-1,4-benzodiazepin-2-one Following General Procedure 4-C using 3-[N'-(tert-butylcarbamate)-L-alaninyl]-amino-5-cyclohexyl-1,3-dihydro-1-methyl-2H-1,4-benzodiazepin-2-one, the title intermediate was prepared as a white foam. The crude material was used immediately.

$C_{19}H_{26}N_4O_2$ (M+H=343.2136); mass spectroscopy found 343.2139.

EXAMPLE 4-H

Synthesis of 3-(L-Alaninyl)amino-2,3-dihydro-1-methyl-7-nitro-5-phenyl-1H-1,4-benzodiazepin-2-one

Step A

Preparation of 2-[N-(α-Isopropylthio)-N'-(benzyloxycarbonyl)glycinyl]-amino-5-nitrobenzophenone A solution of α-(isopropylthio)-N-(benzyloxycarbonyl)glycine (1 eq; prepared according to Zoller, V. and D. Ben-Ishai *Tetrahedron* 1975, 31, 863, incorporated herein by reference) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-5-nitrobenzophenone (0.9 eq.; Acros) and 4-methylmorpholine (2.0 eq.) in dry THF was added via cannulation to the acid chloride. The cooling bath was removed and the reaction stirred at ambient temperature for 5 hours. The reaction was diluted with methylene chloride and washed with 0.5 M citric acid, saturated aqueous NaHCO$_3$, and brine. The organic phase was dried over Na$_2$SO$_4$, filtered, and concentrated. The residue was purified via preparative LC2000 eluting with a gradient of 15–20% ethyl acetate/hexanes giving an off-white foam.

$C_{26}H_{25}N_3O_6S$ (MW=507.61); mass spectroscopy found 507.9.

Anal. calcd for $C_{26}H_{25}N_3O_6S$: C, 61.53; H, 4.96; N, 8.28. Found: C, 61.70; H, 4.99; N, 8.22.

Step B

Preparation of 2-[N-(α-Amino)-N'-(benzyloxycarbonyl)-glycinyl]-amino-5-nitrobenzophenone Ammonia gas was bubbled into a solution 2-[N-(α-isopropylthio)-N'-(benzyloxycarbonyl)-glycinyl]-amino-5-nitrobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step C without further purification.

Step C

Preparation of 3-(Benzyloxycarbonyl)-amino-2,3-dihydro-7-nitro-5-phenyl-1H-1,4-benzodiazepin-2-one 2-[N-(α-Amino)-N'-(benzyloxycarbonyl)-glycinyl]-amino-5-nitrobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over Na$_2$SO$_4$, filtered, and concentrated. The residue was purified via flash chromatography eluting with a gradient of 2–3% isopropyl alcohol/methylene chloride.

$C_{23}H_{18}N_4O_5$ (MW=430.45); mass spectroscopy found (M+H) 431.2.

Anal. calcd for $C_{23}H_{18}N_4O_5$: C, 64.18; H, 4.22; N, 13.02. Found: C, 64.39; H, 4.30; N, 13.07.

Step D

Preparation of 3-(Benzyloxycarbonyl)-amino-2,3-dihydro-1-methyl-7-nitro-5-phenyl-1H-1,4-benzodiazepin-2-one Following General Procedure 4-A and using 3-(benzyloxycarbonyl)-amino-2,3-dihydro-7-nitro-5- phenyl-1H-1,4-benzodiazepin-2-one, the title intermediate was prepared as a yellow foam.

$C_{24}H_{20}N_4O_5$ (MW=444.48); mass spectroscopy found (M+H) 445.2.

Anal. calcd for $C_{24}H_{20}N_4O_5$: C, 64.86; H, 4.54; N, 12.60. Found: C, 65.07; H, 4.55; N, 12.46.

Step E

Preparation of 3-Amino-1,3-dihydro-1-methyl-7-nitro-5-phenyl-2H-1,4-benzodiazepin-2-one Following General Procedure 4-B and using 3-(benzyloxycarbonyl)-amino-2,3-dihydro-1-methyl-7-nitro-5-phenyl-1H-1,4-benzodiazepin-2-one, the title intermediate was prepared as a yellow foam which was used immediately in Step F.

Step F

Preparation of 3-[N'-(tert-Butylcarbamate)-L-alaninyl]-amino-2,3-dihydro-1-methyl-7-nitro-5-phenyl-1H-1,4-benzodiazepin-2-one Following General Procedure D using N-Boc-L-alanine and 3-amino-1,3-dihydro-1-methyl-7-nitro-5-phenyl-2H-1,4-benzodiazepin-2-one, the title intermediate was prepared as a yellow solid.

$C_{24}H_{27}N_5O_6$ (MW=481.56); mass spectroscopy found (M+H) 482.3.

Anal. calcd for $C_{24}H_{27}N_5O_6$: C, 59.88; H, 5.61; N, 14.55. Found: C, 60.22; H, 5.75; N, 13.91.

Step G

Preparation of 3-(L-Alaninyl)-amino-2,3-dihydro-1-methyl-7-nitro-5-phenyl-1 H-1,4-benzodiazepin-2-one Following General Procedure 4-C using 3-[N'-(tert-butylcarbamate)-L-alaninyl]-amino-2,3-dihydro-1-methyl-7-nitro-5-phenyl-1H-1,4-benzodiazepin-2-one, the title intermediate was prepared as a yellow foam. The crude material was used immediately.

EXAMPLE 4-I

Synthesis of 3-(L-Alaninyl)amino-2,3-dihydro-1-methyl-5-(2-fluorophenyl)-1H-1,4-benzodiazepin-2-one

Step A

Preparation of 3-Amino-1,3-dihydro-1-methyl-5-(2-fluorophenyl)-2H-1,4-benzodiazepin-2-one A flask was charged with 3-(benzyloxycarbonyl)-amino-7-bromo-2,3-dihydro-1-methyl-5-(2-fluorophenyl)-1H-1,4-benzodiazepin-2-one (1 eq.; Example 4-D, Step A) and 10% palladium on carbon. Methanol was added, and the flask was placed under a balloon of $H_2$. The reaction was stirred for 21 hours. The mixture was filtered through celite washing with methanol. The filtrate was concentrated to a white solid.

$C_{16}H_{14}FN_3O$ (MW=283.33); mass spectroscopy found (M+H) 284.1.

Step B

Preparation of 3-[N'-(tert-Butylcarbamate)-L-alaninyl]-amino-1,3-dihydro-1-methyl-5-(2-fluorophenyl)-2H-1,4-benzodiazepin-2-one Following General Procedure D using N-Boc-L-alanine and 3-amino-1,3-dihydro-1-methyl-5-(2-fluorophenyl)-2H-1,4-benzodiazepin-2-one, the title intermediate was prepared as a white solid.

$C_{24}H_{27}FN_4O_4$ (MW=454.50); mass spectroscopy found (M+H) 455.4.

Anal. calcd for $C_{24}H_{27}FN_4O_4$: C, 63.44; H, 5.95; N, 12.33. Found: C, 63.64; H, 6.08; N, 12.16.

Step C

Preparation of 3-(L-Alaninyl)-amino-7-bromo-1,3-dihydro-1-methyl-5-(2-fluorophenyl)-2H-1,4-benzodiazepin-2-one Following General Procedure 4-C using 3-[N'-(tert-butylcarbamate)-L-alaninyl]-amino-1,3-dihydro-1-methyl-5-(2-fluorophenyl)-2H-1,4-benzodiazepin-2-one, the title intermediate was prepared as a white foam. The crude material was used immediately.

EXAMPLE 4-J

Synthesis of 3-(L-Alaninyl)-amino-2,3-dihydro-1-methyl-5-(3-fluorophenyl)-1H-1,4-benzodiazepin-2-one

Step A

Preparation of 2-Amino-3'-fluorobenzophenone

A solution of 3-bromofluorobenzene (1 eq.) in THF was cooled to −78° C. under nitrogen and treated with tert-butyllithium (2.05 eq., 1.6 M solution in pentane) at a rate of 40 mL/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over $Na_2SO_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3.

$^1H$ NMR (300 MHz, $CDCl_3$) d 7.44–7.19 (6H, m), 6.74 (1H, d, J=8.0 Hz), 6.61 (1H, dd, J=0.94, 7.9 Hz), 6.10 (2H, bs).

Step B

Preparation of 2-[N-(α-Isopropylthio)-N'-(benzyloxycarbonyl)-glycinyl]-amino-3'-fluorobenzophenone A solution of α-(isopropylthio)-N-(benzyloxycarbonyl) glycine (1 eq; prepared according to Zoller, V. and D. Ben-Ishai *Tetrahedron* 1975, 31, 863, incorporated herein by reference) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-3'-fluorobenzophenone (0.9 eq.) and 4-methylmorpholine (2.0 eq.) in dry THF was added via cannulation to the acid chloride. The cooling bath was removed and the reaction stirred at ambient temperature for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was purified via preparative LC2000 eluting with a gradient of 15→20% ethyl acetate/hexanes giving an off-white foam.

$C_{26}H_{25}N_2O_4S$ (MW=480.60); mass spectroscopy found (M+$NH_4^+$) 498.3.

$^1$H NMR (300 MHz, CDCl$_3$) d 11.39 (1H, s), 8.59 (1H, d, J=6.0 Hz), 7.63–7.55 (2H, m), 7.48–7.27 (9H, m), 7.14 (1H, dt, J=1.2, 8.4 Hz), 5.94 (1H, d, J=7.2 Hz), 5.58 (1H, d, J=8.7 Hz), 5.17 (2H, ABq, J=14.7 Hz), 3.25 (1H, sep, J=6.6 Hz), 1.44 (3H, d, J=6.0 Hz), 1.28 (3H, d, J=6.6 Hz).

Step C

Preparation of 2-[N-(α-Amino)-N'-(benzyloxycarbonyl)-glycinyl]amino-3'-fluorobenzophenone Ammonia gas was bubbled into a solution of 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D

Preparation of 3-(Benzyloxycarbonyl)-amino-2,3-dihydro-5-(3-fluorophenyl)-1H-1,4-benzodiazepin-2-one 2-[N-(α-Amino)-N'-(benzyloxycarbonyl)-glycinyl]-amino-3'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 2→3% isopropyl alcohol/methylene chloride.

$C_{23}H_{18}FN_3O_3$ (MW=403.44); mass spectroscopy found (M+H) 404.4.

Anal. calcd for $C_{23}H_{18}FN_3O_3 \cdot 0.5H_2O$: C, 66.98; H, 4.64; N, 10.18. Found: C, 67.20; H, 4.64; N, 9.77.

Step E

Preparation of 3-(Benzyloxycarbonyl)-amino-2,3-dihydro-1-methyl-5-(3-fluorophenyl)-1H-1,4-benzodiazepin-2-one Following General Procedure 4-A and using 3-(benzyloxycarbonyl)-amino-2,3-dihydro-5-(3-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.3.

Anal. calcd for $C_{24}H_{20}FN_3O_3$: C, 69.06; H, 4.83; N, 10.07. Found: C, 69.33; H, 4.95; N, 9.82.

Step F

Preparation of 3-Amino-1,3-dihydro-1-methyl-5-(3-fluorophenyl)-2H-1,4-benzodiazepin-2-one Following General Procedure 4-B and using 3-(benzyloxycarbonyl)-amino-2,3-dihydro-1-methyl-5-(3-fluorophenyl)-1H-1,4-benzodiazepin-2-one, the title intermediate was prepared as a yellow foam which was used immediately in Step G.

Step G

Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.3.

Anal. calcd for $C_{24}H_{27}FN_4O_4$: C, 63.42; H, 5.99; N, 12.33. Found: C, 63.34; H, 6.01; N, 12.08.

Step H

Preparation of 3-(L-Alaninyl)-amino-2,3-dihydro-1-methyl-5-(3-fluorophenyl)-1H-1,4-benzodiazepin-2-one Following General Procedure 4-C using 3-[N'-(tert-butylcarbamate)-L-alaninyl]-amino-2,3-dihydro-1-methyl-5-(3-fluorophenyl)-1H-1,4-benzodiazepin-2-one, the title intermediate was prepared as a yellow foam. The crude material was used immediately.

EXAMPLE 4-K

Synthesis of 3-(L-Alaninyl)amino-2,3-dihydro-1-methyl-5-(4-fluorophenyl)-1H-1,4-benzodiazepin-2-one Step A Preparation of 2-Amino-4'-fluorobenzophenone A solution of 4-bromofluorobenzene (1 eq.) in THF was cooled to −78° C. under nitrogen and treated with tert-butyllithium (2.05 eq., 1.6 M solution in pentane) at a rate of 40 mL/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over $Na_2SO_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3.

Anal. calcd for $C_{13}H_{10}FNO$: C, 72.55; H, 4.68; N, 6.51. Found: C, 72.80; H, 4.51; N, 6.74.

Step B

Preparation of 2-[N-(α-Isopropylthio)-N'-(benzyloxycarbonyl-glycinyl]-amino-4'-fluorobenzophenone A solution of α-(isopropylthio)-N-(benzyloxycarbonyl) glycine (1 eq; prepared according to Zoller, V. and D. Ben-Ishai *Tetrahedron* 1975, 31, 863, incorporated herein by reference) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-4'-fluorobenzophenone (0.9 eq.) and 4-methylmorpholine (2.0 eq.) in dry THF was added via cannulation to the acid chloride. The cooling bath was removed and the reaction stirred at ambient temperature for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was purified via preparative LC2000 eluting with a gradient of 15→20% ethyl acetate/hexanes giving an off-white foam.

$C_{26}H_{25}N_2O_4S$ (MW=480.60); mass spectroscopy found $(M+NH_4^+)$ 498.2.

$^1$H NMR (300 MHz, CDCl$_3$) d 11.28 (1H, s), 8.56 (1H, d, J=8.4 Hz), 7.78–7.73 (2H, m), 7.61–7.53 (2H, m), 7.36–7.32 (5H, m), 7.20–7.14 (3H, m), 5.98 (1H, d, J=7.5 Hz), 5.57 (1H, d, J=7.8 Hz), 5.16 (2H, ABq, J=14.7 Hz), 3.25 (1H, sep, J=6.0 Hz), 1.43 (3H, d, J=6.3 Hz), 1.27 (3H, d, J=6.6 Hz).

Step C

Preparation of 2-[N-(α-Amino)-N'-(benzyloxycarbonyl)-glycinyl]-amino-4'-fluorobenzophenone Ammonia gas was bubbled into a solution of 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D

Preparation of 3-(Benzyloxycarbonyl)amino-2,3-dihydro-5-(4-fluorophenyl)-1H-1,4-benzodiazepin-2-one 2-[N-(α-Amino)-N'-(benzyloxycarbonyl)-glycinyl]-amino-44'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 2–3% isopropyl alcohol/methylene chloride.

$C_{23}H_{18}FN_3O_3$ (MW=403.44); mass spectroscopy found (M+H) 404.4.

Anal. calcd for $C_{23}H_{18}FN_3O_3 \cdot 1.25H_2O$: C, 64.85; H, 4.85. Found: C, 64.80; H, 4.55.

Step E

Preparation of 3-(Benzyloxycarbonyl)-amino-2,3-dihydro-1-methyl-5-(4-fluorophenyl)-1H-1,4-benzodiazepin-2-one Following General Procedure 4-A and using 3-(benzyloxycarbonyl)-amino-2,3-dihydro-5-(4-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.2.

Anal. calcd for $C_{24}H_{20}FN_3O_3$: C, 69.06; H, 4.83; N, 10.07. Found: C, 69.35; H, 4.93; N, 9.97.

Step F

Preparation of 3-Amino-1,3-dihydro-1-methyl-5-(4-fluorophenyl)-2H-1,4-benzodiazepin-2-one Following General Procedure 4-B and using 3-(benzyloxycarbonyl)-amino-2,3-dihydro-1-methyl-5-(4-fluorophenyl)-1H-1,4-benzodiazepin-2-one, the title intermediate was prepared as a yellow foam which was used immediately in Step G.

Step G

Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.4.

Anal. calcd for $C_{24}H_{27}FN_4O_4 \cdot 1.5H_2O$: C, 59.86; H, 6.28; N, 11.64. Found: C, 60.04; H, 5.62; N, 11.27.

Step H

Preparation of 3-(L-Alaninyl)-amino-2,3-dihydro-1-methyl-5-(4-fluorophenyl)-1H-1,4-benzodiazepin-2-one Following General Procedure 4-C using 3-[N'-(tert-butylcarbamate)-L-alaninyl]-amino-2,3-dihydro-1-methyl-5-(4-fluorophenyl)-1H-1,4-benzodiazepin-2-one, the title intermediate was prepared as a yellow foam. The crude material was used immediately.

EXAMPLE 4-L

Synthesis of 3-(N'-L-Alaninyl)amino-2,3-dihydro-1-isobutyl-5-phenyl-1H-1,4-benzodiazepin-2-one Step A 1,3-Dihydro-5-phenyl-2H-1,4-benzodiazepin-2-one (prepared according to the procedure of M. G. Bock et al., J. Org. Chem. 1987, 52, 3232–3239, incorporated herein by reference) was alkylated with isobutyl iodide using General Procedure 8-G to afford 1,3-dihydro-1-isobutyl-5-phenyl-2H-1,4-benzodiazepin-2-one.

Step B

Following General Procedures 4-D and 4-F and using the product from Step A, 3-amino-1,3-dihydro-1-isobutyl-5-phenyl-2H-1,4-benzodiazepin-2-one was prepared.

Step C

The product from Step B and N-Boc-L-alanine (Sigma) were coupled using General Procedure D, followed by removal of the Boc group using General Procedure 8-J, to afford 3-(N'-L-alaninyl)amino-1,3-dihydro-1-isobutyl-5-phenyl-2H-1,4-benzodiazepin-2-one.

By substituting isopropyl iodide, n-propyl iodide, cyclopropylmethyl iodide and ethyl iodide for isobutyl iodide in Step A above, the following additional intermediates were prepared:

3-(N'-L-alaninyl)amino-1,3-dihydro-1-isopropyl-5-phenyl-2H-1,4-benzodiazepin-2-one
3-(N'-L-alaninyl)amino-1,3-dihydro-1-propyl-5-phenyl-2H-1,4-benzodiazepin-2-one
3-(N'-L-alaninyl)amino-1,3-dihydro-1-cyclopropylmethyl-5-phenyl-2H-1,4-benzodiazepin-2-one
3-(N'-L-alaninyl)amino-1,3-dihydro-1-ethyl-5-phenyl-2H-1,4-benzodiazepin-2-one.

EXAMPLE 4-M

Synthesis of 3-(N'-L-Alaninyl)amino-1-methyl-5-phenyl-1,3,4,5-tetrahydro-2H-1,5-benzodiazepin-2-one

Step A 1,3,4,5-Tetrahydro-5-phenyl-2H-1,5-benzodiazepin-2-one (CAS No. 32900-17-7) was methylated using General Procedure 4-I to afford 1-methyl-5-phenyl-1,3,4,5-tetrahydro-2H-1,5-benzodiazepin-2-one.

Step B

Following General Procedures 4-E and 4-F and using the product from Step A, 3-amino-1-methyl-5-phenyl-1,3,4,5-tetrahydro-2H-1,5-benzodiazepin-2-one was prepared.

Step C

The product from Step B and N-Boc-L-alanine (Sigma) were coupled using General Procedure D, followed by removal of the Boc group using General Procedure 8-N, to afford 3-(N'-L-alaninyl)amino-1-methyl-5-phenyl-1,3,4,5-tetrahydro-2H-1,5-benzodiazepin-2-one.

EXAMPLE 4-N

Synthesis of 3-(N'-L-Alaninyl)amino-2,4-dioxo-1-methyl-5-phenyl-2,3,4,5-tetrahydro-1H-1,5-benzodiazepine 3-Amino-2,4-dioxo-1-methyl-5-phenyl-2,3,4,5-tetrahydro-1H-1,5-benzodiazepine (CAS No. 131604-75-6) was coupled with N-Boc-L-alanine (Sigma) using General Procedure D, followed by removal of the Boc group using General Procedure 4-N, to afford the title compound.

EXAMPLE 4-O

Synthesis of 3-((R)-Hydrazinopropionyl)amino-2,3-dihydro-1-methyl(5-phenyl)-1H-1,4-benzodiazepin-2-one

Part 1

Synthesis of (R)-N,N'-Di-BOC-2-Hydrazinopropionic Acid

Step A

To (S)-(−)-4-benzyl-2-oxazolidanone (Aldrich) in THF cooled to −50° C. was added n-butyl lithium 1.1 eq. (1.6 M in hexane) dropwise. The reaction mixture was allowed to warm to −20° C. and then was re-cooled to −78° C. and propionyl chloride (1.1 eq) was added in one portion. The reaction mixture was allowed to stir an additional 15 min. at −78° C. and then was allowed to warm to room temperature. The reaction was then quenched with a saturated solution of sodium bicarbonate and extracted with ethyl acetate. The organic extracts were washed with water, followed by brine and then dried over sodium sulfate, filtered and concentrated to give (S)-(−)-3-propionyl4-benzyl-2-oxazolidanone.

Step B

To a solution of (S)-(−)-3-propionyl-4-benzyl-2-oxazolidanone in THF at −78° C. was added KHMDS (1.05 eq.) (Aldrich) dropwise. The reaction mixture was allowed to stir at −78° C. for 30 min. and then a precooled solution of di-tert-butyl-azodicarboxylate (Aldrich) was added via a cannula. After 5 min. 2.6 eq. of acetic acid was added. The reaction mixture was then extracted with dichloromethane and the organic layer was washed with 1M potassium phosphate. The organic layer was then dried over sodium sulfate, filtered and concentrated to give (S)-(−)-3-[(R)-N,N'-di-BOC-2-hydrazinopropionyl]-4-benzyl-2-oxazolidanone.

Step C

To (S)-(−)-3-[(R)-N,N'-di-BOC-2-hydrazinopropionyl]-4-benzyl-2-oxazolidanone (0.49 moles) at 0° C. in 8 mL of THF and 3 mL of water was added LiOH (1.7 eq.) and $H_2O_2$ (3.0 eq.) and the reaction mixture was stirred at room temperature for 3 hours. The reaction mixture was then poured into a separatory funnel and diluted with water. The aqueous mixture was extracted with ethyl acetate and then acidified to pH 2.0 with 1N HCl and extracted with ethyl acetate. The organic layer was then dried over sodium sulfate, filtered and solvent removed to give (R)-N,N'-di-BOC-2-hydrazinopropionic acid which was used without further purification.

Part 2

3-Amino-2,3-dihydro-1-methyl-5-phenyl-1H-1,4-benzodiazepin-2-one was coupled to (R)-N,N'-di-BOC-2-hydrazinopropionic acid using General Procedure D. The Boc group was removed by dissolving the Boc-protected compound in a 1:1–2:1 mixture of $CH_2Cl_2$ and trifluoroacetic acid. The resulting solution was stirred until tlc indicated complete conversion, typically 2 hours. The solution was then stripped to dryness and the residue was taken up in ethyl acetate or $CH_2Cl_2$. The solution was washed with saturated aqueous $NaHCO_3$ and the aqueous phase was adjusted to a basic pH, then extracted with ethyl acetate or $CH_2Cl_2$. The organic phase was washed with saturated aqueous NaCl and dried over $MgSO_4$. The solution was stripped free of solvent on a rotary evaporator to afford the title compound.

EXAMPLE 4-P

Synthesis of 3-Amino-2,4-dioxo-1,5-bis-(1-methylethyl)-2,3,4,5-tetrahydro-1H-1,5-benzodiazepine

Step A

Synthesis of 2,4-Dioxo-2,3,4,5-tetrahydro-1H-1,5-benzodiazepine 2,4-Dioxo-2,3,4,5-tetrahydro-1H-1,5-benzodiazepine (CAS No. 49799-48-6) was prepared from 1,2- phenylenediamine (Aldrich) and malonic acid (Aldrich) using the procedure of Claremon, D. A. et al., PCT Application: WO 96/40655, incorporated herein by reference.

Step B

Synthesis of 2,4-Dioxo-1,5-bis-(1-methylethyl)-2,3, 4,5-tetrahydro-1H-1,5-benzodiazepine 2,4-Dioxo-1,5-bis-(1-methylethyl)-2,3,4,5-tetrahydro-1H-1,5-benzodiazepine (CAS No. 113021-84-4) was prepared following General Procedure 4-M using the product from Step A and 2-iodopropane (Aldrich). Purification was by flash chromatography eluting with EtOAc/hexanes (3:7 gradient to 1:1), then recrystalization from EtOAc/hexanes.

Step C

Synthesis of 3-Azido-2,4-dioxo-1,5-bis-(1-methylethyl)-2,3,4,5-tetrahydro-1H-1,5-benzodiazepine Following General Procedure 4-K using the product from Step B, 3-azido-2,4-dioxo-1,5-bis-(1-methylethyl)-2,3,4,5-tetrahydro-1H-1,5-benzodiazepine (CAS No. 186490-50-6) was prepared as a white solid. The product was purified by flash chromatography eluting with hexanes/EtOAc (4:1) to provide a separable 23:1 mixture of pseudo-axial/pseudo-equatorial azides. The pure pseudo-axial azide was used in the next step.

Step D

Synthesis of 3-Amino-2,4-dioxo-1,5-bis-(1-methylethyl)-2,3,4,5-tetrahydro-1H-1,5-benzodiazepine Following General Procedure 4-L using the product from Step C, 3-amino-2,4-dioxo-1,5-bis-(1-methylethyl)-2,3,4,5-tetrahydro-1H-1,5-benzodiazepine (CAS No. 186490-51-7) was prepared as a white solid. Purification was by flash chromatography eluting with $CH_2Cl_2$/MeOH (98:2 gradient to 95:5). The isolated pseudo-axial amine atropisomer was completely converted to the pseudo-equatorial amine atropisomer by heating in toluene to 100–105° C. for 15 minutes, and the pseudo-equatorial amine atropisomer was used in the next step. The isomers were distinguished by $^1$H-NMR in $CDCl_3$. Selected $^1$H-NMR ($CDCl_3$): Pseudo-axial amine 4.40 (s, 1H); Pseudo-equatorial amine 3.96 (s, 1H).

EXAMPLE 4-Q

Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Step A Synthesis of N-(t-Butoxycarbonyl)-R-2-thienylglycine N-(t-Butoxycarbonyl)-R-2-thienylglycine (CAS No. 74462-03-1) was prepared from L-α-(2-thienyl)glycine (Sigma) by the procedure described in Bodansky, M. et al; *The Practice of Peptide Synthesis*; Springer Verlag; 1994, p. 17, incorporated herein by reference.

Step B

Synthesis of 3-[N'-(t-Butoxycarbonyl)-R-2-thienylglycinyl]-amino-2,4-dioxo-1,5-bis-(1-methylethyl)-2,3,4,5-tetrahydro-1H-1,5-benzodiazepine Following General Procedure J above using the product from Example 4-P and the product from Step A above, 3-[N'-(t-butoxycarbonyl)-R-2-thienylglycinyl]-amino-2,4-dioxo-1,5-bis-(1-methylethyl)-2,3,4,5-tetrahydro-1H-1,5-benzodiazepine was prepared as a white foam. Purification was by flash chromatography eluting with $CH_2Cl_2$/EtOAc (9:1 gradient to 5:1).

Step C

Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Following General Procedure 4-N above using the product from Step B, the title compound was prepared as a white solid.

EXAMPLE 4-R

Synthesis of 3-(L-Alaninyl)-amino-2,4-dioxo-1,5-bis-methyl-2,3,4,5-tetrahydro-1H-1,5-benzodiazepine Hydrochloride Step A Synthesis of 2,4-Dioxo-1,5-bis-methyl-2,3,4,5-tetrahydro-1H-1,5-benzodiazepine 2,4-Dioxo-1,5-bis-methyl-2,3,4,5-tetrahydro-1H-1,5-benzodiazepine (CAS No. 23954-54-3) was prepared following General Procedure 4-M using the product from Example 4-P, Step A and iodomethane (Aldrich). The white solid product precipitated during partial concentration of the reaction after work-up, and was isolated by filtration.

Step B

Synthesis of 3-Azido-2,4-dioxo-1,5-bis-methyl-2,3, 4,5-tetrahydro-1H-1,5-benzodiazepine For this substrate, General Procedure 4-K was modified in the following manner. Initially the product from Step A was suspended (not a solution) in THF at −78° C., and following addition of the KN(TMS)$_2$ solution, this suspension was allowed to warm to −35° C. over a period of 12 minutes, during which the suspension became a solution, and was re-cooled to −78° C.; then treated as described in the General Procedure. 3-Azido-2,4-dioxo-1,5-bis-methyl-2,3,4,5-tetrahydro-1H-1,5-benzodiazepine was purified by flash chromatography eluting with $CHCl_3$/EtOAc (7:1), then trituration from hot $CHCl_3$ with hexanes and cooled to −23° C. The product was isolated as a white solid.

Step C

Synthesis of 3-Amino-2,4-dioxo-1,5-bis-methyl-2,3, 4,5-tetrahydro-1H-1,5-benzodiazepine Following General Procedure 4-L using the product from Step B, 3-amino-2,4-dioxo-1,5-bis-methyl-2,3,4,5-tetrahydro-1H-1,5-benzodiazepine was prepared as a white solid. The crude product was used without further purification.

Step D

Synthesis of 3-[N'-(t-Butoxycarbonyl)-L-alaninyl]-amino-2,4-dioxo-1,5-bis-methyl-2,3,4,5-tetrahydro-1H-1,5-benzodiazepine Following General Procedure I above using N-Boc-L-alanine (Novabiochem) and the product from Step C, 3-[N'-

(t-butoxycarbonyl)-L-alaninyl]-amino-2,4-dioxo-1,5-bis-methyl-2,3,4,5-tetrahydro-1H-1,5-benzodiazepine was prepared as a white foam. Purification was by flash chromatography eluting with $CH_2Cl_2$/EtOAc (2:1 gradient to 1:1).

Step E

Synthesis of 3-(L-alaninyl)-amino-2,4-dioxo-1,5-bis-methyl-2,3,4,5-tetrahydro-1H-1,5-benzodiazepine Hydrochloride Following General Procedure 4-N above using the product from Step D, the title compound was prepared as an off-white amorphous solid.

EXAMPLE 4-S

Synthesis of 3-(L-Alaninyl)amino-2,4-dioxo-1,5-bis-(2-methylpropyl)-2,3,4,5-tetrahydro-1H-1,5-benzodiazepine Hydrochloride

Step A

Synthesis of 2,4-Dioxo-1,5-bis-(2-methylpropyl)-2,3,4,5-tetrahydro-1H-1,5-benzodiazepine 2,4-Dioxo-1,5-bis-(2-methylpropyl)-2,3,4,5-tetrahydro-1H-1,5-benzodiazepine was prepared following General Procedure 4-M using the product from Example 4-P, Step A and 1-iodo-2-methylpropane (Aldrich). Purification was by flash chromatography eluting with EtOAc/hexanes (3:7 gradient to 1:1), then recrystalization from EtOAc/hexanes.

Step B

Synthesis of 3-Azido-2,4-dioxo-1,5-bis-(2-methylpropyl)-2,3,4,5-tetrahydro-1H-1,5-benzodiazepine Following General Procedure 4-K (a precipitate formed during the addition of the $KN(TMS)_2$, but dissolved upon addition of the trisyl azide) using the product from Step A, 3-azido-2,4-dioxo-1,5-bis-(2-methylpropyl)-2,3,4,5-tetrahydro-1H-1,5-benzodiazepine was prepared as a white solid. The product was purified by flash chromatography eluting with hexanes/EtOAc (4:1) and a second flash chromatography eluting with $CH_2Cl_2$/hexanes/EtOAc (10:10:1 gradient to 8:6:1).

Step C

Synthesis of 3-Amino-2,4-dioxo-1,5-bis-(2-methylpropyl)-2,3,4,5-tetrahydro-1H-1,5-benzodiazepine Following General Procedure 4-L using the product from Step B, 3-amino-2,4-dioxo-1,5-bis-(2-methylpropyl)-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH).

Step D

Synthesis of 3-[N'-(t-Butoxycarbonyl)-L-alaninyl]-amino-2,4-dioxo-1,5-bis-(2-methylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2-methylpropyl)-2,3,4,5-tetrahydro-1H-1,5-benzodiazepine was prepared as a white foam. Purification was by flash chromatography eluting with $CH_2Cl_2$/EtOAc (3:1 gradient to 3:2).

Step E

Synthesis of 3-(L-Alaninyl)-amino-2,4-dioxo-1,5-bis-(2-methylpropyl)-2,3,4,5-tetrahydro-1H-1,5-benzodiazepine Hydrochloride Following General Procedure 4-N above using the product from Step D, the title compound was prepared as an amorphous white solid.

EXAMPLE 4-T

Synthesis of 3-(S-Phenylglycinyl)amino-2,4-dioxo-1,5-bis-(2-methylpropyl)-2,3,4,5-tetrahydro-1H-1,5-benzodiazepine Hydrochloride

Step A

Synthesis of 3-[N'-(t-Butoxycarbonyl)-S-phenylglycinyl]-amino-2,4-dioxo-1,5-bis-(2-methylpropyl)-2,3,4,5-tetrahydro-1H-1,5-benzodiazepine Following General Procedure J above using the product from Example 4-S, Step C and the Boc-L-phenylglycine (Novabiochem, CAS No. 2900-27-8), 3-[N'-(t-butoxycarbonyl)-S-phenylglycinyl]-amino-2,4-dioxo-1,5-bis-(2-methylpropyl)-2,3,4,5-tetrahydro-1H-1,5-benzodiazepine was prepared as a white foam. Purification was by flash chromatography eluting with $CH_2Cl_2$/EtOAc (9:1 gradient to 5:1).

Step B

Synthesis of 3-(S-Phenylglycinyl)-amino-2,4-dioxo-1,5-bis-(2-methylpropyl)-2,3,4,5-tetrahydro-1H-1,5-benzodiazepine Hydrochloride Following General Procedure 4-N above using the product from Step A, 3-(S-phenylglycinyl)-amino-2,4-dioxo-1,5-bis-(2-methylpropyl)-2,3,4,5-tetrahydro-1H-1,5-benzodiazepine hydrochloride was prepared as an off-white solid.

EXAMPLE 4-U

Synthesis of 3-(L-Alaninyl)amino-2,4-dioxo-1,5-bis-(cyclopropylmethyl)-2,3,4,5-tetrahydro-1H-1,5-benzodiazepine Hydrochloride

Step A

Synthesis of 2,4-Dioxo-1,5-bis-(cyclopropylmethyl)-2,3,4,5-tetrahydro-1H-1,5-benzodiazepine 2,4-Dioxo-1,5-bis-(cyclopropylmethyl)-2,3,4,5-tetrahydro-1H-1,5-benzodiazepine was prepared following General Procedure 4-M using the product from Example 4-P, Step A, and (bromomethyl)cyclopropane (Lancaster). Purification was by flash chromatography eluting with EtOAc/hexanes (3:7 gradient to straight EtOAc), then recrystalization from EtOAc/hexanes.

Step B

Synthesis of 3-Azido-2,4-dioxo-1,5-bis-(cyclopropylmethyl)-2,3,4,5-tetrahydro-1H-1,5-benzodiazepine For this substrate General Procedure 4-K was modified in the following manner. Initially the product from Step A was suspended (not a solution) in THF at −78° C., and following addition of the KN(TMS)$_2$ solution, this suspension was allowed to warm to −30° C., during which the suspension became a solution, and was re-cooled to −78° C. Upon re-cooling to −78° C. a precipitate began to form, therefore the reaction flask containing the mixture was partially raised above the cooling bath until the internal temperature rose to −50° C.; then the trisyl azide solution was added. The cooling bath was removed and the mixture allowed to warm to −20° C. whereupon the mixture had become a nearly homogenous solution, and the AcOH was added. Then the mixture was treated as described in the general procedure. 3-Azido-2,4-dioxo-1,5-bis-(cyclopropylmethyl)-2,3,4,5-tetrahydro-1H-1,5-benzodiazepine was purified by trituration with hot to room temperature EtOAc, followed by recrystalization from hot to −23° C. CHCl$_3$/EtOAc/EtOH (5:5:1) and isolated as a white solid.

Step C

Synthesis of 3-Amino-2,4-dioxo-1,5-bis-(cyclopropylmethyl)-2,3,4,5-tetrahydro-1H-1.5-benzodiazepine Following General Procedure 4-L using the product from Step B, 3-amino-2,4-dioxo-1,5-bis-(cyclopropylmethyl)-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH) followed by recrystalization from warm CH$_2$Cl$_2$/hexanes (1:1) to −23° C.

Step D

Synthesis of 3-[N'-(t-Butoxycarbonyl)-L-alaninyl]-amino-2,4-dioxo-1,5-bis-(cyclopropylmethyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(cyclopropylmethyl)-2,3,4,5-tetrahydro-1H-1,5-benzodiazepine was prepared as a white foam. Purification was by flash chromatography eluting with CH$_2$Cl$_2$/EtOAc (3:1 gradient to 2:1).

Step E

Synthesis of 3-(L-Alaninyl)-amino-2,4-dioxo-1,5-bis-(cyclopropylmethyl)-2,3,4,5-tetrahydro-1H-1,5-benzodiazepine Hydrochloride Following General Procedure 4-N above using the product from Step D, the title compound was prepared as an off-white solid.

EXAMPLE 4-V

Synthesis of 3-(L-Alaninyl)-amino-2,4-dioxo-1,5-bis-(2,2-dimethylpropyl)-2,3,4,5-tetrahydro-1H-1,5-benzodiazepine Hydrochloride

Step A

Synthesis of 2,4-Dioxo-1,5-bis-(2,2-dimethylpropyl)-2,3,4,5-tetrahydro-1H-1,5-benzodiazepine To a stirred suspension of the product from Example 4-P, Step A (1.0 eq., 17.08 g) in DMSO (500 mL) at room temperature was added neopentyl iodide (43.01 g, 2.24 eq., Aldrich) and Cs$_2$CO$_3$ (72.65 g, 2.3 eq., Aldrich). The resulting mixture was heated to 75° C. for 30 minutes, then additional Cs$_2$CO$_3$ (31.59 g, 1.0 eq.) was added and the mixture rapidly stirred at 75° C. for 6 hours. The mixture was allowed to cool and H$_2$O (500 mL) and EtOAc (1000 mL) were added. The phases were partitioned and the organic phase washed with H$_2$O (1×500 mL), 1 M aq. HCl (2×500 mL), and brine (1×500 mL). Then, the organic phase was dried over MgSO$_4$, filtered, concentrated, and purified by flash chromatography eluting with hexanes/EtOAc (3:2 gradient to 2:3) to provide 2,4-dioxo-1,5-bis-(2,2-dimethylpropyl)-2,3,4,5-tetrahydro-1H-1,5-benzodiazepine as a white solid.

Step B

Synthesis of 3-Azido-2,4-dioxo-1,5-bis-(2,2-dimethylpropyl)-2,3,4,5-tetrahydro-1H-1,5-benzodiazepine Following General Procedure 4-K using the product from Step A, 3-azido-2,4-dioxo-1,5-bis-(2,2-dimethylpropyl)-2,3,4,5-tetrahydro-1H-1,5-benzodiazepine was prepared as a white solid. The product was purified by flash chromatography eluting with hexanes/CH$_2$Cl$_2$/EtOAc (10:5:1 gradient to 5:5:1) to provide a separable 13:1 mixture of pseudo-axial/pseudo-equatorial azides. The pure pseudo-axial azide was used in the next step. Selected $^1$H-NMR (CDCl$_3$): Pseudo-axial azide 5.12 (s, 1H); Pseudo-equatorial azide 4.03 (s, 1H).

Step C

Synthesis of 3-Amino-2,4-dioxo-1,5-bis-(2,2-dimethylpropyl)-2,3,4,5-tetrahydro-1H-1,5-benzodiazepine Following General Procedure 4-L using the product from Step B, 3-amino-2,4-dioxo-1,5-bis-(2,2-dimethylpropyl)-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH). The isolated white solid product was identified as a ~4:1 mixture of pseudo-axial and pseudo-equatorial amines atropisomers by $^1$H-NMR. The mixture was heated in toluene to 100° C. for 20 minutes, then re-concentrated to provide the pure pseudo-equatorial amine atropisomer, as a white solid, and this was for the next step. Selected $^1$H-NMR (CDCl$_3$): Pseudo-axial amine 4.59 (s, 1H); Pseudo-equatorial amine 4.03 (s, 1H).

Step D

Synthesis of 3-[N'-(t-Butoxycarbonyl)-L-alaninyl]-amino-2,4-dioxo-1,5-bis-(2,2-dimethylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2,2-dimethylpropyl)-2,3,4,5-tetrahydro-1H-1,5-benzodiazepine was prepared as a white foam. Purification was by flash chromatography eluting with CH$_2$Cl$_2$/EtOAc (4:1 gradient to 5:2).

Step E

Synthesis of 3-(L-Alaninyl)-amino-2,4-dioxo-1,5-bis-(2.2-dimethylpropyl)-2,3,4,5-tetrahydro-1H-1,5-benzodiazepine Hydrochloride Following General Procedure 4-N above using the product from Step D, the title compound was prepared as an off-white solid.

EXAMPLE 4-W

Synthesis of 3-(L-Alaninyl)amino-2,4-dioxo-1,5-bis-phenyl-2,3,4,5-tetrahydro-1H-1,5-benzodiazepine hydrochloride

Step A

Synthesis of 2,4-Dioxo-1,5-bis-phenyl-2,3,4,5-tetrahydro-1H-1,5-benzodiazepine

This procedure is a modification of the procedure described in Chan, D. M. T. *Tetrahedron Lett.* 1996, 37, 9013–9016, incorporated herein by reference. A mixture of the product from Example 4-P, Step A (1.0 eq., 7.50 g), $Ph_3Bi$ (2.2 eq., 41.26 g, Aldrich), $Cu(OAc)_2$ (2.0 eq., 15.48 g, Aldrich), $Et_3N$ (2.0 eq., 8.62 g) in $CH_2Cl_2$ (100 mL) was stirred under $N_2$ at room temperature for 6 days (monitoring by TLC). The solids were removed by filtration through a plug of Celite rinsing with $CH_2Cl_2$/MeOH (3×75 mL). The filtrate was concentrated, dissolved in hot $CH_2Cl_2$/MeOH (9:1) and filtered through a large plug of silica gel eluting with $CH_2Cl_2$/MeOH (9:1, 2L). The filtrate was concentrated and the residue purified by flash chromatography eluting with straight $CH_2Cl_2$ gradient to $CH_2Cl_2$/MeOH (9:1). 2,4-Dioxo-1,5-bis-phenyl-2,3,4,5-tetrahydro-1H-1,5-benzodiazepine crystallized during concentration of the fractions containing the product, and was isolated by filtration as a white solid.

Step B

Synthesis of 3-Azido-2,4-dioxo-1,5-bis-phenyl-2,3,4,5-tetrahydro-1H-1,5-benzodiazepine For this substrate, General Procedure 4-K was modified in the following manner. Initially the product from Step A was suspended (not a solution) in THF at −70° C., and following addition of the $KN(TMS)_2$ solution, this suspension was allowed to warm to −20° C. over a period of 10 minutes, during which the suspension became a solution, and was re-cooled to −70° C.; then treated as described in the general procedure. The title compound was purified by trituration with hot $CHCl_3$/hexanes (1:1) to yield 3-azido-2,4-dioxo-1,5-bis-phenyl-2,3,4,5-tetrahydro-1H-1,5-benzodiazepine as a white solid.

Step C

Synthesis of 3-Amino-2,4-dioxo-1,5-bis-phenyl-2,3,4,5-tetrahydro-1H-1,5-benzodiazepine Following General Procedure 4-L using the product from Step B, 3-amino-2,4-dioxo-1,5-bis-phenyl-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH).

Step D

Synthesis of 3-[N'-(t-Butoxycarbonyl)-L-alaninyl]-amino-2,4-dioxo-1,5-bis-phenyl-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-phenyl-2,3,4,5-tetrahydro-1H-1,5-benzodiazepine was prepared as a white foam. Purification was by flash chromatography eluting with $CH_2Cl_2$/EtOAc (4:1 gradient to 3:1).

Step E

Synthesis of 3-(L-Alaninyl)-amino-2,4-dioxo-1,5-bis-phenyl-2,3,4,5-tetrahydro-1H-1,5-benzodiazepine Hydrochloride Following General Procedure 4-N above using the product from Step D, the title compound was prepared as a white amorphous solid.

EXAMPLE 4-X

Synthesis of 3-Amino-2,3-dihydro-1-methyl-5-phenyl-1H-1,4-benzodiazepin-2-one

Following the method of R. G. Sherrill et al., *J. Org. Chem.*, 1995, 60, 730–734, incorporated herein by reference, and using glacial acetic acid and HBr gas, the title compound was prepared.

EXAMPLE 4-Y

Synthesis of 3-(L-Valinyl)-amino-2,3-dihydro-1-methyl-5-phenyl-1H-1,4-benzodiazepin-2-one

Step A

Synthesis of 3-[N'-(tert-Butylcarbamate)-L-valinyl]-amino-2,3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2,2,1]heptane-1-methanesulfonate (Example 4-B, Step A) was free based by partitioning between methylene chloride and 1M potassium carbonate. The free amine was then coupled with N-Boc-valine following General Procedure D to give the title compound.

$C_{26}H_{32}N_4O_4$ (MW 464.62); mass spectroscopy 464.3.

Anal. Calcd for $C_{26}H_{32}N_4O_4$: C, 67.22; H, 6.94; N, 12.06. Found: C, 67.29; H, 6.79; N, 11.20.

Step B

Synthesis of 3-(L-valinyl)-amino-2,3-dihydro-1-methyl-5-phenyl-1H-1,4-benzodiazepin-2-one Following General Procedure 4-C and using 3-[N'-(tert-butylcarbamate)-L-alaninyl]-amino-2,3-dihydro-1-methyl-5-phenyl-1H-1,4-benzodiazepine-2-one, the title compound was prepared as a white foam.

$C_{21}H_{23}N_4O_2$ (MW 363.48); mass spectroscopy (M+H) 364.2.

EXAMPLE 4-Z

Synthesis of 3-(L-tert-Leucinyl)-amino-2,3-dihydro-1-methyl-5-phenyl-1H-1,4-benzodiazepin-2-one

Step A

Synthesis of 3-[N'-(tert-Butylcarbamate)-L-tert-leucinyl]-amino-2,3-dihydro-1-methyl-5-phenyl-1H-1,4-benzodiazepin-2-one (S)-3-amino-1,3-dihydro-1-methyl-5-phenyl-2H-1,4-benzodiazepin-2-one, (1S)-7,7-dimethyl-2-oxobicyclo[2.2.1]heptane-1-methanesulfonate (Example 4-B, Step A) was free based by partitioning between methylene chloride and 1M potassium carbonate. The free amine was then coupled with N-Boc-tert-leucine following General Procedure D to give the title compound.

$C_{27}H_{35}N_4O_4$ (MW 479.66); mass spectroscopy 479.

Step B

Synthesis of 3-(L-tert-Leucinyl)-amino-2,3-dihydro-1-methyl-5-phenyl-1H-1,4-benzodiazepin-2-one Following General Procedure 4-C and using 3-[N'-(tert-butylcarbamate)-L-tert-leucinyl]-amino-2,3-dihydro-1-methyl-5-phenyl-1H-1,4-benzodiazepine-2-one, the title compound was prepared as a white foam.

Anal. Calcd for $C_{22}H_{25}N_4O_2 \cdot 0.5H_2O$: C, 68.19; H, 7.02; N, 14.40. Found: C, 68.24; H, 7.00; N, 14.00.

EXAMPLE 4-AA

Synthesis of 3-(L-Alaninyl)-amino-2,3-dihydro-1,5-dimethyl-1H-1,4-benzodiazepine 2,3-Dihydro-1,5-dimethyl-1H-1,4-benzodiazepine was prepared following General Procedures 8-I (using methyl iodide), 4-D and 4-F. Coupling of this intermediate with Boc-L-alanine (Novo) using General Procedure D.

The Boc group was removed by dissolving the Boc-protected compound in a 1:1–2:1 mixture of $CH_2Cl_2$ and trifluoroacetic acid. The resulting solution was stirred until tlc indicated complete conversion, typically 2 hours. The solution was then stripped to dryness and the residue was taken up in ethyl acetate or $CH_2Cl_2$. The solution was washed with saturated aqueous $NaHCO_3$ and the aqueous phase was adjusted to a basic pH, then extracted with ethyl acetate or $CH_2Cl_2$. The organic phase was washed with saturated aqueous NaCl and dried over $MgSO_4$. The solution was stripped free of solvent on a rotary evaporator to afford the title compound which was used without further purification.

EXAMPLE 4-AB

Synthesis of 3-(L-3-Thienylglycinyl)amino-2,4-dioxo-1,5-bis-(2,2-dimethylpropyl)-2,3,4,5-tetrahydro-1H-1,5-benzodiazepine

Step A

Synthesis of N-(t-Butoxycarbonyl)-L-3-thienylglycine N-(t-Butoxycarbonyl)-L-3-thienylglycine was prepared from L-α-(3-thienyl) glycine (Sigma) by the procedure described in Bodansky, M. et al; *The Practice of Peptide Synthesis*; Springer Verlag; 1994, p. 17, incorporated herein by reference.

Step B

Synthesis of 3-[N'-(t-Butoxycarbonyl)-L-3-thienylglycinyl]-amino-2,4-dioxo-1,5-bis-(2,2-dimethylpropyl)-2,3,4,5-tetrahydro-1H-1,5-benzodiazepine Following General Procedure D above using the product from Example 4-V, Step C and the product from Step A above, 3-[N'-(t-butoxycarbonyl)-L-3-thienylglycinyl]-amino-2,4-dioxo-1,5-bis-(2,2-dimethylpropyl)-2,3,4,5-tetrahydro-1H-1,5-benzodiazepine was prepared.

Step C

Synthesis of 3-(L-3-Thienylglycinyl)amino-2,4-dioxo-1,5-bis-(2,2-dimethylpropyl)-2,3,4,5-tetrahydro-1H-1,5-benzodiazepine Following General Procedure 4-N above using the product from Step B, the title compound was prepared.

EXAMPLE 4-AC

Synthesis of 2-(L-Alaninyl)-amino-3H-fluoreno[1,9-ef]-2,4-dihydro-1-methyl-1H-1,4-diazepin-3-one

Step A

Preparation of 1-[N-(α-isopropylthio)-N'-(benzyloxycarbonyl -glycinyl]-amino-9-fluorenon A solution of α-(isopropylthio)-N-(benzyloxycarbonyl) glycine (1 eq; prepared according to Zoller, V. and D. Ben-Ishai *Tetrahedron* 1975, 31, 863, incorporated herein by reference) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 1-amino-9-fluorenone (0.9 eq.; Aldrich) and 4-methylmorpholine (2.0 eq., Aldrich) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was triturated with 1:1 diethyl ether/hexanes giving the title compound and a yellow solid.

MS Calcd for $C_{26}H_{25}N_2O_4S$: 461.15 (MH$^+$), found 461.3

Anal. Calcd for $C_{26}H_{24}N_2O_4S$: C, 67.81; H, 5.25; N, 6.08. Found: C, 67.97; H, 5.26; N, 6.14.

Step B

Preparation of 1-[N-(a-amino)-N'-(benzyloxycarbonyl)-glycinyl]-amino-9-fluorenone Ammonia gas was bubbled into a solution 1-[N-(α-isopropylthio)-N'- (benzyloxycarbonyl)-glycinyl]-amino-9-fluorenone (1 eq) in THF at 0° C. After 35 minutes mercury (II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step C without further purification.

Step C

Preparation of 2-(benzyloxycarbonyl)-amino-3H-Fluoreno[1,9-ef]-2,4-dihydro-1H-1,4-diazepin-3-one 1-[N-(α-Amino)-N'-(benzyloxycarbonyl)-glycinyl]-amino-9-fluorenone (1 eq.) was treated with glacial acetic acid and ammonium acetate (4.7 eq.). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was triturated with 3:1 diethyl ether/methylene chloride.

Anal. Calcd for $C_{23}H_{17}N_3O_3 \cdot 0.25\ H_2O$: C, 71.22; H, 4.55; N, 10.83. Found: C, 71.50; H, 4.44; N, 10.84.

Step D

Preparation of 2-(benzyloxycarbonyl)-amino-3H-fluoreno[1,9-ef]-2,4-dihydro-1-methyl-1H-1,4-diazepin-3-one Following General Procedure 4-A above using 2-(benzyloxycarbonyl)-amino-3H-fluoreno[1,9-ef]-2,4- dihydro-1H-1,4-diazepin-3-one, the title intermediate was prepared as a yellow solid.

Anal. Calcd for $C_{24}H_{19}N_3O_3$: C, 72.53; H, 4.82; N, 10.57. Found: C, 72.37; H, 5.01; N, 10.36.

Step E

Preparation of 2-amino-3H-fluoreno[1,9-ef]-2,4-dihydro-1-methyl-1H-1,4-diazepin-3-one Following General Procedure 4-B above using 2-(benzyloxycarbonyl)-amino-3H-fluoreno[1,9-ef]-2,4-dihydro-1-methyl-1H-1,4-diazepin-3-one, the title intermediate was prepared as a yellow foam which was used immediately in Step F.

Step F

Preparation of 2-[N'-(tert-butylcarbamate)-L-alaninyl]-amino-3H-Fluoreno[1,9-ef]-2,4-dihydro-1-methyl-1H-1,4-diazepin-3-one Following General Procedure D using N-Boc Alanine (Novabiochem) and 2-amino-3H-fluoreno[1,9-ef]-2,4-dihydro-1-methyl-1H-1,4-diazepin-3-one, the title intermediate was prepared as a yellow solid.

MS Calcd for $C_{24}H_{27}N_4O_4$: 435.21 (MH$^+$); found 435.29.

Step G

Preparation of 2-(L-alaninyl)-amino-3H-fluoreno[1,9-ef]-2,4-dihydro-1-methyl-1H-1,4-diazepin-3-one Following General Procedure 4-C using 2-[N'-(tert-butylcarbamate)-L-alaninyl]-amino-3H-fluoreno[1,9-ef]-2,4-dihydro-1-methyl-1H-1,4-diazepin-3-one, the title intermediate was prepared as a yellow foam.

EXAMPLE 4-AD

Synthesis of 5-(L-Alaninyl]-amino-7-methyl-1,2,4-triazolo[4,3-d][1,4]benzodiazepin-6(7H)-one

Step A

Preparation of 1,3-dihydro-5-(ethylthio)-1-methyl-2H-1,4-benzodiazepin-2-one

A rapidly stirred solution of 1-methyl-1,2,3,4-tetrahydro-3H-1,4-benzodiazepin-2,5-dione (Showell, G. A. et al. *J. Med. Chem.* 1994, 37, 719, incorporated herein by reference) (1 eq.) and pyridine (1.1 eq., Aldrich) in $CH_2Cl_2$ (0.16 M in dione), cooled to −40 to −45° C. under $N_2$ in an oven-dried flask, was treated dropwise with trifluoromethanesulfonic anhydride (1.1 eq., Aldrich). The resulting mixture (light yellow color; precipitate) was stirred at −40 to −35° C. for 20 minutes and then at 0° C. (ice bath) to 10° C for 14.5 hours (note: ice in Dewar melted slowly overnight). The resulting orange solution (some precipitate) was recooled to 0° C. and treated dropwise with ethanethiol (1.2 eq., Aldrich). The resulting mixture was stirred at 0 to 4° C. under $N_2$ for 8 hours then partitioned between $CH_2Cl_2$ and saturated aqueous $NaHCO_3$. The aqueous phase was extracted thrice with $CH_2Cl_2$. The organic extracts were combined, dried over $Na_2SO_4$, and evaporated in vacuo. The mixture was purified via flash chromatography using a gradient from $CH_2Cl_2$ to 30:70 $CH_2Cl_2$/Ethyl acetate as the eluent.

MS Calcd for $C_{12}H_{15}NOS$: 235.09 (MH+), found 235.0.

Anal. Calcd for $C_{12}H_{14}NOS$: C, 61.51; H, 6.02; N, 11.96. Found: C, 61.55; H, 5.99; N, 11.74.

Step B

Preparation of 7-methyl-1,2,4-triazolo[4,3-d][1,4]benzodiazepin-6(7H)-one

A mixture of 1,3-dihydro-5-(ethylthio)-1-methyl-2H-1,4-benzodiazepin-2-one (1 eq.) and formic hydrazide (5.8 eq. Aldrich) in n-butanol (0.1 M in benzodiazepine) was stirred at reflux under $N_2$ for 24 hours. An additional 1.67 eq. of formic hydrazide was added and refluxing continued an additional 16 hours. The yellow solution was evaporated in vacuo and the residue was purified via flash chromatography eluting with a gradient from 98:2 to 96:4 $CH_2Cl_2$/MeOH.

The product was obtained as a white solid.

MS Calcd for $C_{11}H_{11}N_4O$: 215.09, found 215.3.

Anal Calcd for $C_{11}H_{10}N_4O$: C, 61.67; H, 4.71; N, 26.15. Found: C, 61.56; H, 4.71; N, 26.08.

Step C

Preparation of 5(5H)-azido-7-methyl-1,2,4-triazolo[4,3-d][1,4]benzodiazepin-6(7H)-one Following General Procedure 4-K using 5H-7-methyl-1,2,4-triazolo[4,3-d][1,4]benzodiazepin-6(7H)-one, the title compound was prepared as a pale yellow solid.

MS Calcd for C11H9N7O: 255.09, FDMS found 255.0.

IR (solution in $CHCl_3$) 2138, 2115 cm$^{-1}$.

Step D

Preparation of 5(5H)-amino-7-methyl-1,2,4-triazolo[4,3-d][1,4]benzodiazepin-6(7H)-one A mixture of 5(5H)-azido-7-methyl-1,2,4-triazolo[4,3-d][1,4]benzodiazepin-6(7H)-one in ethyl acetate (0.1 M) under $N_2$ was treated with 10% Pd on carbon (0.4 equiv., Engelhard). The reaction vessel was flushed with $H_2$ and stirring continued for 3 hours under a balloon of $H_2$. The vessel was flushed with $N_2$ and the contents filtered through celite 545 washing with ethyl acetate. The filtrate was concentrated in vacuo to give a white powder.

MS Calcd for $C_{11}H_{12}N_5O$: 230.10 (MH$^+$), found 230.1.

Step E

Preparation of 5(5H)-[N'-(tert-butylcarbamate)-L-alaninyl]-amino-7-methyl-1,2,4-triazolo[4,3-d][1,4]benzodiazepin-6(7H)-one Following General Procedure D using 5(5H)-amino-7-methyl-1,2,4-triazolo[4,3-d][1,4]benzodiazepin-6(7H)-one and N-Boc Alanine (Novabiochem), the title intermediate was prepared as a white foam.

MS Calcd for $C_{19}H_{25}N_6O_4$: 401.19 (MH+), found 401.1.

Anal. Calcd for $C_{19}H_{24}N_6O_4$: C, 55.74; H, 6.15; N, 20.53. Found: C, 56.06; H, 6.42; N, 20.20.

Step F

Preparation of 5(5H)-(L-alaninyl)-amino-7-methyl-1,2,4-triazolo[4,3-d][1,4]benzodiazepin-6(7H)-one Following General Procedure 4-C using 5(5H)-[N'-(tert-butylcarbamate)-L-alaninyl]-amino-7-methyl-1,2,4-triazolo

[4,3-d][1,4]benzodiazepin-6(7H)-one, the title compound was prepared as a white foam.

MS Calcd for $C_{14}H_{17}N_6O_2$: 301.14 (MH$^+$), found 301.1.

EXAMPLE 4-AE

Synthesis of 3-(L-Alaninyl)-amino-2,3-dihydro-1-methyl-5-piperidinyl-1H-1,4-benzodiazepin-2-one Step A Preparation of 3-[N'-tert-butylcarbamate)-L-alaninyl]-amino-2,3-dihydro-1-methyl-5-(1-piperidinyl)-1H-1,4-benzodiazepin-2-one Following General Procedure D above using 3-amino-1,3-dihydro-1-methyl-5-(1-piperidinyl)-2H-1,4-benzodiazepin-2-one (Example 4-A) and N-Boc Alanine (Novabiochem),the title compound was prepared as a white foam.

MS Calcd for $C_{23}H_{33}N_5O_4$ 444.26 (MH$^+$), found 444.4.

Anal. Calcd for $C_{23}H_{33}N_5O_4 \cdot 0.5H_2O$: C, 61.04; H, 7.57; N, 15.47. Found: C, 61.09; H, 7.29; N, 15.21.

Step B

Preparation of 3-(L-alaninyl)-amino-2,3-dihydro-1-methyl-5-(1-piperidinyl)-1H-1,4-benzodiazepin-2-one Following General Procedure 4-C using 3-[N'-tert-butylcarbamate)-L-alaninyl]-amino-2,3-dihydro-1-methyl-5-(1-piperidinyl)-1H-1,4-benzodiazepin-2-one, the title compound was prepared.

EXAMPLE 4-AF

Synthesis of 3-(L-Alaninyl)-amino-2,3-dihydro-5-isopropyl-1-methyl-1H-1,4-benzodiazepin-2-one Step A Preparation of 3-(benzyloxycarbonyl)-amino-2,3-dihydro-5-isopropyl-1H-1,4-benzodiazepin-2-one A slurry of 2-(benzotriazol-1-yl)-N-(benzyloxycarbonyl)glycine (1.1 equiv.; Katritzky, A. R. et al. *J. Org. Chem.* 1990, 55, 2206, incorporated herein by reference) in THF (0.3 M) was cooled to 0° C. and treated with oxalyl chloride (1.1 equiv.) in a dropwise manner. To the slurry was added dropwise DMF (0.1 equiv.); stirring was continued at 0° C. for 1 hour. A solution of 1-(2-aminophenyl)-2-methyl-1-propanone (1.0 equiv.; Robl, J. A. *Synthesis* 1991, 56, incorporated herein by reference) and N-methylmorpholine (2.2 equiv.) in THF (1 M in propanone), pre-cooked to 0° C., was added via cannula. Upon completion of the addition, the reaction was warmed to ambient temperature. The mixture was filtered, washing the filter cake with THF. The filtrate was transferred to a three-neck flask and treated with ammonia gas through a dispersion tube for 15 minutes. Methanol (0.3 M in propanone) was added and the ammonia continued to be bubbled through the solution for 1 hour. The reaction was concentrated, diluted with ethyl acetate,and re-concentrated; this was repeated again. The residue was diluted with ethyl acetate and washed twice with 1 N NaOH. The aqueous washes were back-extracted with ethyl acetate. The combined organics were washed with brine, dried over $Na_2SO_4$, filtered, and concentrated. Acetic acid was added and concentrated in vacuo. The syrup was dissolved in acetic acid (0.6 M in propanone) and treated with ammonium acetate (4.0 equiv.). The reaction was stirred at ambient temperature for 18 hours. The resultant solid was filtered, washing with $H_2O$.

MS Calcd for $C_{20}H_{22}N_3O_3$: 352.17, found 352.5.

Step B

Preparation of 3-(benzyloxycarbonyl)-amino-2,3-dihydro-5-isopropyl-1-methyl-1H-1,4-benzodiazepin-2-one Following General Procedure 4-A using 3-(benzyloxycarbonyl)-amino-2,3-dihydro-5-isopropyl-1H-1,4-benzodiazepin-2-one, the title compound was prepared as a white solid.

MS Calcd for $C_{21}H_{24}N_3O_3$: 366.18 (MH+), found 366.2.

Anal. Calcd for $C_{21}H_{23}N_3O_3 \cdot 0.25H_2O$: C, 68.18; H, 6.40; N, 11.36. Found: C, 68.36; H, 6.28; N, 11,48.

Step C

Preparation of 3-amino-2,3-dihydro-5-isopropyl-1-methyl-1H-1,4-benzodiazepin-2-one Following General Procedure 4-B using 3-(benzyloxycarbonyl)-amino-2,3-dihydro-5-isopropyl-1-methyl-1H-1,4-benzodiazepin-2-one, the title compound was prepared as a white foam.

MS Calcd for $C_{13}H_{18}N_3O$: 232.14 (MH+), found 232.19.

Step D

Preparation of 3-[N'-(tert-butylcarbamate)-L-alaninyl]-amino-2,3-dihydro-5-isopropyl-1-methyl-1H-1,4-benzodiazepin-2-one Following General Procedure D using 3-amino-2,3-dihydro-5-isopropyl-1-methyl-1H-1,4-benzodiazepin-2-one and N-Boc alanine (Novabiochem), the title compound was prepared as a white solid.

MS Calcd for $C_{21}H_{31}N_4O_4$: 403.23 (MH+), found 403.46.

Step E

Preparation of 3-(L-alaninyl)-amino-2,3-dihydro-5-isopropyl-1-methyl-1H-1,4-benzodiazepin-2-one Following General Procedure 4-C using 3-[N'-(tert-butylcarbamate)-L-alaninyl]-amino-2,3-dihydro-5-isopropyl-1-methyl-1H-1,4-benzodiazepin-2-one, the title compound was prepared as a white foam.

MS Calcd for $C_{16}H_{23}N_4O_2$: 303.18 (MH+), found 303.21.

Anal Calcd for $C_{16}H_{22}N_4O_2 \cdot 0.3 H_2O$: C, 62.44; H, 7.40; N, 18.20. Found: C, 62.58; H, 7.10; N, 17.79.

EXAMPLE 4-AG

Synthesis of 3-(L-Alaninyl)-amino-2,3-dihydro-5-n-propyl-1-methyl-1H-1,4-benzodiazepin-2-one Step A Preparation of 1-(2-aminophenyl)-1-butanone A solution of anthranilonitrile (1 equiv., Aldrich) in diethyl ether (2.4 M) was cooled to 0° C. and treated with propylmagnesium chloride (2.5 equiv., Aldrich; 2.0 M in $Et_2O$) in a dropwise manner over the course of an hour. After addition of 25% of the Grignard reagent, an additional 1/10 volume of Et$_2$O was added. The cooling bath was removed and stirring of the suspension continued for 5 hours. The reaction was returned to 0° C. and cautiously quenched with 3 N HCl. The cooling bath was removed and stirring continued for 30 minutes. The mixture was made basic by the addition of solid NaOH. The contents were extracted thrice with ethyl acetate; brine was added to help break up the suspension. The combined extracts were washed with brine, dried over Na$_2$SO$_4$, filtered, and concentrated. The crude residue was chromatographed eluting with 95:5 hexanes/ethyl acetate.

MS Calcd for C$_{10}$H$_{13}$NO: 163.10, found 163.18.

Anal. Calcd for C$_{10}$H$_{13}$NO.0.2 H$_2$O: C, 72.00; H, 8.10; N, 8.40. Found: C, 72.36; H, 8.25; N, 8.76

Step B

Preparation of 3-(benzyloxycarbonyl)-amino-2,3-dihydro-5-isopropyl-1H-1,4-benzodiazepin-2-one A slurry of 2-(benzotriazol-1-yl)-N-(benzyloxycarbonyl) glycine (1.1 equiv.; Katritzky, A. R. et al. *J. Org. Chem.* 1990, 55, 2206, incorporated herein by reference) in THF (0.3 M) was cooled to 0° C. and treated with oxalyl chloride (1.1 equiv.) in a dropwise manner. To the slurry was added dropwise DMF (0.1 equiv.); stirring was continued at 0° C. for 1 hour. A solution of 1-(2-aminophenyl)-1-butanone and N-methylmorpholine (2.2 equiv.) in THF (1 M in butanone), pre-cooled to 0° C., was added via cannula. Upon completion of the addition, the reaction was warmed to ambient temperature. The mixture was filtered, washing the filter cake with THF. The filtrate was transferred to a three-neck flask and treated with ammonia gas through a dispersion tube for 15 minutes. Methanol (0.3 M in butanone) was added and the ammonia continued to be bubbled through the solution for 1 hour. The reaction was concentrated, diluted with ethyl acetate, and re-concentrated; this was repeated again. The residue was diluted with ethyl acetate and washed twice with 1 N NaOH. The aqueous washes were back-extracted with ethyl acetate. The combined organics were washed with brine, dried over Na$_2$SO$_4$, filtered, and concentrated. Acetic acid was added and concentrated in vacuo. The syrup was dissolved in acetic acid (0.6 M in butanone) and treated with ammonium acetate (4.0 equiv.). The reaction was stirred at ambient temperature for 18 hours. The resultant solid was filtered, washing with H$_2$O.

MS Calcd for C$_{20}$H$_{22}$N$_3$O$_3$: 352.17, found 352.4.

Step C

Preparation of 3-(benzyloxycarbonyl)-amino-2,3-dihydro-5-n-propyl-1-methyl-1H-1,4-benzodiazepin-2-one Following General Procedure 4-A using 3-(benzyloxycarbonyl)-amino-2,3-dihydro-5-n-propyl-1H-1,4-benzodiazepin-2-one, the title compound was prepared as a white solid.

MS Calcd for C$_{21}$H$_{24}$N$_3$O$_3$: 366.18 (MH+), found 366.2.

Step D

Preparation of 3-amino-2,3-dihydro-5-n-propyl-1-methyl-1H-1,4-benzodiazepin-2-one Following General Procedure 4-B using 3-(benzyloxycarbonyl)-amino-2,3-dihydro-5-n-propyl-1-methyl-1H-1,4-benzodiazepin-2-one, the title compound was prepared as a white foam. This compound was used immediately in Step E.

Step E

Preparation of 3-[N'-(tert-butylcarbamate)-L-alaninyl]-amino-2,3-dihydro-5-n-propyl-1-methyl-1H-1,4-benzodiazepin-2-one Following General Procedure D using 3-amino-2,3-dihydro-5-n-propyl-1-methyl-1H-1,4-benzodiazepin-2-one and N-Boc alanine (Novabiochem), the title compound was prepared as a white solid.

MS Calcd for C$_{21}$H$_{31}$N$_4$O$_4$: 403.23 (MH+), found 403.4.

Step F

Preparation of 3-(L-alaninyl)-amino-2,3-dihydro-5-n-propyl-1-methyl-1H-1,4-benzodiazepin-2-one Following General Procedure 4-C using 3-[N'-(tert-butylcarbamate)-L-alaninyl]-amino-2,3-dihydro-5-n-propyl-1-methyl-1H-1,4-benzodiazepin-2-one the title compound was prepared as a white foam.

EXAMPLE 4-AH

Synthesis of 3-(L-Alaninyl)amino-4-n-butyl-3,4-dihydro-1-methyl-1H-1,4-benzodiazepin-2,5-dione

Step A

Preparation of 4-n-butyl-3,4-dihydro-1-methyl-1H-1,4-benzodiazepin-2,5-dione

A solution of 13 mmol of 3,4-dihydro-1-methyl-1H-1,4-benzodiazepin-2,5-dione (Tett. Lett. 1994, 50(30), 9051, incorporated herein by reference) in 30 mL dry dimethylformamide is treated, dropwise at 0° C. under nitrogen cover, with one equivalent of potassium-t-butoxide (Aldrich; 1.0 M in THF). After forty-five minutes at 0° C., iodobutane is introduced via syringe over several minutes. The reaction mixture is stirred at ambient temperature seventy-five minutes, diluted with methylene chloride, and then washed with water and saturated sodium chloride. The organic solution is dried over anhydrous sodium sulfate, filtered and concentrated in vacuo to give a yellow oil. Flash column chromatography (silica gel; ethyl acetate/hexane (7/1) eluent) provides pure material as a colorless oil (90% yield).

C$_{14}$H$_{18}$N$_2$O$_2$ (MW=246.3)

Anal. Calcd for C$_{14}$H$_{18}$N$_2$O$_2$: C, 68.27; H, 7.37; N, 11.37. Found: C, 68.53; H, 7.11; N, 11,41.

Step B

Preparation of 3-azido-4-n-butyl-3,4-dihydro-1-methyl-1H-1,4-benzodiazepine-2,5-dione Following General Procedure 4-K using 4-n-butyl-3,4-dihydro-1-methyl-1H-1,4-benzodiazepin-2,5-dione the title intermediate was prepared as a waxy solid.

C$_{14}$H$_{17}$N$_5$O$_2$ (MW=287.3); Exact Mass FAB+ Theory 288.1461 Found 288.1459

Step C

Preparation of 3-amino-4-n-butyl-3,4-dihydro-1-methyl-1H-1,4-benzodiazepine-2,5-dione A solution of 0.4 mmol of azide (see Step B above) in ethyl acetate is treated with 170 mg of 10% Pd/C (Englehard) and hydrogenated overnight via the static pressure of a hydrogen-filled balloon attached to the reaction flask via a syringe and septum. The catalyst is removed by filtration and the filtrate concentrated in vacuo to give a yellow oil. This was purified via chromatography (silica gel; 1 mil Chromatotron plate; 95/5 methylene chloride/methanol[7N ammonia])

Anal. Calcd for $C_{14}H_{19}N_3O_2$: C, 64,35; H, 7.33; N, 16.08. Found: C, 64.58; H, 7.19; N, 15.94.

Step D

Preparation of 3-(N-tert-butylcarbamate-L-alaninyl) amino-4-n-butyl-3,4-dihydro-1-methyl-1H-1,4-benzodiazepin-2,5-dione Following General Procedure D using N-Boc-alanine and the aminobenzodiazepinedione from Step C above, the title intermediate was obtained as an amorphous white solid.

Anal. Calcd. for $C_{22}H_{32}N_4O_5$: C, 61.09; H, 7.46; N, 12.95. Found: C, 60.83; H, 7.51; N, 12.69

Step E

Preparation of 3-(L-alaninyl)amino-4-n-butyl-3,4-dihydro-1-methyl-1,4-benzodiazepin-2,5-dione Following General Procedure 4-C using the Boc-protected intermediate from Step D above, the title intermediate is obtained as a white solid.

$C_{17}H_{24}N_4O_3$(MW=332.4) Exact Mass FAB+Theory MW=333.1927 Found MW=333.1924

EXAMPLE 4-AI

Synthesis of 3-(L-alaninyl)amino-1,3-dihydro-5-ethylthio-1-methyl-2H-1,4-benzodiazepin-2-one Step A Preparation of 1,3-dihydro-5-ethylthio-1-methyl-2H-1,4-benzodiazepin-2-one A solution of 1.0 mmol of 3,4-dihydro-1-methyl-1H-1,4-benzodiazepin-2,5-dione (Tett. Lett. 1994, 50(30), 9051) in 8mL dry dichloromethane (Aldrich Sure Seal), in an oven-dried round bottom flask under nitrogen cover, is treated with 1.1 equivalents of anhydrous pyridine (Mallinkrodt). The reaction is cooled to −51° C. in a dry ice/acetone bath and treated, dropwise via syringe over three minutes, with 1.1 equivalents of trifluoromethanesulfonic anhydride (Aldrich; sealed ampules). The reaction mixture is allowed to stir twenty minutes while maintaining a reaction temperature between −47 and −35° C. The temperature is brought to 0° C. over 1–2 minutes and then maintained at that temperature for one hour. Ethanethiol (3.4 equivalents) is introduced via syringe and the mixture allowed to stir overnight, still immersed in an ice water-filled Dewar. The temperature had risen to 16° C. by morning. The reaction mixture is partitioned between methylene chloride and aqueous sodium bicarbonate. The aqueous portion is further extracted three times with methylene chloride and the combined extracts dried over anhydrous sodium sulfate, filtered and concentrated in vacuo to give a yellow oil. Purification is effected by flash chromatography (silica gel; gradient elution using methylene chloride/ethyl acetate in 100/1, 95/5, 90/10 and 85/15. The title compound is obtained as a colorless oil which crystallizes on standing.

Anal. Calcd for $C_{12}H_{14}N_2OS$: C, 61.51; H, 6.02; N, 11.96. Found: C, 61.55; H, 5.99; N, 11.74.

Step B

Preparation of 3-azido-1,3-dihydro-5-ethylthio-1-methyl-2H-1,4- benzodiazepin-2-one Following General Procedure 4-K using the ethylthiobenzodiazepine intermediate from Step A above, the title intermediate was prepared as a white solid.

Anal. Calcd. for $C_{12}H_3N_5OS$: C, 52.35; H, 4.76; N, 25.44. Found: C, 52.63; H, 4.67; N, 25.39. Step C Preparation of 3-amino-1.3-dihydro-5-ethylthio-1-methyl-2H-1,4-benzodiazepin-2-one A solution of 1.90 mmol of azide (see Step B above) in 13 mL of tetrahydrofuran to which had been added 1 mL of water is treated with an excess of triphenyphospine (2.8 equivalents) added in one portion as a solid. The reaction is stirred at room temperature under nitrogen cover for twenty hours and then diluted with ethyl acetate. The solution is extracted with 1N HCl three times, and the combined extracts are rendered basic by the addition of 5N NaOH. This is extracted three times with ethyl acetate and the combined extracts washed once with saturated aqueous sodium chloride, dried over anhydrous sodium sulfate, filtered and concentrated in vacuo on a rotary evaporator at 20° C. The resulting oil is used immediately.

$C_{12}H_{15}N_3OS$ (MW=249.3) FAB+Exact Mass: Theory 250.1014 Found 250.1011

Step D

Preparation of 3-(N-tert-butylcarbamate-L-alaninyl) amino-1,3-dihydro-5-ethylthio-1-methyl-2H-1,4-benzodiazepin-2-one Following General Procedure D using N-Boc-alanine and the aminobenzodiazepin-2-one from Step C above, the title intermediate was obtained as an amorphous white solid.

Anal. Calcd. for $C_{20}H_{28}N_4O_4S$: C, 57.12; H, 6.71; N, 13.32. Found: C, 56.85; H, 6.77; N, 13.12

Step E

Preparation of 3-(L-alaninyl)amino4-n-butyl-3,4-dihydro-1-methyl-1,4-benzodiazepin-2,5-dione Following General Procedure 4-C using the Boc-protected intermediate from Step D above, the title intermediate is obtained as a colorless oil.

$C_{15}H_{20}N_4O_2S$(MW=320.4) FAB+Exact Mass Theory 321.1385 Found 321.1388.

EXAMPLE 4-AJ

Synthesis of 3-L-Alaninyl-amino-5-phenyl-1-methyl-2H-1,5-diazepin-2-one

Step A

Preparation of 1-phenyl-4-piperidinone

The title intermediate was prepared from aniline (Aldrich) and methyl acrylate (Aldrich) by the literature procedure of Hermant, R. M., et al. *J. Am. Chem. Soc.,* 1990, 112, 1214–1221, incorporated herein by reference.

Step B

Preparation of 5-phenyl-2H-1,5-diazepin-2-one

To the product from Step A (12.54 g, 71.56 mmols) in glacial acetic acid (60 mL) and concentrated sulfuric acid (30 mL) at 0° C. was added sodium azide (5.12 g, 78.7 mmols) in five portions of 1.024 g over a period of 4 hours. The resultant pale yellow mixture was allowed to warm to room temperature with stirring under nitrogen for 17 hours. The mixture was poured onto ice and neutralized to pH 7 with 5 M aq. NaOH. The product was extracted into methylene chloride (2×400 mL) and the combined organic extracts were dried over sodium sulfate, filtered, and concentrated to a pale yellow solid. Flash chromatography purification eluting with EtOAc gradient to EtOAc/MeOH (95:5) yielded 12.37 g (91%) of the title intermediate as a pale yellow solid.

$C_{11}H_{14}N_2O$ (MW. 190.25), mass spectroscopy (MH$^+$), 191.4.

Anal. Calcd. For $C_{11}H_{14}N_2O$: C, 69.45; H, 7.42; N, 14.72, Found: C, 69.74; H, 7.23; N, 15.00.

Step C

Preparation of 5-phenyl-1-methyl-2H-1,5-diazepin-2-one

Following General Procedure 4-G using the product from Step B, methyl iodide, and potassium tert-butoxide, the title intermediate was prepared. HPLC purification eluting with EtOAc yielded the product as a white solid.

$C_{12}H_{16}N_2O$ (MW. 204.27), mass spectroscopy (MH$^+$), 205.2.

Anal. Calcd. For $C_{12}H_{16}N_2O$: C, 70.56; H, 7.90; N, 13.71, Found: C, 70.65; H, 7.70; N, 13.95.

Step D

Preparation of 3-azido-5-phenyl-1-methyl-2H-1,5-diazepin-2-one

Following the General Procedure 4-E using the product from Step C, the title intermediate was prepared. HPLC purification eluting with EtOAc/hexanes (60:40), and a second HPLC purification eluting with methylene chloride/methanol (98:2), yielded the product as a light yellow solid.

$C_{12}H_{15}N_5O$ (MW. 245), mass spectroscopy (MH$^+$), 246.4.

Step E

Preparation of 3-amino-5-phenyl-1-methyl-2H-1,5-diazepin-2-one

Following the General Procedure 4-F using the product from Step D, the title intermediate was prepared as yellow oil which upon standing solidified.

$C_{12}H_{17}N_3O$ (MW. 219), mass spectroscopy (MH$^+$), 220.3.

Anal. Calcd. For $C_{12}H_{17}N_3O$: C, 65.73; H, 7.81; N, 19.16, Found: C, 65.94; H, 7.37; N, 18.85.

Step F

Preparation of 3-[N'-(t-butoxycarbonyl)-L-alaninyl]-amino-5-phenyl-1-methyl-2H-1,5-diazepin-2-one Following General Procedure D using the product from Step E and Boc-L-Alanine (Nova Biochem) the title intermediate was prepared. HPLC purification eluting with EtOAc/hexanes (1:1) afforded the title compound as a white solid.

Exact Mass, anal. cacld. for $C_{20}H_{31}N_4O_4$: Theory, 391.2345, Found, 391.2342.

Step G

Preparation of 3-(L-alaninyl)-amino-5-phenyl-1-methyl-2H-1,5-diazepin-2-one

Following the General Procedure 4-N using the product from Step F the title intermediate was prepared. HPLC purification eluting with 95:5 methylene chloride/methanol gave the title intermediate.

Exact mass anal. calcd. Form. $C_{15}H_{23}N_4O_2$, Theory, 291.1821; Found, 291.1816.

EXAMPLE 4-AK

Synthesis of 3-(S)-Phenylglycinyl]-amino-5-phenyl-1-methyl-2H-2,3,4,5-tetrahydro-1,5-benzodiazepine-2-one Step A Preparation of 3-[N'-(t-Butoxycarbonyl)-(S)-phenylglycinyl]-amino-1-methyl-5-phenyl-1,3,4,5-tetrahydro-2H-1,5-benzodiazepine 2-one Following modified General Procedure J using the product from Example 4-M, Step B, and Boc-L-Phenylglycine (Nova Biochem), the title intermediate was prepared. The modification was that the reaction was only stirred for 6 hours. HPLC purification eluting with 80/20 hexanes/EtOAc afforded the separated diastereomers; isomer 1 (first eluting) and isomer 2 (second eluting).

$C_{29}H_{32}N_4O_4$ (MW 500.60); mass spectroscopy for isomer 1: MH$^+$501.2; MH$^-$, 499.3; mass spectroscopy for isomer 2: MH$^+$501.2; MH$^-$, 499.3.

Step B

Synthesis of 3-((S)-phenylglycinyl)-amino-1-methyl-5-phenyl-1,3,4,5-tetrahydro-2H-1,5-benzodiazepine 2-one Following the General Procedure 4-N using the products (Isomers 1 and 2 brought through reaction sequence separately) from Step A, the title intermediates were prepared. HPLC purification eluting with 95/5 methylene chloride/methanol afforded the title intermediates as light yellow oils.

$C_{24}H_{24}N_4O_2$ (MW 400.48); mass spectroscopy for isomer 1: MH$^+$, 401.3; MH$^-$, 399.2; mass spectroscopy for isomer 2: MH$^+$, 401.2; MH$^-$, 399.3.

EXAMPLE 4-AL

Synthesis of 3-(L-Norvalinyl)-amino-2,4-dioxo-1,5-bis-methyl-2,3,4,5-tetrahydro-1H-1,5-benzodiazepine Step A Preparation of 3-[N'-(t-Butoxycarbonyl)-L-norvalinyl]-amino-2,4-dioxo-1,5-bis-methyl-2,3,4,5-tetrahydro-1H-1,5-benzodiazepine Following General Procedure D using the product from Example 4-R, Step C and Boc-L-norvaline (BACHEM) the title intermediate was prepared. HPLC purification eluting with EtOAc/Hexanes (60:40) afforded the title intermediate as a white solid.

$C_{21}H_{30}N_4O_5$ (MW 418.49).

Anal. Calcd. for $C_{21}H_{30}N_4O_5$ hemihydrate: C, 59.00; H, 7.39; N, 13.10. Found: C, 59.35; H, 7.58; N, 12.86.

Exact Mass calcd. for $C_{21}H_{31}N_4O_5$: Theory 419.2294, Found 419.2289.

Step B

Preparation of 3-(L-norvalinyl)-amino-2,4-dioxo-1,5-bis-methyl-2,3,4,5-tetrahydro-1H-1,5-benzodiazepine Following General Procedure 4-N using the product from Step A, the title intermediate was prepared and used without further purification.

$C_{16}H_{22}N_4O_3$ (MW 318.38)

Exact Mass calcd. for $C_{16}H_{23}N_4O_3$: Theory 319.1770, Found 319.1774.

EXAMPLE 4-AM

Synthesis of 3-(L-norvalinyl)-amino-2,4-dioxo-1-methyl-5-phenyl-2,3,4,5-tetrahydro-1H-1,5-benzodiazepine

Step A

Preparation of 3-[N'-(t-Butoxycarbonyl)-L-norvalinyl)-amino-2,4-dioxo-1-methyl-5-phenyl-2,3,4,5-tetrahydro-1H-1,5-benzodiazepine Following General Procedure D using 3-amino-2,4-dioxo-1-methyl-5-phenyl-2,3,4,5-tetrahydro-1H-1,5-benzodiazepine (CAS No. 131604-75-6) and Boc-L-norvaline (BACHEM) the title intermediate was prepared. HPLC purification with EtOAc/hexanes (1:1) afforded the title intermediate as a white solid.

$C_{26}H_{32}N_4O_5$ (MW 480.57); mass spectroscopy, $MH^+$ 481.2.

Anal. Calcd. for $C_{26}H_{32}N_4O_5$: C, 64.98; H, 6.71; N, 11.66. Found: C, 64.87; H, 6.83; N, 11.53.

Step B

Preparation of 3-(L-norvalinyl)-amino-2,4-dioxo-1-methyl-5-phenyl-2,3,4,5-tetrahydro-1H-1,5-benzodiazepine Following General Procedure 4-N using the product from Step A, the title intermediate was prepared. HPLC purification eluting with methylene chloride/methanol (9:1) afforded the title intermediate as an off white solid.

$C_{21}H_{24}N_4O_3$ (MW 380.45); mass spectroscopy, $MH^+$ 381.1.

Exact Mass calcd. for $C_{21}H_{25}N_4O_3$: Theory 381.1889, Found 381.1928.

EXAMPLE 4-AN

Synthesis of 3-(L-alaninyl)-amino-1,5-bis-methyl-2H-2,3,4,5-tetrahydro-1,5-benzodiazepine-2-one

Step A

Preparation of N,N'-Dimethyl-1,2-phenylenediamine

Following the literature procedures of Stetter, H., *Chem. Ber.*, 1953, 86, 161 and Cheeseman, G. W. H., *J. Chem. Soc.*, 1955, 3308, incorporated herein by reference, the title intermediate was prepared from 1,2-phenylenediamine (Aldrich) as a low melting solid.

$C_8H_{12}N_2$ (MW 136); mass spectroscopy, 136.1.

Exact mass anal. Cacld. for $C_8H_{13}N_2$: Theory, 137.1079, Found, 137.081

Step B

Preparation of 1,5-Bis-methyl-2,3,4,5-tetrahydro-2H-1,5-benzadiazepine-2-one

To a solution of the product from Step A (400 mg, 2.94 mmols) in 5M Aq. HCl (30 mL) was added acrylic acid (0.202 mL, 3.23 mmols, Aldrich) and the mixture heated to reflux for 18 hours. The black mixture was allowed to cool, then poured onto ice and the pH adjusted to 10 with 5M Aq. NaOH. The product was extracted into $CH_2Cl_2$ (200 mL) and washed with water (100 mL) and brine (100 mL). The organic phase was dried over $Na_2SO_4$, filtered, and concentrated to give a black oil. HPLC purification eluting with hexanes/EtOAc (1:1) afforded 364 mg of the title intermediate as a brown oil.

$C_{11}H_{14}N_2O$ (MW 190.25); mass spectroscopy, $MH^+$ 191.4

Anal. Calcd. for $C_{11}H_{14}N_2O$: Theory, C, 69.45; H, 7.42; N, 14.72; Found, C, 69.26; H, 7.40; N, 14.64.

Step C

Preparation of 3-Azido-1,5-bis-methyl-2,3,4,5-tetrahydro-2H-1,5-benzadiazepine-2-one Following General Procedure 4-E using the product from Step B, the title intermediate was prepared. HPLC purification eluting with hexanes/EtOAc (7:3) afforded the title intermediate as a light brown oil.

$C_{11}H_{13}N_5O$ (MW 231.26), mass spectroscopy, $MH^+$ 232.2 Exact mass Anal. Calcd. for $C_{11}H_{14}N_5O$: Theory, 232.1198; Found, 232.1196.

Step D

Preparation of 3-Amino-1,5-bis-methyl-2,3,4,5-tetrahydro-2H-1,5-benzadiazepine-2-one Following procedure 4-F using the product from Step C, the title intermediate was prepared and used without chromatographic purification.

$C_{11}H_{15}N_3O$ (MW 205.26), mass spectroscopy $MH^+$ 206.2.

Exact mass Anal. Calcd. for $C_{11}H_{16}N_3O$: Theory, 206.1293; Found, 206.1295.

Step E

Preparation of 3-[N'-(t-Butoxycarbonyl)-L-alaninyl]-amino-1,5-bis-methyl-2,3,4,5-tetrahydro-2H-1,5-benzadiazepine-2-one Following General Procedure D using the product from Step D and Boc-L-Alanine (Nova Biochem), the title intermediate was prepared. HPLC purification eluting with EtOAc/hexanes (6:4) afforded the title intermediate as a white foamy solid.

$C_{19}H_{28}N_4O_4$ (MW 376.45), mass spectroscopy $MH^+$, 377.4,$MH^-$, 375.3.

Anal. Calcd. for $C_{19}H_{28}N_4O_4$: Theory, C, 60.62; H, 7.50; N, 14.88. Found, C, 60.68; H, 7.42; N, 14.38.

Step F

Preparation of 3-(L-Alaninyl)-amino-1,5-bis-methyl-2,3,4,5-tetrahydro-2H-1,5-benzadiazepine-2-one Following the procedure 4-N using the product from Step E, the title intermediate was prepared. HPLC purification eluting with EtOAc/hexanes (6:4) afforded the title intermediate as a thick yellow oil.

$C_{14}H_{20}N_4O_2$: (MW 276.34), mass spectroscopy, $MH^+$, 277.2.

Using the following procedures, the following additional intermediates can be prepared for use in this invention.

General Procedure C-H

The intermediates shown in Table C-A were synthesized in parallel in using the following procedure:

Step A

To a solution of 3-(tert-butoxycarbonyl)amino-2,3-dihydro-5-phenyl-1H-1,4-benzodiazepin-2-one (CA No. 125:33692: 100 mg, 0.28 mmol) in 1 mL of anhydrous DMF was added 600 μL of a solution of 0.5 M potassium bis(trimethylsilyl)amide (0.30 mmol) in toluene. Neat alkyl halide (0.56 mmol; as indicated in Table C-A) was added immediately in one portion and the reaction mixture was left undisturbed overnight. When an alkyl chloride was used, 1 equivalent of sodium iodide was added to the reaction mixture. After concentration under reduced pressure, the crude reaction residue was partitioned between methylene chloride (2 mL) and aqueous saturated bicarbonate (2 mL) and then passed through a 5 g Extralut QE cartridge (EM Science; Gibbstown, N.J.) using 10 mL of methylene chloride. The resulting filtrate was concentrated under reduced pressure and the crude product was further purified using automated semi-preparative HPLC (YMC 20x50 mm Silica column; gradient elution; 0–5% (5.5 min.), 5–20% (3.5 min.), 20–100% (2 min.), 100% (4 min.) ethyl acetate/methylene chloride, flow rate of 25 mL/min.). Product provided the expected M+1 peak by IEX MS and was carried on without further purification and characterization.

Step B

The product obtained from Step A was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3x with 2 mL portions of methanol and the product was eluted from the column using 6 mL of 2.0 M solution of ammonia/methanol. After concentration under reduced pressure, the product were characterized by IEX MS and carried on without further purification.

Step C

To the crude product obtained from Step B (1.05 equiv.) was added sequentially a 0.3 mM stock solution of $HOBt.H_2O$ (1.05 equiv.) in DMF, a 0.3 mM stock solution of N-t-BOC-L-alanine (1.0 equiv.) in THF and 0.3 mM stock solution of 1-(3-dimethylaminopropyl)-3-ethyl carbodiimide (1.05 equiv.) in THF. After standing undisturbed for 24 h, the reaction mixture was concentrated and the residue redissolved in 2 mL of a 10% methanol/methylene chloride solution. This solution was then filtered through a pre-washed (methanol) 1 g SCX (Varian Sample Preparation) column using an additional 8 mL of the same solvent. For Example C-V a 1 g Si column (Varian Sample Preparation) was used. The filtrate was concentrated under a stream of nitrogen to approximately ⅓ its original volume and then passed over a plug (500 mg) of AG 1-8x anion exchange resin (BioRad; Hercules, Calif.; columns were pre-washed with 1N NaOH, water and methanol) using an additional 10 mL of methanol. The resulting filtrate was concentrated under reduced pressure and the crude product was carried on without further purification after characterization by IEX MS.

Step D

The crude product obtained from Step C was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3x with 2 mL portions of methanol and the product was eluted from the column using 6 mL of 2.0 M solution of ammonia/methanol. After concentration under reduced pressure, the product was characterized by IEX MS and carried on without further purification. The intermediates prepared by this method are shown in Table C-A.

TABLE C-A

Intermediates

| Ex. | Alkyl Halide | Intermediate | MS |
|---|---|---|---|
| C-A | 3-Fluorobenzyl bromide (Aldrich) | 3-(L-alaninyl)amino-5-phenyl-2,3-dihydro-1-(3-fluorobenzyl)-1H-1,4-benzodiazepin-2-one | 431.1 |
| C-B | Benzyl bromide (Aldrich) | 3-(L-alaninyl)amino-5-phenyl-2,3-dihydro-1-(benzyl)-1H-1,4-benzodiazepin-2-one | 513.2 |
| C-C | tert-Butylbenzyl bromide (Aldrich) | 3-(L-alaninyl)amino-5-phenyl-2,3-dihydro-1-(4-tert-butylbenzyl)-1H-1,4-benzodiazepin-2-one | 469.2 |
| C-D | 2-Bromoethylcyclohexane (Fairfield) | 3-(L-alaninyl)amino-5-phenyl-2,3-dihydro-1-(2-cyclohexylethyl)-1H-1,4-benzodiazepin-2-one | 433.2 |
| C-E | 1-Bromo-3,3-dimethylbutane (Wiley) | 3-(L-alaninyl)amino-5-phenyl-2,3-dihydro-1-(3,3-dimethylbutyl)-1H-1,4-benzodiazepin-2-one | 407.2 |
| C-F | Methyl alpha-bromophenylacetate (Aldrich) | 3-(L-alaninyl)amino-5-phenyl-2,3-dihydro-1-(1-methoxycarbonyl-1-phenylmethyl)-1H-1,4-benzodiazepin-2-one | 471.2 |
| C-G | 1-Bromo-2-ethyl-butane (Aldrich) | 3-(L-alaninyl)amino-5-phenyl-2,3-dihydro-1-(2-ethylbutyl)-1H-1,4-benzodiazepin-2-one | 407.2 |
| C-H | Bromomethylcyclohexane (Aldrich) | 3-(L-alaninyl)amino-5-phenyl-2,3-dihydro-1-(cyclohexylmethyl)-1H-1,4-benzodiazepin-2-one | 419.2 |
| C-I | 2-(Bromoethyl)benzene (Aldrich) | 3-(L-alaninyl)amino-5-phenyl-2,3-dihydro-1-(2-phenylethyl)-1H-1,4-benzodiazepin-2-one | 427.2 |
| C-J | 3-(Bromopropyl)benzene (K and K Laboratories) | 3-(L-alaninyl)amino-5-phenyl-2,3-dihydro-1-(3-phenylpropyl)-1H-1,4-benzodiazepin-2-one | 441.2 |
| C-K | N-(2-Bromo-ethyl)phthalimide (Aldrich) | 3-(L-alaninyl)amino-5-phenyl-2,3-dihydro-1-(2-(N-phthalimidyl)ethyl)-1H-1,4-benzodiazepin-2-one | 496.2 |
| C-L | 2-Phenylbenzyl bromide (Aldrich) | 3-(L-alaninyl)amino-5-phenyl-2,3-dihydro-1-(2-biphenylmethyl)-1H-1,4-benzodiazepin-2-one | 489.2 |
| C-M | Tetrahydrofurfuryl bromide (Lancaster) | 3-(L-alaninyl)amino-5-phenyl-2,3-dihydro-1-((2-tetrahydrofuranyl)methyl)-1H-1,4-benzodiazepin-2-one | 407.2 |
| C-N | 2-Bromomethyl-1,4-benzodioxane | 3-(L-alaninyl)amino-5-phenyl-2,3-dihydro-1-(2-(1,4- | 471.2 |

TABLE C-A-continued

Intermediates

| Ex. | Alkyl Halide | Intermediate | MS |
|---|---|---|---|
| | (Acros) | benzodioxanyl)methyl)-1H-1,4-benzodiazepin-2-one | |
| C-O | 3-Bromomethyl-5-chlorobenzo[b]thiophene (Maybridge) | 3-(L-alaninyl)amino-5-phenyl-2,3-dihydro-1-((3-(5-chlorobenzo[b]thienyl))methyl)-1H-1,4-benzodiazepin-2-one | 503.1 |
| C-P | 1-Bromopinacolone (Lancaster) | 3-(L-alaninyl)amino-5-phenyl-2,3-dihydro-1-(3,3-dimethyl-2-oxopropyl)-1H-1,4-benzodiazepin-2-one | 421.1 |
| C-Q | 5-(Bromomethyl)benzofurazan (Maybridge) | 3-(L-alaninyl)amino-5-phenyl-2,3-dihydro-1-(5-benzofurazanylmethyl)-1H-1,4-benzodiazepin-2-one | 455.2 |
| C-R | 3-Phenoxypropyl bromide (Aldrich) | 3-(L-alaninyl)amino-5-phenyl-2,3-dihydro-1-(3-phenoxypropyl)-1H-1,4-benzodiazepin-2-one | 457.2 |
| C-S | 6-(Bromomethyl)-2-(trifluoromethyl)-quinoline (Maybridge) | 3-(L-alaninyl)amino-5-phenyl-2,3-dihydro-1-(6-(2-trifluoromethylquinolinyl)methyl)-1H-1,4-benzodiazepin-2-one | 533.2 |
| C-T | 1-Bromo-2-methylbutane (Aldrich) | 3-(L-alaninyl)amino-5-phenyl-2,3-dihydro-1-(2-methylbutyl)-1H-1,4-benzodiazepin-2-one | 393.2 |
| C-U | Ethyl bromide (Aldrich) | 3-(L-alaninyl)amino-5-phenyl-2,3-dihydro-1-(ethyl)-1H-1,4-benzodiazepin-2-one | 351.2 |
| C-V | 3-Picolyl chloride hydrochloride (Aldrich) | 3-(L-alaninyl)amino-5-phenyl-2,3-dihydro-1-(3-pyridylmethyl)-1H-1,4-benzodiazepin-2-one | 414.1 |
| C-W | 1-(2-Chloroacetyl)-indoline (Maybridge) | 3-(L-alaninyl)amino-5-phenyl-2,3-dihydro-1-(2-oxo-2-(N-indolinyl)ethyl)-1H-1,4-benzodiazepin-2-one | 482.2 |
| C-Y | 4-(Chloromethyl)-3,5-dimethylisoxazole (Aldrich) | 3-(L-alaninyl)amino-5-phenyl-2,3-dihydro-1-((4-(3,5-dimethyl)isoxazolyl)methyl)-1H-1,4-benzodiazepin-2-one. | 432.2 |
| C-Z | 2-Bromoethyl methyl ether (Aldrich) | 3-(L-alaninyl)amino-5-phenyl-2,3-dihydro-1-(2-methoxyethyl)-1H-1,4-benzodiazepin-2-one | 381.2 |

EXAMPLE C-AA

Synthesis of (S)-3-(L-phenylglycinyl)amino-2,3-dihydro-1-methyl-5-phenyl-1H-1,4-benzodiazepin-2-one

Step A

Synthesis of (S)-3-(N'-(tert-Butoxycarbonyl-L-phenylglycinyl)amino-2,3-dihydro-1-methyl-5-phenyl-1H-1,4-benzodiazepin-2-one To a solution of triethyl amine (519 uL, 3.8 mmol) and (S)-3-amino-5-phenyl-2-oxo-1,4-benzodiazepine (1.0 g, 3.8 mmol) (prepared according to the procedure of M. G. Bock et al., *J. Org. Chem.* 1987, 52, 3232–3239, incorporated herein by reference) in 100 mL of anhydrous methylene chloride at −20° C. was added N-Boc-L-phenylglycine fluoride (Carpino et al, J. Org. Chem. 1991, 56, 2611–2614, incorporated herein by reference) in one portion. The reaction mixture was stirred for 15 min. and quenched with saturated aqueous bicarbonate (10 mL). The layers were seperated, the organic layer washed sequentially with saturated aqueous bicarbonate, water and brine and then dried over sodium sulfate. Purification of the crude product using silica gel chromatography (10–50% ethyl acetate/hexane) gave 1.3 g (69%) of a hydroscopic white foam.

NMR data was as follows:
$^1$H NMR (300 MHz, CDCl$_3$): δ=1.35 (br s, 9H), 3.41 (s, 3H), 5.30–5.45 (m, 2H), 5.75–5.95 (m, 1H), 7.15–7.75 (m, 15H).

IR (CDCl$_3$): 1709.7, 1676.6, 1489, 1166.3 cm$^{-1}$.

IEX MS (M+1): 498.0.

Step B

Synthesis of (S)-3-(L-phenylglycinyl)amino-2,3-dihydro-1-methyl-5-phenyl-1H-1,4-benzodiazepin-2-one (S)-3-(N'-(tert-Butoxycarbonyl)-L-phenylglycinyl)amino-2,3-dihydro-1-methyl-5-phenyl-1H-1,4-benzodiazepin-2-one (1.27 g, 2.55 mmol) was added to 50 mL of a stirring solution of 15% TFA in methylene chloride in one portion. After stirring 1 h, the reaction mixture was concentrated under reduced pressure and the residue dissolved in 100 mL of methylene chloride. This solution was washed twice with saturated sodium bicarbonate, once with brine and then dried over sodium sulfate. Purification of the crude product using silica gel column chromatography (5–10% methanol/methylene chloride) gave 743 mg (73%) of a very light green foam.

NMR data was as follows:
$^1$H NMR (CDCl$_3$): δ=2.05 (br s, 1 H), 3.45 (s, 3 H), 5.51 (d, J=8.39 Hz, 1H), 7.15–7.70 (m, 14 H), 8.60 (d, J=830 Hz, 1H).

IR (CDCl$_3$): 1673.3, 1601.1, 1506.1 cm$^{-1}$.

IEX MS (M+1): 399.2.

EXAMPLE C-AB

Synthesis of 3-(L-Alaninyl)amino-2,3-dihydro-1-(2-oxo-2-phenylethyl)-5-phenyl-1H-1,4-benzodiazepin-2-one

Step A

Synthesis of 3-(Benzoxycarbonyl)amino-2,3-dihydro-1-(2-oxo-2-phenylethyl)-5-phenyl-1H-1,4-benzodiazepin-2-one To a solution of 3-(Benzoxycarbonyl)amino-2,3-dihydro-5-phenyl-1H-1,4-benzodiazepin-2-one (Bock, M. G. et al, *Tetrahedron Lett.* 1987, 28, 939, incorporated herein by reference; 4.0 g, 10.4 mmol) in 40 mL of anhydrous DMF at 0° C. was added potassium tert-butoxide (1.51 g, 13.5 mmol) in one portion. The reaction mixture was stirred 20 min. and α-bromoacetophenone (Lancaster; Windham, N.H.; 2.9 g, 14.6 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–5% ethyl acetate/methylene chloride) gave 4.2 g (81%) of an off white foam.

NMR data was as follows:
$^1$H NMR (300 MHz, CDCl$_3$): δ=5.16 (s, 2 H), 5.34 (s, 2 H), 5.50 (d, J=8.33 Hz, 1H), 6.70 (d, J=8.28 Hz, 1H), 7.20–7.70 (m, 12 H), 7.91 (d, J=7.54 Hz, 2 H).

IR (CHCl$_3$): 1706.04, 1685.3, 1505.9, 1489.1, 1450.3, 1244.7 cm$^{-1}$.

IEX MS (M+1): 504.3.

Step B

Synthesis of 3-Amino-2,3-dihydro-1-(2-oxo-2-phenylethyl)-5-phenyl-1H-1,4-benzodiazepin-2-one A solution of 3-(Benzoxycarbonyl)amino-2,3-dihydro-1-(2-oxo-2-phenylethyl)-5-phenyl-1H-1,4-benzodiazepin-2- one (3.7 g, 7.36 mmol) in 100 mL of anhydrous methylene chloride was cooled to 0° C. under nitrogen. A stream of anhydrous HBr gas was then bubbled through this solution for 1 h. The bubbler was removed and the reaction was warmed to room temperature under nitrogen. After stirring 1 h the reaction was concentrated under vacuum and the residue was redissolved in 20 mL of methylene chloride. The crude HBr salt of the product was precipitated from solution using 300 mL of anhydrous ether and collected by filtration as a light yellow solid. After washing with ether, the solid was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 2.27 g of the product was obtained as an orange foam which was carried on without further purification.

NMR data was as follows:

$^1$H NMR (300 MHz, CDCl$_3$): δ=2.60 (br s, 2 H), 4.72 (s, 1H), 5.34 (s, 2 H), 7.10–7.70 (m, 12 H), 7.91 (d, J=7.60 Hz, 2 H).

IEX MS (M+1): 370.2

Step C

Synthesis of 3-(N'-(tert-Butoxycarbonyl)-L-alaninyl)amino-2,3-dihydro-1-(2-oxo-2-phenylethyl)-5-phenyl-1H-1,4-benzodiazepin-2-one To a solution of HOBt-H$_2$O (697 mg, 5.16 mmol), N,N-diisopropylethylamine (900 uL, 5.16 mmol) and N-t-BOC-L-alanine (975 mg, 5.16 mmol) in 20 mL of anhydrous THF at 0° C. was added 1-(3-dimethylaminopropyl)-3-ethyl carbodiimide hydrochloride (EDCI; 986 mg, 5.16 mmol) in one portion. After stirring 5 min., a solution of 3-amino-2,3-dihydro-1-(2-oxo-2-phenylethyl)-5-phenyl-1H-1,4-benzodiazepin-2-one (2.0 g, 5.43 mmol) in 20 mL of anhydrous THF was added via syringe and the reaction mixture was warmed to room temperature and stirred overnight. The reaction mixture was diluted with 200 mL methylene chloride, extracted sequentially with 10% citric acid, saturated sodium bicarbonate, water and brine and then dried over sodium sulfate. Purification of the crude product using silica gel chromatography (10%–30% ethyl acetate/methylene chloride) gave 2.59 g (93%) of a white foam.

NMR data was as follows:

$^1$H NMR (300 MHz, CDCl$_3$): δ=1.30–1.60 (m, 12 H), 4.35 (br s, 1H), 5.00–5.50 (m, 3 H), 5.65–5.70 (m, 1H), 7.15–7.65 (m, 12 H), 7.70–7.80 (m, 1 H), 7.85–7.95 (m, 1H).

IR (CHCl$_3$): 1705.8, 1678.8, 1488.7, 1450.2, 1230.4, 1164.4 cm$^{-1}$.

IEX MS (M+1): 541.2.

Step D

Synthesis of 3-(L-Alaninylamino-2,3-dihydro-1-(2-oxo-2-phenylethyl)-5-phenyl-1H-1,4-benzodiazepin-2-one 3-(N'-(tert-Butoxycarbonyl)-L-alaninyl)amino-2,3-dihydro-1-(2-oxo-2-phenylethyl)-5-phenyl-1H-1,4-benzodiazepin-2-one (2.5 g, 4.63 mmol) was added to 100 mL of a stirring solution of 15% TFA/methylene chloride in one portion. After stirring 2 h, the reaction mixture was concentrated under reduced pressure and the residue was dissolved in 150 mL of methylene chloride. This solution was washed twice with saturated sodium bicarbonate, once with brine and then dried over sodium sulfate. Purification of the crude product using silica gel column chromatography (1–10% methanol/methylene chloride) gave 1.91 g (94%) of the title compound as a white foam.

NMR data was as follows:

$^1$H NMR (300 MHz, CDCl$_3$): δ=1.30–1.50 (m, 3 H), 1.80–2.20 (br s, 2 H), 3.55–3.75 (m, 1H), 5.20–5.45 (m, 2 H), 5.67 (t, J=7.48 Hz, 1H), 7.20–7.65 (m, 12 H), 7.90 (d, J=7.7 Hz, 2 H), 8.80 (dd, J$_1$=25.09 Hz, J$_2$=8.33 Hz, 1H).

EX MS (M+1): 441.2.

EXAMPLE C-AC

Synthesis of 3-(L-Alaninyl)amino-2,3-dihydro-1-(4,4,4-trifluorobutyl)-5-phenyl-1H-1,4-benzodiazepin-2-one Step A Synthesis of 3-(Benzoxycarbonyl)amino-2,3-dihydro-1-(4,4,4-trifluorobutyl)-5-phenyl-1H-1,4-benzodiazepin-2-one To a solution of 3-(benzoxycarbonyl)amino-2,3-dihydro-5-phenyl-1H-1,4-benzodiazepin-2-one (3.7 g, 9.61 mmol) in 40 mL of anhydrous DMF at 0° C. was added potassium tert-butoxide (1.6 g, 14.4 mmol) in one portion. The reaction mixture was stirred 20 min. and 4,4,4-trifluoro-1-bromobutane (Lancaster; Windham, N.H.; 2.6 g, 13.4 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–3% ethyl acetate/methylene chloride) gave 1.52 g (32%) of an off white foam.

NMR data was as follows:

$^1$H NMR (300 MHz, CDCl$_3$): δ=1.50–2.10 (m, 4 H), 3.70–3.90 (m, 1 H), 4.35–4.55 (m, 1 H), 5.15 (s, 2 H), 5.33 (d, J=8.47 Hz, 1 H), 6.67 (d, J=8.40 Hz, 1 H), 7.2–7.70 (m, 14 H).

IR (CHCl$_3$): 1720.4, 1683.0, 1604.8, 1505.5, 1451.1, 1323.9, 1254.5, 1148.4 cm$^{-1}$.

IEX MS (M+1): 496.3.

Step B

Synthesis of 3-Amino-2,3-dihydro-1-(4,4,4-trifluorobutyl)-5-phenyl-1H-1,4-benzodiazepin-2-one A solution of 3-(benzoxycarbonyl)amino-2,3-dihydro-1-(4,4,4-trifluorobutyl)-5-phenyl-1H-1,4-benzodiazepin-2-one (1.42 g, 2.87 mmol) in 50 mL of anhydrous methylene chloride was cooled to 0° C. under nitrogen. A stream of anhydrous HBr gas was slowly bubbled through the solution for 1 h. The bubbler was removed and the reaction was warmed to room temperature under nitrogen. After stirring for 1 h, the reaction was concentrated under vacuum and the residue was redissolved in 10 mL of methylene chloride. The crude HBr salt of the product was precipitated from solution using 90 mL of anhydrous ether and collected by filtration. After washing with ether, the HBr salt was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 1.06 g (100%) of the product was obtained as a white foam which was carried on without further purification. NMR data was as follows:

$^1$H NMR (300 MHz, CDCl$_3$): δ=1.60–2.10 (m, 4 H), 2.76 (br s, 2 H), 3.75–3.85 (m, 1H), 4.40–4.60 (m, 2 H), 7.20–7.70 (m, 9 H).

IEX MS (M+1): 362.1.

Step C

Synthesis of 3-(N'-(tert-Butoxycarbonyl)-L-alaninyl)amino-2,3-dihydro-1-(4,4,4-trifluorobutyl)-5-phenyl-1H-1,4-benzodiazepin-2-one To a solution of HOBt-H$_2$O (373 mg, 2.76 mmol), N,N-diisopropylethylamine (481 uL, 2.76 mmol) and N-t-BOC-L-alanine (522 mg, 2.76 mmol) in 10 mL of anhydrous THF at 0° C. was added 1-(3-dimethylaminopropyl)-3-ethyl carbodiimide hydrochloride (EDCI; 527 mg, 2.76 mmol) in one portion. After stirring 5 min., a solution of 3-amino-2,3-dihydro-1-(4,4,4-trifluorobutyl)-5-phenyl-1H-1,4-benzodiazepin-2-one (1.05 g, 2.91 mmol) in 10 mL of anhydrous THF was added via syringe and the reaction mixture was warmed to room temperature and stirred overnight. The reaction mixture was diluted with 100 mL methylene chloride, extracted sequentially with 10% citric acid, saturated sodium bicarbonate, water and brine and then dried over sodium sulfate. Purification of the crude product using silica gel chromatography (10%–30% ethyl acetate/methylene chloride) gave 1.28 g (83%) of a white foam.

NMR data was as follows:

$^1$H NMR (300 MHz, CDCl$_3$): δ=1.40–2.10 (m, 16 H), 3.70–3.85 (m, 1 H), 4.30–4.55 (m, 2 H), 5.10 (br s, 1H), 5.45–5.55 (m, 1 H), 7.25–7.80 (m, 10 H).

IR (CDCl$_3$): 1676.6, 1605.2, 1488.6, 1450.9, 1393.2, 1338.7, 1324.9, 1253.8, 1150.4 cm$^{-1}$.

IEX MS (M+1): 533.1.

Step D

Synthesis of 3-(L-Alaninyl)amino-2,3-dihydro-1-(4,4,4-trifluorobutyl)-5-phenyl-1H-1,4-benzodiazepin-2-one 3-(N'-(tert-Butoxycarbonyl)-L-alaninyl)amino-2,3-dihydro-1-(4,4,4-trifluorobutyl)-5-phenyl-1H-1,4-benzodiazepin-2-one (1.21 g, 2.27 mmol) was added to 50 mL of a stirring solution of 15% TFA/methylene chloride in one portion. After stirring 2 h, the reaction mixture was concentrated under reduced pressure and the residue was dissolved in 100 mL of methylene chloride. This solution was washed twice with saturated sodium bicarbonate, once with brine and then dried over sodium sulfate. Purification of the crude product using silica gel column chromatography (1–5% methanol/methylene chloride) gave 670 mg (68%) of a light pink foam.

NMR data was as follows:

$^1$H NMR (300 MHz, CDCl$_3$): δ=1.43 (t, J=7.0 Hz, 3 H), 1.60–2.20 (m, 7 H), 3.60–3.85 (m, 2 H), 4.35–4.55 (m, 1H), 5.51 (dd, J$_1$=8.36 Hz, J$_2$=2.48 Hz, 1 H), 7.20–7.70 (m, 9 H), 8.80 (dd, J$_1$=27.73 Hz, J$_2$=8.34 Hz, 1 H).

IEX MS (M+1): 433.2.

EXAMPLE C-AE

Synthesis of 3-[(L-Alaninyl)amino]-2,3-dihydro-1-methyl-5-(2-pyridyl)-1H-1,4-benzodiazepin-2-one Step A Synthesis of 3-Amino-2,3-dihydro-1-methyl-5-(2-pyridyl)-1H-1,4-benzodiazepin-2-one The title compound was synthesized as described in Synth. Commun., 26(4), 721–727 (1996), incorporated herein by reference.

Step B

Synthesis of 3-[(N-tert-Butoxycarbonyl-L-alaninyl)amino]-2,3-dihydro-1-methyl-5-(2-pyridyl)-1H-1,4-benzodiazepin-2-one A solution of L-Boc-alanine (1.74 g, 9.20 mmol), HOBt monohydrate (1.24 g, 9.20 mmol), diisopropylethylamime (1.6 mL, 9.20 mmol) and CH$_2$Cl$_2$ (30 mL) was purged with nitrogen and cooled in an ice bath. To the cold solution was added 1-(3-dimethylaminopropyl)-3-ethylcarbodiimide hydrochloride (1.76 g, 9.20 mmol) followed by a solution of 3-amino-2,3-dihydro-1-methyl-5-(2-pyridyl)-1H-1,4-benzodiazepin-2-one (2.45 g, 9.20 mmol) dissolved in CH$_2$Cl$_2$ (15 mL). The cold bath was removed and the solution stirred overnight at room temperature. The reaction mixture was extracted with H$_2$O, 0.1 N aq. citric acid, 5% aq. NaHCO$_3$, and brine. The remaining CH$_2$Cl$_2$ solution was dried (MgSO$_4$) and concentrated to a tan foam. The title compound was crystallized from CH$_2$Cl$_2$/EtOAc to give 3.47 g (86% yield) of white crystals, mp. 228–229° C.

Anal. Calcd for C$_{23}$H$_{27}$N$_5$O$_4$: C, 63.14; H, 6.22; N, 16.01. Found: C, 63.25; H, 6.15; N, 15.95. MS (FD$^+$) 437 m/z.

Step C

Synthesis of 3-[(L-Alaninyl)amino]-2,3-dihydro-1-methyl-5-(2-pyridyl)-1H-1,4-benzodiazepin-2-one A solution of 3-[(N-tert-butoxycarbonyl-L-alaninyl)amino]-2,3-dihydro-1-methyl-5-(2-pyridyl)-1H-1,4-benzodiazepin-2-one (3.42 g, 7.82 mmol) in CH$_2$Cl$_2$ (90 mL) was cooled in an ice bath and treated with TFA (13.2 mL, 172 mmol). The cold bath was removed and the solution stirred at room temperature for four hours. The reaction mixture was washed with 1 M aq. K$_2$CO$_3$ and the aqueous portion back-extracted with CH$_2$Cl$_2$. The combined extracts were washed with H$_2$O, dried (MgSO$_4$) and concentrated to obtain 1.75 g (66% yield) of the title compound as an off-white foam. MS (IS$^+$) 338 (m/e).

$^1$HNMR (CDCl$_3$): δ=8.76–8.86 (1H, m), 8.63 (1H, m), 8.17 (1H, m), 7.82 (2H, m), 7.60 (1H, m), 7.41 (3H, m), 5.60 (1H, m), 3.63 (1H, m), 3.49 (3H, s), 1.66 (2H, broad), 1.45 (3H, m).

EXAMPLE C-AF

Synthesis of 3-[(L-Alaninyl)amino]-2,3-dihydro-1-(2-N,N-diethylaminoethyl-5-(2-pyridyl)-1H-1,4-benzodiazepin-2-one Step A Synthesis of 3-Amino-2,3-dihydro-1-(2-N,N-diethylaminoethyl)-5-(2-pyridyl)-1H-1,4-benzodiazepin-2-one The title compound was synthesized as described in Synth. Commun., 26(4), 721–727 (1996), incorporated herein by reference.

Step B

Synthesis of 3-[(N-tert-Butoxycarbonyl-L-alaninyl) amino]-2,3-dihydro-1-(2-N,N-diethylaminoethyl)-5-(2-pyridyl)-1H-1,4-benzodiazepin-2-one A solution of L-Boc-alanine (1.80 g, 9.50 mmol), HOBt monohydrate (1.28 g, 9.50 mmol), diisopropylethylamime (1.65 mL, 9.50 mmol) and $CH_2Cl_2$ (40 mL) was purged with nitrogen and cooled in an ice bath. To the cold solution was added 1-(3-dimethylaminopropyl)-3-ethylcarbodiimide hydrochloride (1.82 g, 9.50 mmol) followed by a solution of 3-amino-2,3-dihydro-1-(2-N,N-diethylaminoethyl)-5-(2-pyridyl)-1H-1,4-benzodiazepin-2-one (3.34 g, 9.50 mmol) dissolved in $CH_2Cl_2$ (25 mL). The cold bath was removed and the solution stirred overnight at room temperature. The reaction mixture was extracted with $H_2O$, 5% aq. $NaHCO_3$, and brine. The remaining $CH_2Cl_2$ solution was dried ($MgSO_4$) and concentrated to a tan foam. The title compound was isolated via column chromatography (2% $MeOH/CH_2Cl_2$ to 10% $MeOH/CH_2Cl_2$) to give 3.53 g (71% yield) of yellow foam.

MS (FD$^+$) 522 (m/z).

$^1$HNMR ($CDCl_3$): δ=8.62 (1H, d), 8.11 (1H, m), 7.80 (2H, m), 7.59 (2H, m), 7.32–7.45 (2H, m), 5.54 (1H, m), 5.02–5.18 (1H, m), 4.38 (1H, m), 4.20 (1H, m), 3.83 (1H, m), 2.62 (2H, t), 2.44 (4H, m), 1.40–1.56 (12H, m), 0.88 (6H, m).

Step C

Synthesis of 3-[(L-Alaninyl)amino]-2,3-dihydro-1-(2-N,N-diethylaminoethyl)-5-(2-pyridyl)-1H-1,4-benzodiazepin-2-one The title compound was synthesized using the procedure described in Example C-AE, Step C. A solution of 3-[(N-tert-butoxycarbonyl-L-alaninyl)amino]-2,3-dihydro-1-(2-N,N-diethylaminoethyl)-5-(2-pyridyl)-1H-1,4-benzodiazepin-2-one (3.52 g, 6.73 mmol) was treated with TFA (11.4 mL, 148 mmol) to give 2.61 g (92% yield) the title compound as a light yellow foam.

MS (IS$^+$) 423 (m/e).

$^1$HNMR ($CDCl_3$): δ=8.78–8.93 (1H, m), 8.62 (1H, d), 8.11 (1H, m), 7.80 (2H, m), 7.58 (2H, m), 7.39 (2H, m), 5.58 (1H, m), 4.22 (1H, m), 3.88 (1H, m), 3.61 (1H, m), 2.67 (2H, t), 2.49 (4H, m), 1.73 (2H, broad), 1.42 (3H m), 0.91 (6H, m).

EXAMPLE C-AG

Synthesis of 3-[(L-Alaninyl)amino]-2,3-dihydro-1-(3,3-dimethyl-2-oxobutyl)-5-(2-pyridyl)-1H-1,4-benzodiazepin-2-one

Step A

Synthesis of 3-Amino-2,3-dihydro-1-(3,3-dimethyl-2-oxobutyl)-5-(2-pyridyl)-1H-1,4-benzodiazepin-2-one The title compound was synthesized as described in Synth. Commun., 26(4), 721–727 (1996), incorporated herein by reference.

Step B

Synthesis of 3-[(N-tert-Butoxycarbonyl-L-alaninyl) amino]-2,3-dihydro-1-(3,3-dimethyl-2-oxobutyl)-5-(2-pyridyl)-1H-1,4-benzodiazepin-2-one A solution of L-Boc-alanine (1.57 g, 8.33 mmol), HOBt monohydrate (1.13 g, 8.33 mmol), diisopropylethylamime (1.45 mL, 8.33 mmol) and $CH_2Cl_2$ (40 mL) was purged with nitrogen and cooled in an ice bath. To the cold solution was added 1-(3-dimethylaminopropyl)-3-ethylcarbodiimide hydrochloride (1.60 g, 8.33 mmol) followed by a solution of 3-amino-2,3-dihydro-1-(3,3-dimethyl-2-oxobutyl)-5-(2-pyridyl)-1H-1,4-benzodiazepin-2-one (2.92 g, 8.33 mmol) dissolved in $CH_2Cl_2$ (25 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a yellow foam. The title compound was isolated via column chromatography (20% EtOAc/hexanes to 60% EtOAc/hexanes) to give 4.19 g (96% yield) of light yellow foam.

MS (FD+) 521 (m/z).

$^1$HNMR ($CDCl_3$): δ=8.65 (1H, t), 8.17 (1H, t), 7.90 (1H, t), 7.71–7.85 (1H, m), 7.54 (1H, m), 7.44 (1H, t), 7.37 (1H, d), 7.24–7.32 (1H, m), 7.14 (1H, m), 5.67 (1H, dd), 5.18 (1H, broad), 4.93–5.07 (1H, m), 4.50–4.64 (1H, m), 4.38 (1H, broad), 1.42–1.51 (12H, m), 1.26 (9H, d).

Step C

Synthesis of 3-[(L-Alaninyl)amino]-2,3-dihydro-1-(3,3-dimethyl-2-oxobutyl)-5-(2-pyridyl)-1H-1,4-benzodiazepin-2-one The title compound was synthesized using the procedure described in Example C-AE, Step C. A solution of 3-[(N-tert-butoxycarbonyl-L-alaninyl)amino]-2,3-dihydro-1-(3,3-dimethyl-2-oxobutyl)-5-(2-pyridyl)-1H-1,4-benzodiazepin-2-one (4.18 g, 8.01 mmol) was treated with TFA (13.6 mL, 176 mmol) to give 3.14 g (93% yield) the title compound as an off-white foam.

MS (IS$^+$) 422 (m/e).

$^1$HNMR ($CDCl_3$) δ8.85–8.99 (1H, m), 8.68 (1H, d), 8.20 (1H, t), 7.87 (1H, t), 7.58 (1H, t), 7.42 (2H, m), 7.30 (1H, t), 7.17 (1H, d), 5.72 (1H, m 5.08 (1H, d), 4.60 (1H, d), 3.66 (1H, m), 1.47 (3H, m), 1.28 (9H, m).

EXAMPLE C-AH

Synthesis of 3-[(L-Alaninyl)amino]-2,3-dihydro-1-methyl-5-(2-thiazyl)-1H-1,4-benzodiazepin-2-one

Step A

Synthesis of 3-Amino-2,3-dihydro-1-methyl-5-(2-thiazyl)-1H-1,4-benzodiazepin-2-one The title compound was synthesized in a manner similar to the procedure described in Synth. Commun., 26(4), 721–727 (1996), incorporated herein by reference, starting with 2-(2-aminobenzoyl)thiazole (prepared as described in Tetrahedron, 51(3), 773–786, (1995), incorporated herein by reference).

MS (IS$^+$) 273 (m/e).

$^1$HNMR ($CDCl_3$): δ=7.83–7.94 (2H, m), 7.61 (1H, t), 7.50 (1H, d), 7.34 (2H, m), 4.60 (1H, s), 3.46 (3H, s), 1.97 (2H, broad).

Step B

Synthesis of 3-[(N-tert-Butoxycarbonyl-L-alaninyl) amino]-2,3-dihydro-1-methyl-5-(2-thiazyl)-1H-1,4-benzodiazepin-2-one A solution of L-Boc-alanine (1.85 g, 9.77 mmol), HOBt monohydrate (1.32 g, 9.77 mmol), diisopropylethylamime (1.70 mL, 9.77 mmol) and $CH_2Cl_2$ (30 mL) was purged with nitrogen and cooled in an ice bath. To the cold solution was added 1-(3-dimethylaminopropyl)-3-ethylcarbodiimide hydrochloride (1.87 g, 9.77 mmol) followed by a solution of 3-amino-2,3-dihydro-1-methyl-5-(2-thiazyl)-1H-1,4-benzodiazepin-2-one (2.66 g, 9.77 mmol) dissolved in $CH_2Cl_2$ (20 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a light yellow foam. The title compound was crystallized from EtOAc/hexane to give 3.22 g (74% yield) of white crystals, mp. 196–197° C.

Anal. Calcd for $C_{21}H_{25}N_5O_4S$: C, 56.87; H, 5.68; N, 15.79. Found: C, 56.74; H, 5.75; N, 15.55.

MS ($IS^+$) 444 m/e.

Step C

Synthesis of 3-[(L-Alaninyl)amino]-2,3-dihydro-1-methyl-5-(2-thiazyl)-1H-1,4-benzodiazepin-2-one The title compound was synthesized using the procedure described in Example C-AE, Step C.

EXAMPLE C-AI

Synthesis of 3-[(L-Alaninyl)amino]-2,3-dihydro-1-methyl-5-(thiophen-2-yl)-1H-1,4-benzodiazepin-2-one Step A Synthesis of 3-Amino-2,3-dihydro-1-methyl-5-(2-thiophen-2-yl)-1H-1,4-benzodiazepin-2-one The title compound was synthesized in a manner similar to the procedure described in *Synth. Commun.*, 26(4), 721–727 (1996), incorporated herein by reference, starting with 2-(2-aminobenzoyl)thiophene (prepared as described in *Collect. Czech. Chem. Commun.*, 34(2), 468–478, (1969), incorporated herein by reference).

MS ($IS^+$) 272 (m/e).

$^1$HNMR ($CDCl_3$): δ=7.68 (1H, d), 7.60 (1H, t), 7.48 (1H, m), 7.35 (2H, d), 7.28 (1H, m), 7.15 (1H, d), 7.05 (1H, d), 4.50 (1H, broad), 3.45 (3H s), 2.26 (2H, broad).

Step B

Synthesis of 3-[(N-tert-Butoxycarbonyl-L-alaninyl)amino]-2,3-dihydro-1-methyl-5-(thiophen-2-yl)-1H-1,4-benzodiazepin-2-one The title compound was synthesized in a manner similar to the procedure described in Example C-AH, Step B.

MS ($IS^+$) 443 (m/e).

$^1$HNMR ($CDCl_3$): δ7.69 (1H, d), 7.61 (2H, m), 7.48 (1H, d), 7.27–7.42 (2H, m), 7.18 (1H, m), 7.05 (1H, m), 5.51 (1H, d), 5.13 (1H, broad), 4.36 (1H, broad), 3.44 (3H, s), 1.38–1.57 (12H, m).

Step C

Synthesis of 3-[(L-Alaninyl)amino]-2,3-dihydro-1-methyl-5-(thiophen-2-yl)-1H-1,4-benzodiazepin-2-one The title compound was synthesized in a manner similar to the procedure described in Example C-AE, Step C.

MS ($IS^+$) 343 (m/e).

$^1$HNMR ($CDCl_3$): δ=8.55 (1H, d), 7.68 (1H, d), 7.59 (1H, m), 7.48 (1H, d), 7.36 (1H, d), 7.31 (1H, d), 7.16 (1H, m), 7.04 (1H, t), 5.54 (1H, d 3.58 (1H, m), 3.45 (3H, s), 1.41 (3H, d).

EXAMPLE 5-A

Synthesis of 3-(L-Alaninyl)-amino-2,3-dihydro-1-methyl-5-phenyl-1H-1-benzazepin-2-one Step A Preparation of 1-phenyl-1-[2-N-(α-isopropylthio)-N'-(benzyloxycarbonyl)-glycinyl]-aminophenyl]ethylene A solution of α-(isopropylthio)-N-(benzyloxycarbonyl) glycine (1 eq; prepared according to Zoller, V. and D. Ben-Ishai, *Tetrahedron* 1975, 31, 863, incorporated herein by reference) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was re-cooled to 0° C. A solution of 1-phenyl-1-(2-aminophenyl)ethylene (0.9 eq.; Arienti, A. et al. *Tetrahedron* 1997, 53, 3795, incorporated herein by reference) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was purified via flash chromatography eluting with $CH_2Cl_2$ then 90:10 $CH_2Cl_2$/ethyl acetate giving a pale yellow oil.

$C_{27}H_{28}N_2O_3S$ (MW=460.60); mass spectroscopy ($MH^+$) 461.4.

Anal. Calcd for $C_{27}H_{28}N_2O_3S$: C, 70.41; H, 6.13; N, 6.08. Found: C, 70.42; H, 6.05; N, 6.05.

Step B

Preparation of 3-(benzyloxycarbonyl)-amino-2,3-dihydro-5-phenyl-1H-1-benzazepin-2-one A solution of 1-phenyl-1-[2-N-(α-isopropylthio)-N'-(benzyloxycarbonyl)-glycinyl-aminophenyl]ethylene (1 eq) in acetonitrile under nitrogen was treated with mercury(II) chloride (1.0 equiv.; Aldrich). A white precipitate formed immediately after the mercury(II) chloride had dissolved. The mixture was heated to reflux for 2.5 hours; an additional 0.05 equiv. of mercury(II) chloride was added and refluxing continued for 1 hour. The reaction was cooled to ambient temperature and the mercury salts were filtered washing with methylene chloride. The filtrate was concentrated in vacuo; the resultant residue was taken up in methylene chloride and filtered to remove additional mercury salts. The filtrate was washed with water. The aqueous layer was back-extracted five times with methylene chloride. The combined organics were allowed to stand overnight; additional mercury salts were filtered. The filtrate was dried over $Na_2SO_4$, filtered, and concentrated in vacuo. The crude oil was purified via flash chromatography eluting with a gradient form $CH_2Cl_2$ to 82:18 $CH_2Cl_2$/ethyl acetate giving a tan solid. The solid could be further purified by trituration with diethyl ether which provided a white solid.

$C_{24}H_{20}N_2O_3$ (MW=384.43); mass spectroscopy found (M+H) 385.1.

Step C

Preparation of 3-(benzyloxycarbonyl)-amino-2,3-dihydro-1-methyl-5-phenyl-1H-1-benzazepin-2-one Following General Procedure 4-A and using 3-(benzyloxycarbonyl)-amino-2,3-dihydro-5-phenyl-1H-1-benzazepin-2-one, the title intermediate was prepared as a white solid.

$C_{25}H_{22}N_2O_3$ (MW=398.4); mass spectroscopy found (M+H) 399.2.

Anal. Calcd for $C_{25}H_{22}N_2O_3$: C, 75.36; H, 5.57; N, 7.03. Found: C, 75.21; H, 5.57; N, 7.13.

Step D

Preparation of 3-amino-1,3-dihydro-1-methyl-5-phenyl-2H-1-benzazepin-2-one

Following General Procedure 4-B and using 3-(benzyloxycarbonyl)-amino-2,3-dihydro-1-methyl-5-phenyl-1H-1-benzazepin-2-one, the title intermediate was prepared as an amber oil which was used immediately in Step E.

Step E

Preparation of 3-[N'-(tert-butylcarbamate)-L-alaninyl]-amino-2,3-dihydro-1-methyl-5-phenyl-1H-1-benzazepin-2-one Following General Procedure D using N-Boc Alanine and 3-amino-1,3-dihydro-1-methyl-5-phenyl-2H-1-benzazepin-2-one, the title intermediate was prepared as a white solid.

$C_{25}H_{29}N_3O_4$ (MW=435.57); mass spectroscopy found (M+H) 436.3. $^1$H NMR (300 MHz, CDCl$_3$) d 7.54 (2H, d, J=4.6 Hz), 7.52–725 (18H, m), 5.90 (1H, d, J=5.3 Hz), 5.88 (1H, d, J=5.3 Hz), 5.1 (1H, bs), 4.9 (1H, bs), 4.60 (2H, m), 4.31 (2H, m), 3.48 (6H, s), 1.48 (9H, s), 1.46 (9H, s), 1.43 (3H, d, J=4.5 Hz), 1.40 (3H, d, J=4.1Hz).

Step F

Preparation of 3-(L-alaninyl)-amino-2,3-dihydro-1-methyl-5-phenyl-1H-1-benzazepin-2-one Following General Procedure 4-C using 3-[N'-(tert-butylcarbamate)-L-alaninyl]-amino-2,3-dihydro-1-methyl-5-phenyl-1H-1-benzazepin-2-one, the title intermediate was prepared as a white foam. No further purification was necessary.

$C_{20}H_{21}N_3O_2$ (MW=335.40); mass spectroscopy found (M+H) 336.2.

Anal. Calcd for $C_{20}H_{21}N_3O_2$: C, 71.62; H, 6.31; N, 12.53. Found: C, 71.78; H, 6.54; N, 12.22.

EXAMPLE 5-B

Synthesis of 3-(L-Alaninyl)-amino-2,3,4,5-tetrahydro-1-methyl-5-phenyl-1H-1-benzazepin-2-one

Step A

Preparation of 3-amino-2,3,4,5-tetrahydro-1-methyl-5-phenyl-2H-1-benzazepin-2-one A solution of 3-(benzyloxycarbonyl)-amino-2,3-dihydro-1-methyl-5-phenyl-1H-1-benzazepin-2-one (Example 5-A, Steps A–C) in methanol under nitrogen was treated with 10% palladium on carbon (0.4 equiv.). The reaction vessel was placed under a balloon of hydrogen and stirred for 3 hours. The reaction flask was flushed well with nitrogen and the reaction mixture filtered through celite washing with CH$_2$Cl$_2$. The filtrate was concentrated to a white foam.

$C_{17}H_{18}N_2O$ (MW=266.37); mass spectroscopy found (M+H) 267.1.

Anal. Calcd for $C_{17}H_{18}N_2O$: C, 76.66; H, 6.81; N, 10.52. Found: C, 76.56; H, 6.83; N, 10.38.

Step B

Preparation of 3-[N'-(tert-butylcarbamate)-L-alaninyl]-amino-2,3,4,5-tetrahydro-1-methyl-5-phenyl-1H-1-benzazepin-2-one Following General Procedure D using N-Boc Alanine and 3-amino-2,3,4,5-tetrahydro-1-methyl-5-phenyl-2H-1-benzazepin-2-one, the title intermediate was prepared as a white foam.

$C_{25}H_{31}N_3O_4$ (MW=437.59); mass spectroscopy found (M+H) 438.2.

Anal. Calcd for $C_{25}H_{31}N_3O_4$: C, 68.63; H, 7.14; N, 9.60. Found: C, 68.93; H, 7.13; N, 9.49.

Step C

Preparation of 3-(L-alaninyl)-amino-2,3,4,5-tetrahydro-1-methyl-5-phenyl-1H-1-benzazepin-2-one Following General Procedure 4-C using 3-[N'-(tert-butylcarbamate)-L-alaninyl]-amino-2,3,4,5-tetrahydro-1-methyl-5-phenyl-1H-1-benzazepin-2-one, the title intermediate was prepared as a white foam. No further purification was necesary.

$C_{20}H_{23}N_3O_2$ (MW=337.46); mass spectroscopy found (M+H) 338.2.

Anal. Calcd for $C_{20}H_{23}N_3O_2$: C, 71.19; H, 6.87; N, 12.45. Found: C, 71.38; H, 6.83; N, 12.51.

EXAMPLE 5-C

Synthesis of 3-(L-Alaninyl)-amino-2,3,4,5-tetrahydro-1-methyl-5-phenyl-1H-1-benzazepin-2-one

Step A

Preparation of 3-amino-2,3,4,5-tetrahydro-1-methyl-5-phenyl-2H-1-benzazepin-2-one To a flask containing 300 mL of freshly condensed liquid ammonia at −70° C. was added lithium metal (4.1 equiv.). The dark blue slurry was warmed to −45° C. and treated with a pre-cooled solution of 3-(benzyloxycarbonyl)-amino-2,3-dihydro-1-methyl-5-phenyl-1H-1-benzazepin-2-one (Example 4-AC, Steps A–C) in 30 mL distilled THF. After 10 min a solution of tert-butanol (4.0 equiv.) in distilled THF was added. After an additional 10 min the reaction was quenched with ammonium chloride. The cooling bath was removed and the ammonia allowed to evaporate overnight. The contents were partitioned between CH$_2$Cl$_2$ and saturated aqueous NaHCO$_3$. The organic phase was washed with brine, dried over Na$_2$SO$_4$, filtered, and concentrated. It was purified via liquid chromatography eluting with a gradient from 99:1 to 90:10 CH$_2$Cl$_2$/MeOH.

---

Anal. Calcd for $C_{24}H_{20}N_2O_3$·0.5 H$_2$O: C, 73.27; H, 5.38; N, 7.12. Found: C, 73.41; H, 5.13; N, 7.30.

$C_{17}H_{18}N_2O$ (MW=266.37); mass spectroscopy found (M+H) 267.0.

Step B

Preparation of 3-[N'-(tert-butylcarbamate)-L-alaninyl]-amino-2,3,4,5-tetrahydro-1-methyl-5-phenyl-1H-1-benzazepin-2-one Following General Procedure D using N-Boc-alanine and 3-amino-2,3,4,5-tetrahydro-1-methyl-5-phenyl-2H-1-benzazepin-2-one, the title intermediate was prepared as a white foam.

$C_{25}H_{31}N_3O_4$ (MW=437.59); mass spectroscopy found (M+H) 438.2.

Anal. Calcd for $C_{25}H_{31}N_3O_4$: C, 68.63; H, 7.14; N, 9.60. Found: C, 68.70; H, 7.15; N, 9.54.

Step C

Preparation of 3-(L-alaninyl)-amino-2,3,4,5-tetrahydro-1-methyl-5-phenyl-1H-1-benzazepin-2-one Following General Procedure 4-C using 3-[N'-(tert-butylcarbamate)-L-alaninyl]-amino-2,3,4,5-tetrahydro-1-methyl-5-phenyl-1H-1-benzazepin-2-one, the title intermediate was prepared as a white foam. No further purification was necessary.

$C_{20}H_{23}N_3O_2$ (MW=337.46); mass spectroscopy found (M+H) 338.2. Anal. Calcd for $C_{20}H_{23}N_3O_2$: C, 71.19; H, 6.87; N, 12.45. Found: C, 71.32; H, 6.57; N, 12.24.

E. CYCLIC KETONE DERIVATIVES

General Procedure 6-A

Jones Oxidation Procedure

The compound to be oxidized was stirred in acetone and the Jones reagent was added in portions until the starting material was consumed. The reaction mixture was quenched with isopropanol and the mixture was filtered through Celite and concentrated under reduced pressure. The residue was partitioned between ethyl acetate and water and the organic portion was dried over sodium sulfate and then concentrated under reduced pressure. The crude product was purified by silica gel chromatography and/or recrystallization.

General Procedure 6-B

Swern Oxidation Procedure

To a stirred mixture of oxalyl chloride (0.1.5 mL, 1.2 mmol) in 10 mL of dichloromethane cooled to −78° C. was added DMSO (0.106 mL, 1.5 mmol) and the mixture was stirred for 10 minutes. A solution of the alcohol (0.1828 g, 0.60 mmol) in 20 mL of chloroform was added dropwise. The reaction mixture was stirred at −78° C. for 2 hours, and then 0.5 mL (3.6 mmol) of triethylamine was added. Stirring was continued for 1 hour and then the mixture was allowed to warm to room temperature and stirring was continued at ambient temperature overnight. The mixture was then diluted with 50 mL of dichloromethane, washed with brine (3×), dried over magnesium sulfate, filtered and evaporated to dryness to give the crude product which as typically purified by column chromatography.

F. DIBENZAZEPINONE DERIVATIVES AND RELATED COMPOUNDS

General Procedure 7-A

Preparation of 5-Amino-7-alkyl-5,7-dihydro-6H-dibenz[b,d]azepin-6-one Derivatives

Step A

Following General Procedure 5-A and using 5,7-dihydro-6H-dibenz[b,d]azepin-6-one and an alkyl halide, the 7-alkyl-5,7-dihydro-6H-dibenz[b,d]azepin-6-one was prepared.

Step B

The 7-alkyl-5,7-dihydro-6H-dibenz[b,d]azepin-6-one (1 eq.) was dissolved in THF and isoamylnitrite (1.2 eq.) was added. The mixture was cooled to 0° C. in an ice bath. NaHMDS (1.1 eq., 1M in THF) was added dropwise. After stirring for 1 hour or until the reaction was complete, the mixture was concentrated then acidified with 1N HCl and extracted with EtOAc. The organic portion was dried and concentrated to yield a crude product which was purified by silica gel chromatography.

Step C

The resulting oxime was dissolved in EtOH/NH$_3$ (20:1) and hydrogenated in a bomb using Raney nickel and hydrogen (500 psi) at 100° C. for 10 hours. The resulting mixture was filtered and concentrated to provide an oil which was purified by silica gel chromatography to yield the title compound.

General Procedure 7-B

Preparation of Fluoro-substituted 5,7-dihydro-6H-dibenz[b,d]azepin-6-one Derivatives A modification of the procedure of Robin D. Clark et al. *Tetrahedron*, Vol. 49, No. 7, pp. 1351–1356, 1993, incorporated herein by reference, was used. Specifically, an appropriately substituted N-t-Boc-2-amino-2'-methylbiphenyl was dissolved in THF and cooled to −78° C. s-Butyl lithium (1.3M in cyclohexane, 2.2 eq.) was added slowly so that the temperature remained below −65° C. The resulting mixture was allowed to warm to −25° C. and was stirred at that temperature for 1 hour. The mixture was cooled to −78° C. Dry $CO_2$ was bubbled through the mixture for 30 seconds. The mixture was allowed to warm to ambient temperature then was carefully quenched with water. The mixture was concentrated under reduced pressure then was adjusted to pH 3 with 1N HCl. The mixture was extracted with EtOAc and the organic portion was dried and concentrated to yield a crude material. The crude material was dissolved in methanol and the solution was saturated with HCl. The mixture was heated at reflux for 12 hours then was allowed to cool. The mixture was concentrated to provide crude lactam which was purified by chromatography or crystallization.

General Procedure 7-C

Resolution of 5-Amino-7-methyl-5,7-dihydro-6H-dibenz[b,d]azepin-6-one

In a round bottom flask was added the racemic freebase amine (1.0 eq.) in methanol followed by di-p-toluoyl-D-tartaric acid monohydrate (1.0 eq.). The mixture was concentrated in vacuo to a residue and redissolved in a moderate volume of methanol and allowed to stir at room temperature open to the atmosphere (8–72 hours). The solid was removed by filtration. The enantiomeric excess was determined by chiral HPLC (Chiracel ODR) using 15% acetonitrile and 85% H$_2$O with 0.1% trifluoroacetic acid and a flow rate of 1.0 mL/min at 35° C. The resolved di-p-toluoyl-D-tartaric salt was then dissolved in EtOAc and saturated NaHCO$_3$ until pH 9–10 was reached. The layers were separated and the organic layer was washed again with saturated NaHCO$_3$, H$_2$O, and brine. The organic layer was dried over MgSO$_4$ and the drying agent was removed by filtration. The filtrate was concentrated in vacuo. The free amine was dissolved in MeOH and HCl (12M, 1.0 eq.) was added. The salt was concentrated in vacuo and the resulting film was triturated with EtOAc. The HCl salt was filtered and rinsed with EtOAc. The ee was determined by chiral HPLC.

EXAMPLE 7-A

Synthesis of 5-Amino-7-methyl-5,7-dihydro-6H-dibenz[b,d]azepin-6-one Hydrochloride

Step A

Synthesis of 7-Methyl-5,7-dihydro-6H-dibenz[b,d]azepin-6-one

A round bottom flask was charged with sodium hydride (0.295 g, 7.46 mmol) in 9.0 ml of DMF and treated with 5,7-dihydro-6H-dibenz[b,d]azepin-6-one (1.3 g, 6.22 mmol) (CAS #20011-90-9, prepared as described in Brown, et. al., *Tetrahedron Letters,* No. 8, 667–670, (1971) and references cited therein, which are incorporated herein by reference). After stirring at 60° C. for 1 h, the solution was treated with methyl iodide (1.16 ml, 18.6 mmol) and stirring continued for 17 h with the exclusion of light. After cooling, the reaction was diluted with $CH_2Cl_2/H_2O$, washed with $NaHSO_4$ solution, $H_2O$, and dried over $Na_2SO_4$. Evaporation and flash chromatography ($SiO_2$, $CHCl_3$) gave 0.885 g (63%) of the title compound as a colorless solid.

NMR data was as follows:

$^1$H-nmr ($CDCl_3$): δ=7.62 (d, 2H), 7.26–7.47 (m, 6H), 3.51 (m, 2H), 3.32 (s, 3H).

$C_{15}H_{13}NO$ (MW=223.27); mass spectroscopy (MH+) 223.

Anal. Calcd for $C_{15}H_{13}NO$; C, 80.69 H, 5.87 N, 6.27. Found: C, 80.11 H, 5.95 N, 6.23.

Step B

Synthesis of 7-Methyl-5-oximo-5,7-dihydro-6H-dibenz[b,d]azepin-6-one

The compound isolated above (0.700 g, 3.14 mmol) was dissolved in 20 ml of toluene and treated with butyl nitrite (0.733 ml, 6.28 mmol). The reaction temperature was lowered to 0° C. and the solution was treated with KHMDS (9.42 ml, 0.5 M) under $N_2$ atmosphere. After stirring for 1 h the reaction was quenched with a saturated solution of $NaHSO_4$, diluted with $CH_2Cl_2$ and separated. The organic layer was dried over $Na_2SO_4$ and the title compound purified by chromatography ($SiO_2$, 98:2 $CHCl_3/MeOH$) giving 0.59 g (80%) as a colorless solid.

$C_{15}H_{12}N_2O_2$ (MW=252.275); mass spectroscopy (MH+) 252.

Anal. Calcd for $C_{15}H_{12}N_2O_2$; C, 71.42 H, 4.79 N, 11.10. Found: C, 71.24 H, 4.69 N, 10.87.

Step C

Synthesis of 5-Amino-7-Methyl-5,7-dihydro-6H-dibenz[b,d]azepin-6-one Hydrochloride The oxime isolated above (0.99 g, 3.92 mmol) was hydrogenated in a Parr apparatus at 35 psi over 10% Pd/C (0.46 g) in 3 A ethanol. After 32 h the reaction mixture was filtered through a plug of celite, the filtrate evaporated to a foam and treated with a saturated solution of HCl (g) in $Et_2O$. The resulting colorless solid was filtered, rinsed with cold $Et_2O$ and vacuum dried to give 0.66 g (61%) of the title compound.

NMR data was as follows:

$^1$H-nmr (DMSOd6): δ=9.11 (bs, 3H), 7.78–7.41(m, 8H), 4.83 (s, 1H), 3.25 (s, 3H).

$C_{15}H_{14}N_2O$ HCl (MW=274.753); mass spectroscopy (MH+free base) 238.

Anal. Calcd for $C_{15}H_{14}N_2O$ HCl; C, 65.57 H, 5.50 N, 10.19 Found: C, 65.27 H, 5.67 N, 10.13.

EXAMPLE 7-B

Synthesis of (S)- and (R)-5-(L-Alaninyl)-amino-7-methyl-5,7-dihydro-6H-dibenz[b,d]azepin-6-one

Step A

Synthesis of (S)- and (R)-5-(N-Boc-L-Alaninyl)-amino-7-methyl-5,7-dihydro-6H-dibenz[b,d]azepin-6-one Boc-L-Alanine (0.429 g, 2.26 mmol) (Aldrich) was dissolved in THF and treated with HOBt (0.305 g, 2.26 mmol), and 5-amino-7-methyl-5,7-dihydro-6H-dibenz[b,d]azepin-6-one (0.45 g, 1.89 mmol) (Example 7-A). The temperature was lowered to 0° C. and the reaction mixture treated with EDC (0.449 g, 2.26 mmol) (Alrich) and stirred 17 hours under $N_2$. The reaction mixture was evaporated, the residue diluted with $EtOAc/H_2O$, washed 1.0 N HCl, sat. $NaHCO_3$, brine and dried over $Na_2SO4$. The diastereomers were separated on a Chiralcel OD column using 10% IPA/heptane at 1.5 ml/minute.

Isomer 1: Retention time 3.37 minutes.

NMR data was as follows:

$^1$H-nmr ($CDCl_3$): δ=7.62–7.33 (m, 9H), 5.26 (d, 1H), 5.08 (m, 1H), 4.34 (m, 1H), 3.35 (s, 3H), 1.49 (s, 9H), 1.40 (d, 3H).

Optical Rotation: $[\alpha]_{20}$=−96@589 nm (c=1, MeOH).

$C_{23}H_{27}N_3O_4$ (MW=409.489); mass spectroscopy (MH+) 409.

Anal. Calcd for $C_{23}H_{27}N_3O_4$; C, 67.46 H, 6.64 N, 10.26. Found: C, 68.42 H, 7.02 N, 9.81.

Isomer 2: Retention time 6.08 minutes.

NMR data was as follows:

$^1$H-nmr ($CDCl_3$): δ=7.74 (bd,1H), 7.62–7.32 (m, 8H), 5.28 (d, 1H), 4.99 (m, 1H), 4.36 (m, 1H), 3.35 (s, 3H), 1.49 (s, 9H), 1.46 (d, 3H).

Optical Rotation: $[\alpha]_{20}$=69@589 nm (c=1, MeOH).

$C_{23}H_{27}N_3O_4$ (MW=409.489); mass spectroscopy (MH+) 409.

Anal. Calcd for $C_{23}H_{27}N_3O_4$; C, 67.46 H, 6.64 N, 10.26. Found: C, 67.40 H, 6.62 N, 10.02

Step B

Synthesis of (S)- and (R)-5-(L-Alaninyl)-amino-7-methyl-5,7-dihydro-6H-dibenz[b,d]azepin-6-one Hydrochloride The compounds isolated in Step A (each isomer separately) were dissolved in dioxane and treated with excess HCl (g). After stirring for 17 hours, the title compounds were isolated as colorless solids after evaporation and vacuum drying.

Isomer 1:

$C_{18}H_{19}N_3O_2$.HCl (MW=345.832); mass spectroscopy (MH+ free base) 309.

Optical Rotation: $[\alpha]_{20}=-55@589$ nm (c=1, MeOH).

Isomer 2:

$C_{18}H_{19}N_3O_2 \cdot HCl$ (MW=345.832); mass spectroscopy (MH+ free base) 309.

Optical Rotation: $[\alpha]_{20}=80@589$ nm (c=1, MeOH).

General Procedure 8-G

N-Alkylation of Amides or Lactams

Using Sodium Hydride or Potassium tert-Butoxide

To a slurry of sodium hydride or potassium tert-butoxide (1.1 eq) in 15 mL of dry DMF was added the appropriate amide (0.0042 moles) as a solution in 10 mL of DMF. The alkyl iodide was then added and a thick slurry resulted. The reaction became less thick as time elapsed and when complete by TLC the reaction had become homogeneous. The reaction mixture was poured over ice and extracted into ethyl acetate. The organic layer was washed with water, followed by brine. The organic layer was then dried over sodium sulfate, filtered and concentrated under reduced pressure. The residue was purified by HPLC (LC 2000), eluting with an ethyl acetate/hexane system.

General Procedure 8-I

N-Alkylation of Amides or Lactams Using Cesium Carbonate

To a solution of the amide or lactam in DMF was added cesium carbonate (1.05 eq) and an alkyl iodide (1.1 eq). The mixture was allowed to stir overnight at room temperature and then the reaction mixture was dilluted with ethyl acetate and washed with water, followed by brine. The organic layer was dried over sodium sulfate, filtered and concentrated under reduced pressure. The residue was purified by HPLC (LC 2000), eluting with an ethyl acetate/hexane system.

General Procedure 8-J

BOC Removal Procedure

To an N-Boc protected compound was added $CH_2Cl_2$/TFA (4:1) at room temperature. The reaction mixture was stirred at room temperature for 3 hours and then concentrated. The residue was extracted into dichloromethane and washed with water, saturated sodium bicarbonate, dried over $Na_2SO_4$, filtered and concentrated to give the free amine.

General Procedure AA

Reductive Amination

To a solution of the arylamine in ethanol in a hydrogenation flask was added 1 equivalent of the 2-oxocarboxylic acid ester (e.g., pyruvate ester), followed by 10% palladium on carbon (25 weight percent based on the arylamine). The reaction was hydrogenated at 20 psi $H_2$ on a Parr shaker until complete reaction was indicated by tlc (30 minutes to 16 hours). The reaction mixture was then filtered through a pad of Celite 545 (available from Aldrich Chemical Company, Inc.) and stripped free of solvent on a rotary evaporator. The crude product residue was then further purified via chromatography.

General Procedure AB

First Transesterification Technique

A solution of 1–5 equivalents of the desired alcohol was added to 1 equivalent of sodium hydride in toluene. After off-gassing had ceased, the compound to be transesterified, dissolved in toluene, was added. After 0.5 hours, the reaction was either heated to 40° C. and placed under house vacuum (~20 mmHg), or nitrogen was bubbled through the solution while it was heated at 90° C. The reaction was followed by tlc, and when the reaction was complete the solution was cooled and quenched with water or 1M HCl, and in smaller scale reactions diluted with ethyl acetate. The organic phase was extracted with saturated aqueous $NaHCO_3$, then washed with saturated aqueous NaCl and dried over $MgSO_4$. The solution was stripped free of solvent on a rotary evaporator, and the crude product residue was then further purified by chromatography. Alternatively, the reaction mixture was worked-up by evaporation of the solvents and direct chromatography of the crude mixture.

This procedure is particularly useful in the case of costly and/or high boiling alcohols.

General Procedure AC

Second Transesterification Technique

The compound to be transesterified was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous $NaHCO_3$ was added. The organic phase was washed with saturated aqueous NaCl and dried over $MgSO_4$. The solution was stripped free of solvent on a rotary evaporator, and the crude product residue was then further purified by chromatography.

General Procedure AD

Third Transesterification Technique

The compound to be transesterified was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous $NaHCO_3$ was added. The volume of the reaction mixture was reduced on a rotary evaporator until the excess alcohol was removed and then the remaining residue was taken up in ethyl acetate and additional water was added. The organic phase was washed with saturated aqueous NaCl and dried over $MgSO_4$. The solution was stripped free of solvent on a rotary evaporator, and the crude product residue was then further purified by chromatography.

This procedure is particularly employed in the case of low boiling, inexpensive alcohols, miscible with water.

General Procedure AE

O-Alkylation Technique

To a carboxylic acid compound (prepared, for example, by reductive amination via General Procedure AA to provide for the N-aryl amino acid ester, followed by hydrolysis via Procedure AF) in DMF was added 1.5 equivalents $K_2CO_3$, followed by 1 equivalent of alkylating agent (e.g., tert-butyl bromoacetate). The reaction was stirred at room temperature for 2 hours, then was quenched with water and extracted into ethyl acetate. The organic phase was washed with saturated aqueous $NaHCO_3$, water, and saturated aqueous NaCl, and was then dried over $MgSO_4$. The solution was stripped free of solvent on a rotary evaporator to yield the crude product.

General Procedure AF

Ester Hydrolysis to Free Acid

To a carboxylic ester compound (prepared, for example, by reductive amination via General Procedure AA to provide for the N-aryl amino acid ester) in a 1:1 mixture of $CH_3OH/H_2O$ was added 2–5 equivalents of $K_2CO_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over $MgSO_4$. The solution was stripped free of solvent on a rotary evaporator to yield the crude product.

General Procedure AG

N-Heteroarylation of Alanine

A solution of 1.1 equivalents of L-alanine and 2 equivalents NaOH in DMSO was stirred at room temperature for 1 hour, then 1 equivalent of 2-chlorobenzothiazole was added. The mixture was heated to 100° C. for 4 hours, then cooled to room temperature and poured onto ice. The pH of the resulting aqueous solution was adjusted to ~2, and the precipitated solid was removed by filtration. This solid was then dissolved in 1N NaOH and the resulting solution was filtered through a pad of Celite 545. The pH of the filtrate was adjusted to ~2, and the white precipitate was removed by filtration and washed with water to yield the crude product.

General Procedure AH

EDC Coupling

To a 1:1 mixture of the desired acid and alcohol in $CH_2Cl_2$ at 0° C. was added 1.5 equivalents triethylamine, followed by 2.0 equivalents hydroxybenzotriazole monohydrate, then 1.25 equivalents of ethyl-3-(3-dimethylamino)-propyl carbodiimide.HCl (EDC). The reaction was stirred overnight at room temperature, then transferred to a separatory funnel and washed with water, saturated aqueous $NaHCO_3$, 1N HCl, and saturated aqueous NaCl, and was then dried over $MgSO_4$. The solution was stripped free of solvent on a rotary evaporator to yield the crude product.

General Procedure AI

Oxime or Amine Coupling Technique

The trichlorophenyl ester (1 eq) of a carboxylic acid was stirred in DMF or THF. The oxime or amine (1.2 eq) was added and the mixture was stirred at ambient temperature for 1–4 hours. In cases where the hydrochloride salt form of an amine was used, a suitable base such as N,N-diisopropylethylamine (1.2 eq) was also added. The resulting mixture was concentrated under reduced pressure to yield a crude product which was used without purification or was purified by silica gel chromatography and/or crystallization.

General Procedure AJ

Alkylation Technique

The amine (1 eq), the α-bromo ester (1.1 eq) and a suitable base (such as triethylamine) (2 eq) were stirred in chloroform. The resulting solution was heated at reflux for 4–12 hours. After cooling, the mixture was diluted with chloroform and washed with water. The organic portion was dried (sodium sulfate) and concentrated under reduced pressure. The crude product was purified by silica gel chromatography.

General Procedure AK

Oxime or Alcohol Coupling Technique

The carboxylic acid (1 eq) was stirred in a suitable solvent (such as THF, dioxane or DMF). An alcohol or oxime (1–5 eq) was added. EDC hydrochloride (1.2 eq) and hydroxybenzotriazole hydrate (1 eq) were added. A suitable base (such as 4-methylmorpholine or triethylamine) (0–1 eq) was added. A catalytic amount (0.1 eq) of 4-dimethylaminopyridine was added. The mixture was stirred at ambient temperature and under a dry atmosphere of nitrogen. After 20 hours, the mixture was concentrated under reduced pressure. The resulting concentrate was partitioned between ethyl acetate and water. The organic portion was separated and washed with aqueous sodium bicarbonate and brine. The organic portion was dried (sodium sulfate) and concentrated under reduced pressure. The crude product was used without purification or was purified by silica gel chromatography and/or crystallization.

General Procedure AL

EDC Coupling

The carboxylic acid was dissolved in methylene chloride. The amino acid (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride (EDC) was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product. Pure products were obtained by flash chromatography in an appropriate solvent.

General Procedure AM

Triflate Displacement

To a 0° C. solution of iso-butyl R-(+)-lactate in $CH_2Cl_2$ was added 1.1 equivalents of trifluoromethanesulfonic anhydride. After stirring at room temperature for 20 min, 1.1 equivalents of 2,6-lutidine was added and stirring was continued for 10 min. This solution was then transferred to a flask containing 1 equivalent the arylamine and 1 equivalent N,N-diisopropylethylamine in $CH_2Cl_2$ or $CH_3NO_2$ at 0° C. The reaction was held overnight at room temperature and then stripped free of solvent on a rotary evaporator. The residue was dissolved in ethyl acetate, washed with 5% citric acid, followed by saturated aqueous NaCl, dried over magnesium sulfate or sodium sulfate and then the solution was stripped free of solvent on a rotary evaporator to yield the crude product, which was then purified by chromatography.

General Procedure AN

BOC Removal

The BOC-protected compound was added to a 1:1 mixture of $CH_2Cl_2$ and trifluoroacetic acid, and was stirred until tlc indicated complete conversion, typically 2 h. The solution was then stripped to dryness and the residue was taken up in ethyl acetate and extracted with dilute HCl. The acid reaction was neutralized and extracted with ethyl acetate. The organic phase was washed with saturated aqueous NaCl and dried over $MgSO_4$. The solution was stripped free of solvent on a rotary evaporator to yield the product.

General Procedure AO

Synthesis of Pyruvate Esters

To a mixture of pyruvic acid (8.8 g, 0.1 mol) (Aldrich) in 100 mL of benzene was added iso-butanol (14.82 g, 0.2 mol) and a catalytic amount of p-toluenesulfonic acid. The mixture was then refluxed using a Dean Stark apparatus. After 4 hours, the reaction appeared to be complete with the isolation of 1.8 g (0.1 mol) of water. The benzene and iso-butanol were removed on a rotary evaporator. The residue (14 g, 0.1 mol), which was primarily the pyruvate iso-butyl ester by nmr [$^1$H-Nmr (CDCl$_3$): δ=4.0 (d, 2H), 2.5 (s, 3H), 2.0 (m, 1H), 1.0 (d, 6H)], was used without further purification. By substituting other alcohols in place of iso-butanol (e.g., ethanol, isopropanol, n-butanol, benzyl alcohol and the like), other esters of pyruvic acid can be prepared in a similar manner.

General Procedure AP

Aromatic Nucleophilic Substitution of Fluorobenzenes

A mixture of 1.82 g (10 mmol) of D,L-alanine iso-butyl ester hydrochloride, the fluorobenzene (10 mmol) and 3 g of anhydrous potassium carbonate in 10 mL of DMSO was stirred at 120° C. for 2–5 hours. The reaction mixture was then cooled to room temperature and diluted with 100 mL of ethyl acetate. The ethyl acetate extract was washed with water (3×), dried over $MgSO_4$ and evaporated to dryness to afford the crude product, which was further purified by column chromatography.

General Procedure AQ

Fourth Transesterification Technique

The ester to be transesterified was dissolved in a large excess of the alcohol and 0.3 equivalents of titanium(IV) isopropoxide (Aldrich) was added. The reaction was followed by tlc until complete and then the volatiles were removed at reduced pressure. The resulting crude material was then chromatographed to obtain the desired product.

General Procedure AR

Synthesis on N-BOC Anilines

To a solution of the aniline in THF was added dropwise 1 equivalent of di-tert-butyl dicarbonate (Aldrich) in THF and then 1.5 equivalents of 10N aqueous sodium hydroxide at 0° C. After stirring at room temperature for 16 hours, or heating at 80° C. for 3 hours, if needed, the reaction mixture was diluted with ether and washed with NaHCO$_3$, brine, dried over sodium sulfate and potassium carbonate, concentrated at reduced pressure and chromatographed to afford the N-BOC aniline.

General Procedure AS

Oxime Ester Formation

The trichlorophenyl ester (1 eq.) was stirred in DMF or THF. The oxime (1.2 eq.) was added and the mixture was stirred at ambient temperature for 1 to 4 hours. The resulting mixture was concentrated under reduced pressure and the residue was purified by silica gel chromatography and/or crystallization.

IV. EPOXIDE PREPARATION

General Procedure EA

First Epoxide Opening Procedure

A solution of 5-(S)-[L-alaninyl]-amino-7-methyl-5,7-dihydro-6H-dibenz[b,d]azepin-6-one hydrochloride (1 eq., Ex. 7B) in methanol (0.1 M) was treated with diisopropylethylamine (1.5–2 eq., Aldrich) and the appropriate epoxide (1–3 eq.). The resulting mixture was stirred at room temperature for 96 hr, then concentrated in vacuo. The resulting oil was dissolved in methylene chloride and washed with water. The aqueous layer was re-extracted with methylene chloride then the combined organic extracts were dried over Na$_2$SO$_4$, filtered and concentrated. The crude product was purified by flash chromatography.

General Procedure EB

Second Epoxide Opening Procedure

A solution of 5-(S)-[L-alaninyl]-amino-7-methyl-5,7-dihydro-6H-dibenz[b,d]azepin-6-one hydrochloride (1 eq., Ex. 7B) in methanol (0.1 M) was treated with diisopropylethylamine (1–3 eq., Aldrich) and the appropriate epoxide (1.5–2 eq.). The resulting mixture was heated to 50° C. for 48 hr, then cooled to room temperature and concentrated in vacuo. The resulting oil was dissolved in methylene chloride and washed with water. The aqueous layer was re-extracted with methylene chloride then the combined organic extracts were dried over Na$_2$SO$_4$, filtered and concentrated. The crude product was purified by flash chromatography.

EXAMPLE EB

Synthesis of N-(2(R/S)-hydroxy-2-(3,5-difluorophenyl)ethyl)-L-alanine

Following General Procedure EB and reacting 2-(3,5-difluorophenyl)-1,2-epoxyethane (Example EC1) and L-alanine methyl ester hydrochloride (Bachem), the title compound was isolated after flash chromatography with 3:1 to 1:1 (gradient) hexanes/ethyl acetate.

$C_{12}H_{15}F_2NO_3$ (MW=259.25); mass spectroscopy (MH+) 260.2

$^1$H NMR (CD$_3$OD, 250 MHz, δ) 7.04–6.75 (m, 3H), 4.78–4.64 (m, 1H), 3.71 (s, 3H), 3.49–3.29 (m, 1H), 2.84–2.60 (m, 2H), 1.31 (d, J =5.6Hz, 3H).

General Procedure EC

Preparation of Epoxides

A solution of the appropriate aldehyde (1 eq.) in 1:1 methylene chloride/50% aq. sodium hydroxide (0.15M) was treated with tetrabutylammonium iodide (0.1 eq., Aldrich) and trimethylsulfonium iodide (1.2 eq., Aldrich). The resulting mixture was heated to 50° C. for 24 hours, then cooled to room temperature and washed with water. The aqueous layer was re-extracted with methylene chloride then the combined organic extracts were dried over Na$_2$SO$_4$, filtered and concentrated. The crude product was purified by flash chromatography.

EXAMPLE EC1

Synthesis of 2-(3,5-difluorophenyl)-1,2-epoxyethane

Following General Procedure EC and using 3,5-difluorobenzaldehyde (Aldrich), the title compound was isolated after flash chromatography with 20:1 pentane/diethylether.

$C_8H_6F_2O$ (MW=156.13); mass spectroscopy 156.0

$^1$H NMR (CDCl$_3$, 300 MHz, δ), 6.84–6.70 (m, 3H), 3.84–3.82 (m, 1H), 3.16–3.12 (m, 1H), 2,73–2.70 (m, 1H).

EXAMPLE EC2

Synthesis of 2-(3,4,5-trifluorophenyl)-1,2-epoxyethane

Following General Procedure EC and using 3,4,5-trifluorobenzaldehyde (Strem), the title compound was isolated after flash chromatography with 10:1 pentane/diethylether.

$C_8H_5F_3O$ (MW=174.12); mass spectroscopy 174.1

$^1$H NMR (CDCl$_3$, 300 MHz, δ) 6.94–6.89 (m, 2H), 3.81–3.79 (m, 1H), 3.15–3.12 (m, 1H), 2,69–2.67 (m, 1H).

EXAMPLE EC3

Synthesis of 2-(3,4,5-trifluorophenyl)-1,2-epoxyethane

Following General Procedure EC and using 4-(trifluoromethyl)benzaldehyde (Aldrich), the title compound was isolated after flash chromatography with 10:1 pentane/diethylether.

$C_9H_7F_3O$ (MW=188.15); mass spectroscopy 188.0

$^1$H NMR (CDCl$_3$, 300 MHz, δ) 7.61 (d, J=7.9Hz, 2H), 7.40 (d, J=7.9Hz, 2H), 3.93–3.90 (m, 1H), 3.20–3.17 (m, 1H), 2,78–2.75 (m, 1H).

EXAMPLE EC4

Synthesis of 2-(3,5-bis-(trifluoromethyl)phenyl)-1,2-epoxyethane

Following General Procedure EC and using 3,5-bis-(trifluoromethyl)benzaldehyde (Lancaster), the title compound was isolated after flash chromatography with 10:1 pentane/diethylether.

$C_{10}H_6F_6O$ (MW=256.15); mass spectroscopy 257

$^1$H NMR (CDCl$_3$, 300 MHz, δ) 7.82 (s, 1H), 7.74 (s, 2H), 4.00–3.98 (m, 1H), 3.25–3.22 (m, 1H), 2.80–2.77 (m, 1H).

General Procedure ED

Deprotection of SEM protected alcohol

An appropriate SEM protected alcohol was stirred in 5% HCl in methanol at room temperature for 17 hours. The reaction solution was poured into aqueous saturated NaHCO$_3$ and extracted with dichloromethane. The organic layer was concentrated in vacuo to afford the de-protected product.

V. SYNTHESIS OF INTERMEDIATES

Intermediate A

Synthesis of 5-(S)-(N'-(3-methyl-2-(2-trimethylsilylethyloxy)-methyloxybutyl)-L-alaninyl)-amino-7-methyl-5,7-dihydro-6H-dibenz[b,d]azepin-6-one

Step A

Preparation of Methyl-2-(S)-(2-trimethylsilylethyloxy-)methyloxy-3-methylbutanoate A solution of methyl-2-(S)-hydroxy-3-methylbutanoate (1.0 eq; J. Org. Chem. (1997), 62(7), 2292–2297, incorporated herein by reference) in dichloromethane was stirred with diisopropylethylamine (2.0 eq) under nitrogen. 2-Trimethylsilylethoxymethyl chloride (3 eq; Aldrich) was added dropwise via syringe. The solution was stirred at room temperature for 17 hours. The solution was washed with 1.0N HCl, and the water layer was back extracted with dichloromethane. The organics were combined, dried over Na$_2$SO$_4$, and the solvents removed in vacuo. The residue was purified via radial chromatography using 20% ethyl acetate in hexanes affording the title intermediate as a clear oil.

$^1$H NMR data was as follows:

$^1$H NMR (400 MHz, CDCl$_3$) δ4.71 (2H s), δ3.89 (1H d, J=57 Hz), δ3.72 (3H s), δ3.72–3.57 (2H m), δ2.10–2.03 (1H m), δ0.97–0.86 (8H m), δ0.10 (9H s).

$C_{12}H_{26}O_4Si$ (MW=262.42); mass spectroscopy (M+) 262.

Step B

Preparation of 3-methyl-2-(S)-2-(trimethylsilyl)ethyloxy-methyloxybutanal

A solution of methyl-2-(S)-(2-trimethylsilylethyloxy)methyloxybutyl-3-methylbutanoate (1.0 eq) in toluene was cooled to −78° C. under a nitrogen atmosphere. DIBAL-H (Aldrich, 1.0M in toluene, 1.5 eq) was added dropwise at −78° C. The reaction was stirred at −78° C. for 20 minutes, and methanol was added to quench the reaction. The mixture was stirred for an additional 30 minutes at −78° C., and a 10% aqueous solution of Rochelle's salt was added. The reaction was allowed to warm to room temperature, and stirred for 17 hours. The layers were separated, and the organic layer was concentrated in vacuo. The residue was purified by radial chromatography using 20% ethyl acetate in hexanes, affording the title intermediate as a clear oil.

$^1$H NMR data was as follows:

$^1$H NMR (400 MHz, CDCl$_3$) δ9.61 (1H s), δ4.79–4.72 (1H m), δ4.69–4.63 (2H m), δ3.71–3.56 (2H m), δ2.16–2.01 (1H m), δ1.23 (2H br s), δ1.20–0.82 (6H m), δ0.03 (9H s).

$C_{11}H_{24}O_3Si$ (MW=232.40); mass spectroscopy (MH+) 233.

Step C

Preparation of N-(3-methyl-2-(S)-(2-trimethylsilylethyloxy)methyloxybutyl)-L-alanine, methyl ester 3-methyl-2-(S)-(2-trimethylsilylethyloxy)methyloxybutanal (1.0 eq) was stirred in methanol at room temperature with L-Alanine, methyl ester (0.8 eq; Bachem). Sodium cyanoborohydride (0.5 eq) was added to the solution, and the reaction was stirred for 17 hours. The reaction was made alkaline by addition of aqueous saturated NaHCO$_3$ solution. The mixture was extracted with dichloromethane, dried over sodium sulfate, and concentrated in vacuo. The residue was purified via radial chromatography using 20% ethyl acetate in hexanes to afford the title intermediate as a colorless oil.

$C_{15}H_{33}NO_4Si$ (MW=319.50); mass spectroscopy (MH+) 320

Anal. Calcd for $C_{15}H_{33}NO_4Si$; C 56.39, H 10.41, N 4.38. Found: C56.15, H 10.14, N 4.42.

Step D

Preparation of 5-(S)-(N'-(3-methyl-2-(S)-(2-trimethylsilylethyloxy)methyloxybutyl)-L-alaninyl)-amino-7-methyl-5,7-dihydro-6H-dibenz[b,d]azepin-6-one Following General Procedure II-A, Method B and using N-(3-methyl-2-(S)-(2-trimethylsilylethyloxy)

methyloxybutyl)-L-alanine, methyl ester, the acid was prepared. The residue was used, following General Procedure D, and using 5-(S)-amino-7-methyl-5,7-dihydro-6H-dibenz [b,d]azepin-6-one hydrochloride (Example 7A) to prepare the title intermediate.

$C_{29}H_{43}N_3O_4Si$ (MW=525.77), mass spectroscopy (MH+) 526.

Anal. Calcd. for $C_{29}H_{43}N_3O_4Si$; C 66.25, H 8.24, N 7.99. Found: C 66.10, H 8.13, N 8.13.

Intermediate B

Synthesis of 3-(N'-(3-methyl-2-(S)-(2-trimethylsilylethyloxy)methyloxybutyl)-L-Alaninyl)-amino-2,4-dioxo-1-methyl-5-phenyl-2,3,4,5-tetrahydro-1H-1,5-benzodiazepine Following General Procedure II-A, Method B and using N-(3-methyl-2-(S)-(2-trimethylsilylethyloxy) methyloxybutyl)-L-alanine, methyl ester (Intermediate A, Step C; 1 eq), the free acid was prepared. The residue was used, following General Procedure D, and using 3-amino-2,4-dioxo-1-methyl-5-phenyl-2,3,4,5-tetrahydro-1H-1,5-benzodiazepine (CAS No. 131604-75-6) to prepare the title intermediate.

$C_{30}H_{44}N_4O_5Si$ (MW=568.79), mass spectroscopy (MH+) 569.

Anal Calcd. for $C_{30}H_{44}N_4O_5Si$; C 63.35, H 7.80, N 9.85. Found: C 63.24, H 7.48, N 9.89.

Intermediate C

Synthesis of N-(2-(R/S)-3,5-difluorophenyl-2-hydroxyethyl)-L-alanine

Following General Procedure II-A, Method B, modified by using 3:1 butanol/toluene for extraction of the product in place of ethyl acetate, and using N-(2-(R/S)-3,5-difluorophenyl-2-hydroxyethyl)-L-alanine (Example EB) the title intermediate was prepared.

$^1$H NMR data was as follows:

$^1$H NMR (400 MHz, CD$_3$OD) δ7.04–7.01 (2H m), δ6.89–6.79 (1H m), δ4.97–4.83 (1H m), δ4.00 (1H q, J=7.0 Hz), δ3.27–3.08 (2H m), δ1.54 (3H d, J=2.8 Hz)

$C_{11}H_{13}F_2NO_3$ (MW=245.23); mass spectroscopy (MH+) 246.

EXAMPLE 6

Synthesis of 5-(S)-(N'-(2-(3,5-difluorophenyl)ethyl)-L-alaninyl)-amino-7-methyl-5,7-dihydro-6H-dibenz [b,d]azepin-6-one A solution of 3,5-difluorophenylacetaldehye (CAS 109346-94-3: Elliott, Michael et al. *Pestic. Sci.* (1987), 18(4), 239–44, incorporated herein by reference; 1.4 eq) and 5-(S)-[L-alaninyl]-amino-7-methyl-5,7-dihydro-6H-dibenz [b,d]azepin-6-one hydrochloride (1 eq., Example 7B) with sodium cyanoborohydride (0.6 eq.,Aldrich) in methanol was stirred at room temperature for 1.5 hours. The solvent was removed in vacuo, and the residue dissolved in a mixture of 1:1 aqueous saturated NaHCO$_3$/diethyl ether. The layers were separated, and the aqueous layer was back-extracted with diethyl ether. The organic layers were combined, and concentrated in vacuo. The residue was purified via flash column chromatography using 50% ethyl acetate in hexanes to afford the title compound.

$C_{26}H_{25}F_2N_3O_2$ (MW=449.50); mass spectroscopy (MH+) 450.

Anal. Calcd for $C_{26}H_{25}F_2N_3O_2$; C 69.47, H 5.61, N 9.35, F 8.45. Found: C 69.55, H 5.63, N 9.21, F 8.30.

EXAMPLES 7 AND 8

Synthesis of 5(S)-(N'-(2(R)-hydroxy-2-(3,5-difluorophenyl)ethyl)-L-alaninyl)-amino-7-methyl-5,7-dihydro-6H-dibenz[b,d]azepin-6-one and 5(S)-(N'-(2(S)-hydroxy-2-(3,5-difluorophenyl)ethyl)-L-alaninyl)-amino-7-methyl-5,7-dihydro-6H-dibenz[b,d]azepin-6-one Following General Procedure EB and using 2-(3,5-difluorophenyl)-1,2-epoxyethane (Example EC1), the title compounds were isolated as pure diastereomers after flash chromatography with 1:1 hexanes/ethyl acetate.

Ex. 7 (less polar by TLC): $C_{26}H_{25}F_2N_3O_3$ (MW=465.50); mass spectroscopy (MH+) 466.2

Anal. Calcd for $C_{26}H_{25}F_2N_3O_3$: C, 67.09; H, 5.41; N, 9.03. Found: C, 67.06; H, 5.67; N, 8.75.

Ex. 8 (more polar by TLC): $C_{26}H_{25}F_2N_3O_3$ (MW= 465.50); mass spectroscopy (MH+) 466.2

Anal. Calcd for $C_{26}H_{25}F_2N_3O_3$: C, 67.09; H, 5.41; N, 9.03. Found: C, 67.04; H, 5.46; N, 8.89.

EXAMPLE 9

Synthesis of 5(S)-(N'-(2(R/S)-hydroxy-3-isopropyloxy-propyl)-L-alaninyl)-amino-7-methyl-5,7-dihydro-6H-dibenz[b,d]azepin-6-one Following General Procedure EB and using isopropyl glycidyl ether (Aldrich), the title compound was isolated as a mixture of diastereomers after flash chromatography with 95:5 ethyl acetate/methanol.

$C_{24}H_{31}N_3O_4$ (MW=425.53); mass spectroscopy (MH+) 426.2

Anal. Calcd for $C_{24}H_{31}N_3O_4$: C, 67.74; H, 7.34; N, 9.87. Found: C, 67.90; H, 7.40; N, 9.60.

EXAMPLE 10

Synthesis of 5(S)-(N'-(2(R/S)-hydroxy-butyl)-L-alaninyl)-amino-7-methyl-5,7-dihydro-6H-dibenz[b, d]azepin-6-one Following General Procedure EB and using 1,2-epoxybutane (Aldrich), the title compound was isolated as a mixture of diastereomers after flash chromatography with 9:1 ethyl acetate/methanol.

$C_{22}H_{27}N_3O_3$ (MW=381.48); mass spectroscopy (MH+) 382.4

Anal. Calcd for $C_{22}H_{27}N_3O_3$: C, 69.27; H, 7.13; N, 11.02. Found: C, 69.51; H, 7.14; N, 10.76.

EXAMPLE 11

Synthesis of 5(S)-(N'-(2(R/S),3-dihydroxy-propyl)-L-alaninyl)-amino-7-methyl-5,7-dihydro-6H-dibenz [b,d]azepin-6-one Following General Procedure EB and using glycidol (Aldrich), the title compound was isolated as a mixture of diastereomers after flash chromatography with 7:3 ethyl acetate/methanol.

$C_{21}H_{25}N_3O_4$ (MW=383.45); mass spectroscopy (MH+) 384.3

Anal. Calcd for $C_{21}H_{25}N_3O_4$: C, 65.78; H, 6.57; N, 10.96. Found: C, 64.13; H, 6.17; N, 9.84.

EXAMPLE 12

Synthesis of 5(S)-(N'-(2(R/S)-hydroxy-3-morpholinopropyl)-L-alaninyl)-amino-7-methyl-5,7-dihydro-6H-dibenz[b,d]azepin-6-one Following General Procedure EB and using 3-morpholino-1,2-epoxypropane (Transworld), the title compound was isolated as a mixture of diastereomers after flash chromatography with 9:1 ethyl acetate/methanol.

$C_{25}H_{32}N_4O_4$ (MW=452.56); mass spectroscopy (MH+) 453.2

Anal. Calcd for $C_{25}H_{32}N_4O_4$: C, 66.35; H, 7.13; N, 12.38. Found: C, 65.45; H, 7.21; N, 11.37.

EXAMPLE 13

Synthesis of 5(S)-(N'-(2(R/S)-hydroxy-tetradecyl)-L-alaninyl)-amino-7-methyl-5,7-dihydro-6H-dibenz[b,d]azepin-6-one Following General Procedure EB and using 1,2-epoxytetradecane (Aldrich), the title compound was isolated as a mixture of diastereomers after flash chromatography with 100% ethyl acetate.

$C_{32}H_{47}N_3O_3$ (MW=521.75); mass spectroscopy (MH+) 522.4

Anal. Calcd for $C_{32}H_{47}N_3O_3$: C, 73.67; H, 9.08; N, 8.05. Found: C, 73.77; H, 8.16; N, 8.11.

EXAMPLE 14

Synthesis of 5(S)-(N'-(2(R/S)-hydroxy-octyl)-L-alaninyl)-amino-7-methyl-5,7-dihydro-6H-dibenz[b,d]azepin-6-one Following General Procedure EB and using 1,2-epoxyoctane (Aldrich), the title compound was isolated as a mixture of diastereomers after flash chromatography with 100% ethyl acetate.

$C_{26}H_{35}N_3O_3$ (MW=437.58); mass spectroscopy (MH+) 438.2

Anal. Calcd for $C_{26}H_{35}N_3O_3$: C, 71.37; H, 8.06; N, 9.60. Found: C, 67.61; H, 7.28; N, 8.93.

EXAMPLES 15 AND 16

Synthesis of 5(S)-(N'-(2(R)-hydroxy-2-(3,4,5-trifluorophenyl)ethyl)-L-alaninyl)-amino-7-methyl-5,7-dihydro-6H-dibenz[b,d]azepin-6-one and 5(S)-(N'-(2(S)-hydroxy-2-(3,4,5-trifluorophenyl)ethyl)-L-alaninyl)-amino-7-methyl-5,7-dihydro-6H-dibenz[b,d]azepin-6-one Following General Procedure EB and using 2-(3,4,5-trifluorophenyl)-1,2-epoxyethane (Example EC2), the title compounds were isolated as pure diastereomers after flash chromatography with 100% ethyl acetate.

Ex. 15 (less polar by TLC): $C_{26}H_{24}F_3N_3O_3$ (MW=483.49); mass spectroscopy (MH+) 484.5

Anal. Calcd for $C_{26}H_{24}F_3N_3O_3$: C, 64.59; H, 5.00; N, 8.69. Found: C, 64.60; H, 4.99; N, 8.76.

Ex. 16 (more polar by TLC): $C_{26}H_{24}F_3N_3O_3$ (MW=483.49); mass spectroscopy (MH+) 484.5

Anal. Calcd for $C_{26}H_{24}F_3N_3O_3$: C, 64.59; H, 5.00; N, 8.69. Found: C, 64.71; H, 4.93; N, 8.74.

EXAMPLES 17 AND 18

Synthesis of 5(S)-(N'-(2(R)-hydroxy-2-(4-(trifluoromethyl)phenyl)ethyl)-L-alaninyl)-amino-7-methyl-5,7-dihydro-6H-dibenz[b,d]azepin-6-one and 5(S)-(N'-(2(S)-hydroxy-2-(4-(trifluoromethyl)phenyl)ethyl)-L-alaninyl)-amino-7-methyl-5,7-dihydro-6H-dibenz[b,d]azepin-6-one Following General Procedure EB and using 2-(4-(trifluoromethyl)phenyl)-1,2-epoxyethane (Example EC3), the title compounds were isolated as pure diastereomers after flash chromatography with 100% ethyl acetate.

Ex. 17 (less polar by TLC): $C_{27}H_{26}F_3N_3O_3$ (MW=497.52); mass spectroscopy (MH+) 498.3

Anal. Calcd for $C_{27}H_{26}F_3N_3O_3$: C, 65.18; H, 5.27; N, 8.45. Found: C, 64.60; H, 5.31; N, 8.32.

Ex. 18 (more polar by TLC): $C_{27}H_{26}F_3N_3O_3$ (MW=497.52); mass spectroscopy (MH+) 498.3

Anal. Calcd for $C_{27}H_{26}F_3N_3O_3$: C, 65.18; H, 5.27; N, 8.45. Found: C, 66.12; H, 5.46; N, 8.77.

EXAMPLES 19 AND 20

Synthesis of 5(S)-(N'-(2(R)-hydroxy-2-(3,5-bis-(trifluoromethyl)phenyl)ethyl)-L-alaninyl)-amino-7-methyl-5,7-dihydro-6H-dibenz[b,d]azepin-6-one and 5(S)-(N'-(2(S)-hydroxy-2-(3,5-bis-(trifluoromethyl)phenyl)ethyl)-L-alaninyl)-amino-7-methyl-5,7-dihydro-6H-dibenz[b,d]azepin-6-one Following General Procedure EB and using 2-(3,5-bis-(trifluoromethyl)phenyl)-1,2-epoxyethane (Example EC4), the title compounds were isolated as pure diastereomers after flash chromatography with 100% ethyl acetate.

Ex. 19 (less polar by TLC): $C_{28}H_{25}F_6N_3O_3$ (MW=565.52); mass spectroscopy (MH+) 566.5

Anal. Calcd for $C_{28}H_{25}F_6N_3O_3$: C, 59.47; H, 4.46; N, 7.43. Found: C, 61.24; H, 4.63; N, 7.71.

Ex. 20 (more polar by TLC): $C_{28}H_{25}F_6N_3O_3$ (MW=565.52); mass spectroscopy (MH+) 566.5

Anal. Calcd for $C_{28}H_{25}F_6N_3O_3$: C, 59.47; H, 4.46; N, 7.43. Found: C, 59.51; H, 4.40; N, 7.26.

EXAMPLES 21 AND 22

Synthesis of 5(S)-(N'-(2(R)-hydroxy-2-(3,3,3-trifluoro)-propyl)-L-alaninyl)-amino-7-methyl-5,7-dihydro-6H-dibenz[b,d]azepin-6-one and 5(S)-(N'-(2(S)-hydroxy-2-(3,3,3-trifluoro)-propyl)-L-alaninyl)-amino-7-methyl-5,7-dihydro-6H-dibenz[b,d]azepin-6-one Following General Procedure EA and using 3,3,3-trifluoro-1,2-epoxypropane (Lancaster), the title compounds were isolated as pure diastereomers after flash chromatography with 100% ethyl acetate.

Ex. 21 (less polar by TLC): $C_{21}H_{22}F_3N_3O_3$ (MW=421.42); mass spectroscopy (MH+) 422.1

Anal. Calcd for $C_{21}H_{22}F_3N_3O_3$: C, 59.85; H, 5.26; N, 9.97. Found: C, 59.86; H, 5.54; N, 9.69.

Ex. 22 (more polar by TLC): $C_{21}H_{22}F_3N_3O_3$ (MW=421.42); mass spectroscopy (MH+) 422.1

Anal. Calcd for $C_{21}H_{22}F_3N_3O_3$: C, 59.85; H, 5.26; N, 9.97. Found: C, 59.42; H, 5.37; N, 9.85.

EXAMPLE 23

Synthesis of 5-(S)-(N'-(3-methyl-2-butanone)-L-alaninyl)-amino-7-methyl-5,7-dihydro-6H-dibenz[b,d]azepin-6-one A solution of 5-(S)-[L-alaninyl]-amino-7-methyl-5,7-dihydro-6H-dibenz[b,d]azepin-6-one hydrochloride (Example 7B, 1.0 eq) in dichloromethane was stirred at 0° C. with DIEA (2 eq). Bromo-3-methyl-2-butanone (2 eq; Org. Syn., 1988, Coll. Vol6, p193, incorporated herein by reference) in dichloromethane was added dropwise via addition funnel. The reaction mixture was allowed to warm to room temperature, and stirring was continued for 17 hours. The stirring was stopped, and the solvents removed in vacuo to yield a yellow oil. This oil was purified by radial chromatography on silica gel using ethyl acetate as the eluent to afford title compound.

$^1$H NMR data was as follows:

$^1$H NMR (400 MHz, CDCl$_3$) δ8.64 (1H d, J=7.8 Hz), δ7.59–7.22 (8H m), δ5.30 (1H d, J=7.8 Hz), δ3.81 (1H d, J=19.1 Hz), δ3.39 (1H d, J=19.1 Hz), δ3.29 (3H s), δ3.07 (1H q, J=6.8 Hz), δ2.63–2.54 (1H m) δ1.22 (3H d, =7.1 Hz), δ1.15–1.02 (6H m).

$C_{23}H_{27}N_3O_3$ (MW=393.48); mass spectroscopy (MH+) 394.

EXAMPLE 24

Synthesis of 5-(S)-(N'-(3-methyl-2-(S)-hydroxybutyl)-L-alaninyl)-amino-7-methyl-5,7-dihydro-6H-dibenz[b,d]azepin-6-one Following General Procedure ED and using 5-(S)-(N'-(3-methyl-2-(S)-(2-trimethylsilylethyloxy)methyloxybutyl)-L-alaninyl)-amino-7-methyl-5,7-dihydro-6H-dibenz[b,d]azepin-6-one (Intermediate A), the title compound was prepared. $C_{23}H_{29}N_3O_3$ (MW=395.51); mass spectroscopy (MH+) 396.

Anal. Calcd. for $C_{23}H_{29}N_3O_3$; C 69.85, H 7.39, N 10.62. Found: C 69.74, H 7.45, N 10.52.

EXAMPLE 25

Synthesis of 3-(N'-(3-methyl-2-(S)-2-(hydroxybutyl)-L-Alaninyl)-amino-2,4-dioxo-1-methyl-5-phenyl-2,3,4,5-tetrahydro-1H-1,5-benzodiazepine Following General Procedure ED above, and using 3-(N'-(3-methyl-2-(S)-2-(trimethylsilyl)ethyoxymethyloxybutyl)-L-Alaninyl)-amino-2,4-dioxo-1-methyl-5-phenyl-2,3,4,5-tetrahydro-1H-1,5-benzodiazepine (Intermediate B), the title compound was prepared.

$C_{24}H_{30}N_4O_4$ (MW=438.53); mass spectroscopy (MH+) 439.

Anal. Calcd. for $C_{24}H_{30}N_4O_4$; C 65.73, H 6.90, N 12.78. Found: C 63.76, H 6.81, N 12.22.

EXAMPLE 26

Synthesis of 3-(N'-(2-(R/S)-3,5-difluorophenyl-2-hydroxyethyl)-L-alaninyl)-amino-2,4-dioxo-1-methyl-5-phenyl-2,3,4,5-tetrahydro-1H-1,5-benzodiazepine Following General Procedure D and using 3-amino-2,4-dioxo-1-methyl-5-phenyl-2,3,4,5-tetrahydro-1H-1,5-benzodiazepine (CAS No. 131604-75-6) and N-(2-(R/S)-3,5-difluorophenyl-2-hydroxyethyl)-L-alanine (Intermediate C), the title compound was prepared.

$C_{27}H_{26}F_2N_4O_4$ (MW=508.52); mass spectroscopy (MH+) 509.

Anal. Calcd. for $C_{27}H_{26}F_2N_4O_4$ C 63.77, H 5.15, N 11.02. Found: C 63.57, H 5.65, N 9.74.

EXAMPLE 2

Synthesis of 5-(S)-{N'-[(1RS,2SR)-1,2,3,4-tetrahydro-1-hydroxy-2-naphthyl]alaninyl}-amino-7-methyl-5,7-dihydro-6H-dibenz[b,d]azepin-6-one Step A Synthesis of 1,2,3,4-tetrahydro-naphthalene-1,2-dione-2-oxime To the mixture of t-BuOK (1.2 eq.) in THF at 0° C. was added a solution of isoamylnitrite (1.2 eq.) and α-tetralone (Aldrich) (1.0 eq.) in THF dropwise. The reaction mixture was warmed to RT and stirred at RT for 2 h. The reaction mixture was stripped to dryness, mixed with ice-cooled HCl (1M), extracted with EtOAc, washed with brine, dried over MgSO$_4$, filtered and concentrated. The residue was purified with flash chromatography (silica gel, 2:1 hexane/EtOAc) to give the title compound.

$C_{10}H_9NO_2$ (MW=175.186); mass spectroscopy (MH$^+$) 176.

Anal. Calcd for $C_{10}H_9NO_2$: C, 68.56 H, 5.18 N, 8.00; Found: C, 68.81 H, 5.20 N 7.98.

Step B

Synthesis of (1,2,3,4-tetrahydro-1-hydroxy-2-naphthyl)-amine

The compound made in Step A above (1.0 eq.) was dissolved in THF, cooled to 0° C. LAH(2.0 eq.) in THF (1M) was added slowly. The reaction mixture was allowed to warm to RT. The reaction mixture was stirred at RT overnight. The reaction mixture was cooled in an ice-bath, worked up with EtOH and saturated potassium sodium tartrate solution, extracted with CH$_2$Cl$_2$, washed with brine, and dried over Na$_2$SO$_4$. The residue was purified by acid/base extractions to give the title compound.

$C_{10}H_{13}NO$ (MW=163.219); mass spectroscopy (MH$^+$) 164.

Step C

Synthesis of N'-(1,2,3,4-tetrahydro-1-hydroxy-2-naphthyl)-alanine ethyl ester

Following General Procedure AM using Ethyl-D-lactate (Fluka) and the compound made in B above, the title compound was prepared.

$C_{15}H_{21}NO_3$ (MW=263.335); mass spectroscopy (MH$^+$) 264.

Step D

Synthesis of N-(3a,4,5,9b-tetrahydronaphth[2,1-d] oxazol -2(3H)-one)-alanine ethyl ester To a solution of the compound made in C above (1 eq.) in CH$_2$Cl$_2$ under N$_2$ at 0° C., Et$_3$N (1 eq.) and carbonyldiimidazole (1 eq.) in CH$_2$Cl$_2$ were added and the mixture was stirred for 3 h. Another 1 eq. of carbonyldiimidazole in CH$_2$Cl$_2$ was added and stirred at 0° C. for 1 h. The reaction mixture was stirred at RT for 3 h. Water was added, stirred for 15 min, extracted with CH$_2$Cl$_2$, washed with water, dried over Na$_2$SO$_4$, filtered, and concentrated. The residue was purified with flash chromatography (silica gel, 2:1 hexane/EtOAc) to give the title compound.

$C_{16}H_{19}NO_4$ (MW=289.329); mass spectroscopy (MH$^+$) 290.

Step E

Synthesis of N-(3a,4,5,9b-tetrahydronaphth[2,1-d] oxazol -2(3H)-one)-alanine

Following General Procedure II-A, Method B using the compound made in D above, the title compound was prepared.

$C_{14}H_{15}NO_4$ (MW=261.276); mass spectroscopy (MH$^+$) 262.

Step F

Synthesis of 5-(S)-{N'-[(3a RS,9a SR)-3a,4,5,9b-tetrahydronaphth[2,1-d]oxazol-2(3H)-one]-alaninyl}-amino-7-methyl-5,7-dihydro-6H-dibenz[b,d]azepin-6-one Following General Procedure D using the compound made in E above and 5-(S)-amino-7-methyl-5,7-dihydro- 6H-dibenz[b,d]azepin-6-one hydrochloride (Example 7A), the title compound was prepared, which was purified by flash chromatography (silica gel, 5% MeOH/CH$_2$Cl$_2$).

$C_{29}H_{27}N_3O_4$ (MW=481.549); mass spectroscopy (MH$^+$) 482.

Anal. Calcd for $C_{29}H_{27}N_3O_4$: C, 72.33 H, 5.65 N, 8.73; Found: C, 72.44 H, 5.90 N 8.55.

Step G

Synthesis of 5-S-{N'-[(1RS,2SR)-1,2,3,4-tetrahydro-1-hydroxy-2-naphthyl]alaninyl}amino-7-methyl-5,7-dihydro-6H-dibenz[b,d]azepin-6-one The compound made in F above was heated under reflux with 2 N NaOH in EtOH/H$_2$O (2:1) for 20 min. The reaction mixture was stripped to dryness, extracted with EtOAc, washed with water, and dried over Na$_2$SO$_4$. Evaporation and SCX column purification [5% MeOH(7N NH$_3$)/CH$_2$Cl$_2$] gave the title compound as a mixture of four diastereomers.

$C_{28}H_{29}N_3O_3$ (MW=455.555); mass spectroscopy (MH$^+$) 456.

Anal. Calcd for $C_{28}H_{29}N_3O_3$: C, 73.82 H, 6.42 N, 9.22; Found: C, 73.87 H, 6.30 N 9.46.

Four isomers were isolated by HPLC (reversed phase, H$_2$O/CH$_3$CN with 0.1% TFA), SCX column purification [5% MeOH(7N NH$_3$)/CH$_2$Cl$_2$] and chromatography [silica gel, 5% MeOH(7N NH$_3$)/CH$_2$Cl$_2$]:

Isomer 1: $^1$H-nmr(CDCl$_3$): δ=8.20 [d, 1H, (—CONH—)]
Isomer 2: $^1$H-nmr(CDCl$_3$): δ=8.38 [d, 1H, (—CONH—)]
Isomer 3: $^1$H-nmr(CDCl$_3$): δ=8.60 [d, 1H, (—CONH—)]
Isomer 4: $^1$H-nmr(CDCl$_3$): δ=9.03 [d, 1H, (—CONH—)]

EXAMPLE 28

Synthesis of 5-(S)-{N'-[(1RS,2RS)-1,2,3,4-tetrahydro-1-hydroxy-2-naphthyl]alaninyl}-amino-7-methyl-5,7-dihydro-6H-dibenz[b,d]azepin-6-one

Step A

Synthesis of N-[(1RS,2RS)-1,2,3,4-tetrahydro-1-hydroxy-2-naphthyl]-alanine ethyl ester Following General Procedure AM using Ethyl-D-lactate (Fluka) and N-[(1RS,2RS)-1,2,3,4-tetrahydro-1-hydroxy-2-naphthyl]-amine (Liebigs Ann. Chem. 1992, pp273, incorporated herein by reference), the title compound was prepared. $C_{15}H_{21}NO_3$ (MW=263.335); mass spectroscopy (MH$^+$) 264.

Step B

Synthesis of N-[(1RS,2RS)-1,2,3,4-tetrahydro-1-hydroxy-2-naphthyl]-alanine lithium salt Following General Procedure II-A, Method B, and using the compound made in A above except without work-up, the title compound was obtained by stripping the reaction mixture to dryness.

$C_{13}H_{16}NO_3Li$ (MW=241.241); mass spectroscopy (MH$^+$) 242.

Step C

Synthesis of 5-(S)-{N'-[(1RS,2RS)-1,2,3,4-tetrahydro-1-hydroxy-2-naphthyl]-alaninyl}-amino-7-methyl-5,7-dihydro-6H-dibenz[b,d]azepin-6-one Following General Procedure D using the compound made in B above and 5-(S)-amino-7-methyl-5,7-dihydro-6H-dibenz[b,d]azepin-6-one hydrochloride (Example 7A), the title compound was prepared as a mixture of three diastereomers, which were separated with HPLC (reversed phase, 0.1%TFA in CH$_3$CN/H$_2$O) and SCX column [5% MeOH (7N NH$_3$)/CH$_2$Cl$_2$] to give the following isomers:

Isomer 1: $^1$H-nmr(CDCl$_3$): δ=8.70 [d, 1H, (—CONH—)]; $C_{28}H_{29}N_3O_3$ (MW=455.555); mass spectroscopy (MH$^+$) 456.

Isomer 2: $^1$H-nmr(CDCl$_3$): δ=9.31 [d, 1H, (—CONH—)]; $C_{28}H_{29}N_3O_3$ (MW=455.555); mass spectroscopy (MH$^+$) 456; Anal. Calcd for $C_{28}H_{29}N_3O_3$: C, 73.82 H, 6.42 N, 9.22; Found: C, 74.05 H, 6.51 N 8.96.

A mixture of isomer 2 and isomer 3: $^1$H-nmr(CDCl$_3$): δ=9.31 [d, (—CONH—)], 8.95 [d, (—CONH—)]; $C_{28}H_{29}N_3O_3$ (MW=455.555); mass spectroscopy (MH$^+$) 456; Anal. Calcd for $C_{28}H_{29}N_3O_3$ with 1/4 H$_2$O: C, 73.09 H, 6.48 N, 9.14; Found: C, 73.08 H, 6.77 N 8.79.

EXAMPLE 29

Synthesis of 5-(S)-[N'-(2-α-tetralone)-L-alaninyl]-amino-7-methyl-5,7-dihydro-6H-dibenz[b,d]azepin-6-one hydrochloride Following General Procedure 6-A using 5-(S)-{N'-[(1RS,2RS)-1,2,3,4-tetrahydro-1-hydroxy-2-naphthyl]-L-alaninyl}-amino-7-methyl-5,7-dihydro-6H-dibenz[b,d]azepin-6-one and a mixture of isomer 2 and 3 from Example 29, the free base of the title compound was prepared as a mixture of two diastereomers, which were treated with HCl/dioxane respectively to give isomer 1 and isomer 2 of the hydrochlorides.

Isomer 1: Exact mass spectroscopy: calc. for $C_{28}H_{28}N_3O_3$=454.2131, Found 454.2135; Anal. Calcd for $C_{28}H_{27}N_3O_3$ with 1/2 dioxane: C, 67.46 H, 6.05 N, 7.87; Found: C, 67.06 H, 5,74 N 7.49.

Isomer 2: Exact mass spectroscopy: calc. for $C_{28}H_{28}N_3O_3$=454.2131, Found 454.2126; Anal. Calcd for $C_{28}H_{29}N_3O_3$ with 1 dioxane: C, 66.48 H, 6.29 N, 7.27; Found: C, 66.32 H, 5.97 N 7.42.

EXAMPLE 30

Synthesis of 5-(S)-[N'-(1,2,3,4-tetrahydro-2-naphthyl)-L-alaninyl]-amino-7-methyl-5,7-dihydro-6H-dibenz[b,d]azepin-6-one A mixture of 5-(S)-(L-alaninyl)-amino-7-methyl-5,7-dihydro-6H-dibenz[b,d]azepin-6-one (Example 7-B) (1.00 eq.), β-tetralone (Aldrich) (1.00 eq.) and titanium(IV) isopropoxide (Aldrich) (1.25 eq.) was stirred at RT for 1 h and then diluted with MeOH. NaBH$_3$CN (0.67 eq.) was added and stirred at RT overnight. Water was added, diluted with EtOAc, filtered, and concentrated to give a residue, which was purified by SCX column [3% MeOH(7N NH$_3$)/CH$_2$Cl$_2$] and flash chromatography [silica gel, 3% MeOH (7N NH$_3$)/CH$_2$Cl$_2$] to give the title compound.

$C_{28}H_{29}N_3O_2$ (MW=439.556); mass spectroscopy (MH$^+$) 440.

$^1$H-nmr(CDCl$_3$): δ=9.50(m, 1H), 7.60–7.11 (m, 12H), 5.28–5.20 (m, 1H), 3.39–2.86 (m, 8H), 2.15–2.10 (m, 1H), 1.56–1.21 (m, 6H).

EXAMPLE 31

Synthesis of 5-(S)-{N'-[(1RS,2SR)-1-hydroxy-2-cyclohexyl]alaninyl}-amino-7-methyl-5,7-dihydro-6H-dibenz[b,d]azepin-6-one Following the procedure in Example 28 using cis-2-aminocyclohexanol hydrochloride (ACROS), the title compound was prepared.

Exact mass spectroscopy: Calc. for $C_{24}H_{30}N_3O_3$: 408.2287; Found 408.2283.

Anal. Calcd for $C_{24}H_{29}N_3O_3$: C, 70.74 H, 7.17 N, 10.31; Found: C, 70.72 H, 7.23 N 10.41.

EXAMPLE 32

Synthesis of 5-(S)-[N'-(4-methylpentyl)-L-alaninyl]-amino-7-methyl-5,7-dihydro-6H-dibenz[b,d]azepin-6-one To a solution of 5-(S)-(L-alaninyl)-amino-7-methyl-5,7-dihydro-6H-dibenz[b,d]azepin-6-one (Example 7-B) (2.00 eq.) in MeOH was added a few drops of HCl-MeOH, 4-methyl-1-pentanal (1.00 eq.) (made by following the procedure described in Tetrahedron Letter, No.31, 1975, pp2647, incorporated herein by reference) and molecular sieves. $NaBH_3CN$ (0.67 eq.) was added. The pH of the reaction mixture was maintained at 5–6 by adding HCl-MeOH. The reaction mixture was stirred at RT overnight. The reaction mixture was basified, extracted with EtOAc, dried over $Na_2SO_4$. Concentration and flash chromatography [silica gel, 5% MeOH (7 N $NH_3$)/$CH_2Cl_2$] gave the title compound. Exact mass spectroscopy: Calc. for $C_{24}H_{32}N_3O_2$: 394.2495; Found 394.2499.

Anal. Calcd for $C_{24}H_{31}N_3O_2$ with 4/5 $H_2O$: C, 70.66 H, 8.07 N, 10.30; Found: C, 70.25 H, 7.58 N 10.64.

EXAMPLE 3

Cellular Screen for the Detection of Inhibitors of β-Amyloid Production

A compound of formula I above was assayed for its ability to inhibit β-amyloid production in a cell line possessing the Swedish mutation. This screening assay employed cells (K293. =human kidney cell line) which were stably transfected with the gene for amyloid precursor protein 751 (APP751) containing the double mutation $Lys_{651}Met_{652}$ to $Asn_{651}Leu_{652}$ (APP751 numbering) in the manner described in International Patent Application Publication No. 94/10569[8] and Citron et al.[16]. This mutation is commonly called the Swedish mutation and the cells, designated as "293 751 SWE", were plated in Corning 96-well plates at $2–4 \times 10^4$ cells per well in Dulbecco's minimal essential media (Sigma, St. Louis, Mo.) plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 μL of a compound of formula I (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media. From each well, 100 μL of conditioned media or appropriate dilutions thereof were transferred into an ELISA plate precoated with antibody 266 [P. Seubert, Nature (1992) 359:325–327][17] against amino acids 13–28 of β-amyloid peptide as described in International Patent Application Publication No. 94/10569[8] and stored at 4° C. overnight. An ELISA assay employing labelled antibody 3D6 [P. Seubert, Nature (1992) 359:325–327][17] against amino acids 1–5 of β-amyloid peptide was run the next day to measure the amount of β-amyloid peptide produced.

Cytotoxic effects of the compounds were measured by a modification of the method of Hansen, et al.[18]. To the cells remaining in the tissue culture plate was added 25 μL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562nm}$ and the $OD_{650nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compound was assayed for β-amyloid peptide production inhibition activity in cells using this assay. The results of this assay demonstrate that the compounds of formula I inhibit β-amyloid peptide production by at least 30% as compared to the control when employed at 10 μg/mL.

EXAMPLE 34

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) Nature 373:523–527].[19] Depending upon which compound is being tested, the compound is usually formulated at between 1 and 10 mg/mL. Because of the low solubility factors of the compounds, they may be formulated with various vehicles, such as corn oil (Safeway, South San Francisco, Calif.); 10% ethanol in corn oil; 2-hydroxypropyl-β-cyclodextrin (Research Biochemicals International, Natick Mass.); and carboxy-methyl-cellulose (Sigma Chemical Co., St. Louis Mo.).

The mice are dosed subcutaneously with a 26 gauge needle and 3 hours later the animals are euthanized via $CO_2$ narcosis and blood is taken by cardiac puncture using a 1 cc 25G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/ml aprotinin, 5 mM EDTA, pH 8.0, 10 μg/ml leupeptin], thereby reducing the final concentration of guanidine to 0.5 M, before centrifugation at 16,000×g for 20 minutes at 4° C. Samples are further diluted, if necessary, to achieve an optimal range for the ELISA measurements by the addition of casein buffer with 0.5 M guanidine hydrochloride added. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266 [P. Seubert, *Nature* (1992) 359:325–327][17], is specific to amino acids 13–28 of β-amyloid. The antibody 3D6 [Johnson-Wood et al., *PNAS USA* (1997) 94:1550–1555],[20] which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/ml (11 pM) and shows no cross-reactivity to the endogenous murine β-amyloid peptide at concentrations up to 1 ng/ml.

The configuration of the sandwich ELISA quantitating the level of β-amyloid (aa 1–42) employs the mAb 21F12 [Johnson-Wood et al., *PNAS USA* (1997) 94:1550–1555][20] (which recognizes amino acids 33–42 of β-amyloid ) as the capture antibody. Biotinylated 3D6 is also the reporter antibody in this assay which has a lower limit of sensitivity of ~125 pg/ml (28 pM).

The 266 and 21F12 capture mAbs are coated at 10 μg/ml into 96 well immunoassay plates (Costar, Cambidge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed ≧3 times with wash buffer between each step of the assay. The biotinylated 3D6, diluted to 0.5 μg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The calorimetric substrate, Slow TMB-ELISA (Pierce, Cambridge Mass.), is added and allowed to react for 15 minutes, after which the enzymatic reaction is stopped with addition of 2 N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5gm/l thimerosal, 8.5 gm/l sodium chloride, 0.5 ml Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

Formulations other than those described above can also be used for oral delivery and intravenous delivery to a mammal. For oral delivery, the compound can be mixed with either 100% corn oil or, alternatively, in a solution containing 80% corn oil, 19.5% oleic acid and 0.5% labrafil. The compound can be mixed with the above solutions in concentrations ranging from 1 mg/mL to 10 mg/mL. The compound in solution is preferably administered orally to the mammal at a dose volume of 5 mL/kg of body weight. For IV delivery, the compound is preferably mixed with a solution of 3% ethanol, 3% solutol HS-15 and 94% saline. The compound is preferably mixed with the above solution in concentrations ranging from 0.25 mg/mL to 5 mg/mL. The compound in solution is preferably administered by IV to the mammal at a dose volume of 2 mL/kg of body weight.

From the foregoing description, various modifications and changes in the composition and method will occur to those skilled in the art. All such modifications coming within the scope of the appended claims are intended to be included therein.

What is claimed is:

1. A compound having the formula:

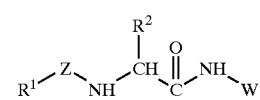

wherein:

R[1] is selected from the group consisting of:
A) alkyl of from 1 to 20 carbon atoms;
B) alkenyl of from 2 to 10 carbon atoms and 1–2 sites of alkenyl unsaturation;
C) alkynyl of from 2 to 10 carbon atoms and from 1–2 sites of alkynyl unsaturation;
D) cycloalkyl of from 3 to 12 carbon atoms;
E) cycloalkenyl of from 4 to 8 carbon atoms;
F) substituted alkyl of from 1 to 10 carbon atoms, having from 1 to 3 substituents selected from:
1) alkoxy having the formula alkyl-O— wherein alkyl is as defined in A herein;
2) substituted alkoxy of the formula substituted alkyl-O— wherein substituted alkyl is as defined in F herein;
3) cycloalkyl as defined in D herein;
4) substituted cycloalkyl as defined in I herein;
5) cycloalkenyl as defined in E herein;
6) substituted cycloalkenyl as defined in J herein;
7) acyl selected from alkyl-C(O)—, substituted alkyl-C(O)—, cycloalkyl-C(O)—, substituted cycloalkyl-C(O)—, optionally substituted aryl-C(O)—, optionally substituted heteroaryl-C(O)— and optionally substituted heterocyclic-C(O)— wherein alkyl is defined in A herein; wherein substituted alkyl is defined in F herein; wherein cycloalkyl is defined in D herein; wherein substituted cycloalkyl is defined in I herein; wherein optionally substituted aryl is defined in F25 herein; wherein optionally substituted heteroaryl is defined in F27 herein; and wherein optionally substituted heterocyclic is defined in F29 herein;

8) acylamino having the formula —C(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;

9) acyloxy selected from alkyl-C(O)O—, substituted alkyl-C(O)O—, cycloalkyl-C(O)O—, optionally substituted aryl-C(O)O—, optionally substituted heteraryl-C(O)O— and optionally substituted heterocyclic-C(O)O— wherein alkyl is defined in A herein; wherein substituted alkyl is defined in F herein; wherein cycloalkyl is defined in D herein; wherein optionally substituted aryl is defined in F25 herein; wherein optionally substituted heteroaryl is defined in F27 herein; and wherein optionally substituted heterocyclic is defined in F29 herein;

10) amino;

11) substituted amino having the formula —N(R)$_2$ wherein each R is independently selected from the group consisting of:
   a) hydrogen;
   b) alkyl as defined in A herein;
   c) substituted alkyl as defined in F herein;
   d) alkenyl as defined in B herein;
   e) substituted alkenyl as defined in G herein;
   f) alkynyl as defined in C herein;
   g) substituted alkynyl as defined in H herein;
   h) optionally substituted aryl as defined in F25 herein;
   i) cycloalkyl as defined in D herein;
   j) substituted cycloalkyl as defined in I herein;
   k) optionally substituted heteroaryl as defined in F27 herein;
   l) optionally substituted heterocyclic as defined in F29 hereof; and wherein one of R can also be hydrogen or R and R together with the nitrogen atom to which they are joined form an optionally substituted heterocyclic as defined in F29 herein;

12) aminoacyl having the formula —NRC(O)R wherein each R is independently hydrogen, alkyl, substituted alkyl, optionally substituted aryl, optionally substituted heteroaryl, or optionally substituted heterocyclic wherein alkyl is defined in A herein, wherein substituted alkyl is defined in F herein; wherein optionally substituted aryl is defined in F25 herein; wherein heteroaryl is defined in F27 herein; and wherein optionally substituted heterocyclic is defined in F29 herein;

13) aminoacyloxy having the formula —NRC(O)OR wherein each R is independently hydrogen, alkyl, substituted alkyl, optionally substituted aryl, optionally substituted heteroaryl, or optionally substituted heterocyclic wherein alkyl is defined in A herein, wherein substituted alkyl is defined in F herein, wherein optionally substituted aryl is defined in F25 herein, wherein optionally substituted heteroaryl is defined in F27 herein, and wherein optionally substituted heterocyclic is defined in F29 herein;

14) oxyacylamino having the formula —OC(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein, wherein optionally substituted aryl is defined in F25 herein, wherein optionally substituted heteroaryl is defined in F27 herein, and wherein optionally substituted heterocyclic is defined in F29 herein;

15) cyano;

16) halo selected from fluoro, chloro, brimo and iodo;

17) hydroxy;

18) carboxyl;

19) optionally substituted carboxyalkyl having the formula —C(O)O alkyl and —C(O)O substituted alkyl wherein alkyl is as defined in A and substituted alkyl is as defined in F;

20) keto;

21) thioketo;

22) thiol;

23) thioalkoxy having the formula —S-alkyl, wherein alkyl is defined in A herein;

24) substituted thioalkoxy having the formula —S-substituted alkyl, wherein substituted alkyl is defined in F herein;

25) optionally substituted aryl having 6 to 14 carbon atoms and optionally substituted with 1 to 5 substituents selected from:
   a) acyloxy as defined in F9 herein;
   b) hydroxy;
   c) acyl as defined in F7 herein;
   d) alkyl as defined in A herein;
   e) alkoxy as defined in F1 herein;
   f) alkenyl as defined in B herein;
   g) alkynyl as defined in C herein;
   h) substituted alkyl as defined in F herein;
   i) substituted alkoxy as defined in F2 herein;
   j) substituted alkenyl as defined in G herein;
   k) substituted alkynyl as defined in H herein;
   l) amino;
   m) substituted amino as defined in F11 herein;
   n) aminoacyl as defined in F12 herein;
   o) acylamino as defined in F8 herein;
   p) optionally substituted alkaryl in which the alkyl moiety has 1 to 8 carbon atoms and the aryl has 6 to 10 carbon atoms and is optionally substituted as defined in F25 herein;
   q) optionally substituted aryl as defined in F25 herein;
   r) optionally substituted aryloxy as defined in F26 herein;
   s) azido;
   t) carboxyl;
   u) optionally substituted carboxylalkyl as defined in F19 herein;
   v) cyano;
   w) halo as defined in F16 herein;
   x) nitro;
   y) optionally substituted heteroaryl as defined in F27 herein;
   z) optionally substituted heterocyclic as defined in F29 herein;

aa) aminoacyloxy as defined in F13 herein;
bb) oxyacylamino as defined in F14 herein;
cc) thioalkoxy as defined in F23 herein;
dd) substituted thioalkoxy as defined in F24 herein;
ee) optionally substituted thioaryloxy having the formula aryl-S— wherein aryl is optionally substituted as defined in F25 herein;
ff) optionally substituted thioheteroaryloxy having the formula heteroaryl-S— wherein heteroaryl is optionally substituted as defined in F27 herein;
gg) —SO-alkyl wherein alkyl is as defined in A herein;
hh) —SO-substituted alkyl wherein substituted alkyl is as defined in F herein;
ii) —SO-optionally substituted aryl wherein optionally substituted aryl is as defined in F25 herein;
jj) —SO-optionally substituted heteroaryl wherein optionally substituted heteroaryl is as defined in F27 herein;
kk) —SO$_2$-alkyl wherein alkyl is as defined in A herein;
ll) —SO$_2$-substituted alkyl wherein substituted alkyl is as defined in F herein;
mm) —SO$_2$-optionally substituted aryl wherein optionally substituted aryl is as defined in F25 herein;
nn) —SO$_2$-optionally substituted heteroaryl wherein optionally substituted heteroaryl is as defined in F27 herein; and
oo) trihalomethyl wherein halo is as defined in F16 herein;
26) optionally substituted aryloxy having the formula aryl-O— wherein aryl is optionally substituted aryl as defined in F25 herein;
27) optionally substituted heteroaryl having 1 to 15 ring carbon atoms and 1 to 4 ring heteroatoms selected from oxygen, nitrogen and sulfur and optionally substituted with 1 to 5 substituents selected from the same group of substituents as defined for optionally substituted aryl in F25 herein;
28) optionally substituted heteroaryloxy having the formula —O-heteroaryl wherein heteroaryl is optionally substituted heteroaryl as defined in F27 herein;
29) optionally substituted saturated or unsaturated heterocyclic from 1 to 15 ring carbon atoms and 1 to 4 ring heteroatoms selected from nitrogen, sulfur and oxygen and optionally substituted with 1 to 5 substituents selected from the same group of substituents as defined for substituted alkyl in F herein;
30) optionally substituted heterocycloxy having the formula —O-heterocyclic wherein heterocyclic is defined as optionally substituted heterocyclic on F29 hereof;
31) hydroxyamino;
32) alkoxyamino wherein alkoxy is as defined in F1;
33) nitro;
34) —SO-alkyl wherein alkyl is as defined in A herein;
35) —SO-substituted alkyl wherein substituted alkyl is as defined in F herein;
36) —SO-optionally substituted aryl wherein aryl is optionally substituted as defined in F25 herein;
37) —SO-optionally substituted heteroaryl wherein optionally substituted heteroaryl is as defined in F27 herein;
38) —SO$_2$-alkyl wherein alkyl is as defined in A herein;
39) —SO$_2$-substituted alkyl wherein substituted alkyl is as defined in F herein;
40) —SO$_2$-optionally substituted aryl wherein optionally substituted aryl is as defined in F25 herein;
41) —SO$_2$-optionally substituted heteroaryl wherein optionally substituted heteroaryl is as defined in F27 herein,
G) substituted alkenyl having 2 to 10 carbon atoms and having of from 1 to 3 substituents selected from the group consisting of:
1) alkoxy having the formula alkyl-O— wherein alkyl is as defined in A herein;
2) substituted alkoxy of the formula substituted alkyl-O— wherein substituted alkyl is as defined in F herein;
3) cycloalkyl as defined in D herein;
4) substituted cycloalkyl as defined in I herein;
5) cycloalkoxy;
6) substituted cycloalkoxy;
7) acyl as defined in F7 herein;
8) acylamino as defined in F8 herein;
9) acyloxy as defined in F9 herein;
10) amino;
11) substituted amino as defined in F11 herein;
12) aminoacyl as defined in F12 herein;
13) aminoacycloxy as defined in F13 herein;
14) cyano;
15) halo selected from fluoro, cholo, brimo and iodo;
16) hydroxy;
17) carboxyl;
18) optionally substituted carboxyalkyl having the formula —C(O)O-alkyl and —C(O)O-substituted alkyl wherein alkyl is as defined in A and substituted alkyl is as defined in F;
19) keto;
20) thioketo;
21) thiol;
22) thioalkoxy as defined in F23 herein;
23) substituted thioalkoxy as defined in F24 herein;
24) optionally substituted aryl as defined in F25 herein;
25) optionally substituted heteroaryl as defined in F27 herein;
26) optionally substituted saturated or unsaturated heterocyclic as defined in F29 herein;
27) optionally substituted heterocycloxy as defined in F30 herein;
28) nitro;
29) —SO-alkyl wherein alkyl is as defined in A herein;
30) —SO-substituted alkyl wherein substituted alkyl is as defined in F herein;
31) —SO-aryl wherein optionally substituted aryl is optionally substituted as defined in F25 herein;
32) —SO-optionally substituted heteroaryl wherein optionally substituted heteroaryl is as defined in F27 herein;
33) —SO$_2$-alkyl wherein alkyl is as defined in A herein;
34) —SO$_2$-substituted alkyl wherein substituted alkyl is as defined in F herein;

153

35) —SO$_2$-optionally substituted aryl wherein optionally substituted aryl is as defined in F25 herein; and 36) —SO$_2$-optionally substituted heteroaryl wherein optionally substituted heteroaryl is as defined in F27 herein;

H) substituted alkynyl having 2 to 10 carbon atoms having 1–2 sites of alkynyl unsaturation and having 1 to 3 substituents selected from the same group of substituents as defined for substituted alkenyl in G herein;

I) substituted cycloalkyl having 3 to 12 carbon atoms and having from 1 to 5 substituents selected from the same group of substituents as defined for substituted alkyl in F herein;

J) substituted cycloalkenyl as defined in E herein having from 1 to 5 substituents selected from the same group of substituents as defined for substituted alkyl in F herein;

K) optionally substituted aryl as defined in F25 herein;

L) optionally substituted heteroaryl as defined in F27 herein; and

M) optionally substituted heterocyclic as defined in F29 herein;

$R^2$ is selected from the group consisting of:

N) alkyl as defined in A herein;

O) substituted alkyl as defined in F herein;

P) alkenyl of from 2 to 8 carbon atoms and 1–2 sites of alkenyl unsaturation;

Q) substituted alkenyl as defined in G herein;

R) alkynyl of from 2 to 8 carbon atoms and from 1–2 sites of alkynyl unsaturation;

S) substituted alkynyl as defined in H herein;

T) cycloalkyl of from 3 to 12 carbon atoms;

U) optionally substituted aryl as defined in F25 herein;

V) optionally substituted heteroaryl as defined in F27 herein; and

W) optionally substituted heterocyclic as defined in F29 herein;

Z is represented by the formula —T—CX'X"V— wherein:

T is selected from the group consisting of a bond covalently linking $R^1$ to —CX'X", oxygen, sulfur and —NR$^6$ wherein $R^6$ is hydrogen, acyl as defined in F7 herein, alkyl as defined in A herein, optionally substituted aryl as defined in F25 herein or optionally substituted heteroaryl as defined in F27 herein;

X' and X" are independently selected from hydrogen, hydroxy or fluoro or together form oxo with the proviso that when T is oxygen, sulfur or —NR$^6$ then X' and X" are each hydrogen;

V is alkylene having 1 to 10 carbon atoms or substituted alkylene having 1 to 10 carbon atoms in the alkylene moiety and having 1 to 3 substituents selected from the with the same group of substituents as defined for substituted alkenyl in G herein with the proviso that V is not carbonyl; and W is cyclic group selected from the group consisting of:

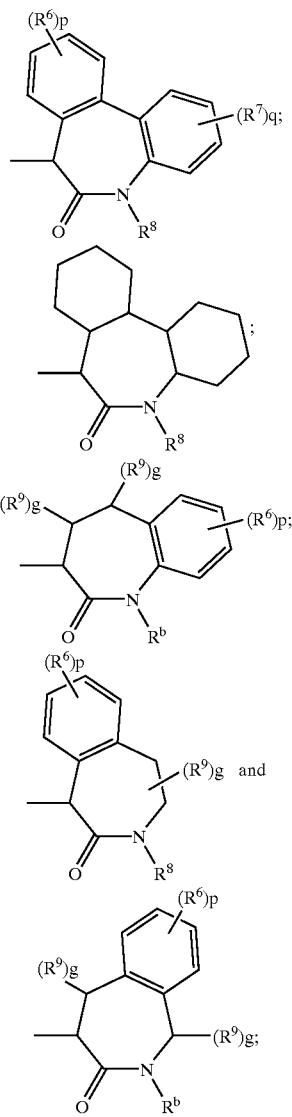

wherein:

each $R^6$ and $R^7$ is independently selected from the group consisting of acyl as defined in F7 herein, acylamino as defined in F8 herein, acyloxy as defined in F9 herein, alkenyl having 2 to 10 carbon atoms, substituted alkenyl as defined in G herein, alkoxy as defined in F1 herein, substituted alkoxy as defined in F2 herein, alkyl as defined in A herein, substituted alkyl as defined in F herein, alkynyl having 2 to 10 carbon atoms, substituted alkynyl as defined in H herein, amino, substituted amino as defined in F11, aminoacyl as defined in F12 herein, optionally substituted aryl as defined in F25 herein, optionally substituted aryloxy as defined in F26 herein, carboxyl, carboxyalkyl as defined in F19 herein, cyano, cycloalkyl having 3 to 12 carbon atoms, substituted cycloalkyl as defined in I herein, halo, optionally substituted heteroaryl as defined in F27 herein, optionally substituted heterocyclic as defined in F29 herein, nitro, thioalkoxy as defined in F24 herein, substituted thioalkoxy as defined in F25 herein, optionally substituted thioaryloxy having the formula optionally substituted aryl-S— wherein optionally substituted aryl is as defined in F25, thioheteroaryloxy having the formula heteroaryl-S— wherein heteroaryl is optionally substituted heteroaryl as defined in F27 herein, —SO-alkyl wherein alkyl is as defined in A herein, —SO-substituted alkyl wherein substituted alkyl is as defined in F herein, —SO-optionally substituted aryl, wherein optionally substituted aryl is as defined in F25 herein, —SO-optionally substituted heteroaryl wherein —SO²-substituted alkyl wherein substituted alkyl is as defined in F, —SO₂-optionally substituted aryl wherein optionally substituted aryl is as defined in F25 herein, and —SO₂-optionally substituted heteroaryl wherein optionally substituted heteroaryl is as defined in F27 herein;

$R^8$ is selected from the group consisting of hydrogen, alkyl as defined in A herein, substituted alkyl as defined in F herein, alkenyl having 2 to 10 carbon atoms, substituted alkenyl as defined in G herein, alkynyl having 2 to 10 carbon atoms, substituted alkynyl as defined in H herein, acyl as defined in F7 herein, optionally substituted aryl as defined in F25 herein, cycloalkyl having 3 to 12 carbon atoms, substituted cycloalkyl as defined in I herein, cycloalkenyl as defined in E herein, substituted cycloalkenyl as defined in J herein, optionally substituted heteroaryl as defined in F27 herein, and optionally substituted heterocyclic as defined in F29 herein;

$R^9$ is independently selected from the group consisting of alkyl as defined in A hereto, substituted alkyl as defined in F herein, alkenyl having 2 to 10 carbon atoms, substituted alkenyl as defined in G herein, alkynyl having 2 to 10 carbon atoms, substituted alkynyl as defined in H herein, optionally substituted aryl as defined in F25 herein, cycloalkyl having 3 to 12 carbon atoms, substituted cycloalkyl as defined in I herein, cycloalkenyl as defined in E, substituted cycloalkenyl as defined in J herein, optionally substituted heteroaryl as defined in F27 herein, and optionally substituted heterocyclic as defined in F29 herein; g is 0, 1 or 2; p is 0, 1, 2, 3 or 4; and q is 0, 1, 2, 3, or 4; or a pharmaceutically acceptable salt thereof.

2. The compound according to claim 1 wherein W has the formula:

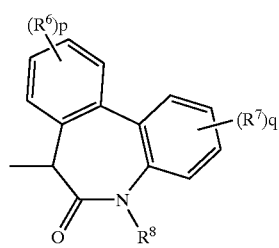

wherein $R^6$, $R^7$, $R^8$, p and q are as defined in claim 1.

3. The compound according to claim 1 wherein W has the formula:

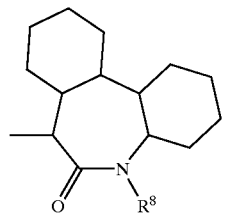

wherein $R^8$ is as defined in claim 1.

4. The compound according to claim 1 wherein W has the formula:

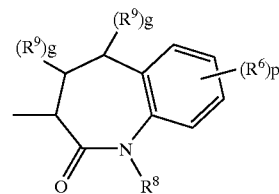

wherein $R^6$, $R^8$, $R^9$, g and p are as defined in claim 1.

5. The compound according to claim 1 wherein W has the formula:

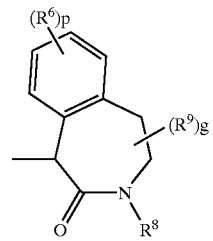

wherein $R^6$, $R^8$, $R^9$, g and p are as defined in claim 1.

6. The compound according to claim 1 wherein W has the formula:

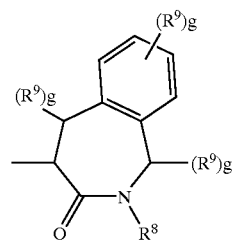

wherein $R^6$, $R^8$, $R^9$, g and p are as defined in claim 1.

7. The compound according to claim 2, 3, 4, 5 or 6 wherein V is alkylene having 1 to 6 carbon atoms.

8. A pharmaceutical composition comprising a pharmaceutically acceptable carrier and a pharmaceutically effective amount of a compound or mixture of compounds according to claim 2, 3, 4, 5 or 6.

9. A method for inhibiting β-amyloid peptide release and/or its synthesis in a cell which method comprises administering to such a cell an amount of a compound or a mixture of compounds according to claim 2, 3, 4, 5 or 6 effective in inhibiting the cellular release and/or synthesis of β-amyloid peptide.

10. A method for treating a human patient with Alzheimer's Disease in order to inhibit further deterioration in the condition of that patient which method comprises administering to said patient a pharmaceutical composition comprising a pharmaceutically acceptable inert carrier and an effective amount of a compound or a mixture of compounds according to claim 3, 4, 5 or 6.

11. A method for inhibiting β-amyloid peptide release and/or its synthesis in a cell which method comprises administering to such a cell an amount of a compound or a mixture of compounds according to claim 1 effective in inhibiting the cellular release and/or synthesis of β-amyloid peptide.

12. A method for treating a human patient with Alzheimer's disease in order to inhibit further deterioration in the condition of that patient which method comprises administering to said patient a pharmaceutical composition comprising a pharmaceutical inert carrier and an effective amount of a compound or a mixture of compounds according to claim 1.

13. The method according to claim 11 or 12 wherein $R^1$ is selected from the group consisting of phenyl, 1-naphthyl, 2-naphthyl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl)phenyl, 3,5-dimethoxyphenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5,6-pentafluorophenyl, 2,5-dimethylphenyl, 4-phenylphenyl, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyridin-2-yl, pyridin-3-yl, pyridin-4-yl, fluoropyridyls (including 5-fluoropyridin-3-yl), chloropyridyls (including 5-chloropyridin-3-yl), thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetraol-5-yl, allyl, 2-(cyclohexyl)ethyl, (CH$_3$)$_2$CH═CHCH$_2$CH$_2$CH(CH$_3$)—, φC(O)CH$_2$—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl) methyl, (2-methoxyphenyl)methyl, (3-methoxyphenyl)methyl, (3-hydroxyphenyl)methyl, (4-hydroxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH$_3$OC(O)CH$_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH$_3$CH═CH—, CH$_3$CH$_2$CH═CH—, (4-chlorophenyl)C(O)CH$_2$—, 4-(fluorophenyl)-NHC(O)CH$_2$—, 1-phenyl-n-butyl, (φ)$_2$CHNHC(O)CH$_2$CH$_2$—, (CH$_3$)$_2$NC(O)CH$_2$—, methylcarbonylmethyl, (2,4-dimethylphenyl)C(O)CH$_2$—, 4-methoxyphenyl-C(O)CH$_2$—, phenyl-C(O)CH$_2$—, CH$_3$C(O)N(φ)—, ethenyl, methylthiomethyl, (CH$_3$)$_3$CNHC(O)CH$_2$—, 4-fluorophenyl-C(O)CH$_2$—, diphenylmethyl, phenoxymethyl, 3,4-methylenedioxyphenyl-CH$_2$—, benzo[b]thiophen-3-yl, (CH$_3$)$_3$COC(O)NHCH$_2$—, trans-styryl, H$_2$NC(O)CH$_2$CH$_2$—, 2-trifluoromethylphenyl-C(O)CH$_2$, φC(O)NHCH(φ)CH$_2$—, mesityl, CH$_3$CH(═NHOH)CH$_2$—, 4-CH$_3$-φ-NHC(O)CH$_2$CH$_2$—, φC(O)CH(φ)CH$_2$—, (CH$_3$)$_2$CHC(O)NHCH(φ)—, CH$_3$CH$_2$OCH$_2$—, CH$_3$OC(O)CH(CH$_3$)(CH$_2$)$_3$—, 2,2,2-trifluoroethyl, 1-(trifluoromethyl)ethyl, 2-CH$_3$-benzofuran-3-yl, 2-(2,4-dichlorophenoxy)ethyl, φSO$_2$CH$_2$—, 3-cyclohexyl-n-propyl, CF$_3$CH$_2$CH$_2$CH$_2$— and N-pyrrolidinyl.

14. The method according claim 11 or 12 wherein $R^2$ is independently selected from the group consisting of alkyl, substituted alkyl, alkenyl, cycloalkyl, optionally substituted aryl, optionally substituted heteroaryl and optionally substituted heterocyclic.

15. The method according to claim 14 wherein $R^2$ is selected from the group consisting of methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyridin-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)═CH$_2$, —CH$_2$CH═CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl, pyridyl, —CH$_2$-naphthyl, —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl and thien-3-yl.

16. The method according to claim 11 or 12 wherein $R^8$ is selected from the group of hydrogen, alkyl, substituted alkyl and cycloalkyl.

17. The method according to claim 16 wherein $R^8$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, and cyclohexyl.

18. The method according to claim 11 or 12 wherein $R^9$ is hydrogen, alkyl or substituted alkyl.

19. The method according to claim 11 or 12 wherein said compounds is selected from the group consisting of:

5-(S)-(N'-(2-(3,5-difluorophenyl)ethyl)-L-alaninyl)-amino-7-methyl-5,7-dihydro-6H-dibenz[b,d]azepin-6-one 5(S)-(N'-(2(R)-hydroxy-2-(3,5-difluorophenyl)ethyl)-L-alaninyl)-amino-7-methyl-5,7-dihydro-6H-dibenz[b,d]azepin-6-one 5(S)-(N'-(2(S)-hydroxy-2-(3,5-difluorophenyl)ethyl)-L-alaninyl)-amino-7-methyl-5,7-dihydro-6H-dibenz[b,d]azepin-6-one 5(S)-(N'-(2(R/S)-hydroxy-3-isopropyloxy-propyl)-L-alaninyl)-amino-7-methyl-5,7-dihydro-6H-dibenz[b,d]azepin-6-one 5(S)-(N'-(2(R/S)-hydroxy-butyl)-L-alaninyl)-amino-7-methyl-5,7-dihydro-6H-dibenz[b,d]azepin-6-one 5(S)-(N'-(2(R/S)-3-dihydroxy-propyl)-L-alaninyl)-amino-7-methyl-5,7-dihydro-6H-dibenz[b,d]azepin-6-one 5(S)-(N'-(2(R/S)-hydroxy-3-morpholinopropyl)-L-alaninyl)-amino-7-methyl-5,7-dihydro-6H-dibenz[b,d]azepin-6-one 5(S)-(N'-(2(R/S)-hydroxy-tetradecyl)-L-alaninyl)-amino-7-methyl-5,7-dihydro-6H-dibenz[b,d]azepin-6-one 5(S)-(N'-(2(R/S)-hydroxy-octyl)-L-alaninyl)-amino-7-methyl-5,7-dihydro-6H-dibenz[b,d]azepin-6-one 5(S)-(N'-(2(R)-hydroxy-2-(3,4,5-trifluorophenyl)ethyl)-L-alaninyl)-amino-7-methyl-5,7-dihydro-6H-dibenz[b,d]azepin-6-one 5(S)-(N'-(2(S)-hydroxy-2-(3,4,5-trifluorophenyl)ethyl)-L-alaninyl)-amino-7-methyl-5,7-dihydro-6H-dibenz[b,d]azepin-6-one 5(S)-(N'-(2(R)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,3,3-trifluoro)-propyl)-L-alaninyl)-amino-7-methyl-5,7-dihydro-6H-dibenz[b,d]azepin-6-one 5(S)-(N'-(2(S)-hydroxy-2-(3,3,3-trifluoro)-propyl)-L-alaninyl)-amino-7-methyl-5,7-dihydro-6H-dibenz[b,d]azepin-6-one 5-(S)-(N'-(3-methyl-2-butanone)-L-alaninyl)-amino-7-methyl-5,7-dihydro-6H-dibenz[b,d]azepin-6-one 5-(S)-(N'-(3-methyl-2-(S)-hydroxybutyl)-L-alaninyl)-amino-7-methyl-5,7-dihydro-6H-dibenz[b,d]azepin-6-one 5-[N'-(S)-2-(4-methylpentyl)amino-3-methylbutyryl-L-alaninyl]-amino-7-methyl-5,7-dihydro-6H-dibenz[b,d]azepin-6-one 5-(S)-{N'-[(1RS,2SR)-1,2,3,4-tetrahydro-1-hydroxy-2-naphthyl]alaninyl}-amino-7-methyl-5,7-dihydro-6H-dibenz[b,d]azepin-6-one 5-(S)-[N'-(2-α-tetralone)-L-alaninyl]-amino-7-methyl-5,7-dihydro-6H-dibenz[b,d]azepin-6-one hydrochloride 5-(S)-[N'-(1,2,3,4-tetrahydro-2-naphthyl)-L-alaninyl]-amino-7-methyl-5,7-dihydro-6H-dibenz[b,d]azepin-6-one 5-(S)-{N'-[(1RS,2SR)-1-hydroxy-2-cyclohexyl]alaninyl}-amino-7-methyl-5,7-dihydro-6H-dibenz[b,d]azepin-6-one, and 5-(S)-[N'-(4-methylpentyl)-L-alaninyl]-amino-7-methyl-5,7-dihydro-6H-dibenz[b,d]azepin-6-one.

20. A pharmaceutical composition comprising a pharmaceutically acceptable carrier and a pharmaceutically effective amount of a compound or mixtures of compounds according to claim 1.

21. The pharmaceutical composition according to claim 20 wherein $R^1$ is selected from the group consisting of phenyl, 1-naphthyl, 2-naphthyl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl)phenyl, 3,5-dimethoxyphenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5,6-pentafluorophenyl, 2,5-dimethylphenyl, 4-phenylphenyl, 2-fluoro-3-trifluoromethylphenyl, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyridin-2-yl, pyridin-3-yl, pyridin-4-yl, fluoropyridyls (including 5-fluoropyridin-3-yl), chloropyridyls (including 5-chloropyridin-3-yl), thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetrazol-5-yl, allyl, 2-(cyclohexyl)ethyl, (CH$_3$)$_2$CH=CHCH$_2$CH$_2$CH(CH$_3$)—, φC(O)CH$_2$—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl)methyl, (2-methoxyphenyl)methyl, (3-methoxyphenyl)methyl, (3-hydroxyphenyl)methyl, (4-hydroxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, $CH_3OC(O)CH_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, $CH_3CH=CH$—, $CH_3CH_2CH=CH$—, (4-chlorophenyl)C(O)$CH_2$—, 4-(fluorophenyl)-NHC(O)$CH_2$—, 1-phenyl-n-butyl, $(\phi)_2CHNHC(O)CH_2CH_2$—, $(CH_3)_2NC(O)CH_2$—, methylcarbonylmethyl, (2,4-dimethylphenyl)C(O)$CH_2$—, 4-methoxyphenyl-C(O)$CH_2$—, phenyl-C(O)$CH_2$—, $CH_3C(O)N(\phi)$—, ethenyl, methylthiomethyl, $(CH_3)_3CNHC(O)CH_2$—, 4-fluorophenyl-C(O)$CH_2$—, diphenylmethyl, phenoxymethyl, 3,4-methylenedioxyphenyl-$CH_2$—, benzo[b]thiophen-3-yl, $(CH_3)_3COC(O)NHCH_2$—, trans-styryl, $H_2NC(O)CH_2CH_2$—, 2-trifluoromethylphenyl-C(O)$CH_2$, $\phi C(O)NHCH(\phi)CH_2$—, mesityl, $CH_3CH(=NHOH)CH_2$—, 4-$CH_3$-$\phi$-NHC(O)$CH_2CH_2$—, $\phi C(O)CH(\phi)CH_2$—, $(CH_3)_2CHC(O)NHCH(\phi)$—, $CH_3CH_2OCH_2$—, $CH_3OC(O)CH(CH_3)(CH_2)_3$—, 2,2,2-trifluoroethyl, 1-(trifluoromethyl)ethyl, 2-$CH_3$-benzofuran-3-yl, 2-(2,4-dichlorophenoxy)ethyl, $\phi SO_2CH_2$—, 3-cyclohexyl-n-propyl, $CF_3CH_2CH_2CH_2$— and N-pyrrolidinyl.

22. The pharmaceutical composition according to claim 20 wherein $R^2$ is independently selected from the group consisting of alkyl, substituted alkyl, alkenyl, cycloalkyl, optionally substituted aryl, optionally substituted heteroaryl and optionally substituted heterocyclic.

23. The pharmaceutical composition according to claim 22 wherein $R^2$ is selected from the group consisting of methyl, ethyl, n-propyl, iso-propyl, n-butyl, iso-butyl, sec-butyl, tert-butyl, —$CH_2CH(CH_2CH_3)_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —$CH_2$-cyclopropyl, —$CH_2$-cyclohexyl, —$CH_2CH_2$-cyclopropyl, —$CH_2CH_2$-cyclohexyl, —$CH_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-$(CH_3)_2NCH_2CH_2CH_2O$-benzyl, p-$(CH_3)_3COC(O)CH_2O$-benzyl, p-(HOOC$CH_2O$)-benzyl, 2-aminopyridin-6-yl, p-(N-morpholino-$CH_2CH_2O$)-benzyl, —$CH_2CH_2C(O)NH_2$, —$CH_2$-imidazol-4-yl, —$CH_2$-(3-tetrahydrofuranyl), —$CH_2$-thiophen-2-yl, —$CH_2$(1-methyl)cyclopropyl, —$CH_2$-thiophen-3-yl, thiophen-3-yl, thiophen-2-yl, —$CH_2$—C(O)O-t-butyl, —$CH_2$—C$(CH_3)_3$, —$CH_2CH(CH_2CH_3)_2$, 2-methylcyclopentyl, cyclohex-2-enyl, —CH[CH$(CH_3)_2$]COOCH$_3$, —$CH_2CH_2N(CH_3)_2$, —$CH_2C(CH_3)=CH_2$, —$CH_2CH=CHCH_3$ (cis and trans), —$CH_2OH$, —CH(OH)$CH_3$, —CH(O-t-butyl)$CH_3$, —$CH_2OCH_3$, —$(CH_2)_4$NH-Boc, —$(CH_2)_4NH_2$, —$CH_2$-pyridyl, pyridyl, —$CH_2$-naphthyl, —$CH_2$-(N-morpholino), p-(N-morpholino-$CH_2CH_2O$)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynapht-2-yl, —$CH_2CH_2SCH_3$, thien-2-yl and thien-3-yl.

24. The pharmaceutical composition according to claim 20 wherein $R^8$ is selected from the group consisting of hydrogen, alkyl, substituted alkyl and cycloalkyl.

25. The pharmaceutical composition according to claim 24 wherein $R^8$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, and cyclohexyl.

26. The pharmaceutical composition according to claim 20 wherein $R^9$ is hydrogen, alkyl or substituted alkyl.

27. The pharmaceutical composition according to claim 20 wherein said compound is selected from the group consisting of:

5-(S)-(N'-(2-(3,5-difluorophenyl)ethyl)-L-alaninyl)-amino-7-methyl-5,7-dihydro-6H-dibenz[b,d]azepin-6-one 5(S)-(N'-(2(R)-hydroxy-2-(3,5-difluorophenyl)ethyl)-L-alaninyl)-amino-7-methyl-5,7-dihydro-6H-dibenz[b,d]azepin-6-one 5(S)-(N'-(2(S)-hydroxy-2-(3,5-difluorophenyl)ethyl)-L-alaninyl)-amino-7-methyl-5,7-dihydro-6H-dibenz[b,d]azepin-6-one 5(S)-(N'-(2(R/S)-hydroxy-3-isopropyloxy-propyl)-L-alaninyl)-amino-7-methyl-5,7-dihydro-6H-dibenz[b,d]azepin-6-one 5(S)-(N'-(2(R/S)-hydroxy-butyl)-L-alaninyl)-amino-7-methyl-5,7-dihydro-6H-dibenz[b,d]azepin-6-one 5(S)-(N'-(2(R/S)-3-dihydroxy-propyl)-L-alaninyl)-amino-7-methyl-5,7-dihydro-6H-dibenz[b,d]azepin-6-one 5(S)-(N'-(2(R/S)-hydroxy-3-morpholinopropyl)-L-alaninyl)-amino-7-methyl-5,7-dihydro-6H-dibenz[b,d]azepin-6-one 5(S)-(N'-(2(R/S)-hydroxy-tetradecyl)-L-alaninyl)-amino-7-methyl-5,7-dihydro-6H-dibenz[b,d]azepin-6-one 5(S)-(N'-(2(R/S)-hydroxy-octyl)-L-alaninyl)-amino-7-methyl-5,7-dihydro-6H-dibenz[b,d]azepin-6-one 5(S)-(N'-(2(R)-hydroxy-2-(3,4,5-trifluorophenyl)ethyl)-L-alaninyl)-amino-7-methyl-,7-dihydro-6H-dibenz[b,d]azepin-6-one 5(S)-(N'-(2(S)-hydroxy-2-(3,4,5-trifluorophenyl)ethyl)-L-alaninyl)-amino-7-methyl-5,7-dihydro-6H-dibenz[b,d]azepin-6-one 5(S)-(N'-(2(R)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,3,3-trifluoro)-propyl)-L-alaninyl)-amino-7-methyl-5,7-dihydro-6H-dibenz[b,d]azepin-6-one 5(S)-(N'-(2(S)-hydroxy-2-(3,3,3-trifluoro)-propyl)-L-alaninyl)-amino-7-methyl-5,7-dihydro-6H-dibenz[b,d]azepin-6-one 5-(S)-(N'-(3-methyl-2-butanone)-L-alaninyl)-amino-7-methyl-5,7-dihydro-6H-dibenz[b,d]azepin-6-one 5-(S)-(N'-(3-methyl-2-(S)-hydroxybutyl)-L-alaninyl)-amino-7-methyl-5,7-dihydro-6H-dibenz[b,d]azepin-6-one 5-[N'-(S)-2-(4-methylpentyl)amino-3-methylbutyryl-L-alaninyl]-amino-7-methyl-5,7-dihydro-6H-dibenz[b,d]azepin-6-one 5-(S)-{N'-[(1RS,2SR)-1,2,3,4-tetrahydro-1-hydroxy-2-naphthyl]alaninyl}-amino-7-methyl-5,7-dihydro-6H-dibenz[b,d]azepin-6-one 5-(S)-[N'-(2-α-tetralone)-L-alaninyl]-amino-7-methyl-5,7-dihydro-6H-dibenz[b,d]azepin-6-one hydrochloride 5-(S)-[N'-(1,2,3,4-tetrahydro-2-naphthyl)-L-alaninyl]-amino-7-methyl-5,7-dihydro-6H-dibenz[b,d]azepin-6-one 5-(S)-{N'-[(1RS,2SR)-1-hydroxy-2-cyclohexyl]alaninyl}-amino-7-methyl-5,7-dihydro-6H-dibenz[b,d]azepin-6-one, and 5-(S)-[N'-(4-methylpentyl)-L-alaninyl]-amino-7-methyl-5,7-dihydro-6H-dibenz[b,d]azepin-6-one.

28. The compound according to claim 1 wherein $R^1$ is selected from the group consisting of phenyl, 1-naphthyl, 2-naphthyl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl)phenyl, 3,5-dimethoxyphenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5,6-pentafluorophenyl, 2,5-dimethylphenyl, 4-phenylphenyl, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyridin-2-yl, pyridin-3-yl, pyridin-4-yl, fluoropyridyls (including 5-fluoropyridin-3-yl), chloropyridyls (including 5-chloropyridin-3-yl), thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetraol-5-yl, allyl, 2-(cyclohexyl)ethyl, (CH$_3$)$_2$CH=CHCH$_2$CH$_2$CH(CH$_3$)—, φC(O)CH$_2$—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl)methyl, (2-methoxyphenyl)methyl, (3-methoxyphenyl)methyl, (3-hydroxyphenyl)methyl, (4-hydroxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH$_3$OC(O)CH$_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH$_3$CH=CH—, CH$_3$CH$_2$CH=CH—, (4-chlorophenyl)C(O)CH$_2$—, 4-(fluorophenyl)-NHC(O)CH$_2$—, 1-phenyl-n-butyl, (φ)$_2$CHNHC(O)CH$_2$CH$_2$—, (CH$_3$)$_2$NC(O)CH$_2$—, methylcarbonylmethyl, (2,4-dimethylphenyl)C(O)CH$_2$—, 4-methoxyphenyl-C(O)CH$_2$—, phenyl-C(O)CH$_2$—, CH$_3$C(O)N(φ)—, ethenyl, methylthiomethyl, (CH$_3$)$_3$CNHC(O)CH$_2$—, 4-fluorophenyl-C(O)CH$_2$—, diphenylmethyl, phenoxymethyl, 3,4-methylenedioxyphenyl-CH$_2$—, benzo[b]thiophen-3-yl, (CH$_3$)$_3$COC(O)NHCH$_2$—, trans-styryl, H$_2$NC(O)CH$_2$CH$_2$—, 2-trifluoromethylphenyl-C(O)CH$_2$, φC(O)NHCH(φ)CH$_2$—, mesityl, CH$_3$CH(=NHOH)CH$_2$—, 4-CH$_3$-φ-NHC(O)CH$_2$CH$_2$—, φC(O)CH(φ)CH$_2$—, (CH$_3$)$_2$CHC(O)NHCH(φ)—, CH$_3$CH$_2$OCH$_2$—, CH$_3$OC(O)CH(CH$_3$)(CH$_2$)$_3$—, 2,2,2-trifluoroethyl, 1-(trifluoromethyl)ethyl, 2-CH$_3$-benzofuran-3-yl, 2-(2,4-dichlorophenoxy)ethyl, φSO$_2$CH$_2$—, 3-cyclohexyl-n-propyl, CF$_3$CH$_2$CH$_2$CH$_2$— and N-pyrrolidinyl.

29. The compound according to claim 1 wherein $R^2$ is independently selected from the group consisting of alkyl, substituted alkyl, alkenyl, cycloalkyl, optionally substituted aryl, optionally substituted heteroaryl and optionally substituted heterocyclic.

30. The compound according to claim 29 wherein $R^2$ is selected from the group consisting of methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyridin-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl, pyridyl, —CH$_2$-naphthyl, —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl and thien-3-yl.

31. The compound according to claim 1 wherein $R^8$ is selected from the group consisting of hydrogen, alkyl, substituted alkyl and cycloalkyl.

32. The compound according to claim 31 wherein $R^8$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, and cyclohexyl.

33. The compound according to claim 1 wherein $R^9$ is hydrogen, alkyl or substituted alkyl.

34. The compound according to claim 1 wherein said compound is selected from the group consisting of:

5-(S)-(N'-(2-(3,5-difluorophenyl)ethyl)-L-alaninyl)-amino-7-methyl-5,7-dihydro-6H-dibenz[b,d]azepin-6-one 5(S)-(N'-(2(R)-hydroxy-2-(3,5-difluorophenyl)ethyl)-L-alaninyl)-amino-7-methyl-5,7-dihydro-6H-dibenz[b,d]azepin-6-one 5(S)-(N'-(2(S)-hydroxy-2-(3,5-difluorophenyl)ethyl)-L-alaninyl)-amino-7-methyl-5,7-dihydro-6H-dibenz[b,d]azepin-6-one 5(S)-(N'-(2(R/S)-hydroxy-3-isopropyloxy-propyl)-L-alaninyl)-amino-7-methyl-5,7-dihydro-6H-dibenz[b,d]azepin-6-one 5(S)-(N'-(2(R/S)-hydroxy-butyl)-L-alaninyl)-amino-7-methyl-5,7-dihydro-6H-dibenz[b,d]azepin-6-one 5(S)-(N'-(2(R/S)-3-dihydroxy-propyl)-L-alaninyl)-amino-7-methyl-5,7-dihydro-6H-dibenz[b,d]azepin-6-one 5(S)-(N'-(2(R/S)-hydroxy-3-morpholinopropyl)-L-alaninyl)-amino-7-methyl-5,7-dihydro-6H-dibenz[b,d]azepin-6-one 5(S)-(N'-(2(R/S)-hydroxy-tetradecyl)-L-alaninyl)-amino-7-methyl-5,7-dihydro-6H-dibenz[b,d]azepin-6-one 5(S)-(N'-(2(R/S)-hydroxy-octyl)-L-alaninyl)-amino-7-methyl-5,7-dihydro-6H-dibenz[b,d]azepin-6-one 5(S)-(N'-(2(R)-hydroxy-2-(3,4,5-trifluorophenyl)ethyl)-L-alaninyl)-amino-7-methyl-5,7-dihydro-6H-dibenz[b,d]azepin-6-one 5(S)-(N'-(2(S)-hydroxy-2-(3,4,5-trifluorophenyl)ethyl)-L-alaninyl)-amino-7-methyl-5,7-dihydro-6H-dibenz[b,d]azepin-6-one 5(S)-(N'-(2(R)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(4-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(S)-hydroxy-2-(3,5-bis-(trifluoromethyl)phenyl)ethyl)-L-alaninyl)-amino-7-methyl-5,7-dihydro-6H-dibenz[b,d]azepin-6-one 5(S)-(N'-(2(R)-hydroxy-2-(3,3,3-trifluoro)-propyl)-L-alaninyl)-amino-7-methyl-5,7-dihydro-6H-dibenz[b,d]azepin-6-one 5(S)-(N'-(2(S)-hydroxy-2-(3,3,3-trifluoro)-propyl)-L-alaninyl)-amino-7-methyl-5,7-dihydro-6H-dibenz[b,d]azepin-6-one 5-(S)-(N'-(3-methyl-2-butanone)-L-alaninyl)-amino-7-methyl-5,7-dihydro-6H-dibenz[b,d]azepin-6-one 5-(S)-(N'-(3-methyl-2-(S)-hydroxybutyl)-L-alaninyl)-amino-7-methyl-5,7-dihydro-6H-dibenz[b,d]azepin-6-one 5-[N'-(S)-2-(4-methylpentyl)amino-3-methylbutyryl-L-alaninyl]-amino-7-methyl-5,7-dihydro-6H-dibenz[b,d]azepin-6-one 5-(S)-{N'-[(1RS,2SR)-1,2,3,4-tetrahydro-1-hydroxy-2-naphthyl]alaninyl}-amino-7-methyl-5,7-dihydro-6H-dibenz[b,d]azepin-6-one 5-(S)-[N'-(2-α-tetralone)-L-alaninyl]-amino-7-methyl-5,7-dihydro-6H-dibenz[b,d]azepin-6-one hydrochloride 5-(S)-[N'-(1,2,3,4-tetrahydro-2-naphthyl)-L-alaninyl]-amino-7-methyl-5,7-dihydro-6H-dibenz[b,d]azepin-6-one 5-(S)-{N'-[(1RS,2SR)-1-hydroxy-2-cyclohexyl]alaninyl}-amino-7-methyl-5,7-dihydro-6H-dibenz[b,d]azepin-6-one and 5-(S)-[N'-(4-methylpentyl)-L-alaninyl]-amino-7-methyl-5,7-dihydro-6H-dibenz[b,d]azepin-6-one.

* * * * *